US011022598B2

(12) United States Patent
Huff et al.

(10) Patent No.: US 11,022,598 B2
(45) Date of Patent: Jun. 1, 2021

(54) DEVICES AND METHODS FOR SAMPLE ANALYSIS

(71) Applicant: ABBOTT LABORATORIES, Abbott Park, IL (US)

(72) Inventors: Jeffrey B. Huff, Lincolnshire, IL (US); Mark A. Hayden, Ingleside, IL (US); Peter J. Karabatsos, Glencoe, IL (US); Andrew S. Schapals, Pleasant Prairie, WI (US); Anthony S. Muerhoff, Kenosha, WI (US); M. Felicia Bogdan, Gurnee, IL (US); Thomas Leary, Kenosha, WI (US); Shelley R. Holets-McCormack, Waukegan, IL (US); Sophie Laurenson, Basel-Land (CH); Andrew T. Fischer, Euless, TX (US); Richard Haack, Skokie, IL (US); Stefan Hershberger, Highland Park, IL (US); Dustin House, Carrollton, TX (US); Lei Qiao, Lake Bluff, IL (US); M. Shawn Murphy, Allen, TX (US); Mark R. Pope, Grayslake, IL (US); Edna M. Prieto-Ballengee, Dallas, TX (US); QiaoQiao Ruan, Kildeer, IL (US); Pathik Soni, Chicago, IL (US); Sergey Tetin, Lindenhurst, IL (US); Lyle Yarnell, Richardson, TX (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 15/724,213

(22) Filed: Oct. 3, 2017

(65) Prior Publication Data
US 2018/0188230 A1    Jul. 5, 2018

Related U.S. Application Data

(63) Continuation of application No. PCT/US2016/025787, filed on Apr. 2, 2016.
(Continued)

(51) Int. Cl.
*G01N 33/487* (2006.01)
*G01N 33/543* (2006.01)
(Continued)

(52) U.S. Cl.
CPC .. *G01N 33/48721* (2013.01); *B01L 3/502761* (2013.01); *G01N 33/5308* (2013.01);
(Continued)

(58) Field of Classification Search
CPC ....... G01N 33/48721; G01N 33/54306; G01N 33/5308; B01L 3/502761
See application file for complete search history.

(56) References Cited

U.S. PATENT DOCUMENTS

| 5,187,096 A | 2/1993 | Giaever et al. |
|---|---|---|
| 5,241,070 A | 8/1993 | Law |

(Continued)

FOREIGN PATENT DOCUMENTS

| EP | 2 825 501 A1 | 1/2015 |
|---|---|---|
| JP | 2007-017155 A | 1/2007 |

(Continued)

OTHER PUBLICATIONS

U.S. Appl. No. 15/724,200 (US 2018/0095067), filed Oct. 3, 2017 (Apr. 5, 2018).
(Continued)

*Primary Examiner* — Melanie Brown
(74) *Attorney, Agent, or Firm* — Baker Botts L.L.P.

(57) ABSTRACT

Methods, devices, and systems for analyte analysis using a nanopore are disclosed. The methods, devices, and systems
(Continued)

utilize a first and a second binding member that each specifically bind to an analyte in a biological sample. The method further includes detecting and/or counting a cleavable tag attached to the second binding member and correlating the presence and/or the number of tags to presence and/or concentration of the analyte. Certain aspects of the methods do not involve a tag, rather the second binding member may be directly detected/quantitated. The detecting and/or counting may be performed by translocating the tag/second binding member through a nanopore. Devices and systems that are programmed to carry out the disclosed methods are also provided.

12 Claims, 54 Drawing Sheets

Specification includes a Sequence Listing.

Related U.S. Application Data

(60) Provisional application No. 62/279,488, filed on Jan. 15, 2016, provisional application No. 62/278,303, filed on Jan. 13, 2016, provisional application No. 62/142,872, filed on Apr. 3, 2015.

(51) Int. Cl.
  *G01N 33/53* (2006.01)
  *B01L 3/00* (2006.01)

(52) U.S. Cl.
  CPC *G01N 33/54306* (2013.01); *B01L 2300/0645* (2013.01); *B01L 2400/0406* (2013.01); *G01N 2458/10* (2013.01)

(56) References Cited

U.S. PATENT DOCUMENTS

| | | | |
|---|---|---|---|
| 5,270,163 A | 12/1993 | Gold et al. | |
| 5,352,803 A | 10/1994 | Mattingly | |
| 5,359,093 A | 10/1994 | Adamczyk et al. | |
| 5,468,646 A | 11/1995 | Mattingly et al. | |
| 5,475,096 A | 12/1995 | Gold et al. | |
| 5,496,925 A | 3/1996 | Mattingly | |
| 5,543,524 A | 8/1996 | Mattingly et al. | |
| 5,567,588 A | 10/1996 | Gold et al. | |
| 5,573,904 A | 11/1996 | Mattingly | |
| 5,593,896 A | 1/1997 | Adamczyk et al. | |
| 5,595,877 A | 1/1997 | Gold et al. | |
| 5,620,850 A | 4/1997 | Bamdad et al. | |
| 5,637,459 A | 6/1997 | Burke et al. | |
| 5,683,867 A | 11/1997 | Biesecker et al. | |
| 5,696,253 A | 12/1997 | Bruice et al. | |
| 5,705,337 A | 1/1998 | Gold et al. | |
| 5,783,699 A | 7/1998 | Mattingly et al. | |
| 6,013,785 A | 1/2000 | Bruice et al. | |
| 6,015,714 A | 1/2000 | Baldarelli et al. | |
| 6,027,496 A | 2/2000 | Loomis et al. | |
| 6,294,063 B1 | 9/2001 | Becker et al. | |
| 6,413,792 B1 | 7/2002 | Sauer et al. | |
| 6,428,959 B1 | 8/2002 | Deamer | |
| 6,464,842 B1 | 10/2002 | Golovchenko et al. | |
| 6,565,727 B1 | 5/2003 | Shenderov | |
| 6,627,067 B1 | 9/2003 | Branton et al. | |
| 6,679,841 B2 | 1/2004 | Bojan et al. | |
| 6,773,566 B2 | 8/2004 | Shenderov | |
| 6,783,643 B2 | 8/2004 | Golovchenko et al. | |
| 6,911,132 B2 | 6/2005 | Pamula et al. | |
| 7,070,921 B2 | 7/2006 | Huang et al. | |
| 7,591,936 B2 | 9/2009 | Sarrut | |
| 7,718,445 B2 | 5/2010 | Martin | |
| 7,906,293 B2 | 3/2011 | Mattingly et al. | |
| 8,287,808 B2 | 10/2012 | Krupenkin et al. | |
| 8,637,242 B2 | 1/2014 | Shen et al. | |
| 8,895,292 B2 | 11/2014 | Söderlund et al. | |
| 8,940,147 B1* | 1/2015 | Bartsch | G01N 27/44791 204/601 |
| 9,017,937 B1* | 4/2015 | Turner | C12Q 1/6869 435/6.1 |
| 2002/0028457 A1 | 3/2002 | Empedocles | |
| 2002/0043463 A1 | 4/2002 | Shenderov | |
| 2002/0197645 A1 | 12/2002 | Martin | |
| 2003/0082633 A1 | 5/2003 | Martin et al. | |
| 2003/0141189 A1 | 7/2003 | Lee et al. | |
| 2003/0211502 A1 | 11/2003 | Sauer et al. | |
| 2004/0149580 A1 | 8/2004 | Flory | |
| 2005/0006224 A1 | 1/2005 | Golovchenko et al. | |
| 2005/0126905 A1 | 6/2005 | Golovchenko et al. | |
| 2006/0121544 A1 | 6/2006 | Boge et al. | |
| 2007/0242105 A1 | 10/2007 | Srinivasan et al. | |
| 2008/0187915 A1 | 8/2008 | Polonsky et al. | |
| 2008/0274513 A1 | 11/2008 | Shenderov et al. | |
| 2010/0181195 A1 | 7/2010 | Garcia Tello | |
| 2010/0282609 A1 | 11/2010 | Pollack et al. | |
| 2010/0292101 A1 | 11/2010 | So | |
| 2010/0307922 A1 | 12/2010 | Wu | |
| 2011/0091989 A1 | 4/2011 | Sista et al. | |
| 2011/0212848 A1 | 9/2011 | Duffy et al. | |
| 2011/0308950 A1 | 12/2011 | Sakai et al. | |
| 2012/0080361 A1 | 4/2012 | Walavalkar et al. | |
| 2012/0141997 A1 | 6/2012 | Meagher et al. | |
| 2012/0268804 A1 | 10/2012 | Hadwen | |
| 2013/0116128 A1 | 5/2013 | Shen et al. | |
| 2013/0126358 A1 | 5/2013 | Lee et al. | |
| 2013/0217103 A1 | 8/2013 | Bauer | |
| 2013/0330247 A1 | 12/2013 | Wilson et al. | |
| 2013/0345088 A1 | 12/2013 | Noji et al. | |
| 2014/0174927 A1 | 6/2014 | Bashir et al. | |
| 2014/0291152 A1 | 10/2014 | Conoci et al. | |
| 2015/0069329 A1 | 3/2015 | Jeon et al. | |
| 2015/0209779 A1* | 7/2015 | Harrer | G01N 33/48728 204/451 |
| 2016/0041179 A1 | 2/2016 | Ju et al. | |
| 2018/0067038 A1 | 3/2018 | Fathollahi et al. | |
| 2018/0111126 A1* | 4/2018 | Osmus | B01L 3/50273 |

FOREIGN PATENT DOCUMENTS

| | | |
|---|---|---|
| JP | 2008-505631 A | 2/2008 |
| JP | 2009-534653 A | 9/2009 |
| JP | 2012-230105 A | 11/2012 |
| JP | 2012-526556 A | 11/2012 |
| JP | 2013-172724 A | 9/2013 |
| JP | 2014-521956 A | 8/2014 |
| JP | 2014-169920 A | 9/2014 |
| WO | WO 00/34527 A2 | 6/2000 |
| WO | WO 02/29076 A1 | 4/2002 |
| WO | WO 2004/085609 A2 | 10/2004 |
| WO | WO 2007/136386 A2 | 11/2007 |
| WO | WO 2009/111431 A2 | 9/2009 |
| WO | WO 2010/040227 A1 | 4/2010 |
| WO | WO 2010/117470 A2 | 10/2010 |
| WO | WO 2011/023949 A2 | 3/2011 |
| WO | WO 2011/057197 A2 | 5/2011 |
| WO | WO 2011/137533 A1 | 11/2011 |
| WO | WO 2012/121310 A1 | 9/2012 |
| WO | WO 2013/066441 A2 | 5/2013 |
| WO | WO 2013/167952 A1 | 11/2013 |
| WO | WO 2013/167955 A1 | 11/2013 |
| WO | WO 2014/062551 A1 | 4/2014 |
| WO | WO 2014/066704 A1 | 5/2014 |
| WO | WO 2014/144898 A1 | 9/2014 |
| WO | WO 2015/031849 A1 | 3/2015 |

OTHER PUBLICATIONS

U.S. Appl. No. 15/724,203, filed Oct. 3, 2017.
Adamczyk et al., "Chemiluminescence quenching of pteroic acid-N-sulfonyl-acridinium-9-carboxamide conjugates by folate binding protein," Bioorg. Med. Chem. Lett. 14:2313-2317 (2004).

(56) References Cited

OTHER PUBLICATIONS

Adamczyk et al., "Chemiluminescent acridinium-9-carboxamide boronic acid probes: Application to a homogeneous glycated hemoglobin assay," Bioorg. Med. Chem. Lett. 16:1324-1328 (2006).
Adamczyk et al., "Chemiluminescent N-Sulfonyl acridinium-9-Carboxamides and Their Application in Clinical Assays," Luminescence Biotechnology: Instruments and Applications, CRC Press, pp. 77-105 (2002).
Adamczyk et al., "Intrinsic factor-mediated modulation of cyanocobalamin-N-sulfonyl-acridinium-9-carboxamide chemiluminescence," Biorg. Med. Chem. Lett. 14:3917-3921 (2004).
Adamczyk et al., "Linker-Mediated Modulation of the Chemiluminescent Signal from N10-(3-Sulfopropyl)—N-sulfonylacridinium-9-carboxamide Tracers," Bioconjugate Chem. 11:714-724 (2000).
Adamczyk et al., "Neopentyl 3-Triflyloxypropanesulfonate. A Reactive Sulfopropylation Reagent for the Preparation of Chemiluminescent Labels," J. Org. Chem. 63:5636-5639 (1998).
Adamczyk et al., "Regiodependent Luminescence Quenching of Biotinylated N-Sulfonyl-acridinium-9-carboxamides by Avidin," Org. Lett. 5(21):3779-3782 (2003).
Adamczyk et al., "Synthesis of a Chemiluminescent Acridinium Hydroxylamine (AHA) for the Direct Detection of Abasic Sites in DNA," Org. Lett. 1(5):779-781 (1999).
Adamczyk et al., Modulation of the Chemiluminescent Signal from N10—(3-Sulfopropyl)-N-Sulfonylacridinium-9-carboxamides, Tetrahedron 55:10899-10914 (1999).
Agasti et al., "Photocleavable DNA Barcode-Antibody Conjugates Allow Sensitive and Multiplexed Protein Analysis in Single Cells," J. Am. Chem. Soc., 134:18499-18502 (2012).
Banta et al., "Replacing Antibodies: Engineering New Binding Proteins," Annu. Rev. Biomed. Eng. 15:93-113 (2013).
Behar et al., "Tolerance of the archaeal Sac7d scaffold protein to alternative library designs: characterization of anti-immunoglobulin G Affitins," Protein Engineering, Design & Selection 26(4):267-275 (2013).
Burgess et al., "An Approach to Photolabile, Fluorescent Protecting Groups," J. Org. Chem. 62:5165-5168 (1997).
Chatterjee et al., "Droplet-based microfluidics with nonaqueous solvents and solutions," Lab Chip, 6:199-206 (2006).
Crawford et al., "Pepetide aptamers: Tools for biology and drug discovery," Brief Funct Genomic Proteomic 2:72-79 (2003).
Dutz et al., "Magnetic particle hyperthermia-a promising tumour therapy?" Nanotechnology, 25:452001 (2014).
Fan et al., "General digital microfluidic platform manipulating dielectric and conductive droplets by dielectrophoresis and electrowetting," Lab Chip, 9:1236-1242 (2009).
Gilbreth et al., "Structural insights for engineering binding proteins based on non-antibody scaffolds," Current Opinion in Structural Biology 22:413-420 (2012).
Gottlin et al., "Isolation of Novel EGFR-Specific VHH Domains," Journal of Biomolecular Screening, 14:77-85 (2009).
Guillier et al., "Linkers and Cleavage Strategies in Solid-Phase Organic Synthesis and Combinatorial Chemistry," Chem. Rev. 100:2091-2157 (2000).
Hall et al., "Hybrid pore formation by directed insertion of α-haemolysin into solid-state nanopores," Nature Nanotechnology, 5:874-877 (2010).
Haugland, Handbook of Fluorescent Probes and Research Chemicals, 6th Edition (1996) (Table of Contents).
Heller, "Electrical Wiring of Redox Enzymes," Acc. Chem. Res. 23(5):128-134 (1990).
Heng et al., "Sizing DNA Using a Nanometer-Diameter Pore," Biophy J 87:2905-2911 (2004).
Hille, B, 2001, Ion Channels of Excitable Membranes, 3rd Ed., Sinauer Associates, Inc., Sunderland, Mass.
Holt et al., "Domain antibodies: proteins for therapy," Trends in Biotechnology 21(11):484-490 (2003).
International Search Report dated Aug. 26, 2016 in International Application No. PCT/US2016/025785.

International Search Report dated Sep. 22, 2016 in International Application No. PCT/US2016/025787.
Jirage et al., "Nanotubule-Based Molecular-Filtration Membranes," Science, 278:655-658 (1997).
Kasianowiscz et al., "Characterization of individual polynucleotide molecules using a membrane channel," PNAS USA 93:13770-13773 (1996).
Kassies et al., "Combined AFM and confocal fluorescence microscope for applications in bio-nanotechnology," J Microsc 217(Part 1):109-116 (2005).
Kazane et al., "Site-specific DNA-antibody conjugates for specific and sensitive immune-PCR," PNAS USA 109(10):3731-3736 (2012).
Kowalczyk et al., "Modeling the conductance and DNA blockade of solid-state nanopores," Nanotech., 22:315101 (2011).
Kwok et al., "Nanopore Fabrication by Controlled Dielectric Breakdown," Supplementary Information Section 8, DNA Translocation (2014).
Kwok et al., "Nanopore Fabrication by Controlled Dielectric Breakdown," PLoS ONE 9(3):e92880 (2014).
Lee et al., "Studies on a Dithiane-Protected Benzoin Photolabile Safety Catch Linker for Solid-Phase Synthesis," J. Org. Chem. 64:3454-3460 (1999).
Li et al., "DNA molecules and configurations in a solid-state nanopore microscope," Nature Materials 2:611-615 (2003).
Li et al., "Ion-beam sculpting at nanometer length scales," Nature 412:166-169 (2001).
Li et al., "Quantized tunneling current in the metallic nanogaps formed by electrodeposition and etching," Applied Physics Lett. 77(24):3995-3997 (2000).
Lo et al., "Novel roll-to-roll lift-off patterned active-matrix display on flexible polymer substrate," Microelectronic Engineering 86:979-983 (2009).
Mattingly et al., "Chemiluminescent N-Sulfonylacridinium-9-Carboxamides and Their Application in Clinical Assays," Chapter 5, Luminescence Biotechnology: Instruments and Applications; Dyke, K. V. Ed.; CRC Press: Boca Raton, pp. 77-105 (2002).
Mattingly, "Chemiluminescent 10-Methyl-Acridinium-9-(N-Sulphonylcarboxamide) Salts. Synthesis and Kinetics of Light Emission," J. Biolumin. Chemilumin. 6:107-114 (1991).
McCapra et al., "Chemiluminescence Involving Peroxide Decompositions," Photochem. Photobiol. 4:1111-1121 (1965).
McEnaney et al., "Antibody-Recruiting Molecules: An Emerging Paradigm for Engaging Immune Function in Treating Human Disease," ACS Chem. Biol. 7:1139-1151 (2012).
Menon et al., "Fabrication and Evaluation of Nanoelectrode Ensembles," Anal Chem 67:1920-1928 (1995).
Millward et al., "Iterative in Situ Click Chemistry Assembles a Branched Capture Agent and Allosteric Inhibitor for Akt1," J. Am. Chem. Soc. 133:18280-18288 (2011).
Murphy et al., "Fast photoinduced electron transfer through DNA intercalation," Proc. Natl Acad Sci USA 91:5315-5319 (1994).
Patel et al., "Selection of a high-affinity WW domain against the extracellular region of VEGF receptor isoform-2 from a combinatorial library using CIS display," Protein Engineering, Design & Selection 26(4):307-315 (2013).
Polak and Van Noorden, Introduction to Immunocytochemistry, 2nd ed., Springer Verlag, N.Y. (1997), (Table of Contents).
Rader, "Chemically programmed antibodies," Trends in Biotechnology 32(4):186-197 (2014).
Rauch et al., "On the Structure of Mitochondrial Porins and its Homologies with Bacterial Porins," Biochem Biophys Res Comm 200(2):908-915 (1994).
Razavi et al., "Stable and versatile active acridinium esters I," Luminescence 15:239-244 (2000).
Razavi et al., "Stable and versatile active acridinium esters II," Luminescence 15: 245-249 (2000).
Reverdatto et al., "Combinatorial Library of Improved Peptide Aptamers, CLIPs to Inhibit RAGE Signal Transduction in Mammalian Cells," PLoS ONE 8(6):e65180 (2013).
Shum et al., "Nucleic Acid Aptamers as Potential Therapeutic and Diagnostic Agents for Lymphoma," J Cancer Ther. 4:872-890 (2013).

(56) References Cited

OTHER PUBLICATIONS

Storm et al., "Fabrication of solid-state nanopores with single-nanometre precision," Nature Materials 2:537-540 (2003).

Szabo et al., "DNA Translocation Across Planar Bilayers Containing *Bacillus subtilis* Ion Channels," J. Biol. Chem. 272(40):25275-25282 (1997).

Szabo et al., "Double-stranded DNA can be translocated across a planar membrane containing purified mitochondrial porin," FASEB J. 12:495-502 (1998).

Tiede et al., "Adhiron: a stable and versatile peptide display scaffold for molecular recognition applications," Protein Engineering, Design & Selection 27(5):145-155 (2014).

Tropini et al., "Multi-Nanopore Force Spectroscopy for DNA Analysis," Biophysical Journal, 92:1632-1637 (2007).

Walsh et al., "Laser-assisted photothermal heating of a plasmonic nanoparticle-suspended droplet in a microchannel," Analyst, 140:1535-1542 (2015).

Wells, High Throughput Bioanalytical Sample Preparation. Methods and Automation Strategies, Progress in Pharmaceutical and Biomedical Analysis, vol. 5, Elsevier (2003) (Table of Contents).

Xiang et al., "A Controllable Electrochemical Fabrication of Metallic Electrodes with a Nanometer/Angstrom-Sized Gap Using an Electric Double Layer as Feedback," Angew. Chem. Int. Ed. 44:1265-1268 (2005).

Zhang et al., "Tumor-Targeted Drug Delivery with Aptamers," Curr Med Chem. 18:4185-4194 (2011).

Zhu et al., "Nucleic Acid Aptamers: An Emerging Frontierin Cancer Therapy," Chem Commun 48:10472-10480 (2012).

U.S. Appl. No. 15/724,200, Dec. 26, 2018 Non-Final Office Action.

U.S. Appl. No. 15/724,200, Oct. 17, 2018 Response to Restriction Requirement.

U.S. Appl. No. 15/724,200, Aug. 30, 2018 Restriction Requirement.

U.S. Appl. No. 15/724,203, Jan. 10, 2019 Response to Restriction Requirement.

U.S. Appl. No. 15/724,203, Dec. 20, 2018 Restriction Requirement.

U.S. Appl. No. 15/724,200, Jun. 6, 2019 Non-Final Office Action.

U.S. Appl. No. 15/724,203, Feb. 6, 2019 Non-Final Office Action.

Fair et al., "Chemical and Biological Applications of Digital-Microfluidic Devices," IEEE Design & Test of Computers, 24(1):10-24 (2007).

Punnamaraju, "Voltage and Photo Induced Effects in Droplet-Interface-Bilayer Lipid Membranes," Ph.D. Dissertation, University of Cincinnati, pp. 1-160 (2011).

U.S. Appl. No. 15/724,203, filed Oct. 7, 2019 Final Office Action.

Tahvildari et al., "Integrating nanopore sensors within microfluidic channel arrays using controlled breakdown," Lab on a Chip 15:1407-1411 (2015).

\* cited by examiner

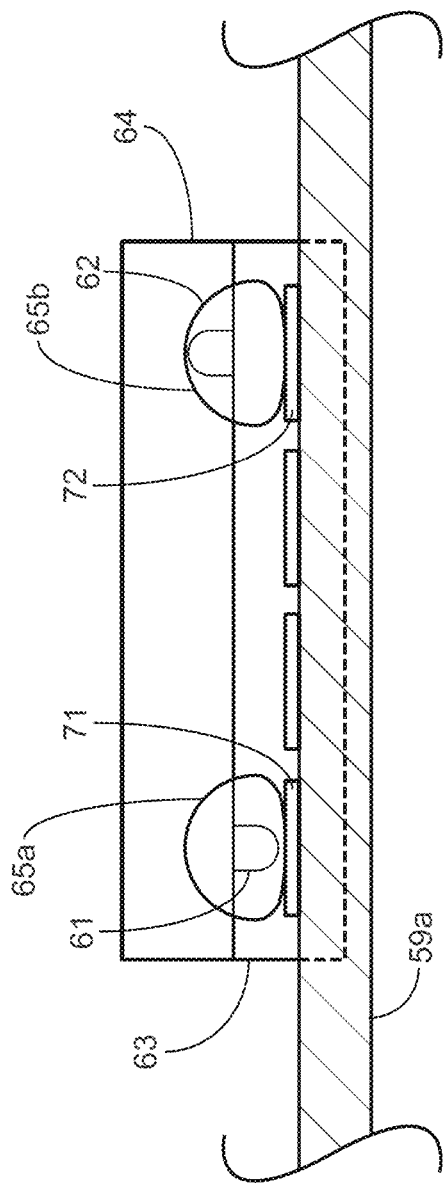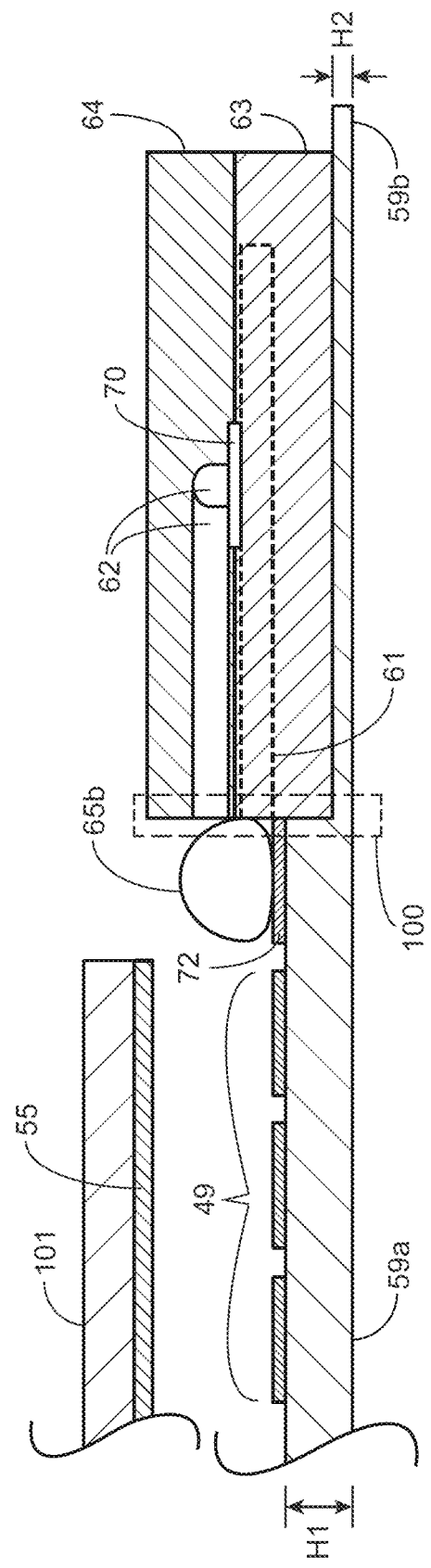
FIG. 2E

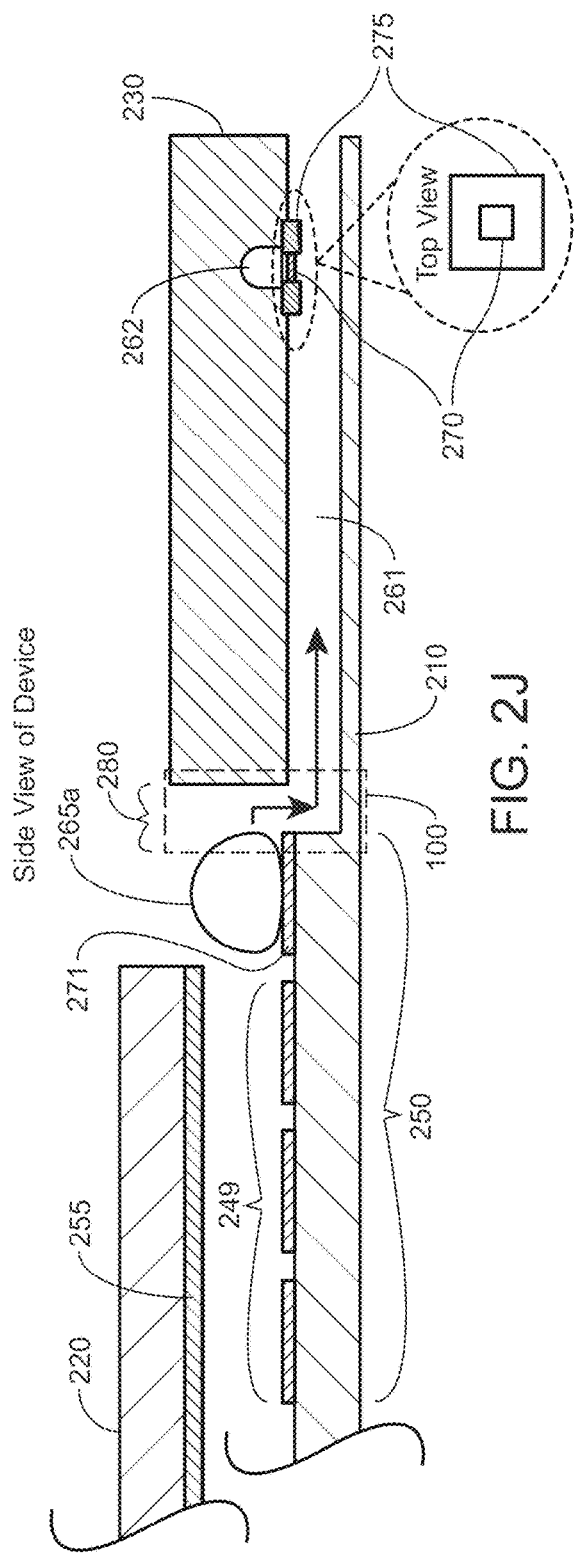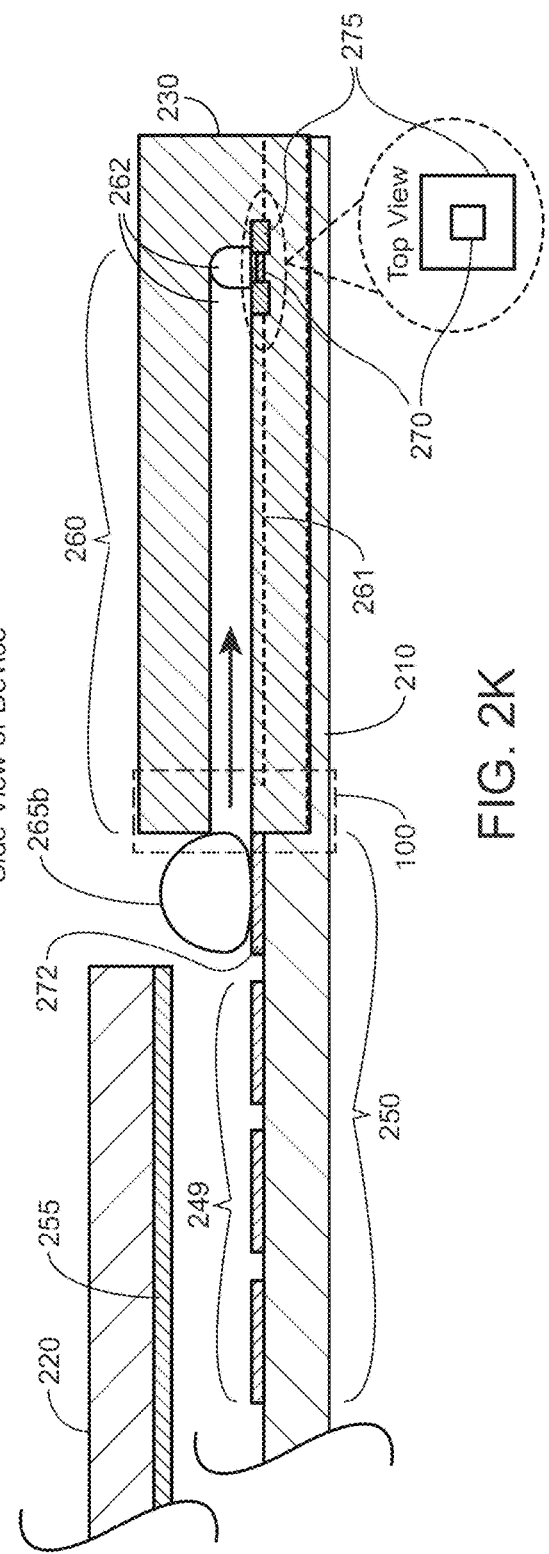

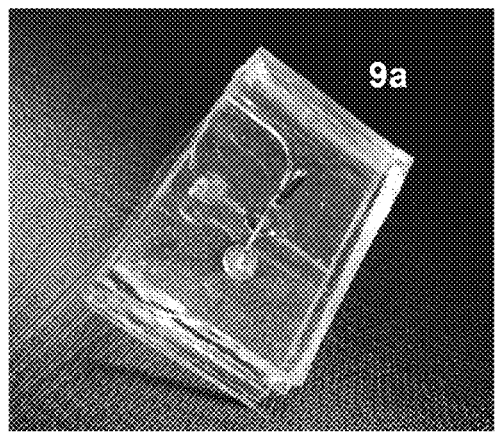 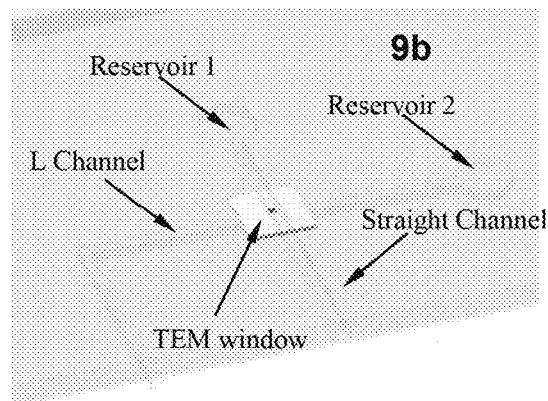
FIG. 14C

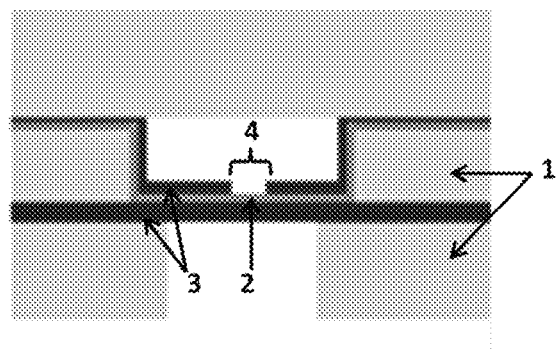

FIG. 35

| Parameter | Value |
|---|---|
| nanopore size | 10 nm |
| nanopore morphology | spherical cylinder |
| SiNx membrane size | infinitely large |
| SiNx membrane thickness | 50 nm |
| SiNx membrane roughness ($R_a$) | 0 nm |
| SiNx charge density | -30 mC/m² |
| silicon resistivity | 30 Ω-cm |
| electrolyte concentration | 1 M KCl |
| sensing voltage | -200 to +200 mV |
| channel height | 725 μm |
| $SiO_2$ diameter | 0 - 4,500 nm |
| $SiO_2$ charge density | -50 mC/m² |
| $SiO_2$ thickness | 100 nm |

FIG. 36

SEQUENCE LISTING

<160> NUMBER OF SEQ ID NOS: 11

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agtcatacga gtcacaagtc atcctaagat accatacaca taccaagttc                50

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 2
gaacttggta tgtgtatggt atcttaggat gacttgtgac tcgtatgact    50

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcccagtgtc tttgtaggag gagcagcgcg tcaatgtggc tgacggacca tggcagatag    60

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ctatctgcca tggtccgtca gccacattga cgcgctgctc ctcctacaaa gacactgggc    60

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctatctgcca tggtccgtca g    21

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaaaaaggtc cgcatcgact gcattca    27

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccctcgtccc cagctacgcc t    21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
aggcgtagct ggggacgagg g                                            21

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
caagcccggt cgtaa                                                   15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttacgaccgg gcttg                                                   15

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttacgaccgg gcttg                                                   15
```

DEVICES AND METHODS FOR SAMPLE ANALYSIS

CROSS-REFERENCE TO RELATED APPLICATIONS

This application is a continuation of International Patent Application No. PCT/US2016/025787, filed Apr. 2, 2016, which claims the benefit of U.S. Provisional Patent Application Nos. 62/142,872 filed Apr. 3, 2015, 62/278,303 filed Jan. 13, 2016, and 62/279,488 filed Jan. 15, 2016, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 8, 2018, is named 003168_1930_SL.txt and is 2,963 bytes in size.

TECHNICAL FIELD

This disclosure relates to methods, devices, and systems for analyte analysis using a nanopore device, e.g., operably coupled with a microfluidic device.

BACKGROUND

Methods and devices that can accurately analyze analyte(s) of interest in a sample are essential for diagnostics, prognostics, environmental assessment, food safety, detection of chemical or biological warfare agents and the like. Such methods and devices not only need to be accurate, precise and sensitive but are also advantageous when a minute sample is to be analyzed quickly and with minimal instrumentation. As such, there in an interest in methods and devices with improved sample analysis capabilities.

SUMMARY

Embodiments of the present disclosure relate to methods, systems, and devices for analysis of analyte(s) in a sample. In certain embodiments, the sample may be a biological sample.

The method for analysis of an analyte in a sample may involve contacting the sample with a first binding member, where the first binding member is immobilized on a solid support and where the first binding member specifically binds to the analyte; contacting the solid support with a second binding member, where the second binding member specifically binds to the analyte and wherein the second binding member includes a cleavable tag attached thereto; removing second binding member not bound to the analyte bound to the first binding member; cleaving the tag attached to the second binding member that is bound to the analyte bound to the first binding member; translocating the cleaved tag through or across a nanopore in a layer; determining the number of tags translocating through the layer; determining concentration of the analyte in the sample based on the number of tags translocating through the layer. In certain embodiments, the concentration of the analyte may be determined by counting the number of tags translocating through the layer per unit time. In other embodiments, the concentration of the analyte may be determined by determining the time at which the number of tags translocating through the layer reaches a threshold or by setting a period of time and counting cumulative number of counts in the set period of time.

In another embodiment, the method may include combining the sample containing the target analyte with a known amount of the target analyte or a competitor molecule, where the target analyte (combined with the sample) or the competitor molecule are attached to a tag via a cleavable linker to produce a tagged analyte or tagged competitor molecule, respectively, and the tagged analyte or tagged competitor molecule compete with the target analyte for binding to a first binding member. The method may further include contacting the combined sample with the first binding member, where the first binding member is immobilized on a solid support and where the first binding member specifically binds to the target analyte (and to the tagged analyte or tagged competitor molecule); contacting the solid support with buffer for an optional washing step; cleaving the tag attached to the tagged analyte or tagged competitor that is bound to the first binding member immobilized on the solid support; translocating the cleaved tag through or across a nanopore in a layer; determining the number of tags translocating through the layer; determining concentration of the analyte in the sample based on the number of tags translocating through the layer. In certain embodiments, the concentration of the analyte may be determined by counting the number of tags translocating through the layer per unit time. In other embodiments, the concentration of the analyte may be determined by determining the time at which the number of tags translocating through the layer reaches a threshold or by setting a period of time and counting cumulative number of counts in the set period of time. In this embodiment, the number of tags translocated through the nanopore or the time at which the number of tags translocating through the layer reaches a threshold may be inversely correlated to the concentration of the analyte in the sample. For example, the lower count or the longer the time period for reaching a threshold, the higher the concentration of the target analyte in the sample.

In one aspect, the present invention relates to a method for measuring or detecting an analyte present in a biological sample. The method comprising contacting the sample with a first binding member, wherein the first binding member is immobilized on a solid support and wherein the first binding member specifically binds to the analyte; contacting the analyte with a second binding member, wherein the second binding member specifically binds to the analyte and wherein the second binding member comprises a cleavable tag attached thereto; removing second binding member not bound to the analyte bound to the first binding member; cleaving the tag attached to the second binding member that is bound to the analyte bound to the first binding member; translocating the cleaved tag through or across one or more nanopores in a layer; and assessing the tag translocating through the layer, wherein measuring the number of tags translocating through the layer measures the amount of analyte present in the sample, or wherein detecting tags translocating through the layer detects that the analyte is present in the sample. In some embodiments, measuring the tags translocating through the layer is assessed, wherein the number of tags translocating through the layer measures the amount of analyte present in the sample. In some embodiments, detecting the tags translocating through the layer is assessed, wherein detecting tags translocating through the layer detects that the analyte is present in the sample.

In one aspect, the present invention relates to a method for measuring or detecting an analyte present in a biological sample. The method comprising contacting the sample with a first binding member, wherein the first binding member is immobilized on a solid support and wherein the first binding member specifically binds to the analyte; contacting the analyte with a second binding member, wherein the second binding member specifically binds to the analyte and wherein the second binding member comprises an aptamer; removing aptamer not bound to the analyte bound to the solid substrate; dissociating the aptamer bound to the analyte and translocating the dissociated aptamer through or across one or more nanopores in a layer; and assessing the aptamer translocating through the layer, wherein measuring the number of aptamers translocating through the layer measures the amount of analyte present in the sample, or wherein detecting aptamers translocating through the layer detects that the analyte is present in the sample. In some embodiments, measuring the aptamers translocating through the layer is assessed, wherein the number of aptamers translocating through the layer measures the amount of analyte present in the sample. In some embodiments, detecting the aptamers translocating through the layer is assessed, wherein detecting tags translocating through the layer detects that the analyte is present in the sample.

In one aspect, the present invention relates to an integrated digital microfluidics nanopore device comprising a bottom substrate, comprising an array of electrodes; a top substrate spaced apart from the bottom substrate; and a nanopore layer disposed in between the bottom and top substrates. The device includes a proximal portion and a distal portion and the nanopore layer is disposed in the distal portion. The array of electrodes in the proximal portion is configured to generate a droplet. The array of electrodes are configured to position the droplet across the nanopore layer such that the droplet is split by the nanopore layer into a first portion and a second portion, wherein at least two electrodes of the array of electrodes are positioned across the nanopore layer, where the two electrodes form an anode and a cathode and operate to drive current through a nanopore in the nanopore layer when a liquid droplet is positioned across the nanopore layer.

In one aspect, the present invention relates to an integrated digital microfluidics nanopore device comprising a bottom substrate, comprising an array of electrodes; a top substrate spaced apart from the bottom substrate and comprising an electrode; and a nanopore layer disposed in between the bottom and top substrates. The device includes a proximal portion and a distal portion and the nanopore layer is disposed in the distal portion. The array of electrodes and the electrode in the proximal portion are configured to generate a droplet. The array of electrodes and the electrode are configured to position the droplet across the nanopore layer such that the nanopore layer splits the droplet into a first portion and a second portion, wherein at least one electrode of the array of electrodes is in contact with the first portion of a droplet positioned across the nanopore layer and the electrode in the top substrate is positioned to contact the second portion of the droplet positioned across the nanopore layer, where the two electrodes form an anode and a cathode and operate to drive current through a nanopore in the nanopore layer when a liquid droplet is positioned across the nanopore layer.

In one aspect, the present invention relates to a method for measuring or detecting an analyte present in a biological sample. The method comprising contacting the sample with a binding member, wherein the binding member is immobilized on a solid support and wherein the binding member specifically binds to the analyte; contacting the sample, which may contain analyte bound to the binding member, with a labeled analyte, wherein the labeled analyte is labeled with a cleavable tag; removing labeled analyte not bound to the binding member; cleaving the tag attached to the labeled analyte that is bound to the binding member; translocating the cleaved tag through or across one or more nanopores in a layer; and assessing the tag translocating through the layer, wherein measuring the number of tags translocating through the layer measures the amount of analyte present in the sample, or detecting tags translocating through the layer detects that the analyte is present in the sample. In some embodiments, measuring the tags translocating through the layer is assessed, wherein the number of tags translocating through the layer measures the amount of analyte present in the sample. In some embodiments, detecting the tags translocating through the layer is assessed, wherein detecting tags translocating through the layer detects that the analyte is present in the sample.

In one aspect, the present invention relates to a method for measuring or detecting an analyte present in a biological sample. The method comprising contacting the sample with a binding member, wherein binding member is immobilized on a solid support and wherein binding member specifically binds to the analyte; contacting the sample, which may contain analyte bound to the binding member, with a labeled analyte, wherein the labeled analyte comprises an aptamer; removing labeled analyte not bound to the binding member; dissociating the aptamer bound to the labeled analyte that is bound to the binding member and translocating the dissociated aptamer through or across one or more nanopores in a layer; and assessing the aptamer translocating through the layer, wherein measuring the number of aptamers translocating through the layer measures the amount of analyte present in the sample, or detecting aptamers translocating through the layer detects that the analyte is present in the sample. In some embodiments, measuring the aptamers translocating through the layer is assessed, wherein the number of aptamers translocating through the layer measures the amount of analyte present in the sample. In some embodiments, detecting the aptamers translocating through the layer is assessed, wherein detecting tags translocating through the layer detects that the analyte is present in the sample.

In one aspect, the present invention relates to a method for measuring or detecting an analyte present in a biological sample. The method comprising contacting the sample with a binding member, wherein the binding member specifically binds to the analyte, and the binding member is labeled with a cleavable tag; contacting the sample, which may contain analyte bound to the binding member, with an immobilized analyte, wherein the immobilized analyte is immobilized on a solid support; removing binding member not bound to the immobilized analyte; cleaving the tag attached to the binding member that is bound to the immobilized analyte; translocating the cleaved tag through or across one or more nanopores in a layer; and assessing the tag translocating through the layer, wherein measuring the number of tags translocating through the layer measures the amount of analyte present in the sample, or detecting tags translocating through the layer detects that the analyte is present in the sample. In some embodiments, measuring the tags translocating through the layer is assessed, wherein the number of tags translocating through the layer measures the amount of analyte present in the sample. In some embodiments, the tags translocating through the layer is assessed, wherein detecting tags translocating through the layer detects that the analyte is present in the sample.

In one aspect, the present invention relates to a method for measuring or detecting an analyte present in a biological sample. The method comprises contacting the sample with a binding member, wherein the binding member specifically binds to the analyte, and the binding member comprises an aptamer; contacting the sample, which may contain analyte bound to the binding member, with a immobilized analyte, wherein the immobilized analyte is immobilized on a solid support; removing binding member not bound to the immobilized analyte; dissociating the aptamer bound to the binding member that is bound to the immobilized analyte and translocating the dissociated aptamer through or across one or more nanopores in a layer; and assessing the aptamer translocating through the layer, wherein measuring the number of aptamers translocating through the layer measures the amount of analyte present in the sample, or detecting aptamers translocating through the layer detects that the analyte is present in the sample. In some embodiments, measuring the aptamers translocating through the layer is assessed, wherein the number of aptamers translocating through the layer measures the amount of analyte present in the sample. In some embodiments, detecting the aptamers translocating through the layer is assessed, wherein detecting tags translocating through the layer detects that the analyte is present in the sample.

In certain aspects, the tag may be an anionic polymer, a cationic polymer, or a nanoparticle. In certain cases, the tag may include an anionic polymer, such as, an oligonucleotide polymer. In certain cases, the oligonucleotide polymer may be a deoxyribonucleic acid or a ribonucleic acid. In certain cases, the oligonucleotide polymer may be a DNA aptamer or a RNA aptamer, where the aptamer does not bind to the analyte. In exemplary cases, the tag may include a nanoparticle which may be a positively charged nanoparticle or a negatively charged nanoparticle.

In certain embodiments, the tag may be spherical tag, such as, a dendrimer, a bead, a nanoparticle, e.g., a nanobead, and the like. In certain embodiments, the tag may not be linear or substantially linear or elongate in shape, such as, a polymer of ribose or deoxyribose units, an oligonucleotide, and a nucleic acid, for example, DNA or RNA.

In certain cases, the first and the second binding members may be aptamers, antibodies or receptors. For example, the first binding member may be a receptor and the second binding member may be an antibody or the first binding member may be an antibody and the second binding member may be a receptor. In certain instances, the first binding member may be a first antibody and the second binding member may be a second antibody.

In certain instances, the tag may be negatively charged and the translocating may include applying a positive potential across the layer thereby translocating the tag across the layer.

In certain instances, the tag may be positively charged and the translocating may include applying a negative potential across the layer thereby translocating the tag across the layer.

In other embodiments, the tag may be a nucleic acid and the tag may be hybridized to an oligonucleotide that includes a sequence complementary to sequence of the tag prior to the translocating.

In another embodiment, a method for measuring an analyte present in a biological sample by using an aptamer as the second binding member is provided. For example, the method may include contacting the sample with a first binding member, where the first binding member is immobilized on a solid support and where the first binding member specifically binds to the analyte; contacting the analyte with a second binding member, wherein the second binding member specifically binds to the analyte and wherein the second binding member comprises an aptamer; removing aptamer not bound to the analyte bound to the solid substrate; dissociating the aptamer from the analyte that is bound to the solid substrate and translocating the dissociated aptamer through nanopore(s) in a layer; determining the number of aptamers translocating through the layer; measuring the analyte in the sample based on the number of aptamers translocating through the layer. In this embodiment, the second binding member is not attached to a tag as the second binding member is directly detected by the nanopore(s).

The aptamer may be a DNA aptamer or a RNA aptamer. The first binding member may be an antibody. In certain instance, the analyte may be a ligand and the first binding member may be a receptor.

Also disclosed herein are methods for simultaneously analyzing multiple different analytes in a sample, for example, the method may include analysis of a first and a second analyte; a first, a second, and a third analyte; and so on. In certain cases, the method for analysis of plurality of different analytes in a sample may include contacting the sample with a plurality of different first binding members, where a first binding member of the different first binding members binds specifically to a first analyte of the plurality of the different analytes, a second binding member of the different first binding members binds specifically to a second analyte of the plurality of the different analytes, and so on. The method may further include contacting the different analytes with a plurality of second binding members, where a first binding member of the plurality of second binding members binds to the first analyte, a second binding member of the plurality of second binding members binds to the second analyte, and so on. In certain instances, each of the plurality of different second binding members may include a tag that is distinct or distinguishable from each other (e.g., each of the different second binding members has a different tag). For example, the first binding member of the plurality of the second binding members may include a first tag, the second binding member of the plurality of the second binding members may include a second tag, and so on, where the first and second tags are distinguishable from each other. Distinguishing the tags can be done using any suitable method, e.g., based on the nature or characteristic properties of the tags.

The method may further include removing unbound second binding members; cleaving the tags attached to the plurality of second binding members bound to the analytes; translocating the tags through nanopores in a layer; determining the number of each of the tags translocating through the layer; measuring the plurality of different analytes in the sample based on the number of each of the tags translocating through the layer. In certain embodiments, the concentration of the analyte may be determined by counting the number of tags translocating through the layer per unit time. In other embodiments, the concentration of the analyte may be determined by determining the time at which the number of tags translocating through the layer reaches a threshold. As noted herein, in certain cases, the second binding members may be a plurality of aptamers and these aptamers are not attached to a tag as the aptamers are counted. In these embodiments, the aptamers may be dissociated from the analyte prior to translocating through or across a nanopore(s).

In certain cases, the different tags, such as the different aptamers, may be distinguishable from each other via nanopore force spectroscopy, optical means or electrical means or a combination thereof.

Also provided herein are kits, systems and devices for carrying out the disclosed methods. The kits, systems and devices may be used to perform analyte analysis in an automated or a semi-automated manner and optionally may include disposable/consumable components that are utilized for analyte analysis. Automated and semi-automated devices may utilize microfluidics. Exemplary microfluidics include digital microfluidics (DMF), surface acoustic wave (SAW) microfluidics, droplet based microfluidic device, and the like. Exemplary microfluidics also include a fully integrated DMF and nanopore device, or a fully integrated SAW and nanopore device. In certain cases, the device for carrying out the disclosed methods may be a digital microfluidics device used in conjunction with a nanopore device. In other embodiments, the device for carrying out the disclosed methods may be an integrated digital microfluidics nanopore device. These devices may be single-use devices or may be reusable (used multiple times for analyte analysis). The digital microfluidic and nanopore devices described herein may provide miniaturized, low cost analyte analysis and may be fabricated using low cost technologies.

Also disclosed herein is an integrated digital microfluidics nanopore device comprising a microfluidics module and a nanopore module; the microfluidics module, comprising an array of electrodes spaced apart from a single electrode sized to overlap with at least a portion of the array of electrodes, where the array of electrodes and the single electrode transport at least one droplet of fluid to a transfer electrode in the array of electrodes, wherein the transfer electrode is positioned at an interface that operatively couples the microfluidics module and the nanopore module; the nanopore module comprising a first microchannel positioned on a first surface of a first substrate; a second microchannel positioned on a first surface of a second substrate; wherein the first surface of the first substrate is in contact with the first surface of the second substrate thereby enclosing the first microchannel and the second microchannel to provide a first capillary channel and a second capillary channel, respectively, wherein at least the first capillary channel extends to the interface between the microfluidics module and the nanopore module and is adjacent to the transfer electrode, and is positioned to receive a fluid droplet positioned on the transfer electrode; wherein the first capillary channel intersects with the second capillary channel, wherein a nanopore layer is positioned in between the first and second substrates at the location where the first and the second capillary channels intersect.

In certain embodiments, the array of electrodes may comprise a first and a second transfer electrodes each of which transfer electrodes are configured to position a fluid droplet over a surface of the transfer electrodes, wherein the first capillary channel extends to the interface between the microfluidics module and the nanopore module, is adjacent to the first transfer electrode and is positioned to receive a fluid droplet located on the first transfer electrode and wherein the second capillary extends to the interface between the microfluidics module and the nanopore module, is adjacent to the second transfer electrode and is positioned to receive a fluid droplet located on the second transfer electrode.

In certain embodiments, the second capillary channel may not extend to the interface and may not be connected to the electrodes of the microfluidics module and may be connected to a vent or a reservoir on one or both ends of the second capillary. In certain cases, the second capillary is connected to a first reservoir at one end and a second reservoir at the other end.

In certain embodiments, the first reservoir and/or the second reservoir comprises a fluid to be positioned across from the first capillary channel at the intersection which fluid facilitates operation of the nanopore layer to drive current through a nanopore of the nanopore layer. In certain embodiments, the first capillary channel and/or the second capillary channel varies in cross sectional width across a length of the capillary such that the width decreases at the intersection compared to the width on either sides of the intersection.

In some embodiments, the first capillary comprises a first pair of electrodes and the second capillary comprises a second pair of electrodes, wherein the first pair of electrodes is positioned in the first capillary channel and flank the nanopore in the nanopore layer and wherein second pair of electrodes is positioned in the second capillary channel and flank the nanopore in the nanopore layer. The droplets may be droplets comprising a molecule to be detected and/or counted by transporting through the nanopore in the nanopore layer.

In certain embodiments, the fluid droplets have different compositions and are a first droplet and a second droplet, the first droplet comprising a molecule to be detected and/or counted by transporting across the nanopore layer through the nanopore and the second droplet comprising a conductive fluid lacking the molecule, where the conductive fluid facilitates transport of the molecule across the nanopore layer via the nanopore.

In certain embodiments, the first capillary channel comprises a first electrode positioned proximal to the nanopore layer and the second capillary channel comprising a second electrode positioned proximal to the nanopore layer, wherein each of the first and second electrodes are exposed in the capillary channels such that they are in contact with a fluid present in the capillary channels and wherein the first and second electrodes operate to drive current through a nanopore in the nanopore layer when a liquid is positioned across the nanopore layer in the first and second capillary channels.

In certain embodiments, the transfer electrode and the first capillary channel are on substantially the same plane, and wherein the fluid droplet is aligned with an opening of the first capillary channel.

In some embodiments, the transfer electrode is at a plane higher than the first capillary channel and wherein the device is configured with a vertical port for transferring the fluid droplet down to an opening of the first capillary channel.

In a particular embodiment, the first surface of the first substrate comprises a first area on which the array of electrodes is disposed and a second area in which the first microchannel is formed, wherein the array of electrodes is on a plane higher than the plane at which the first microchannel is formed.

In some embodiments, the second substrate comprises a notch at a side edge located at the interface, wherein the notch is aligned over the first capillary channel and provides a vertical port for transport of a droplet located at the transfer electrode to the opening of the first capillary channel.

In some cases, the single electrode extends over the transfer electrode and is in bi-planar configuration with the transfer electrode and wherein the single electrode and the transfer electrode operate to move the fluid droplet to the transfer electrode.

In other cases, the single electrode extends over the transfer electrodes and is in bi-planar configuration with the transfer electrodes and wherein the single electrode and the transfer electrodes operate to move the fluid droplets to the transfer electrodes.

In certain embodiments, the single electrode does not extend over the transfer electrode and is not in bi-planar configuration with the transfer electrode, wherein the fluid droplet is moved to the transfer electrode by using coplanar electrodes.

In certain embodiments, the single electrode does not extend over the transfer electrodes and is not in bi-planar configuration with the transfer electrodes, wherein the fluid droplets are moved to the transfer electrodes by using coplanar electrodes.

Thus, using the devices, kits, systems and methods as described herein, analyte present in a biological sample can be measured, and a patient can be diagnosed.

In another aspect, the present invention relates to a method of measuring or detecting an analyte present in a biological sample comprising (a) contacting the sample with a first binding member, wherein the first binding member is immobilized on a solid support and wherein the first binding member specifically binds to the analyte, (b) contacting the analyte with a second binding member, wherein the second binding member specifically binds to the analyte and wherein the second binding member comprises a cleavable tag attached thereto, (c) removing second binding member not bound to the analyte bound to the first binding member, (d) cleaving the tag attached to the second binding member bound to the analyte bound to the first binding member, (e) translocating the tag through one or more nanopores in a layer, and (f) assessing the tag translocating through the layer, wherein measuring the number of tags translocating through the layer measures the amount of analyte present in the sample, or wherein detecting tags translocating through the layer detects that the analyte is present in the sample.

In another aspect, the present invention relates to a method of measuring or detecting an analyte of interest present in a biological sample comprising (a) contacting the sample with a solid support, a first specific binding member, and a second specific binding member, wherein the solid support comprises an immobilization agent, the first specific binding member comprises a ligand for the immobilization agent and the first specific binding member specifically binds the analyte of interest, the second specific binding member comprises a cleavable tag, and the second specific binding member specifically binds the analyte of interest, wherein a solid support/first specific binding member/analyte of interest/second specific binding member complex is formed, (b) removing second specific binding member not bound to the solid support/first specific binding member/analyte/second specific binding member complex, (c) cleaving the tag attached to the labeled analyte bound to the second specific binding member in the solid support/first specific binding member/analyte of interest/second specific binding member complex, (d) translocating the tag through one or more nanopores in a layer, and (e) assessing the tags translocating through the layer, wherein measuring the number of tags translocating through the layer measures the amount of analyte present in the sample, or wherein detecting tags translocating through the layer detects that the analyte is present in the sample.

In another aspect, the present invention relates to a method of measuring or detecting an analyte present in a biological sample comprising (a) contacting the sample with a first binding member, wherein the first binding member is immobilized on a solid support and wherein the first binding member specifically binds to the analyte, (b) contacting the analyte with a second binding member, wherein the second binding member specifically binds to the analyte and wherein the second binding member comprises an aptamer, (c) removing aptamer not bound to the analyte bound to the solid substrate, (d) dissociating the aptamer bound to the analyte, (e) translocating the dissociated aptamer through one or more nanopores in a layer, and (f) assessing the aptamer translocating through the layer, wherein measuring the number of aptamers translocating through the layer measures the amount of analyte present in the sample, or wherein detecting aptamers translocating through the layer detects that the analyte is present in a the sample.

In one aspect, the present invention relates to an integrated digital microfluidics nanopore device comprising: a first substrate, comprising an array of electrodes; a second substrate spaced apart from the first substrate; and a nanopore layer disposed between the first and second substrates, wherein the array of electrodes are configured to position the droplet across the nanopore layer such that the droplet is split by the nanopore layer into a first portion and a second portion, wherein at least two electrodes of the array of electrodes are positioned across the nanopore layer, where the two electrodes form an anode and a cathode and operate to drive current through a nanopore in the nanopore layer when a liquid droplet is positioned across the nanopore layer.

In yet another aspect, the present invention relates to an integrated digital microfluidics nanopore device comprising: a first substrate, comprising an array of electrodes; a second substrate spaced apart from the first substrate; and a nanopore layer disposed between the first and second substrates, wherein the array of electrodes are configured to position a droplet across the nanopore layer such that the nanopore layer splits the droplet into a first portion and a second portion, wherein at least one electrode of the array of electrodes is in contact with the first portion of a droplet positioned across the nanopore layer and the electrode in the second substrate is positioned to contact the second portion of the droplet positioned across the nanopore layer, where the two electrodes form an anode and a cathode and operate to drive current through a nanopore in the nanopore layer when a liquid droplet is positioned across the nanopore layer.

In yet another aspect, the present invention relates to a method for measuring or detecting an analyte present in a biological sample comprising: (a) contacting the sample with a binding member, wherein the binding member is immobilized on a solid support and wherein the binding member specifically binds to the analyte, (b) contacting the sample with a labeled analyte, wherein the labeled analyte is labeled with a cleavable tag, (c) removing labeled analyte not bound to the binding member, (d) cleaving the tag attached to the labeled analyte bound to the binding member, (e) translocating the tag through one or more nanopores in a layer, and (f) assessing the tags translocating through the layer, wherein measuring the number of tags translocating through the layer measures the amount of analyte present in the sample, or wherein detecting tags translocating through the layer detects that the analyte is present in the sample.

In yet another aspect, the present invention relates to a method for measuring or detecting an analyte present in a biological sample, the method comprising: (a) contacting the sample with a binding member, wherein binding member is immobilized on a solid support and wherein binding member specifically binds to the analyte, (b) contacting the sample with a labeled analyte, wherein the labeled analyte comprises an aptamer; (c) removing labeled analyte not bound to the binding member, (d) dissociating the aptamer bound to the labeled analyte and translocating the dissociated aptamer through one or more nanopores in a layer, and (e) assessing the aptamer translocating through the layer, wherein measuring the number of aptamers translocating through the layer measures the amount of analyte present in the sample, or wherein detecting aptamers translocating through the layer detects that the analyte is present in the sample.

In yet another aspect, the present invention relates to a method for measuring or detecting an analyte present in a biological sample comprising: (a) contacting the sample with a binding member, wherein the binding member specifically binds to the analyte, and the binding member is labeled with a cleavable tag, (b) contacting the sample with a immobilized analyte, wherein the immobilized analyte is immobilized on a solid support, (c) removing binding member not bound to the immobilized analyte, (d) cleaving the tag attached to the binding member bound to the immobilized analyte, (e) translocating the tag through one or more nanopores in a layer, and (f) assessing the tag translocating through the layer, wherein measuring the number of tags translocating through the layer measures the amount of analyte present in the sample, or wherein detecting tags translocating through the layer detects that the analyte is present in the sample.

In yet another aspect, the present invention relates to a method for measuring or detecting an analyte present in a biological sample comprising: (a) contacting the sample with a binding member, wherein the binding member specifically binds to the analyte, and the binding member comprises an aptamer, (b) contacting the sample with a immobilized analyte, wherein the immobilized analyte is immobilized on a solid support, (c) removing binding member not bound to the immobilized analyte, (d) dissociating the aptamer bound to the binding member bound to the immobilized analyte and translocating the dissociated aptamer through one or more nanopores in a layer, and (e) assessing the aptamer translocating through the layer, wherein measuring the number of aptamers translocating through the layer measures the amount of analyte present in the sample, or wherein detecting aptamers translocating through the layer detects that the analyte is present in the sample.

In yet another aspect, the present invention relates to an integrated digital microfluidics nanopore device comprising a microfluidics module and a nanopore module; the microfluidics module comprising an array of electrodes, wherein the array of electrodes transports at least one droplet of fluid to a first transfer position in the array of electrodes, wherein the first transfer position is at an interface between the microfluidics module and the nanopore module; the nanopore module comprising: a first capillary channel; and a second capillary channel; wherein at least the first capillary channel extends to the interface and is adjacent to the first transfer position, and is positioned to receive a fluid droplet positioned at the first transfer position; wherein the first capillary channel intersects with the second capillary channel, wherein a nanopore layer is positioned in between the first and second capillary channels at the location where the first and the second capillary channels intersect.

In yet another aspect, the present invention relates to a method for measuring an analyte present in a biological sample comprising: (a) contacting the sample with a first binding member, wherein the first binding member is immobilized on a solid support and wherein the first binding member specifically binds to the analyte, (b) contacting the analyte with a second binding member, wherein the second binding member specifically binds to the analyte and wherein the second binding member comprises a cleavable tag attached thereto, (c) removing second binding member not bound to the analyte bound to the first binding member, (d) cleaving the tag attached to the second binding member bound to the analyte bound to the first binding member, (e) translocating the tag through one or more nanopores in a layer, and (f) assessing the tag translocating through the layer, wherein each tag translocating through the layer is a translocation event, wherein measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference standard comprising a calibration curve, standard addition, or digital polymerase chain reaction, wherein the standard curve in subsection i) is determined by measuring the number of translocation events for control concentrations of analyte during a set period of time; wherein the standard curve in subsection ii) is determined by measuring the time it takes for a set number of translocation events to occur for control concentrations of analyte; and wherein the standard curve in subsection iii) is determined by measuring the average time between translocation events to occur for control concentrations of analyte.

In yet another aspect, the present invention relates to a method for measuring an analyte present in a biological sample comprising: (a) contacting the sample with a first binding member, wherein the first binding member is immobilized on a solid support and wherein the first binding member specifically binds to the analyte, (b) contacting the analyte with a second binding member, wherein the second binding member specifically binds to the analyte and wherein the second binding member comprises an aptamer, (c) removing aptamer not bound to the analyte bound to the solid substrate, (d) dissociating the aptamer bound to the analyte, and (e) translocating the dissociated aptamer through one or more nanopores in a layer; and (f) assessing the aptamer translocating through the layer, wherein each aptamer translocating through the layer is a translocation event, wherein measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference standard comprising a calibration curve, standard addition, or digital polymerase chain reaction, wherein the standard curve in subsection i) is determined by measuring the number of translocation events for control concentrations of analyte during a set period of time; wherein the standard curve in subsection ii) is determined by measuring the time it takes for a set number of translocation events to occur for control concentrations of analyte; and wherein the standard curve in subsection iii) is determined by measuring the average time between translocation events to occur for control concentrations of analyte.

In yet another aspect, the present invention relates to method for measuring an analyte present in a biological sample comprising: (a) contacting the sample with a binding member, wherein the binding member is immobilized on a solid support and wherein the binding member specifically binds to the analyte, (b) contacting the sample with a labeled analyte, wherein the labeled analyte is labeled with a cleavable tag, (c) removing labeled analyte not bound to the binding member, (d) cleaving the tag attached to the labeled analyte bound to the binding member, (e) translocating the tag through one or more nanopores in a layer, and (f) assessing the tags translocating through the layer, wherein each tag translocating through the layer is a translocation event, wherein measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference standard comprising a calibration curve, standard addition, or digital polymerase chain reaction, wherein the standard curve in subsection i) is determined by measuring the number of translocation events for control concentrations of analyte during a set period of time; wherein the standard curve in subsection ii) is determined by measuring the time it takes for a set number of translocation events to occur for control concentrations of analyte; and wherein the standard curve in subsection iii) is determined by measuring the average time between translocation events to occur for control concentrations of analyte.

In another aspect, the present invention relates to a method for measuring an analyte present in a biological sample comprising: (a) contacting the sample with a binding member, wherein binding member is immobilized on a solid support and wherein binding member specifically binds to the analyte, (b) contacting the sample with a labeled analyte, wherein the labeled analyte comprises an aptamer, (c) removing labeled analyte not bound to the binding member, (d) dissociating the aptamer bound to the labeled analyte and translocating the dissociated aptamer through one or more nanopores in a layer, and (e) assessing the aptamer translocating through the layer, wherein each aptamer translocating through the layer is a translocation event, wherein measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference standard comprising a calibration curve, standard addition, or digital polymerase chain reaction, wherein the standard curve in subsection i) is determined by measuring the number of translocation events for control concentrations of analyte during a set period of time; wherein the standard curve in subsection ii) is determined by measuring the time it takes for a set number of translocation events to occur for control concentrations of analyte; and wherein the standard curve in subsection iii) is determined by measuring the average time between translocation events to occur for control concentrations of analyte.

In yet another aspect, the present invention relates to a method for measuring an analyte present in a biological sample comprising: (a) contacting the sample with a binding member, wherein the binding member specifically binds to the analyte, and the binding member is labeled with a cleavable tag, (b) contacting the sample with a immobilized analyte, wherein the immobilized analyte is immobilized on a solid support, (c) removing binding member not bound to the immobilized analyte, (d) cleaving the tag attached to the binding member bound to the immobilized analyte, (e) translocating the tag through one or more nanopores in a layer, and (f) assessing the tag translocating through the layer, wherein each tag translocating through the layer is a translocation event, wherein measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference standard comprising a calibration curve, standard addition, or digital polymerase chain reaction, wherein the standard curve in subsection i) is determined by measuring the number of translocation events for control concentrations of analyte during a set period of time; wherein the standard curve in subsection ii) is determined by measuring the time it takes for a set number of translocation events to occur for control concentrations of analyte; and wherein the standard curve in subsection iii) is determined by measuring the average time between translocation events to occur for control concentrations of analyte.

In yet another aspect, the present invention relates to a method for measuring an analyte present in a biological sample comprising: (a) contacting the sample with a binding member, wherein the binding member specifically binds to the analyte, and the binding member comprises an aptamer, (b) contacting the sample with a immobilized analyte, wherein the immobilized analyte is immobilized on a solid support, (c) removing binding member not bound to the immobilized analyte, (d) dissociating the aptamer bound to the binding member bound to the immobilized analyte and translocating the dissociated aptamer through one or more nanopores in a layer, and (e) assessing the aptamer translocating through the layer, wherein each aptamer translocating through the layer is a translocation event, wherein measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference standard comprising a calibration curve, standard addition, or digital polymerase chain reaction, wherein the standard curve in subsection i) is determined by measuring the number of translocation events for control concentrations of analyte during a set period of time; wherein the standard curve in subsection ii) is determined by measuring the time it takes for a set number of translocation events to occur for control concentrations of analyte; and wherein the standard curve in subsection iii) is determined by measuring the average time between translocation events to occur for control concentrations of analyte.

In yet another aspect, the present invention relates to a method for measuring or detecting an analyte present in a biological sample comprising: (a) contacting the sample with a binding member, wherein the binding member is immobilized on a solid support, the binding member comprises a cleavable tag attached thereto, and the binding member specifically binds to the analyte, (b) removing binding member not bound to the analyte, (c) cleaving the tag attached to the binding member bound to the analyte, (d) translocating the tag through one or more nanopores in a layer, and (e) assessing the tag translocating through the layer, wherein each tag translocating through the layer is a translocation event, wherein measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference comprising a calibration curve, standard addition, or digital polymerase chain reaction.

In yet another aspect, the present invention relates to an integrated digital microfluidics nanopore-enabled device comprising: a microfluidics module and a nanopore-enabled module; the microfluidics module, comprising an array of electrodes spaced apart from a single electrode sized to overlap with at least a portion of the array of electrodes, where the array of electrodes and the single electrode transport at least one droplet of fluid to a transfer electrode in the array of electrodes, wherein the transfer electrode is positioned at an interface between the microfluidics module and the nanopore-enabled module; the nanopore-enabled module comprising: a first microchannel positioned on a first surface of a first substrate; a second microchannel positioned on a first surface of a second substrate; wherein the first surface of the first substrate is in contact with the first surface of the second substrate thereby enclosing the first microchannel and the second microchannel to provide a first capillary channel and a second capillary channel, respectively, wherein at least the first capillary channel extends to the interface between the microfluidics module and the nanopore-enabled module and is adjacent to the transfer electrode, and is positioned to receive a fluid droplet positioned on the transfer electrode; wherein the first capillary channel intersects with the second capillary channel, wherein a layer is positioned in between the first and second substrates at the location where the first and the second capillary channels intersect, wherein the layer is devoid of a nanopore and separates an ionic liquid present in the first and second capillary channels, wherein the first and second capillary channels are in electrical connection with electrodes for driving a voltage from the first to the second capillary channel or vice versa for creating a nanopore in the layer at the intersection of the first and second capillary channels.

In yet another aspect, the present invention relates to a method for generating a nanopore in an integrated digital microfluidics nanopore-enabled device, the method comprising: providing an integrated digital microfluidics nanopore-enabled device as previously described herein; applying a voltage in the first and second capillary channels to drive current through the layer; measuring conductance across the layer; terminating application of voltage upon detection of a conductance indicative of generation of a nanopore in the layer.

In yet another aspect, the present invention relates to an integrated digital microfluidics nanopore device comprising: a first substrate comprising an array of electrodes; a second substrate spaced apart from the first substrate; an opening in the first or second substrate in fluid communication with a nanopore layer comprising a nanopore; and a pair of electrodes configured to apply an electric field through the nanopore, wherein the array of electrodes are configured to transport at least one droplet of fluid to the opening.

In yet another aspect, the present invention relates to a pair of integrated digital microfluidics nanopore devices comprising: a first integrated digital microfluidics nanopore device described previously herein, wherein the single electrode is a first single electrode, and the capillary channel is a first capillary channel; and a second integrated digital microfluidics nanopore device comprising: a third substrate, comprising a fifth side and a sixth side opposite the fifth side, wherein the fifth side comprises an array of electrodes; a fourth substrate spaced apart from the third substrate, wherein the fourth substrate comprises a seventh side facing the fifth side of the third substrate and a eight side opposite the seventh side, wherein the seventh side comprises a second single electrode and wherein the nanopore layer is disposed on the eight side, wherein the fourth substrate comprises a second capillary channel extending from the seventh side to the eight side of the fourth substrate, wherein the nanopore layer is positioned over an opening of the capillary channel, wherein the nanopore layer is interposed between the second substrate and the fourth substrate such that the nanopore provides an electroosmotic conduit between the first capillary channel and the second capillary channel, wherein the pair of detection electrodes comprises a second detection electrode that is the second single electrode.

In yet another aspect, the present invention relates to an integrated digital microfluidics nanopore-enabled device comprising: a first substrate, comprising a first side and a second side opposite the first side, wherein the first side comprises an array of electrodes; a second substrate spaced apart from the first substrate, wherein the second substrate comprises a third side facing the first side of the first substrate and a fourth side opposite the third side; a nanopore-enabled layer devoid of a nanopore and disposed on an external side of the device, wherein the external side is selected from the second side or the fourth side, wherein one of the first or second substrates comprising the external side comprises a capillary channel extending from the first side to the second side of the first substrate, or the third side to the fourth side of the second substrate, wherein the nanopore-enabled layer is positioned over an opening of the capillary channel; and a pair of electrodes configured to apply an electric field across the nanopore-enabled layer, wherein the array of electrodes are configured to transport at least one droplet of fluid to the capillary channel.

In yet another aspect, the present invention relates to a method for generating a nanopore in an integrated digital microfluidics nanopore-enabled device comprising: providing an integrated digital microfluidics nanopore-enabled device described previously herein; submerging both sides of the nanopore-enabled layer in an ionic liquid such that the ionic liquid on each side of the layer is in electrical contact with either one of the pair of detection electrodes; applying a voltage between the pair of detection electrodes to drive current through the layer; measuring conductance across the layer; terminating application of voltage upon detection of a conductance indicative of generation of a nanopore in the layer.

In another aspect, the present invention relates to a composition comprising a binding member, a tag and a spacer.

In yet another aspect, the present invention relates to an integrated digital microfluidics nanopore device comprising: a first substrate, comprising an array of electrodes; a second substrate spaced apart from the first substrate; and a nanopore layer having a first surface and a second surface disposed between the first and second substrates, wherein the array of electrodes are configured to position a first droplet at the first surface of the nanopore layer, wherein at least two electrodes of the array of electrodes are positioned across the nanopore layer, where the two electrodes form an anode and a cathode and operate to drive current through a nanopore in the nanopore layer when a liquid droplet is at the first surface of the nanopore layer.

In yet another aspect, the present invention relates to an integrated digital microfluidics nanopore device comprising a microfluidics module and a nanopore module; the microfluidics module comprising an array of electrodes, where the array of electrodes transport at least one droplet of fluid to a transfer position in the array of electrodes, wherein the transfer position is at an interface between the microfluidics module and the nanopore module; the nanopore module comprising: a first capillary channel extending from the transfer position to a nanopore layer.

In yet another aspect, the present invention relates to an integrated digital microfluidics nanopore device comprising: a first substrate, comprising an array of electrodes; a second substrate spaced apart from the first substrate; a first nanopore layer having one or more nanopores therein; a second nanopore layer having one or more nanopores therein; and at least two electrodes for creating an electric field to drive tags through a nanopore in the first and second nanopore layers.

In yet another aspect, the present invention relates to a kit comprising any of the aforementioned devices for use in any of the aforementioned methods.

In yet another aspect, the present invention relates to a method of using any of the aforementioned devices for measuring or detecting an analyte present in a biological sample or for diagnosing a patient or screening a blood supply.

In yet another aspect, the present invention relates to a method for measuring or detecting an analyte of interest present in a biological sample comprising (a) contacting the sample with a solid support, a binding member, and a labeled analyte that is labeled with a cleavable tag, wherein the solid support comprises an immobilization agent, the binding member comprises a ligand for the immobilization agent, and the binding member specifically binds the analyte of interest to form either a solid support/binding member/analyte of interest complex or a solid support/binding member/labeled analyte complex; (b) removing labeled analyte not bound to the binding member in the solid support/binding member/labeled analyte complex; (c) cleaving the tag attached to the labeled analyte bound to the binding member in the solid support/binding member/labeled analyte complex; (d) translocating the tag through one or more nanopores in a layer; and (e) assessing the tags translocating through the layer, wherein measuring the number of tags translocating through the layer measures the amount of analyte present in the sample, or wherein detecting tags translocating through the layer detects that the analyte is present in the sample.

In yet another aspect, the present invention relates to a method for measuring or detecting an analyte of interest present in a biological sample comprising (a) contacting the sample with a solid support, a binding member, and exogenous analyte, wherein the solid support comprises an immobilization agent, the exogenous analyte comprises a ligand for the immobilization agent and binds the solid support so as to form a solid support/immobilized analyte complex, and the binding member comprises a cleavable tag and specifically binds the analyte of interest to form either a solid support/analyte of interest/binding member complex or a solid support/immobilized analyte/binding member complex; (b) removing binding member not bound in either the solid support/immobilized analyte/binding member complex or the solid support/analyte of interest/binding member complex; (c) cleaving the tag attached to the binding member in the solid support/immobilized analyte/binding member complex; (d) translocating the tag through one or more nanopores in a layer; and (e) assessing the tags translocating through the layer, wherein measuring the number of tags translocating through the layer measures the amount of analyte present in the sample, or wherein detecting tags translocating through the layer detects that the analyte is present in the sample.

In yet another aspect, the present invention relates to a method for measuring or detecting an analyte of interest present in a biological sample, the method comprising (a) contacting the sample with a solid support, a binding member, and a labeled analyte that is labeled with a cleavable tag, wherein the solid support comprises an immobilization agent, the binding member comprises a ligand for the immobilization agent, and the binding member specifically binds the analyte of interest so as to form either a solid support/binding member/analyte of interest complex or a solid support/binding member/labeled analyte complex; (b) removing labeled analyte not bound to the binding member in the solid support/binding member/labeled analyte complex; (c) cleaving the tag attached to the labeled analyte bound to the binding member in the solid support/binding member/labeled analyte complex; (d) translocating the tag through one or more nanopores in a layer; and (e) assessing the tags translocating through the layer, wherein measuring the number of tags translocating through the layer measures the amount of analyte present in the sample, or wherein detecting tags translocating through the layer detects that the analyte is present in the sample.

In yet another aspect, the present invention relates to a method for measuring or detecting an analyte of interest present in a biological sample, the method comprising (a) contacting the sample with a solid support, a binding member, and exogenous analyte, wherein the solid support comprises an immobilization agent, the exogenous analyte comprises a ligand for the immobilization agent and binds the solid support so as to form a solid support/immobilized analyte complex, and the binding member comprises a cleavable tag and specifically binds the analyte of interest so as to form either a solid support/analyte of interest/binding member complex or a solid support/immobilized analyte/binding member complex; (b) removing binding member not bound in either the solid support/immobilized analyte/binding member complex or the solid support/analyte of interest/binding member complex; (c) cleaving the tag attached to the binding member in the solid support/immobilized analyte/binding member complex; (d) translocating the tag through one or more nanopores in a layer; and (e) assessing the tags translocating through the layer, wherein measuring the number of tags translocating through the layer measures the amount of analyte present in the sample, or wherein detecting tags translocating through the layer detects that the analyte is present in the sample.

In yet another aspect, the present invention relates to a method for measuring or detecting an analyte of interest present in a biological sample, the method comprising (a) contacting the sample with a solid support, a binding member, and a labeled analyte that is labeled with an aptamer, wherein the solid support comprises an immobilization agent, the binding member comprises a ligand for the immobilization agent, and the binding member specifically binds the analyte of interest so as to form either a solid support/binding member/analyte of interest complex or a solid support/binding member/labeled analyte complex; (b) removing labeled analyte not bound to the binding member in the solid support/binding member/labeled analyte complex; (c) dissociating the aptamer attached to the labeled analyte bound to the binding member in the solid support/binding member/labeled analyte complex; (d) translocating the dissociated aptamer through one or more nanopores in a layer; and (e) assessing the aptamer translocating through the layer, wherein measuring the number of aptamers translocating through the layer measures the amount of analyte present in the sample, or wherein detecting aptamers translocating through the layer detects that the analyte is present in the sample.

In yet another aspect, the present invention relates to a method for measuring or detecting an analyte of interest present in a biological sample, the method comprising (a) contacting the sample with a solid support, a binding member, and exogenous analyte, wherein the solid support comprises an immobilization agent, the exogenous analyte comprises a ligand for the immobilization agent and binds the solid support so as to form a solid support/immobilized analyte complex, and the binding member comprises an aptamer and specifically binds the analyte of interest so as to form either a solid support/analyte of interest/binding member complex or a solid support/immobilized analyte/binding member complex; (b) removing binding member not bound in either the solid support/immobilized analyte/binding member complex or the solid support/analyte of interest/binding member complex; (c) dissociating the aptamer bound to the binding member in the solid support/immobilized analyte/binding member complex; (d) translocating the tag through one or more nanopores in a layer; and (e) assessing the tags translocating through the layer, wherein measuring the number of tags translocating through the layer measures the amount of analyte present in the sample, or wherein detecting tags translocating through the layer detects that the analyte is present in the sample.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 2C-2L depict schematics of exemplary integrated devices in which a microfluidics module is fluidically connected to a nanopore module. The nanopore module includes a nanopore in a layer physically separating two microfluidic channels at a location where the two microfluidic channels intersect.

FIGS. 14A-14C depict fabrication and design of a nanopore module, according to embodiments of the present disclosure.

FIGS. 24A-24C display the scatter plot (level duration versus level of blockage) for plots obtained using showing translocation events through: (FIG. 24A) nanopores comprised of regular double stranded DNA ("dsDNA"); (FIG. 24B) nanopores comprised of DBCO-modified dsDNA; and (FIG. 24C) nanopores comprised of dsDNA stars.

FIG. 26A discloses NP-8 (8) (Oligo 8-1 (SEQ ID NO: 6) and Oligo 8-2 (SEQ ID NO: 7) joined by two photocleavable moieties ("PC") and FIG. 26B discloses NP-8 (8) (Oligo 8-1 (SEQ ID NO: 6) and Oligo 8-2 (SEQ ID NO: 7) joined by two photocleavable moieties ("PC") and NP-9 (9) (SEQ ID NO: 8). FIG. 26B also discloses "AAA AAA GGT CCG CAT CGA CTG CAT TCA" as SEQ ID NO: 6.

FIG. 35 shows a schematic diagram of a nanopore chamber design in a silicon nanopore module, according to embodiments of the present disclosure.

FIG. 36 shows a table listing the physical parameters used for COMSOL electrical field simulations in a nanopore chamber of a silicon nanopore module, according to embodiments of the present disclosure.

DETAILED DESCRIPTION

Figure 1B:
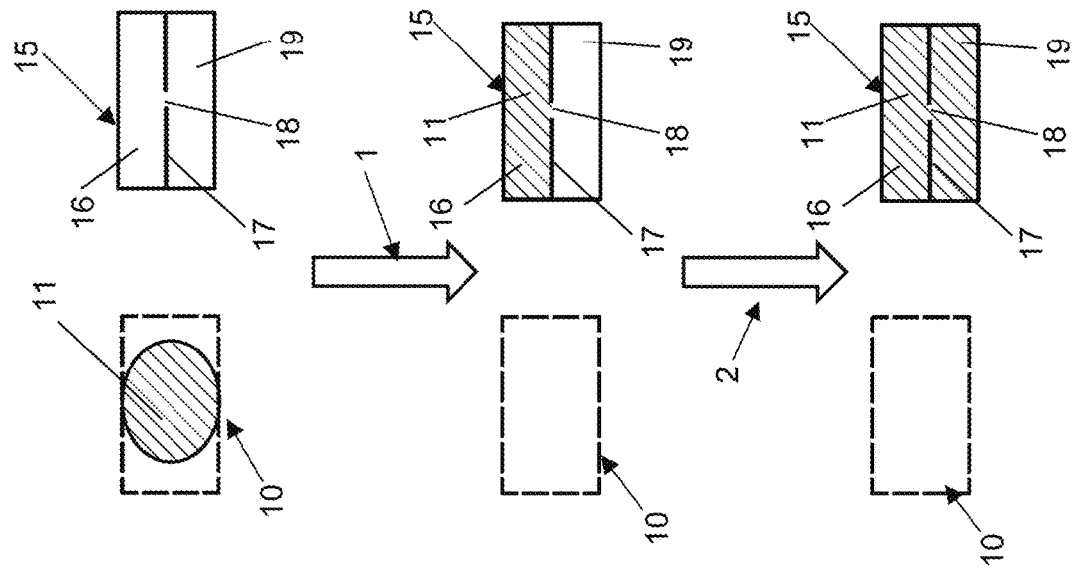
FIG. 1A and FIG. 1B depict a microfluidics device 10 used in conjunction with a nanopore device 15.

Embodiments of the present disclosure relate to methods, systems, and devices for analysis of analyte(s) in a sample. In certain embodiments, the sample may be a biological sample.

1. Definitions

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting.

"Comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Affinity" and "binding affinity" as used interchangeably herein refer to the tendency or strength of binding of the binding member to the analyte. For example, the binding affinity may be represented by the equilibrium dissociation constant ($K_D$), the dissociation rate ($k_d$), or the association rate ($k_a$).

"Analog" as used herein refers to a molecule that has a similar structure to a molecule of interest (e.g., nucleoside analog, nucleotide analog, sugar phosphate analog, analyte analog, etc.). An analyte analog is a molecule that is structurally similar to an analyte but for which the binding member has a different affinity.

"Aptamer" as used herein refers to an oligonucleotide or peptide molecule that can bind to pre-selected targets including small molecules, proteins, and peptides among others with high affinity and specificity. Aptamers may assume a variety of shapes due to their propensity to form helices and single-stranded loops. An oligonucleotide or nucleic acid aptamer can be a single-stranded DNA or RNA (ssDNA or ssRNA) molecule. A peptide aptamer can include a short variable peptide domain, attached at both ends to a protein scaffold.

"Bead" and "particle" are used herein interchangeably and refer to a substantially spherical solid support.

"Component," "components," or "at least one component," refer generally to a capture antibody, a detection reagent or conjugate, a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum, whole blood, tissue aspirate, or plasma sample, in accordance with the methods described herein and other methods known in the art. Some components can be in solution or lyophilized for reconstitution for use in an assay.

"Control" as used herein refers to a reference standard for an analyte such as is known or accepted in the art, or determined empirically using acceptable means such as are commonly employed. A "reference standard" is a standardized substance which is used as a measurement base for a similar substance. For example, there are documented reference standards published in the U.S. Pharmacopeial Convention (USP-NF), Food Chemicals Codex, and Dietary Supplements Compendium (all of which are available at http://www.usp.org), and other well-known sources. Methods for standardizing references are described in the literature. Also well-known are means for quantifying the amounts of analyte present by use of a calibration curve for analyte or by comparison to an alternate reference standard. A standard curve can be generated using serial dilutions or solutions of known concentrations of analyte, by mass spectroscopy, gravimetric methods, and by other techniques known in the art. Alternate reference standards that have been described in the literature include standard addition (also known as the method of standard addition), or digital polymerase chain reaction.

"Digital microfluidics (DMF)," "digital microfluidic module (DMF module)," or "digital microfluidic device (DMF device)" as used interchangeably herein refer to a module or device that utilizes digital or droplet-based microfluidic techniques to provide for manipulation of discrete and small volumes of liquids in the form of droplets. Digital microfluidics uses the principles of emulsion science to create fluid-fluid dispersion into channels (principally water-in-oil emulsion). It allows the production of monodisperse drops/bubbles or with a very low polydispersity. Digital microfluidics is based upon the micromanipulation of discontinuous fluid droplets within a reconfigurable network. Complex instructions can be programmed by combining the basic operations of droplet formation, translocation, splitting, and merging.

Digital microfluidics operates on discrete volumes of fluids that can be manipulated by binary electrical signals. By using discrete unit-volume droplets, a microfluidic operation may be defined as a set of repeated basic operations, i.e., moving one unit of fluid over one unit of distance. Droplets may be formed using surface tension properties of the liquid. Actuation of a droplet is based on the presence of electrostatic forces generated by electrodes placed beneath the bottom surface on which the droplet is located. Different types of electrostatic forces can be used to control the shape and motion of the droplets. One technique that can be used to create the foregoing electrostatic forces is based on dielectrophoresis which relies on the difference of electrical permittivities between the droplet and surrounding medium and may utilize high-frequency AC electric fields. Another technique that can be used to create the foregoing electrostatic forces is based on electrowetting, which relies on the dependence of surface tension between a liquid droplet present on a surface and the surface on the electric field applied to the surface.

"Drag-tag" refers to a mobility modifier. The drag-tag may be genetically engineered, highly repetitive polypeptides ("protein polymers") that are designed to be large, water-soluble, and completely monodisperse. Positively charged arginines may be deliberately introduced at regular intervals into the amino acid sequence to increase the hydrodynamic drag without increasing drag-tag length. Drag-tags are described in U.S. Patent Publication No. 20120141997, which is incorporated herein by reference.

"Enzymatic cleavable sequence" as used herein refers to any nucleic acid sequence that can be cleaved by an enzyme. For example, the enzyme may be a protease or an endonuclease, such as a restriction endonuclease (also called restriction enzymes). Restriction endonucleases are capable of recognizing and cleaving a DNA molecule at a specific DNA cleavage site between predefined nucleotides. Some endonucleases, such as for example FokI, comprise a cleavage domain that cleaves the DNA unspecifically at a certain position regardless of the nucleotides present at this position. In some embodiments, the specific DNA cleavage site and the DNA recognition site of the restriction endonuclease are identical.

"Globular protein" refers to a water soluble protein that has a roughly spherical shape. Examples of globular proteins include but are not limited to ovalbumin, beta-globulin, C-reactive protein, fibrin, hemoglobin, IgG, IgM, and thrombin.

"Label" or "detectable label" as used interchangeably herein refers to a tag attached to a specific binding member or analyte by a cleavable linker.

"Nanoparticle(s)" and "nanobead(s)" are used interchangeably herein and refer to a nanobead or nanoparticle sized to translocate through or across a nanopore used for counting the number of nanobeads/nanoparticles traversing through it.

"Nucleobase" or "Base" means those naturally occurring and synthetic heterocyclic moieties commonly known in the art of nucleic acid or polynucleotide technology or peptide nucleic acid technology for generating polymers. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Nucleobases can be linked to other moieties to form nucleosides, nucleotides, and nucleoside/tide analogs.

"Nucleoside" refers to a compound consisting of a purine, deazapurine, or pyrimidine nucleobase, e.g., adenine, guanine, cytosine, uracil, thymine, 7-deazaadenine, 7-deazaguanosine, that is linked to the anomeric carbon of a pentose sugar at the 1' position, such as a ribose, 2'-deoxyribose, or a 2',3'-di-deoxyribose.

"Nucleotide' as used herein refers to a phosphate ester of a nucleoside, e.g., a mono-, a di-, or a triphosphate ester, wherein the most common site of esterification is the hydroxyl group attached to the C-5 position of the pentose.

"Nucleobase polymer" or "nucleobase oligomer" refers to two or more nucleobases that are connected by linkages to form an oligomer. Nucleobase polymers or oligomers include, but are not limited to, poly- and oligonucleotides (e.g., DNA and RNA polymers and oligomers), poly-and oligo-nucleotide analogs and poly- and oligonucleotide mimics, such as polyamide or peptide nucleic acids. Nucleobase polymers or oligomers can vary in size from a few nucleobases to several hundred nucleobases or to several thousand nucleobases. The nucleobase polymers or oligomers may include from about 2 to 100 nucleobases or from about 8000 to 10000 nucleobases. For example, the nucleobase polymers or oligomers may have at least about 2 nucleobases, at least about 5 nucleobases, at least about 10 nucleobases, at least about 20 nucleobases, at least about 30 nucleobases, at least about 40 nucleobases, at least about 50 nucleobases, at least about 60 nucleobases, at least about 70 nucleobases, at least about 80 nucleobases, at least about 90 nucleobases, at least about 100 nucleobases, at least about 200 nucleobases, at least about 300 nucleobases, at least about 400 nucleobases, at least about 500 nucleobases, at least about 600 nucleobases, at least about 700 nucleobases, at least about 800 nucleobases, at least about 900 nucleobases, at least about 1000 nucleobases, at least about 2000 nucleobases, at least about 3000 nucleobases, at least about 4000 nucleobases, at least about 5000 nucleobases, at least about 6000 nucleobases, at least about 7000 nucleobases, at least about 8000 nucleobases, at least about 9000 nucleobases, or at least about 10000 nucleobases.

"One or more nanopores in a layer" means that in a single membrane structure or multiple membrane structures there is either one nanopore, or there are multiple nanopores (e.g., two or more) next to each other (e.g., side by side). When one or more nanopores are present (e.g., one, two, three, four, five, six, or other number of nanopores as technically feasible), optionally they are present side by side (e.g., next to each other) or in series (e.g., one nanopore in one layer present separate from or stacked onto (e.g., above or on top of) another nanopore in another layer, etc.), or in alternate structure such as would be apparent to one skilled in the art. Optionally, such nanopores are independently addressable, e.g., by each being within its own separate compartment (e.g., walled off from any other nanopore), or alternately can be addressed by an independent detection circuit.

"Polymer brush" refers to a layer of polymers attached with one end to a surface. The polymers are close together and form a layer or coating that forms its own environment. The brushes may be either in a solvent state, when the dangling chains are submerged into a solvent, or in a melt state, when the dangling chains completely fill up the space available. Additionally, there is a separate class of polyelectrolyte brushes, when the polymer chains themselves carry an electrostatic charge. The brushes may be characterized by the high density of grafted chains. The limited space then leads to a strong extension of the chains, and unusual properties of the system. Brushes may be used to stabilize colloids, reduce friction between surfaces, and to provide lubrication in artificial joints "Polynucleotides" or "oligonucleotides" refer to nucleobase polymers or oligomers in which the nucleobases are connected by sugar phosphate linkages (sugar-phosphate backbone). Exemplary poly- and oligonucleotides include polymers of 2'-deoxyribonucleotides (DNA) and polymers of ribonucleotides (RNA). A polynucleotide may be composed entirely of ribonucleotides, entirely of 2'-deoxyribonucleotides or combinations thereof. "Nucleic acid" encompasses "polynucleotide" and "oligonucleotides" and includes single stranded and double stranded polymers of nucleotide monomers.

"Polynucleotide analog" or "oligonucleotide analog" refers to nucleobase polymers or oligomers in which the nucleobases are connected by a sugar phosphate backbone comprising one or more sugar phosphate analogs. Typical sugar phosphate analogs include, but are not limited to, sugar alkylphosphonates, sugar phosphoramidites, sugar alkyl- or substituted alkylphosphotriesters, sugar phosphorothioates, sugar phosphorodithioates, sugar phosphates and sugar phosphate analogs in which the sugar is other than 2'-deoxyribose or ribose, nucleobase polymers having positively charged sugar-guanidyl interlinkages such as those described in U.S. Pat. Nos. 6,013,785 and 5,696,253.

As used herein, a "pore" (alternately referred to herein as "nanopore") or "channel" (alternately referred to herein as "nanopore" or a "nanochannel") refers to an orifice, gap, conduit, or groove in a membrane/layer, where the pore or channel is of sufficient dimension that allows passage or analysis of a single molecule (e.g., a tag) at one time (e.g., one-by-one, as in a series).

"Receptor" as used herein refers to a protein-molecule that recognizes and responds to endogenous-chemical signals. When such endogenous-chemical signals bind to a receptor, they cause some form of cellular/tissue-response. Examples of receptors include, but are not limited to, neural receptors, hormonal receptors, nutrient receptors, and cell surface receptors.

As used herein, "spacer" refers to a chemical moiety that extends the cleavable group from the specific binding member, or which provides linkage between the binding member and the support, or which extends the label/tag from the photocleavable moiety. In some embodiments, one or more spacers may be included at the N-terminus or C-terminus of a polypeptide or nucleotide-based tag or label in order to distance optimally the sequences from the specific binding member. Spacers may include but are not limited to 6-aminocaproic acid, 6-aminohexanoic acid; 1,3-diamino propane; 1,3-diamino ethane; polyethylene glycol (PEG) polymer groups, short amino acid sequences, and such as polyglycine sequences, of 1 to 5 amino acids. In some embodiments, the spacer is a nitrobenzyl group, dithioethylamino, 6 carbon spacer, 12 carbon spacer, or 3-(9-((3-carboxypropyl)(tosyl)carbamoyl)acridin-10-ium-10-yl)propane-1-sulfonate.

"Specific binding partner" or "specific binding member" as used interchangeably herein refers to one of two or more different molecules that specifically recognize the other molecule compared to substantially less recognition of other molecules. The one of two different molecules has an area on the surface or in a cavity, which specifically binds to and is thereby defined as complementary with a particular spatial and polar organization of the other molecule. The molecules may be members of a specific binding pair. For example, a specific binding member may include, but is not limited to, a protein, such as a receptor, an enzyme, and an antibody.

As used herein, "tag" or "tag molecule" both refer to the molecule (e.g., cleaved from the second binding member or an aptamer dissociated from the target analyte) that is translocated through or across a nanopore and provides an indication of the level of analyte in a sample. These terms refer to a single tag molecule or a plurality of the same tag molecule. Likewise "tags", unless specified otherwise, refers to one or one or more tags.

Figure 29:
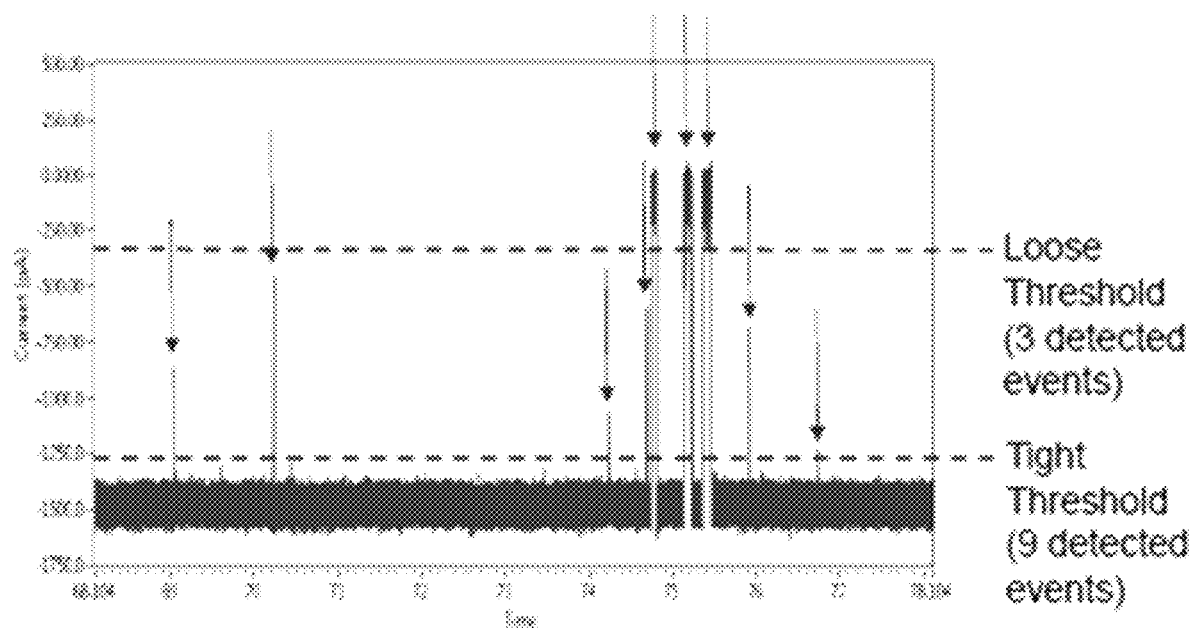
FIG. 29 displays the means by which a threshold for digital signal counting is determined.

"Threshold" as used herein refers to an empirically determined and subjective cutoff level above which acquired data is considered "signal", and below which acquired data is considered "noise". The use of a threshold for digital signal counting is depicted in FIG. 29. A computer program based on CUSUM (Cumulative Sums Algorithm) is employed to process acquired data and detect events based on threshold input from the user. Variation between users is avoided by detection of any many events as possible followed by filtering the data afterwards for specific purposes. For example, as can be seen from this figure, events detected above the set threshold impact the population of events that are counted as signal. With a "loose" threshold a lesser number of events will be counted as signal. With a "tight" threshold a greater number of events will be counted as signal. Setting the threshold as loose or tight is a subjective choice based on the desired sensitivity or specificity for an assay, and whether in a given assessment false positives or false negatives would be preferred. Current blockade signatures from DNA translocations were calculated to be 1.2 nA, which was based on an empirical formula relating current change to the diameter of DNA and the thickness of the nanopore membrane (H. Kwok, et al., *PLoS ONE*, 9(3), 392880, 2014).

As used herein, reference to movement (e.g., of a nanoparticles, tag, tag molecule, or other) "through or across" a nanopore means alternately, through, or across, in other words, from one side to another of a nanopore, e.g., from the cis to the trans side, or vice versa.

"Tracer" as used herein refers to an analyte or analyte fragment conjugated to a tag or label, wherein the analyte conjugated to the tag or label can effectively compete with the analyte for sites on an antibody specific for the analyte. For example, the tracer may be an analyte or analog of the analyte, such as cyclosporine or its analog ISA247, vitamin D and its analogs, sex hormones and their analogs, etc.

"Translocation event" as used herein refers to an event in which a tag translocates through or across (e.g., from the cis to trans side or vice versa) the layer or nanopore.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety to disclose and describe the methods and/or materials in connection with which the publications are cited. The materials, methods, and examples disclosed herein are illustrative only and not intended to be limiting.

2. Methods for Analyte Analysis

Provided herein are methods for analyte analysis. The method may involve single molecule counting. In certain embodiments, a method for analyte analysis may involve assessing an analyte present in a sample. In certain embodiments, the assessing may be used for determining presence of and/or concentration of an analyte in a sample. In certain embodiments, the method may also be used for determining presence of and/or concentration of a plurality of different analytes present in a sample.

Provided herein are methods for measuring or detecting an analyte present in a biological sample. The method includes contacting the sample with a first binding member, wherein the first binding member is immobilized on a solid support and wherein the first binding member specifically binds to the analyte; contacting the analyte with a second binding member, wherein the second binding member specifically binds to the analyte and wherein the second binding member includes a cleavable tag attached thereto; removing second binding member not bound to the analyte bound to the first binding member; cleaving the tag attached to the second binding member that is bound to the analyte bound to the first binding member; translocating the cleaved tag through or across one or more nanopores in a layer; detecting or measuring tags translocating through the layer; and assessing the tag translocating through the layer, wherein measuring the number of tags translocating through the layer measures the amount of analyte present in the sample, or wherein detecting tags translocating through the layer detects that the analyte is present in the sample. In some embodiments, measuring the tags translocating through the layer is assessed, wherein the number of tags translocating through the layer measures the amount of analyte present in the sample. In some embodiments, detecting the tags translocating through the layer is assessed, wherein detecting tags translocating through the layer detects that the analyte is present in the sample.

Provided herein are methods for measuring or detecting an analyte present in a biological sample. The method includes contacting the sample with a first binding member, wherein the first binding member is immobilized on a solid support and wherein the first binding member specifically binds to the analyte; contacting the analyte with a second binding member, wherein the second binding member specifically binds to the analyte and wherein the second binding member includes an aptamer; removing aptamer not bound to the analyte bound to the solid substrate; dissociating the aptamer bound to the analyte and translocating the dissociated aptamer through or across one or more nanopores in a layer; and assessing the aptamer translocating through the layer, wherein measuring the number of aptamers translocating through the layer measures the amount of analyte present in the sample, or detecting aptamers translocating through the layer detects that the analyte is present in the sample. In some embodiments, measuring the aptamers translocating through the layer is assessed, wherein the number of aptamers translocating through the layer measures the amount of analyte present in the sample. In some embodiments, detecting the aptamers translocating through the layer is assessed, wherein detecting tags translocating through the layer detects that the analyte is present in the sample.

In some embodiments, each tag, such as an aptamer, translocating through the layer is a translocation event. Measuring the number of translocation events measures the amount of analyte present in the sample. In some embodiments, the amount of analyte present in the sample can be determined by counting the number of translocation events during a set period of time and correlating the number of translocation events to a control. The standard curve can be determined by measuring the number of translocation events for control concentrations of analyte during a set period of time. In some embodiments, the amount of analyte present in the sample can be determined by measuring the amount of time for a set number of translocation events to occur and correlating to a control. The standard curve can be determined by measuring the time it takes for a set number of translocation events to occur for control concentrations of analyte. In some embodiments, the amount of analyte present in the sample can be determined by measuring the average time between translocation events to occur and correlating to a control. The standard curve can be determined by measuring the average time between translocation events to occur for control concentrations of analyte. In some embodiments, the control can be a reference standard comprising a calibration curve, standard addition, or digital polymerase chain reaction.

In exemplary cases, the method may include contacting the sample with a first binding member ("binding members" alternately referred to as "specific binding members," and as described in section c) below), where the first binding member is immobilized on a solid support and where the first binding member specifically binds to the analyte; contacting the analyte with a second binding member, which second binding member specifically binds to the analyte and which second binding member includes a cleavable tag ("tag" as defined herein and described in section d) below) attached thereto; removing second binding member not bound to the analyte bound to the first binding member; cleaving the tag attached to the second binding member that is bound to the analyte bound to the first binding member; translocating the tag through nanopores in a layer; determining the number of tags translocating through the layer; determining concentration of the analyte in the sample based on the number of tags translocating through the layer. In certain embodiments, the concentration of the analyte may be determined by counting the number of tags translocating through the layer per unit time. In other embodiments, the concentration of the analyte may be determined by determining the time at which the number of tags translocating through the layer reaches a threshold.

The sample may be any test sample containing or suspected of containing an analyte of interest. As used herein, "analyte", "target analyte", "analyte of interest" are used interchangeably and refer to the analyte being measured in the methods and devices disclosed herein. Analytes of interest are further described below.

"Contacting" and grammatical equivalents thereof as used herein refer to any type of combining action which brings a binding member into sufficiently close proximity with the analyte of interest in the sample such that a binding interaction will occur if the analyte of interest specific for the binding member is present in the sample. Contacting may be achieved in a variety of different ways, including combining the sample with a binding member, exposing a target analyte to a binding member by introducing the binding member in close proximity to the analyte, and the like.

In certain cases, the first binding member may be immobilized on a solid support. As used herein, "immobilized" refers to a stable association of the first binding member with a surface of a solid support. By "stable association" is meant a physical association between two entities in which the mean half-life of association is one day or more, e.g., under physiological conditions. In certain aspects, the physical association between the two entities has a mean half-life of two days or more, one week or more, one month or more, including six months or more, e.g., 1 year or more, in PBS at 4° C. According to certain embodiments, the stable association arises from a covalent bond between the two entities, a non-covalent bond between the two entities (e.g., an ionic or metallic bond), or other forms of chemical attraction, such as hydrogen bonding, Van der Waals forces, and the like.

The solid support having a surface on which the binding reagent is immobilized may be any convenient surface in planar or non-planar conformation, such as a surface of a microfluidic chip, an interior surface of a chamber, an exterior surface of a bead (as defined herein), or an interior and/or exterior surface of a porous bead. For example, the first binding member may be attached covalently or non-covalently to a bead, e.g., latex, agarose, sepharose, streptavidin, tosylactivated, epoxy, polystyrene, amino bead, amine bead, carboxyl bead, or the like. In certain embodiments, the bead may be a particle, e.g., a microparticle. In some embodiments, the microparticle may be between about 0.1 nm and about 10 microns, between about 50 nm and about 5 microns, between about 100 nm and about 1 micron, between about 0.1 nm and about 700 nm, between about 500 nm and about 10 microns, between about 500 nm and about 5 microns, between about 500 nm and about 3 microns, between about 100 nm and about 700 nm, or between about 500 nm and 700 nm. For example, the microparticle may be about 4-6 microns, about 2-3 microns, or about 0.5-1.5 microns. Particles less than about 500 nm are sometimes considered nanoparticles. Thus, the microparticle optionally may be a nanoparticle between about 0.1 nm and about 500 nm, between about 10 nm and about 500 nm, between about 50 nm and about 500 nm, between about 100 nm and about 500 nm, about 100 nm, about 150 nm, about 200 nm, about 250 nm, about 300 nm, about 350 nm, about 400 nm, about 450 nm, or about 500 nm.

In certain embodiments, the bead may be a magnetic bead or a magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, NiO/Fe. Examples of ferrimagnetic materials include $NiFe_2O_4$, $CoFe_2O_4$, $Fe_3O_4$ (or $FeO.Fe_2O_3$). Beads can have a solid core portion that is magnetic and is surrounded by one or more non-magnetic layers. Alternately, the magnetic portion can be a layer around a non-magnetic core. The solid support on which the first binding member is immobilized may be stored in dry form or in a liquid. The magnetic beads may be subjected to a magnetic field prior to or after contacting with the sample with a magnetic bead on which the first binding member is immobilized.

After the contacting step, the sample and the first binding member may be incubated for a sufficient period of time to allow for the binding interaction between the binding member and analyte to occur. In addition, the incubating may be in a binding buffer that facilitates the specific binding interaction. The binding affinity and/or specificity of the first binding member and/or the second binding member may be manipulated or altered in the assay by varying the binding buffer. In some embodiments, the binding affinity and/or specificity may be increased by varying the binding buffer. In some embodiments, the binding affinity and/or specificity may be decreased by varying the binding buffer.

The binding affinity and/or specificity of the first binding member and/or the second binding member may be measured using the disclosed methods and device described below. In some embodiments, the one aliquot of sample is assayed using one set of conditions and compared to another aliquot of sample assayed using a different set of conditions, thereby determining the effect of the conditions on the binding affinity and/or specificity. For instance, changing or altering the condition can be one or more of removing the target analyte from the sample, adding a molecule that competes with the target analyte or the ligand for binding, and changing the pH, salt concentration, or temperature. Additionally or alternatively, a duration of time can be the variable and changing the condition may include waiting for a duration of time before again performing the detection methods.

In some embodiments, after the tag or aptamer passes through the pore of a nanopore device, the device can be reconfigured to reverse the movement direction of the tag or aptamer such that the tag or aptamer can pass through the pore again and be re-measured or re-detected, for example, in a confirmatory assay on an infectious disease assay to confirm the measured results.

The binding buffer may include molecules standard for antigen-antibody binding buffers such as, albumin (e.g., BSA), non-ionic detergents (Tween-20, Triton X-100), and/or protease inhibitors (e.g., PMSF). In certain cases, the binding buffer may be added to the microfluidic chip, chamber, etc., prior to or after adding the sample. In certain cases, the first binding member may be present in a binding buffer prior to contacting with the sample. The length of time for binding interaction between the binding member and analyte to occur may be determined empirically and may depend on the binding affinity and binding avidity between the binding member and the analyte. In certain embodiments, the contacting or incubating may be for a period of 5 sec to 1 hour, such as, 10 sec-30 minutes, or 1 minute-15 minutes, or 5 minutes-10 minutes, e.g., 10 sec, 15 sec, 30 sec, 1 minute, 5 minutes, 10 minutes, 15 minutes, 30 minutes, 45 minutes, 1 hour or 2 hours. Other conditions for the binding interaction, such as, temperature, salt concentration, may also be determined empirically or may be based on manufacturer's instructions. For example, the contacting may be carried out at room temperature (21° C.-28° C., e.g., 23° C.-25° C.), 37° C., or 4° C. In certain embodiments, an optional mixing of the sample with the first binding member may be carried out during the contacting step.

Following complex formation between the immobilized first binding member and the analyte, any unbound analyte may be removed from the vicinity of the first binding member along with the sample while the complex of the first binding member and the analyte may be retained due to its association with the solid support. Optionally, the solid support may be contacted with a wash buffer to remove any molecules non-specifically bound to the solid support.

After the first contacting step, and the optional removal of sample and/or optional wash steps, the complex of the first binding member and the analyte may be contacted with a second binding member, thereby leading to the formation of a sandwich complex in which the analyte is bound by the two binding members. An optional mixing of the second member with the first binding member-analyte complex may be carried out during the second contacting step. In some embodiments, immobilization of the analyte molecules with respect to a surface may aid in removal of any excess second binding members from the solution without concern of dislodging the analyte molecule from the surface. In some embodiments, the second binding member may include a tag, such as a cleavable tag, attached thereto.

As noted above, the second contacting step may be carried out in conditions sufficient for binding interaction between the analyte and the second binding member. Following the second contacting step, any unbound second binding member may be removed, followed by an optional wash step. Any unbound second binding member may be separated from the complex of the first binding member-analyte-second binding member by a suitable means such as, droplet actuation, electrophoresis, electrowetting, dielectrophoresis, electrostatic actuation, electric field mediated, electrode mediated, capillary force, chromatography, centrifugation, or aspiration. Upon removal of any unbound second binding member from the vicinity of the complex of the first binding member-analyte-second binding member, the tag attached to the second binding member present in the complex of the first binding member-analyte-second binding member may be separated by a suitable means. In some embodiments, the tag is cleaved or disassociated from the complex which remains after removal of unbound reagents. For example, the tag may be attached to the second binding member via a cleavable linker ("cleavable linker" as described in section f) below). The complex of the first binding member-analyte-second binding member may be exposed to a cleavage agent that mediates cleavage of the cleavable linker.

In certain embodiments, the separation of the tag from the first binding member-analyte-second binding member complex is carried out under conditions that do not result in disruption of the complex, resulting in release of only the tag from the complex. In other cases, the separation of the tag from the first binding member-analyte-second binding member complex is carried out under conditions that may result in disruption of the complex, resulting in release of the tag, as well as one or more of the second binding member, the analyte, the first binding member from the complex. In certain embodiments, the size of the nanopore used for counting the tag may prevent the second binding member, the analyte, the first binding member from translocating through the nanopore. In other embodiments, where the complex of second binding member, the analyte, the first binding member is retained on the solid support, the nanopore may not be sized to exclude the second binding member, the analyte, and the first binding member.

The separation step results in the generation of a free tag that can be caused to translocate through or across a nanopore or nanopore layer (as described in section f) below) under the influence of an electric field. In certain cases, the cleavage step may result in separation of substantially all the tag molecule(s) attached to each of the second binding member in the first binding member-analyte-second binding member complex. The number of tag molecules can be correlated to the number of analyte molecules in the complex which are proportional to the concentration of the analyte in the sample. In certain embodiments, the correlation between the counted tag and the analyte concentration may be direct (higher number of tag molecules relates to higher analyte concentration). In embodiments where a tagged competitor or tagged analyte, such as a tracer (as defined herein), is combined with the sample, which tagged competitor or tagged analyte competes with the analyte in the sample for binding to the first binding member, the correlation between the counted tag and the analyte concentration may be inverse (lower number of tag molecules relates to higher analyte concentration). The correlation between the number of tag molecules and analyte concentration, whether direct or inverse, may be linear or logarithmic. Thus, the number of tag molecules translocating through the nanopore may be used to determine analyte concentration in the sample. In certain embodiments, the concentration of the analyte may be determined by counting the number of tags translocating through the layer per unit time. In other embodiments, the concentration of the analyte may be determined by determining the time at which the number of tags translocating through the layer reaches a threshold. In certain embodiments, the number of tag molecules translocating through or across a nanopore may be determined by the frequency of current blockage at the nanopore per unit time. Signal detection is further described in section g) below. As described in section d) below, the tag molecule may be a nanoparticle or a nanobead ("nanoparticle" and "nanobead" as defined herein).

The number of tags incorporated in the second binding member (i.e., the number of tags in the tag/second binding member conjugate) provides a defined stoichiometry with the analyte. In certain embodiments, a tag may be attached to the second binding member using a procedure that yields a consistent number of tag(s) attached to each second binding member. The number of tags may be optimized based on the speed of counting. A faster read rate may be obtained by including more tags on the binding member as the count rate is dependent on the concentration. The number of tags may be optimized based on the stoichiometry of tag incorporation, for example 1:1 or 1:4 incorporation rate. In some embodiments, there is a 1:5 incorporation rate. For example, one second binding member may have 1 tag molecule, 2 tag molecules, 3 tag molecules, 4 tag molecules, or up to 10 tag molecules attached thereto. In some embodiments, one second binding member may have 5 tag molecules attached thereto. A number of conjugation methods for conjugating a tag to a second binding member (e.g., a peptide, a polypeptide, a nucleic acid) are known, any of which may be used to prepare tagged second binding members for use in the present methods and devices. For example, site specific conjugation of a tag to an analyte specific antibody may be carried out using thiol-maleimide chemistry, amine-succinimidyl chemistry, THIOBRIDGE™ technology, using antibodies with a C- or N-terminal hexahistidine tag, antibodies with an aldehyde tag, copper-free click reaction, and the like.

In some embodiments, the methods can measure the amount of analyte by determining the number of translocation events. In some embodiments, one or more translocation event(s) can correspond to a binding event between a binding member and an analyte depending on the stoichiometry of tag incorporation into the specific binding member. For example, if one tag is incorporated per binding member, then one translocation event represents the binding of the binding member to the analyte; if two tags are incorporated per binding member, then two translocation events represents the binding of the binding member to the analyte; if three tags are incorporated per binding member, then three translocation events represents the binding of the binding member to the analyte, etc.

In another embodiment, the second binding member may be an aptamer that specifically binds to the analyte. In this embodiment, a tag may not be attached to the aptamer. Rather, the aptamer is counted as it translocates through or across a nanopore, i.e., the aptamer serves a dual function of being the second binding member and being the tag. In these embodiments, the aptamer in the complex of first binding member-analyte-aptamer complex may be dissociated from the complex by any suitable method. For example, prior to translocation through or across a nanopore, the aptamer bound to the complex of first binding member-analyte may be dissociated via a denaturation step. The denaturation step may involve exposure to a chaotropic reagent, a high salt solution, an acidic reagent, a basic reagent, solvent, or a heating step. The aptamer may then be translocated through or across a nanopore and the number of aptamer molecules translocating through or across a nanopore may be used to determine concentration of the analyte in the sample.

As noted herein, the tag or aptamer may include a nucleic acid. In certain embodiments, the counting step using a nanopore does not include determining the identity of the tag or the aptamer by determining identity of at least a portion of the nucleic acid sequence present in the tag/aptamer. For example, the counting step may not include determining a sequence of the tag/aptamer. In other embodiments, the tag/aptamer may not be sequenced, however, identity of the tag/aptamer may be determined to the extent that one tag/aptamer may be distinguished from another tag/aptamer based on a differentiable signal associated with the tag/aptamer due its size, conformation, charge, amount of charge and the like. Identification of tag/aptamer may be useful in methods involving simultaneous analysis of a plurality of different analytes in a sample, for example, two, three, four, or more different analytes in a sample.

In certain embodiments, the simultaneous analysis of multiple analytes in a single sample may be performed by using a plurality of different first and second binding members where a pair of first and second binding members is specific to a single analyte in the sample. In these embodiments, the tag associated with the second binding member of a first pair of first and second binding members specific to a single analyte may be distinguishable from the tag associated with the second binding member of a second pair of first and second binding members specific to a different analyte. As noted above, a first tag may be distinguishable from second tag based on difference in dimensions, charge, etc.

In some embodiments, the concentration of an analyte in the fluid sample that may be substantially accurately determined is less than about 5000 fM (femtomolar), less than about 3000 fM, less than about 2000 fM, less than about 1000 fM, less than about 500 fM, less than about 300 fM, less than about 200 fM, less than about 100 fM, less than about 50 fM, less than about 25 fM, less than about 10 fM, less than about 5 fM, less than about 2 fM, less than about 1 fM, less than about 500 aM (attomolar), less than about 100 aM, less than about 10 aM, less than about 5 aM, less than about 1 aM, less than about 0.1 aM, less than about 500 zM (zeptomolar), less than about 100 zM, less than about 10 zM, less than about 5 zM, less than about 1 zM, less than about 0.1 zM, or less.

In some cases, the limit of detection (e.g., the lowest concentration of an analyte which may be determined in solution) is about 100 fM, about 50 fM, about 25 fM, about 10 fM, about 5 fM, about 2 fM, about 1 fM, about 500 aM (attomolar), about 100 aM, about 50 aM, about 10 aM, about 5 aM, about 1 aM, about 0.1 aM, about 500 zM (zeptomolar), about 100 zM, about 50 zM, about 10 zM, about 5 zM, about 1 zM, about 0.1 zM, or less. In some embodiments, the concentration of analyte in the fluid sample that may be substantially accurately determined is between about 5000 fM and about 0.1 fM, between about 3000 fM and about 0.1 fM, between about 1000 fM and about 0.1 fM, between about 1000 fM and about 0.1 zM, between about 100 fM and about 1 zM, between about 100 aM and about 0.1 zM, or less.

The upper limit of detection (e.g., the upper concentration of an analyte which may be determined in solution) is at least about 100 fM, at least about 1000 fM, at least about 10 pM (picomolar), at least about 100 pM, at least about 100 pM, at least about 10 nM (nanomolar), at least about 100 nM, at least about 1000 nM, at least about 10 μM, at least about 100 µM, at least about 1000 µM, at least about 10 mM, at least about 100 mM, at least about 1000 mM, or greater.

In some cases, the presence and/or concentration of the analyte in a sample may be detected rapidly, usually in less than about 1 hour, e.g., 45 minutes, 30 minutes, 15 minutes, 10 minutes, 5 minutes, 1 minute, or 30 seconds.

In certain embodiments, at least some steps of the methods described herein may be carried out on a digital microfluidics device, such as the device described in section 3, below. In certain embodiments, the methods of the present disclosure are carried out using a digital microfluidics device in conjunction with a nanopore device. For example, the digital microfluidics device and the nanopore device may be separate devices and a droplet containing the cleaved tag(s) or the dissociated aptamer(s) may be generated in the microfluidics device and transported to the nanopore device. In certain embodiments, a droplet containing the cleaved tag(s) or the dissociated aptamer(s) may be aspirated from the microfluidics device and transported to the nanopore device using pipette operated by a user or a robot.

In certain embodiments, the methods of the present disclosure are carried out using a device in which a digital microfluidics module is integrated with a nanopore module, such as the device described below. In certain embodiments, the digital microfluidics module and the nanopore module may be reversibly integrated. For example, the two modules may be combined physically to form the integrated device and which device could then be separated into the individual modules. In certain embodiments, the methods of the present disclosure are carried out using a disposable cartridge that includes a microfluidics module with a built-in a nanopore module. Exemplary embodiments of the devices used for performing the methods provided herein are described further in the next section.

In certain cases, the microfluidics device or the microfluidics module of the device integrated (reversibly or fully) with the nanopore module may include a first substrate and a second substrate arranged in a spaced apart manner, where the first substrate is separated from the second substrate by a gap/space, and where at least the steps of contacting the sample with a first binding member, contacting the analyte with a second binding member, removing second binding member not bound to the analyte bound to the first binding member, and cleaving the tag attached to the second binding member (that remains bound to the analyte bound to the first binding member) is carried out in the space/gap between the first and second substrates.

Exemplary embodiments of the present method include generating a droplet of the sample and combining the droplet of the sample with a droplet containing the first binding member to generate a single droplet. The first binding member may be immobilized on a solid substrate, such as, a bead (e.g., a magnetic bead). The single droplet may be incubated for a time sufficient to allow binding of the first binding member to an analyte present in the sample droplet. Optionally, the single droplet may be agitated to facilitate mixing of the sample with the first binding member. Mixing may be achieved by moving the single droplet back and forth, moving the single droplet around over a plurality of electrodes, splitting a droplet and then merging the droplets, or using SAWs, and the like. Next, the single droplet may be subjected to a magnetic force to retain the beads at a location in the device while the droplet may be moved away and replaced with a droplet containing a second binding member. An optional wash step may be performed, prior to adding the second binding member, by moving a droplet of wash buffer to the location at which the beads are retained using the magnetic force. After a period of time sufficient for the second binding member to bind the analyte bound to the first binding member, the droplet containing the second binding member may be moved away while the beads are retained at the first location. The beads may be washed using a droplet of wash buffer followed by contacting the beads with a droplet containing a cleavage reagent to cleave the tag attached to the second binding member. In embodiments where the tag is attached to the second binding member via a photocleavable linker, the beads may be exposed to light of the appropriate wavelength to cleave the linker. In certain cases, the beads may be exposed to a droplet of buffer prior to cleavage of the photocleavable linker. Optionally, after the washing step to remove any unbound second binding member, a droplet containing buffer may be left covering the beads, the magnetic force retaining the beads at the first location may be removed and the buffer droplet containing the beads may be moved to a second location at which the photocleavage may be carried out. The droplet containing the cleaved tags may then be moved to the nanopore device or the nanopore module portion of the integrated device. In embodiments using aptamer as the second binding member, after the washing step to remove any unbound aptamer, a droplet containing buffer may be left covering the beads, the magnetic force retaining the beads at the first location may be removed and the buffer droplet containing the beads may be moved to a second location at which the dissociation of the aptamer may be carried out. In other embodiments, after the washing step, the beads may be exposed to a droplet of a reagent for dissociating aptamer bound to the analyte. A droplet containing the dissociated aptamer may be moved to the nanopore while the beads may be retained in place using a magnet. The droplet containing the dissociated aptamer may be moved to the nanopore device or the nanopore module portion of the integrated device.

In an alternate embodiment, the first binding member may be immobilized on a surface of the first or the second substrate at a location in the gap/space. The step of contacting a sample with the first binding member may include moving a droplet of the sample to the location in the gap/space at which the first binding member is immobilized. The subsequent steps may be substantially similar to those described above for first binding member immobilized on magnetic beads.

After the cleaving/dissociating step, the droplet containing the cleaved tag(s)/dissociated aptamer(s) may be moved to the nanopore device or the nanopore module of the integrated device. As noted above, the droplet(s) may be moved using a liquid transfer system, such as a pipette. In certain cases, the microfluidic module may be fluidically connected to the nanopore module. Fluidic connection may be achieved by connecting the microfluidics module to the nanopore module via a channel or by placing the nanopore module within the microfluidics module, either reversibly or during the manufacturing process of the integrated device. Such devices are further described in the following section.

In the above embodiments, optionally, after the combining, a droplet may be manipulated (e.g., moved back and forth, moved in a circular direction, oscillated, split/merged, exposed to SAW, etc.) to facilitate mixing of the sample with the assay reagents, such as, the first binding member, second binding member, etc.

The moving of the droplets in the integrated microfluidics nanopore device may be carried out using electrical force (e.g., electrowetting, dielectrophoresis, electrode-mediated, opto-electrowetting, electric-field mediated, and electrostatic actuation) pressure, surface acoustic waves and the like. The force used for moving the droplets may be determined based on the specifics of the device, which are described in the following sections a) through g) below, and for the particular device described in section 3.

a) Multiplexing

The methods may include one or more (or alternately two or more) specific binding members to detect one or more (or alternately two or more) target analytes in the sample in a multiplexing assay. Each of the one or more (or alternately two or more) specific binding members binds to a different target analyte and each specific binding member is labeled with a different tag and/or aptamer. For example, a first specific binding member binds to a first target analyte, a second specific binding member binds to a second target analyte, a third specific binding member binds to a third target analyte, etc. and the first specific binding member is labeled with a first tag and/or aptamer, the second specific binding member is labeled with a second tag and/or aptamer, the third specific binding member is labeled with a third tag and/or aptamer, etc. In some embodiments, a first condition causes the cleavage or release of the first tag if the first specific binding member is labeled with a tag or the dissociation or release of the first aptamer if the first specific binding member is labeled with an aptamer, a second condition causes the cleavage or release of the second tag if the second specific binding member is labeled with a tag or the dissociation or release of the second aptamer if the second specific binding member is labeled with an aptamer, a third condition causes the cleavage or release of the third tag if the third specific binding member is labeled with a tag or the dissociation or release of the third aptamer if the third specific binding member is labeled with an aptamer, etc. In some embodiments, the conditions of the sample can be changed at various times during the assay, allowing detection of the first tag or aptamer, the second tag or aptamer, the third tag or aptamer, etc., thereby detecting one or more (or alternately two or more) target analytes. In some embodiments, the one or more (or alternately two or more) cleaved tags and/or dissociated aptamers are detected simultaneously through the pore based on the residence duration in the nanopore, magnitude of current impedance, or a combination thereof.

b) Exemplary Target Analytes

As will be appreciated by those in the art, any analyte that can be specifically bound by a first binding member and a second binding member may be detected and, optionally, quantified using methods and devices of the present disclosure.

In some embodiments, the analyte may be a biomolecule. Non-limiting examples of biomolecules include macromolecules such as, proteins, lipids, and carbohydrates. In certain instances, the analyte may be hormones, antibodies, growth factors, cytokines, enzymes, receptors (e.g., neural, hormonal, nutrient, and cell surface receptors) or their ligands, cancer markers (e.g., PSA, TNF-alpha), markers of myocardial infarction (e.g., troponin, creatine kinase, and the like), toxins, drugs (e.g., drugs of addiction), metabolic agents (e.g., including vitamins), and the like. Non-limiting embodiments of protein analytes include peptides, polypeptides, protein fragments, protein complexes, fusion proteins, recombinant proteins, phosphoproteins, glycoproteins, lipoproteins, or the like.

In certain embodiments, the analyte may be a post-translationally modified protein (e.g., phosphorylated, methylated, glycosylated protein) and the first or the second binding member may be an antibody specific to a post-translational modification. A modified protein may be bound to a first binding member immobilized on a solid support where the first binding member binds to the modified protein but not the unmodified protein. In other embodiments, the first binding member may bind to both the unmodified and the modified protein, and the second binding member may be specific to the post-translationally modified protein.

In some embodiments, the analyte may be a cell, such as, circulating tumor cell, pathogenic bacteria, viruses (including retroviruses, herpesviruses, adenoviruses, lentiviruses, Filoviruses (ebola), hepatitis viruses (e.g., A, B, C, D, and E); HPV, etc.; spores; etc.

A non-limiting list of analytes that may be analyzed by the methods presented herein include Aβ42 amyloid beta-protein, fetuin-A, tau, secretogranin II, prion protein, Alpha-synuclein, tau protein, neurofilament light chain, parkin, PTEN induced putative kinase 1, DJ-1, leucine-rich repeat kinase 2, mutated ATP13A2, Apo H, ceruloplasmin, Peroxisome proliferator-activated receptor gamma coactivator-1 alpha (PGC-1α), transthyretin, Vitamin D-binding Protein, proapoptotic kinase R (PKR) and its phosphorylated PKR (pPKR), CXCL13, IL-12p40, CXCL13, IL-8, Dkk-3 (semen), p14 endocan fragment, Serum, ACE2, autoantibody to CD25, hTERT, CAI25 (MUC 16), VEGF, sIL-2, Osteopontin, Human epididymis protein 4 (HE4), Alpha-Fetoprotein, Albumin, albuminuria, microalbuminuria, neutrophil gelatinase-associated lipocalin (NGAL), interleukin 18 (IL-18), Kidney Injury Molecule-1 (KIM-1), Liver Fatty Acid Binding Protein (L-FABP), LMP1, BARF1, IL-8, carcinoembryonic antigen (CEA), BRAF, CCNI, EGRF, FGF19, FRS2, GREB1, and LZTS1, alpha-amylase, carcinoembryonic antigen, CA 125, IL8, thioredoxin, beta-2 microglobulin levels—monitor activity of the virus, tumor necrosis factor-alpha receptors—monitor activity of the virus, CA15-3, follicle-stimulating hormone (FSH), leutinizing hormone (LH), T-cell lymphoma invasion and metastasis 1 (TIAM1), N-cadherin, EC39, amphiregulin, dUTPase, secretory gelsolin (pGSN), PSA (prostate specific antigen), thymosin 1315, insulin, plasma C-peptide, glycosylated hemoglobin (HBA1c), C-Reactive Protein (CRP), Interleukin-6 (IL-6), ARHGDIB (Rho GDP-dissociation inhibitor 2), CFL1 (Cofilin-1), PFN1 (profilin-1), GSTP1 (Glutathione S-transferase P), S100A11 (Protein S100-A11), PRDX6 (Peroxiredoxin-6), HSPE1 (10 kDa heat shock protein, mitochondrial), LYZ (Lysozyme C precursor), GPI (Glucose-6-phosphate isomerase), HIST2H2AA (Histone H2A type 2-A), GAPDH (Glyceraldehyde-3-phosphate dehydrogenase), HSPG2 (Basement membrane-specific heparan sulfate proteoglycan core protein precursor), LGALS3BP (Galectin-3-binding protein precursor), CTSD (Cathepsin D precursor), APOE (Apolipoprotein E precursor), IQGAP1 (Ras GTPase-activating-like protein IQGAP1), CP (Ceruloplasmin precursor), and IGLC2 (IGLC1 protein), PCDGF/GP88, EGFR, HER2, MUC4, IGF-IR, p27(kip1), Akt, HER3, HER4, PTEN, PIK3CA, SHIP, Grb2, Gab2, PDK-1 (3-phosphoinositide dependent protein kinase-1), TSC1, TSC2, mTOR, MIG-6 (ERBB receptor feedback inhibitor 1), S6K, src, KRAS, MEK mitogen-activated protein kinase 1, cMYC, TOPO II topoisomerase (DNA) II alpha 170 kDa, FRAP1, NRG1, ESR1, ESR2, PGR, CDKN1B, MAP2K1, NEDD4-1, FOXO3A, PPP1R1B, PXN, ELA2, CTNNB1, AR, EPHB2, KLF6, ANXA7, NKX3-1, PITX2, MKI67, PHLPP, adiponectin (ADIPOQ), fibrinogen alpha chain (FGA), leptin (LEP), advanced glycosylation end product-specific receptor (AGER aka RAGE), alpha-2-HS-glycoprotein (AHSG), angiogenin (ANG), CD14 molecule (CD14), ferritin (FTH1), insulin-like growth factor binding protein 1 (IGFBP1), interleukin 2 receptor, alpha (IL2RA), vascular cell adhesion molecule 1 (VCAM1) and Von Willebrand factor (VWF), myeloperoxidase (MPO), ILla, TNFα, perinuclear anti-neutrophil cytoplasmic antibody (p-ANCA), lactoferrin, calprotectin, Wilm's Tumor-1 protein, Aquaporin-1, MLL3, AMBP, VDAC1, *E. coli* enterotoxins (heat-labile exotoxin, heat-stable enterotoxin), influenza HA antigen, tetanus toxin, diphtheria toxin, botulinum toxins, Shiga toxin, Shiga-like toxin I, Shiga-like toxin II, *Clostridium difficile* toxins A and B, etc.

Exemplary targets of nucleic acid aptamers that may be measured in a sample such as an environmental sample, a biological sample obtained from a patient or subject in need using the subject methods and devices include: drugs of abuse (e.g. cocaine), protein biomarkers (including, but not limited to, Nucleolin, nuclear factor-kB essential modulator (NEMO), CD-30, protein tyrosine kinase 7 (PTK7), vascular endothelial growth factor (VEGF), MUC 1 glycoform, immunoglobulin g Heavy Chains (IGHM), Immunoglobulin E, αvβ3 integrin, α-thrombin, HIV gp120, NF-κB, E2F transcription factor, HER3, Plasminogen activator inhibitor, Tenascin C,CXCL12/SDF-1, prostate specific membrane antigen (PSMA), gastric cancer cells, HGC-27); cells (including, but not limited to, non-small cell lung cancer (NSCLC), colorectal cancer cells, (DLD-1), H23 lung adenocarcinoma cells, Ramos cells, T-cell acute lymphoblastic leukemia (T-ALL) cells, CCRF-CEM, acute myeloid leukemia (AML) cells (HL60), small-cell lung cancer (SCLC) cells, NCIH69, human glioblastoma cells, U118-MG, PC-3 cells, HER-2-overexpressing human breast cancer cells, SK-BR-3, pancreatic cancer cell line (Mia-PaCa-2)); and infectious agents (including, but not limited to, *Mycobacterium tuberculosis, Staphylococcus aureus, Shigella dysenteriae, Escherichia coli* O157:H7, *Campylobacter jejuni, Listeria monocytogenes, Pseudomonas aeruginosa, Salmonella* O8, *Salmonella enteritidis*).

Exemplary targets of protein or peptide aptamers that may be measured in a sample obtained from a patient or subject in need using the subject methods and devices include, but are not limited to: HBV core capsid protein, CDK2, E2F transcription factor, Thymidylate synthase, Ras, EB 1, and Receptor for Advanced Glycated End products (RAGE). Aptamers, and use and methods of production thereof are reviewed in e.g., Shum et al., J Cancer Ther. 2013 4:872; Zhang et al., Curr Med Chem. 2011; 18:4185; Zhu et al., Chem Commun (Camb). 2012 48:10472; Crawford et al., Brief Funct Genomic Proteomic. 2003 2:72; Reverdatto et al., PLoS One. 2013 8:e65180.

c) Samples

As used herein, "sample", "test sample", "biological sample" refer to fluid sample containing or suspected of containing an analyte of interest. The sample may be derived from any suitable source. In some cases, the sample may comprise a liquid, fluent particulate solid, or fluid suspension of solid particles. In some cases, the sample may be processed prior to the analysis described herein. For example, the sample may be separated or purified from its source prior to analysis; however, in certain embodiments, an unprocessed sample containing the analyte may be assayed directly. The source of the analyte molecule may be synthetic (e.g., produced in a laboratory), the environment (e.g., air, soil, fluid samples, e.g., water supplies, etc.), an animal, e.g., a mammal, a plant, or any combination thereof. In a particular example, the source of an analyte is a human bodily substance (e.g., bodily fluid, blood, serum, plasma, urine, saliva, sweat, sputum, semen, mucus, lacrimal fluid, lymph fluid, amniotic fluid, interstitial fluid, lung lavage, cerebrospinal fluid, feces, tissue, organ, or the like). Tissues may include, but are not limited to skeletal muscle tissue, liver tissue, lung tissue, kidney tissue, myocardial tissue, brain tissue, bone marrow, cervix tissue, skin, etc. The sample may be a liquid sample or a liquid extract of a solid sample. In certain cases, the source of the sample may be an organ or tissue, such as a biopsy sample, which may be solubilized by tissue disintegration/cell lysis.

A wide range of volumes of the fluid sample may be analyzed. In a few exemplary embodiments, the sample volume may be about 0.5 nL, about 1 nL, about 3 nL, about 0.01 L, about 0.1 µL, about 1 µL, about 5 µL, about 10 µL, about 100 µL, about 1 mL, about 5 mL, about 10 mL, or the like. In some cases, the volume of the fluid sample is between about 0.01 µL and about 10 mL, between about 0.01 µL and about 1 mL, between about 0.01 µL and about 100 µL, or between about 0.1 µL and about 10 µL.

In some cases, the fluid sample may be diluted prior to use in an assay. For example, in embodiments where the source of an analyte molecule is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, about 100-fold, or greater, prior to use.

In some cases, the sample may undergo pre-analytical processing. Pre-analytical processing may offer additional functionality such as nonspecific protein removal and/or effective yet cheaply implementable mixing functionality. General methods of pre-analytical processing may include the use of electrokinetic trapping, AC electrokinetics, surface acoustic waves, isotachophoresis, dielectrophoresis, electrophoresis, or other pre-concentration techniques known in the art. In some cases, the fluid sample may be concentrated prior to use in an assay. For example, in embodiments where the source of an analyte molecule is a human body fluid (e.g., blood, serum), the fluid may be concentrated by precipitation, evaporation, filtration, centrifugation, or a combination thereof. A fluid sample may be concentrated about 1-fold, about 2-fold, about 3-fold, about 4-fold, about 5-fold, about 6-fold, about 10-fold, about 100-fold, or greater, prior to use.

In certain embodiments, the analyte is not amplified (i.e., the copy number of the analyte is not increased) prior to the measurement of the analyte. For example, in cases where the analyte is DNA or RNA, the analyte is not replicated to increase copy numbers of the analyte. In certain cases, the analyte is a protein or a small molecule.

d) Specific Binding Members

As will be appreciated by those in the art, the binding members will be determined by the analyte to be analyzed. Binding members for a wide variety of target molecules are known or can be readily found or developed using known techniques. For example, when the target analyte is a protein, the binding members may include proteins, particularly antibodies or fragments thereof (e.g., antigen-binding fragments (Fabs), Fab' fragments, F(ab')₂ fragments, recombinant antibodies, chimeric antibodies, single-chain Fvs ("scFv"), single chain antibodies, single domain antibodies, such as variable heavy chain domains ("VHH"; also known as "VHH fragments") derived from animals in the Camelidae family (VHH and methods of making them are described in Gottlin et al., Journal of Biomolecular Screening, 14:77-85 (2009)), recombinant VHH single-domain antibodies, and $V_N$AR fragments, disulfide-linked Fvs ("sdFv"), and anti-idiotypic ("anti-Id") antibodies, and functionally active epitope-binding fragments of any of the above, full-length polyclonal or monoclonal antibodies, antibody-like fragments, etc.), other proteins, such as receptor proteins, Protein A, Protein C, or the like. In case where the analyte is a small molecule, such as, steroids, bilins, retinoids, and lipids, the first and/or the second binding member may be a scaffold protein (e.g., lipocalins) or a receptor. In some cases, binding member for protein analytes may be a peptide. For example, when the target analyte is an enzyme, suitable binding members may include enzyme substrates and/or enzyme inhibitors which may be a peptide, a small molecule and the like. In some cases, when the target analyte is a phosphorylated species, the binding members may comprise a phosphate-binding agent. For example, the phosphate-binding agent may comprise metal-ion affinity media such as those describe in U.S. Pat. No. 7,070,921 and U.S. Patent Application No. 20060121544.

In certain cases, at least one of the binding members may be an aptamer, such as those described in U.S. Pat. Nos. 5,270,163, 5,475,096, 5,567,588, 5,595,877, 5,637,459, 5,683,867, 5,705,337. Nucleic acid aptamers (e.g., single-stranded DNA molecules or single-stranded RNA molecules) may be developed for capturing virtually any target molecule. Aptamers bind target molecules in a highly specific, conformation-dependent manner, typically with very high affinity, although aptamers with lower binding affinity can be selected. Aptamers may distinguish between target analyte molecules based on very small structural differences such as the presence or absence of a methyl or hydroxyl group and certain aptamers can distinguish between D- and L-enantiomers and diastereomers. Aptamers may bind small molecular targets, including drugs, metal ions, and organic dyes, peptides, biotin, and proteins. Aptamers can retain functional activity after biotinylation, fluorescein labeling, and when attached to glass surfaces and microspheres.

Nucleic acid aptamers are oligonucleotides that may be single stranded oligodeoxynucleotides, oligoribonucleotides, or modified oligodeoxynucleotide or oligoribonucleotides. "Modified" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl; 2'-fluoro-; 2'-halo or 2-azido-ribose, carbocyclic sugar analogues a-anomeric sugars; epimeric sugars such as arabinose, xyloses or lyxoses, pyranose sugars, furanose sugars, and sedoheptulose. In some embodiments, the binding member comprises a nucleic acid comprising a nucleotide sequence set forth in any one of SEQ ID NOs: 1-11.

Peptide aptamers may be designed to interfere with protein interactions. Peptide aptamers may be based on a protein scaffold onto which a variable peptide loop is attached, thereby constraining the conformation of the aptamer. In some cases, the scaffold portion of the peptide aptamer is derived from Bacterial Thioredoxin A (TrxA).

When the target molecule is a carbohydrate, potentially suitable capture components (as defined herein) include, for example, antibodies, lectins, and selectins. As will be appreciated by those of ordinary skill in the art, any molecule that can specifically associate with a target molecule of interest may potentially be used as a binding member.

For certain embodiments, suitable target analyte/binding member complexes can include, but are not limited to, antibodies/antigens, antigens/antibodies, receptors/ligands, ligands/receptors, proteins/nucleic acid, enzymes/substrates and/or inhibitors, carbohydrates (including glycoproteins and glycolipids)/lectins and/or selectins, proteins/proteins, proteins/small molecules, etc.

In a particular embodiment, the first binding member may be attached to a solid support via a linkage, which may comprise any moiety, functionalization, or modification of the support and/or binding member that facilitates the attachment of the binding member to the support. The linkage between the binding member and the support may include one or more chemical or physical (e.g., non-specific attachment via van der Waals forces, hydrogen bonding, electrostatic interactions, hydrophobic/hydrophilic interactions; etc.) bonds and/or chemical spacers providing such bond(s).

In certain embodiments, a solid support may also comprise a protective, blocking, or passivating layer that can eliminate or minimize non-specific attachment of non-capture components (e.g., analyte molecules, binding members) to the binding surface during the assay which may lead to false positive signals during detection or to loss of signal. Examples of materials that may be utilized in certain embodiments to form passivating layers include, but are not limited to: polymers, such as poly(ethylene glycol), that repel the non-specific binding of proteins; naturally occurring proteins with this property, such as serum albumin and casein; surfactants, e.g., zwitterionic surfactants, such as sulfobetaines; naturally occurring long-chain lipids; polymer brushes, and nucleic acids, such as salmon sperm DNA.

Certain embodiments utilize binding members that are proteins or polypeptides. As is known in the art, any number of techniques may be used to attach a polypeptide to a wide variety of solid supports. A wide variety of techniques are known to add reactive moieties to proteins, for example, the method outlined in U.S. Pat. No. 5,620,850. Further, methods for attachment of proteins to surfaces are known, for example, see Heller, Acc. Chem. Res. 23:128 (1990).

As explained herein, binding between the binding members and the analyte, is specific, e.g., as when the binding member and the analyte are complementary parts of a binding pair. In certain embodiments, the binding member binds specifically to the analyte. By "specifically bind" or "binding specificity," it is meant that the binding member binds the analyte molecule with specificity sufficient to differentiate between the analyte molecule and other components or contaminants of the test sample. For example, the binding member, according to one embodiment, may be an antibody that binds specifically to an epitope on an analyte. The antibody, according to one embodiment, can be any antibody capable of binding specifically to an analyte of interest. For example, appropriate antibodies include, but are not limited to, monoclonal antibodies, bispecific antibodies, minibodies, domain antibodies (dAbs) (e.g., such as described in Holt et al. (2014) Trends in Biotechnology 21:484-490), and including single domain antibodies sdAbs that are naturally occurring, e.g., as in cartilaginous fishes and camelid, or which are synthetic, e.g., nanobodies, VHH, or other domain structure), synthetic antibodies (sometimes referred to as antibody mimetics), chimeric antibodies, humanized antibodies, antibody fusions (sometimes referred to as "antibody conjugates"), and fragments of each, respectively. As another example, the analyte molecule may be an antibody and the first binding member may be an antigen and the second binding member may be a secondary antibody that specifically binds to the target antibody or the first binding member may be a secondary antibody that specifically binds to the target antibody and the second binding member may be an antigen.

In some embodiments, the binding member may be chemically programmed antibodies (cpAbs) (described in Rader (2014) Trends in Biotechnology 32:186-197), bispecific cpAbs, antibody-recruiting molecules (ARMs) (described in McEnaney et al. (2012) ACS Chem. Biol. 7:1139-1151), branched capture agents, such as a triligand capture agent (described in Millward et al. (2011) J. Am. Chem. Soc. 133:18280-18288), engineered binding proteins derived from non-antibody scaffolds, such as monobodies (derived from the tenth fibronectin type III domain of human fibronectin), affibodies (derived from the immunoglobulin binding protein A), DARPins (based on Ankyrin repeat modules), anticalins (derived from the lipocalins bilin-binding protein and human lipocalin 2), and cysteine knot peptides (knottins) (described in Gilbreth and Koide, (2012) Current Opinion in Structural Biology 22:1-8; Banta et al. (2013) Annu. Rev. Biomed. Eng. 15:93-113), WW domains (described in Patel et al. (2013) Protein Engineering, Design & Selection 26(4):307-314), repurposed receptor ligands, affitins (described in Béhar et al. (2013) 26:267-275), and/or Adhirons (described in Tiede et al. (2014) Protein Engineering, Design & Selection 27:145-155).

According to one embodiment in which an analyte is a biological cell (e.g., mammalian, avian, reptilian, other vertebrate, insect, yeast, bacterial, cell, etc.), the binding members may be ligands having specific affinity for a cell surface antigen (e.g., a cell surface receptor). In one embodiment, the binding member may be an adhesion molecule receptor or portion thereof, which has binding specificity for a cell adhesion molecule expressed on the surface of a target cell type. In use, the adhesion molecule receptor binds with an adhesion molecule on the extracellular surface of the target cell, thereby immobilizing or capturing the cell, the bound cell may then be detected by using a second binding member that may be the same as the first binding member or may bind to a different molecule expressed on the surface of the cell.

In some embodiments, the binding affinity between analyte molecules and binding members should be sufficient to remain bound under the conditions of the assay, including wash steps to remove molecules or particles that are non-specifically bound. In some cases, for example in the detection of certain biomolecules, the binding constant of the analyte molecule to its complementary binding member may be between at least about $10^4$ and about $10^6$ $M^{-1}$, at least about $10^5$ and about $10^9$ $M^{-1}$, at least about $10^7$ and about $10^9$ $M^{-1}$, greater than about $10^9$ $M^{-1}$, or greater.

e) Tag or Label

The methods described herein may include a specific binding member bound to a tag, such as a label, to analyze an analyte by impedance. The incorporated tags or labels do not substantially interfere with the conduct of the reaction scheme. For example, the incorporated tag or label does not interfere with the binding constant of or the interaction between the analyte and its complementary binding member. The size and number of incorporated tags or labels may be related to the speed of capture and read rate. The speed of capture and read rate may be increased by increasing the size and/or number of incorporated tags or labels. For example, the size and number of incorporated tags or labels may increase the charge and increase the capture zone of the nanopore. The incorporated tag or labels do not alter the binding member kinetics, for example, antibody kinetics, or the reaction scheme. Exemplary tags include polymers such as, an anionic polymer or a cationic polymer (e.g., a polypeptide with a net positive charge, such as, polyhistidine or polylysine), where the polymer is about 5-1000 residues in length; a protein (e.g., a globular protein) which does not cross react with the binding member and/or interfere with the assay, a dendrimer, e.g., a DNA dendrimer; and a charged nanoparticle, e.g., a nanobead. A polymer tag may include a nucleic acid, such as, a deoxyribonucleic acid or a ribonucleic acid. A polymer tag may include a nucleobase polymer. In certain cases, the tag may be DNA or a RNA aptamer, where the aptamer does not bind to the analyte. In cases, where the tag is an aptamer, it may be optionally denatured prior to the translocation through the nanopore. A polymer tag or a nanoparticle (e.g., a nanobead) may be sufficiently large to generate a reproducible signal as it translocates through or across a nanopore. Aptamers may be 20-220 bases in length, e.g., 20-60 bases long. The size of the nanoparticle (e.g., a nanobead or a dendrimer) may range from about 1 nm to about 950 nm in diameter for example, 10 nm-900 nm, 20 nm-800 nm, 30 nm-700 nm, 50 nm-600 nm, 80 nm-500 nm, 100 nm-500 nm, 200 nm-500 nm, 300 nm-500 nm, or 400 nm-500 nm in diameter, e.g., 10 nm, 20 nm, 30 nm, 50 nm, 100 nm, 200 nm, 300 nm, 400 nm, 500 nm, 600 nm, 700 nm, 800 nm, or 900 nm. When used as a tag, a preferred size for nanoparticle is one that can pass through or across a nanopore (as further described herein). In certain cases, the nanobead/nanoparticle may be made of a material that has a net negative or positive charge or can be treated to have a net negative or positive charge. Exemplary nanobeads/nanoparticles include those made from organic or inorganic polymers. Organic polymers include polymers such as, polystyrene, carbon, polyacrylamide, etc. Inorganic polymers include silicon or metal nanobeads/nanoparticles. In certain cases, the nanobeads/nanoparticles may not be magnetic.

In certain cases, the tag may be a single stranded DNA or RNA. The single stranded DNA or RNA may be hybridized to a probe molecule prior to translocation through or across a nanopore. In certain cases, the method may include analysis of multiple analytes in a single sample. The second binding members that bind to the different analytes in a sample may include different single stranded DNA or RNA attached thereto as tags and the different single stranded DNA or RNA may be hybridized to different probes that further distinguish the different single stranded DNA or RNA from each other as they traverse though the nanopores. In other embodiments, the tags attached to the different second binding members may have different hairpin structures (e.g., length of the hairpin structure) that are distinguishable when the tags pass through or across a nanopore. In yet another embodiment, the tags attached to the different second binding members may have different lengths that are distinguishable when the tags traverse through or across the nanopores—for example, the tags may be double stranded DNA of different lengths (e.g., 25 bp, 50 bp, 75 bp, 100 bp, 150 bp, 200 bp, or more). In certain cases, the tags attached to the different second binding members may have different lengths of polyethylene glycol (PEG) or may be DNA or RNA modified differentially with PEG.

It is noted that reference to a tag or a tag molecule encompasses a single tag or a single tag molecule as well as multiple tags (that all may be identical). It is further noted that the nanopore encompasses a single nanopore as well as multiple nanopores present in a single layer, such as, a substrate, a membrane, and the like. As such, counting the number of tags translocating through or across a nanopore in a layer/sheet/membrane refers to counting multiple tags translocating through or across one or more nanopores in a layer/sheet/membrane. Nanopores may be present in a single layer, such as a substrate or a membrane, the layer may be made of any suitable material that is electrically insulating or has a high electrical resistance, such as a lipid bilayer, a dielectric material, e.g., silicon nitride and silica, atomically thin membrane such as graphene, silicon, silicene, molybdenum disulfide ($MoS_2$), etc., or a combination thereof.

The tag may be any size or shape. In some embodiments, the tag may be a nanoparticle or a nanobead about 10 and 950 nm in diameter, e.g., 20-900 nm, 30-800 nm, 40-700 nm, 50-600 nm, 60-500 nm, 70-400 nm, 80-300 nm, 90-200 nm, 100-150 nm, 200-600 nm, 400-500 nm, 2-10 nm, 2-4 nm, or 3-4 nm in diameter. The tag may be substantially spherical, for example a spherical bead or nanobead, or hemi-spherical. The tag may be a protein about 0.5 kDa to about 50 kDa in size, e.g., about 0.5 kDa to about 400 kDa, about 0.8 kDa to about 400 kDa, about 1.0 kDa to about 400 kDa, about 1.5 kDa to about 400 kDa, about 2.0 kDa to about 400 kDa, about 5 kDa to about 400 kDa, about 10 kDa to about 400 kDa, about 50 kDa to about 400 kDa, about 100 kDa to about 400 kDa, about 150 kDa to about 400 kDa, about 200 kDa to about 400 kDa, about 250 kDa to about 400 kDa, about 300 kDa to about 400 kDa, about 0.5 kDa to about 300 kDa, about 0.8 kDa to about 300 kDa, about 1.0 kDa to about 300 kDa, about 1.5 kDa to about 300 kDa, about 2.0 kDa to about 300 kDa, about 5 kDa to about 300 kDa, about 10 kDa to about 300 kDa, about 50 kDa to about 300 kDa, about 100 kDa to about 300 kDa, about 150 kDa to about 300 kDa, about 200 kDa to about 300 kDa, about 250 kDa to about 300 kDa, about 0.5 kDa to about 250 kDa, about 0.8 kDa to about 250 kDa, about 1.0 kDa to about 250 kDa, about 1.5 kDa to about 250 kDa, about 2.0 kDa to about 250 kDa in size, about 5 kDa to about 250 kDa, about 10 kDa to about 250 kDa, about 50 kDa to about 250 kDa, about 100 kDa to about 250 kDa, about 150 kDa to about 250 kDa, about 200 kDa to about 250 kDa, about 0.5 kDa to about 200 kDa, about 0.8 kDa to about 200 kDa, about 1.0 kDa to about 200 kDa, about 1.5 kDa to about 200 kDa, about 2.0 kDa to about 200 kDa in size, about 5 kDa to about 200 kDa, about 10 kDa to about 200 kDa, about 50 kDa to about 200 kDa, about 100 kDa to about 200 kDa, about 150 kDa to about 200 kDa, about 0.5 kDa to about 100 kDa, about 0.8 kDa to about 100 kDa, about 1.0 kDa to about 100 kDa, about 1.5 kDa to about 100 kDa, about 2.0 kDa to about 100 kDa, about 5 kDa to about 100 kDa, about 10 kDa to about 100 kDa, about 50 kDa to about 100 kDa, about 0.5 kDa to about 50 kDa, about 0.8 kDa to about 50 kDa, about 1.0 kDa to about 50 kDa, about 1.5 kDa to about 50 kDa, about 2.0 kDa to about 50 kDa, about 5 kDa to about 50 kDa, about 10 kDa to about 50 kDa. about 10 kDa to about 90 kDa, about 10 kDa to about 80 kDa, about 10 kDa to about 70 kDa, about 10 kDa to about 60 kDa, about 20 kDa to about 90 kDa, about 20 kDa to about 80 kDa, about 20 kDa to about 70 kDa, about 20 kDa to about 60 kDa, about 40 kDa to about 90 kDa, about 40 kDa to about 80 kDa, about 40 kDa to about 70 kDa, or about 40 kDa to about 60 kDa.

In certain embodiments, the tag may be a nanoparticle. As noted herein, the nanoparticle may be reversibly (e.g., cleavably) attached to the second binding member. In certain aspects, the nanoparticle may be a nanobead of a defined diameter which may the property of the nanobead measured by the nanopore layer. In certain cases, the methods, systems, and devices of the present disclosure may be used to simultaneously analyze a plurality of different analytes in a sample. For such analysis a plurality of second binding members that each specifically bind to a cognate analyte may be used. Each of the different second binding member may be attached to a different sized nanobead that may be used to identify the second binding member. For example, the different nanobead tags may have different diameters, such as, 1 nm, 2 nm, 4 nm, 6 nm, 8 nm, 10 nm, 12 nm, 14 nm, or larger, such as up to 20 nm, 30 nm, 50 nm, 100 nm, 200 nm, 300 nm, 400 nm, 500 nm, 600 nm, 700 nm, 800 nm, 900 nm, 950 nm, or 990 nm.

In certain embodiments, the nanobeads of different diameters may all translocate through a nanopore layer having nanopores of a single diameter, where the different sized nanobeads may be identified based on the residence duration in the nanopore, magnitude of current impedance, or a combination thereof. In certain cases, a stacked nanopore layer device containing multiple nanopore layers, where a first layer may have nanopores of a first diameter and the second layer may have nanopores of a second diameter may be used to detect and count the nanobeads translocating through or across the nanopores. The multiple nanopore layers may be arranged in a manner such that layer with nanopores of a larger diameter is placed upstream to layer having nanopores of a smaller diameter. Exemplary stacked nanopore layers are disclosed in US20120080361.

Exemplary nanoparticles that may be used as tags in the present methods include gold nanoparticles or polystyrene nanoparticles ranging in diameter from 5 nm-950 nm.

In certain cases, the tag may be a polymer, such as, a nucleic acid. The presence of the tag may be determined by detecting a signal characteristic of the tag, such as a signal related to the size or length of the polymer tag. The size or length of the polymer tag can be determined by measuring its residence time in the pore or channel, e.g., by measuring duration of transient blockade of current.

Elements which can be part of, all of, associated with, or attached to the tag or label include: a nanoparticle; gold particle; silver particle; silver, copper, zinc, or other metal coating or deposit; polymer; drag-tag (as defined herein); magnetic particle; buoyant particle; metal particle; charged moiety; dielectrophoresis tag, silicon dioxide, with and without impurities (e.g., quartz, glass, etc.); poly(methylmethacrylate) (PMMA); polyimide; silicon nitride; gold; silver; quantum dot (including CdS quantum dot); carbon dot; a fluorophore; a quencher; polymer; polystyrene; Janus particle; scattering particle; fluorescent particle; phosphorescent particle; sphere; cube; insulator; conductor; barcoded or labeled particle; porous particle; solid particle; nanoshell; nanorod; microsphere; analyte such as a virus, cell, parasite and organism; nucleic acid; protein; molecular recognition element; spacer; PEG; dendrimer; charge modifier; magnetic material; enzyme; DNA including aptamer sequence; amplifiable DNA; repeated sequence of DNA; fusion or conjugate of detectable elements with molecular recognition elements (e.g., engineered binding member); anti-antibody aptamer; aptamer directed to antibody-binding protein; absorbed or adsorbed detectable compound; heme; luciferin; a phosphor; an azido, or alkyne (e.g., terminal or non-terminal alkyne) or other click chemistry participant.

In certain embodiments, the tag may be chosen to provide a rate of capture that is sufficiently high to enable a rapid analysis of a sample. In certain embodiments, the capture rate of the tag may be about 1 event per 10 seconds, 1 event per 5 seconds, 1 event per second or higher. In certain embodiments, linear polymer tags, such as, ribose polymers, deoxyribose polymers, oligonucleotides, DNA, or RNA may be used. Typically for 1 nM solution of DNA, capture rates are approximately 1 event $sec^{-1}$ using a solid-state nanopore ($Si_3N_4$), with no salt gradient, a voltage of 200-800 mV, and a salt (KCl) concentration of 1 M.

In certain cases, linear polymer tags, such as, ribose polymers, deoxyribose polymers, oligonucleotides, DNA, or RNA may not be used as the capture rate for these tags may be too low for certain applications. Tags that are hemispherical, spherical or substantially spherical in shape rapidly translocate through the nanopores and thus shorten the assay duration may be used in applications requiring faster tag counting. In certain cases, the size of the spherical or hemispherical tag may be chosen based on the capture rate needed for the assay. For example, for a higher capture rate, spherical or hemispherical tags of larger size may be selected. In certain cases, the tag may be spherical tag, such as, a nanoparticle/nanobead that has a capture rate about a 10 times, 30 times, 50 times, 100 times, 300 times, 500 times, or a 1000 times faster than capture rate for a linear tag, such as, a DNA tag, under the same measurement conditions.

In some embodiments, the tag may be conjugated to an antibody, for example, a CPSP antibody conjugate. In some embodiments, the tag may be conjugated to an antibody with a spacer, for example, a CPSP antibody conjugate with a spacer. In some embodiments, the tag may be may be conjugated to an oligonucleotide and an antibody, for example, a CPSP oligonucleotide-antibody conjugate. In some embodiments, the tag may be may be conjugated to an oligonucleotide and an antibody with a spacer, for example, a CPSP oligonucleotide-antibody conjugate with spacer. In some embodiments, the tag may be may be conjugated to an oligonucleotide, for example, a CPSP oligonucleotide conjugate. In some embodiments, the spacer includes a nitrobenzyl group, dithioethylamino, 6 carbon spacer, 12 carbon spacer, or 3-(9-((3-carboxypropyl)(tosyl)carbamoyl) acridin-10-ium-10-yl)propane-1-sulfonate. In some embodiments, the spacer comprises a nitrobenzyl group, and the tag is a DNA molecule. In some embodiments, the spacer is dithioethylamino and the tag is a carboxylated nanoparticle. In some embodiments, the spacer is 3-(9-((3-carboxypropyl) (tosyl)carbamoyl)acridin-10-ium-10-yl)propane-1-sulfonate and the tag is an oligonucleotide. In some embodiments, the spacer comprises a 6 carbon spacer or a 12 carbon spacer and the tag is biotin.

f) Cleavable Linker

The tags used in the methods described herein may be attached to specific binding member by a generic linker. The cleavable linker ensures that the tag can be removed. The generic linker may be a cleavable linker. For example, the tag may be attached to the second binding member via a cleavable linker. The complex of the first binding member-analyte-second binding member may be exposed to a cleavage agent that mediates cleavage of the cleavable linker. The linker can be cleaved by any suitable method, including exposure to acids, bases, nucleophiles, electrophiles, radicals, metals, reducing or oxidizing agents, light, temperature, enzymes etc. Suitable linkers can be adapted from standard chemical blocking groups, as disclosed in Greene & Wuts, Protective Groups in Organic Synthesis, John Wiley & Sons. Further suitable cleavable linkers used in solid-phase synthesis are disclosed in Guillier et al. (Chem. Rev. 100:2092-2157, 2000). The linker may be acid-cleavable, base-cleavable or photocleavable. A redox reaction may be part of the cleavage scheme. The cleavable linker may be a charged polymer.

The linker may be a photocleavable linker, a chemically cleavable linker, or a thermally cleavable linker. In embodiments, the linker may be thermal-sensitive cleavable linker. Where the linker is a photocleavable group, the cleavage agent may be light of appropriate wavelength that disrupts or cleaves the photocleavable group. In many embodiments, the wavelength of light used to cleave the photocleavable linking group ranges from about 180 nm to 400 nm, e.g., from about 250 nm to 400 nm, or from about 300 nm to 400 nm. It is preferable that the light required to activate cleavage does not affect the other components of the analyte. Suitable linkers include those based on O-nitrobenzyl compounds and nitroveratryl compounds. Linkers based on benzoin chemistry can also be used (Lee et al., J. Org. Chem. 64:3454-3460, 1999). In some embodiments, the photocleavable linker may be derived from the following moiety:

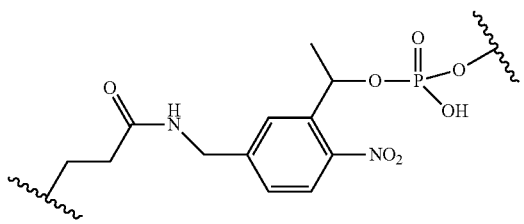

Alternatively, where the cleavage linker is a chemically cleavable group, the cleavage agent may be a chemical agent capable of cleaving the group. A chemically cleavable linker may be cleaved by oxidation/reduction-based cleavage, acid-catalyzed cleavage, base-catalyzed cleavage, or nucleophilic displacement. For example, where the linking group is a disulfide, thiol-mediated cleavage with dithiothreitol or betamercaptoethanol may be used to release the tag. In yet other embodiments where the linking group is a restriction site, the agent is a catalytic agent, such as an enzyme which may be a hydrolytic enzyme, a restriction enzyme, or another enzyme that cleaves the linking group. For example, the restriction enzyme may be a type I, type II, type IIS, type III and type IV restriction enzyme.

In some embodiments, the cleavage linker is an enzymatic cleavable sequence. In one aspect of any of the embodiments herein, an enzymatic cleavable sequence is a nucleic acid sequence of 2, 3, 4, 5, 6, 7, 8, 9 or 10 nucleotides in length. In one embodiment, the enzymatic cleavable sequence comprises a sequence of at least 10 nucleotides. In one embodiment, the enzymatic cleavable sequence comprises a sequence of between 2 and 20 nucleotides. In one embodiment, the enzymatic cleavable sequence comprises a sequence of between 2 and 15 nucleotides. In one embodiment, the enzymatic cleavable sequence comprises a sequence of between 4 and 10 nucleotides. In one embodiment, the enzymatic cleavable sequence comprises a sequence of between 4 and 15 nucleotides.

For example, the cleavable linker may be an acridinium, ethers such as substituted benzyl ether or derivatives thereof (e.g., benzylhydryl ether, indanyl ether, etc.) that can be cleaved by acidic or mild reductive conditions (e.g., hydrogen peroxide to produce an acridone and a sulfonamide), a charged polymer generated using P-elimination, where a mild base can serve to release the product, acetals, including the thio analogs thereof, where detachment is accomplished by mild acid, particularly in the presence of a capturing carbonyl compound, photolabile linkages (e.g., O-nitrobenzoyl, 7-nitroindanyl, 2-nitrobenzhydryl ethers or esters, etc.), or peptide linkers, which are subject to enzymatic hydrolysis (e.g., enzymatic cleavable linkers), particularly where the enzyme recognizes a specific sequence, such as a peptide for Factor Xa or enterokinase. Examples of linkers include, but are not limited to, disulfide linkers, acid labile linkers (including dialkoxybenzyl linkers), Sieber linkers, indole linkers, t-butyl Sieber linkers, electrophilically cleavable linkers, nucleophilically cleavable linkers, photocleavable linkers, cleavage under reductive conditions, oxidative conditions, cleavage via use of safety-catch linkers, and cleavage by elimination mechanisms.

Electrophilically cleaved linkers are typically cleaved by protons and include cleavages sensitive to acids. Suitable linkers include the modified benzylic systems such as trityl, p-alkoxybenzyl esters and p-alkoxybenzyl amides. Other suitable linkers include tert-butyloxycarbonyl (Boc) groups and the acetal system. The use of thiophilic metals, such as nickel, silver or mercury, in the cleavage of thioacetal or other sulphur-containing protecting groups can also be considered for the preparation of suitable linker molecules.

For nucleophilic cleavage, groups such as esters that are labile in water (i.e., can be cleaved simply at basic pH) and groups that are labile to non-aqueous nucleophiles, can be used. Fluoride ions can be used to cleave silicon-oxygen bonds in groups such as triisopropyl silane (TIPS) or t-butyldimethyl silane (TBDMS).

A linker susceptible to reductive cleavage may be used such as with disulphide bond reduction. Catalytic hydrogenation using palladium-based catalysts has been used to cleave benzyl and benzyloxycarbonyl groups.

Oxidation-based approaches are well known in the art. These include oxidation of p-alkoxybenzyl groups and the oxidation of sulphur and selenium linkers. Aqueous iodine to cleave disulphides and other sulphur or selenium-based linkers may also be used.

Safety-catch linkers are those that cleave in two steps. In a preferred system the first step is the generation of a reactive nucleophilic center followed by a second step involving an intra-molecular cyclization that results in cleavage. For example, levulinic ester linkages can be treated with hydrazine or photochemistry to release an active amine, which can then be cyclised to cleave an ester elsewhere in the molecule (Burgess et al., J. Org. Chem. 62:5165-5168, 1997).

Elimination reactions may also be used. For example, the base-catalysed elimination of groups such as Fmoc and cyanoethyl, and palladium-catalysed reductive elimination of allylic systems, may be used.

Where the linker is a thermal cleavable linker or thermal-sensitive linker, the cleavage agent may be localized temperature elevation above a threshold to disrupt or cleave the thermal cleavable group. In some embodiments, the temperature may be elevated in a localized region using microwave irradiation to induce particle hyperthermia. Particle hyperthermia methods may be used, such as those reviewed in Dutz and Hergt (Nanotechnology, 25:452001 (2014)) and described in U.S. Pat. No. 7,718,445, U.S. Patent Publication No. 20030082633, International Patent Publication No. WO 2002029076, and U.S. Patent Publication No. 20020197645, which are each incorporated herein by reference. In some embodiments, the temperature elevation may be achieved photothermally by transferring energy from light to an absorbing target, such as a dye, pigment, or water. In one aspect, the source of light is a laser. In some embodiments, the elevated temperature may cause the thermal separation of double-stranded DNA.

g) Nanopore layer

In the present disclosure, detecting and/or counting the tag (e.g., polymer, aptamer, nanoparticle) may be carried out by translocating the tag through or across a nanopore or nanochannel. In some embodiments, detecting and/or counting the tag (e.g., polymer, aptamer, nanoparticle) may be carried out by translocating the tag through or across at least one or more nanopores or nanochannels. In some embodiments, at least to or more nanopores or nanochannels are presented side by side or in series. In some embodiments, the nanopore or nanochannel is dimensioned for translocation of not more than one tag at a time. Thus, the dimensions of the nanopore in some embodiments will typically depend on the dimensions of the tag to be examined. A tag with a double-stranded region can require a nanopore dimension greater than those sufficient for translocation of a tag which is entirely single-stranded. In addition, a nanoparticle tag such as a nanobead tag can require larger pores or channels than oligomer tags. Typically, a pore of about 1 nm diameter can permit passage of a single stranded polymer, while pore dimensions of 2 nm diameter or larger will permit passage of a double-stranded nucleic acid molecule. In some embodiments, the nanopore or nanochannel is selective for a single stranded tag (e.g., from about 1 nm to less than 2 nm diameter) while in other embodiments, the nanopore or nanochannel is of a sufficient diameter to permit passage of double stranded polynucleotides (e.g., 2 nm or larger). The chosen pore size provides an optimal signal-to noise ratio for the analyte of interest.

In some embodiments, the pore may be between about 0.1 nm and about 1000 nm in diameter, between about 50 nm and about 1000 nm, between about 100 nm and 1000 nm, between about 0.1 nm and about 700 nm, between about 50 nm and about 700 nm, between about 100 nm and 700 nm, between about 0.1 nm and about 500 nm, between about 50 nm and about 500 nm, or between about 100 nm and 500 nm. For example, the pore may be about 0.1 nm, about 0.2 nm, about 0.3 nm, about 0.4 nm, about 0.5 nm, about 0.6 nm, about 0.7 nm, about 0.8 nm, about 0.9 nm, about 1.0 nm, about 1.5 nm, about 2.0 nm, about 2.5 nm, about 3.0 nm, about 3.5 nm, about 4.0 nm, about 4.5 nm, about 5.0 nm, about 7.5 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 150 nm, about 200 nm, about 250 nm, about 300 nm, about 3500 nm, about 400 nm, about 450 nm, about 500 nm, about 550 nm, about 600 nm, about 650 nm, about 700 nm, about 750 nm, about 800 nm, about 850 nm, about 900 nm, about 950 nm, or about 1000 nm in diameter.

In general, nanopores are shorter in length than nanochannels. A nanochannel is substantially longer than a nanopore and may be useful in applications where increasing the time it takes for a molecule to translocate through it (as compared to the time for translocating through or across a nanopore of the same diameter) is desirable. Length of a nanopore may range from about 0.1 nm to less than about 200 nm. Length of a nanochannel may range from about 500 nm to about 100 μm, or longer. The diameter of a nanopore and a nanochannel may be similar.

Various types of nanopores may be used for analyzing the tags/aptamer. These include, among others, biological nanopores that employ a biological pore or channel embedded in a membrane. Another type of nanopore layer is a solid state nanopore in which the channel or pore is made whole or in part from a fabricated or sculpted solid state component, such as silicon. In some embodiments, the nanopore is a solid state nanopore produced using controlled dielectric breakdown. In some embodiments, the nanopore is a solid state nanopore produced by a method other than controlled dielectric breakdown.

In certain embodiments, the length of a nanopore may be up to about 200 nm, e.g., from about 0.1 nm to about 30 nm, from about 10 to about 80 nm, from about 1 to about 50 nm, from about 0.1 nm to about 0.5 nm, from about 0.3 nm to about 1 nm, from about 1 nm to about 2 nm, from about 0.3 nm to about 10 nm, or from about 10 to about 30 nm. The number of nanopores in a nanopore layer may be about 1, 2, 3, 4, 5, 10, 30, 100, 300, 1000, 3000, 10000, 30000, 100000, 300000 or more. The distance between nanopores in a layer between center to center may be about 100 nm to about 300 nm, about 300 nm to about 500 nm, about 500 nm to about 1000 nm, for example, 100 nm, 150 nm, 200 nm, or 300 nm.

In certain embodiments, multiple nanopore layers, each containing on or more nanopores, can be arranged in series with with each other, for detecting and/or counting the tag (e.g., polymer, aptamer, nanoparticle). In this case, detecting and/or counting the tag may be carried out by translocating the tag through or across each nanopore layer. As such, counting the number of tags translocating through or across a nanopore in a layer/sheet/membrane refers to counting multiple tags translocating through or across one or more nanopores in one or more layer/sheet/membrane. In certain embodiments, when more than one nanopore layers are present (e.g., one, two, three, four, five, six, or other number of nanopore layers as technically feasible), optionally they are present in series wherein at least one nanopore in one layer is separate from or stacked onto (e.g., above or on top of) another nanopore in another layer, etc.). Where the nanopore layers are in series, at least two electrodes can be used to create an alectric field to drive tags through the pores and, optionally, additional electrodes positioned between the nanopore layers can further provide driving current.

i) Biological Pores

For detecting and, optionally, counting the tags/aptamer, any biological pore with channel dimensions that permit translocation of the tags can be used. Two broad categories of biological channels are suitable for the methods disclosed herein. Non-voltage gated channels allow passage of molecules through the pore without requiring a change in the membrane potential to activate or open the channel. On the other hand, voltage gated channels require a particular range of membrane potential to activate channel opening. Most studies with biological nanopores have used α-hemolysin, a mushroom-shaped homo-oligomeric heptameric channel of about 10 nm in length found in *Staphylococcus aureus*. Each subunit contributes two beta strands to form a 14 strand anti-parallel beta barrel. The pore formed by the beta barrel structure has an entrance with a diameter of approximately 2.6 nm that contains a ring of lysine residues and opens into an internal cavity with a diameter of about 3.6 nm. The stem of the hemolysin pore, which penetrates the lipid bilayer, has an average inside diameter of about 2.0 nm with a 1.5 nm constriction between the vestibule and the stem. The dimensions of the stem are sufficient for passage of single-stranded nucleic acids but not double-stranded nucleic acids. Thus, α-hemolysin pores may be used as a nanopore selective for single-stranded polynucleotides and other polymers of similar dimensions.

In other embodiments, the biological nanopore is of a sufficient dimension for passage of polymers larger than a single-stranded nucleic acid. An exemplary pore is mitochondrial porin protein, a voltage dependent anion channel (VDAC) localized in the mitochondrial outer membrane. Porin protein is available in purified form and, when reconstituted into artificial lipid bilayers, generates functional channels capable of permitting passage of double-stranded nucleic acids (Szabo et al., 1998, FASEB J. 12:495-502). Structural studies suggest that porin also has a beta-barrel type structure with 13 or 16 strands (Rauch et al., 1994, Biochem Biophys Res Comm 200:908-915). Porin displays a larger conductance compared conductance of pores formed by α-hemolysin, maltoporin (LamB), and gramicidin. The larger conductance properties of porin support studies showing that the porin channel is sufficiently dimensioned for passage of double-stranded nucleic acids. Pore diameter of the porin molecule is estimated at 4 nm. The diameter of an uncoiled double-stranded nucleic acid is estimated to be about 2 nm.

Another biological channel that may be suitable for scanning double stranded polynucleotides are channels found in *B. subtilis* (Szabo et al., 1997, J. Biol. Chem. 272:25275-25282). Plasma membrane vesicles made from *B. subtilis* and incorporated into artificial membranes allow passage of double-stranded DNA across the membrane. Conductance of the channels formed by *B. subtilis* membrane preparations is similar to those of mitochondrial porin. Although there is incomplete characterization (e.g., purified form) of these channels, it is not necessary to have purified forms for the purposes herein. Diluting plasma membrane preparations, either by solubilizing in appropriate detergents or incorporating into artificial lipid membranes of sufficient surface area, can isolate single channels in a detection apparatus. Limiting the duration of contact of the membrane preparations (or protein preparations) with the artificial membranes by appropriately timed washing provides another method for incorporating single channels into the artificial lipid bilayers. Conductance properties may be used to characterize the channels incorporated into the bilayer.

In certain cases, the nanopores may be hybrid nanopores, where a biological pore is introduced in a solid state nanopore, e.g., a nanopore fabricated in a non-biological material. For example, o-haemolysin pore may be inserted into a solid state nanopore. In certain cases, the nanopores may be a hybrid nanopore described in Hall et al., Nature Nanotechnology, 28 Nov. 2010, vol. 5, pg. 874-877.

ii) Solid State Pores

In other embodiments, analysis of the tags is carried out by translocating the tag through or across a nanopore or nanochannel fabricated from non-biological materials. Nanopores or nanochannels can be made from a variety of solid state materials using a number of different techniques, including, among others, chemical deposition, electrochemical deposition, electroplating, electron beam sculpting, ion beam sculpting, nanolithography, chemical etching, laser ablation, focused ion beam, atomic layer deposition, and other methods well known in the art (see, e.g., Li et al., 2001, Nature 412:166-169; and WO 2004/085609).

In particular embodiments, the nanopores may be the nanopores described in WO13167952A1 or WO13167955A1. As described in WO13167952A1 or WO13167955A1, nanopores having an accurate and uniform pore size may be formed by precisely enlarging a nanopore formed in a membrane. The method may involve enlarging a nanopore by applying a high electric potential across the nanopore; measuring current flowing through the nanopore; determining size of the nanopore based in part on the measured current; and removing the electric potential applied to the nanopore when the size of the nanopore corresponds to a desired size. In certain cases, the applied electric potential may have a pulsed waveform oscillating between a high value and a low value, the current flowing through the nanopore may be measured while the electric potential is being applied to the nanopore at a low value.

Solid state materials include, by way of example and not limitation, any known semiconductor materials, insulating materials, and metals coated with insulating material. Thus, at least part of the nanopore(s) may comprise without limitation silicon, silica, silicene, silicon oxide, graphene, silicon nitride, germanium, gallium arsenide, or metals, metal oxides, and metal colloids coated with insulating material.

To make a pore of nanometer dimensions, various feedback procedures can be employed in the fabrication process. In embodiments where ions pass through a hole, detecting ion flow through the solid state material provides a way of measuring pore size generated during fabrication (see, e.g., U.S. Published Application No. 2005/0126905). In other embodiments, where the electrodes define the size of the pore, electron tunneling current between the electrodes gives information on the gap between the electrodes. Increases in tunneling current indicate a decrease in the gap space between the electrodes. Other feedback techniques will be apparent to the skilled artisan.

In some embodiments, the nanopore is fabricated using ion beam sculpting, as described in Li et al., 2003, Nature Materials 2:611-615. In some embodiments, the nanopore is fabricated using high current, as described in WO13167952A1 or WO13167955A1. In other embodiments, the nanopores may be made by a combination of electron beam lithography and high energy electron beam sculpting (see, e.g., Storm et al., 2003, Nature Materials 2:537-540). A similar approach for generating a suitable nanopore by ion beam sputtering technique is described in Heng et al., 2004, Biophy J 87:2905-2911. The nanopores are formed using lithography with a focused high energy electron beam on metal oxide semiconductor (CMOS) combined with general techniques for producing ultrathin films. In other embodiments, the nanopore is constructed as provided in U.S. Pat. Nos. 6,627,067; 6,464,842; 6,783,643; and U.S. Publication No. 2005/0006224 by sculpting of silicon nitride.

In some embodiments, the nanochannels can be constructed as a gold or silver nanotube. These nanochannels are formed using a template of porous material, such as polycarbonate filters prepared using a track etch method, and depositing gold or other suitable metal on the surface of the porous material. Track etched polycarbonate membranes are typically formed by exposing a solid membrane material to high energy nuclear particles, which creates tracks in the membrane material. Chemical etching is then employed to convert the etched tracks to pores. The formed pores have a diameter of about 10 nm and larger. Adjusting the intensity of the nuclear particles controls the density of pores formed in the membrane. Nanotubes are formed on the etched membrane by depositing a metal, typically gold or silver, into the track etched pores via an electroless plating method (Menon et al., 1995, Anal Chem 67:1920-1928). This metal deposition method uses a catalyst deposited on the surface of the pore material, which is then immersed into a solution containing Au(I) and a reducing agent. The reduction of Au(I) to metallic Au occurs on surfaces containing the catalyst. Amount of gold deposited is dependent on the incubation time such that increasing the incubation time decreases the inside diameter of the pores in the filter material. Thus, the pore size may be controlled by adjusting the amount of metal deposited on the pore. The resulting pore dimension is measured using various techniques, for instance, gas transport properties using simple diffusion or by measuring ion flow through the pores using patch clamp type systems. The support material is either left intact, or removed to leave gold nanotubes. Electroless plating technique is capable of forming pore sizes from less than about 1 nm to about 5 nm in diameter, or larger as required. Gold nanotubes having pore diameter of about 0.6 nm appears to distinguish between Ru(bpy)2+2 and methyl viologen, demonstrating selectivity of the gold nanopores (Jirage et al., 1997, Science 278:655-658). Modification of a gold nanotube surface is readily accomplished by attaching thiol containing compounds to the gold surface or by derivatizing the gold surface with other functional groups. This features permits attachment of pore modifying compounds as well as sensing labels, as discussed herein. Devices, such as the cis/trans apparatuses used for biological pores described herein, can be used with the gold nanopores to analyze single coded molecules.

Where the mode of detecting the tag involves current flow through the tag (e.g., electron tunneling current), the solid state membrane may be metalized by various techniques. The conductive layer may be deposited on both sides of the membrane to generate electrodes suitable for interrogating the tag along the length of the chain, for example, longitudinal electron tunneling current. In other embodiments, the conductive layer may be deposited on one surface of the membrane to form electrodes suitable for interrogating tag across the pore, for example, transverse tunneling current. Various methods for depositing conductive materials are known, including, sputter deposition (i.e., physical vapor deposition), non-electrolytic deposition (e.g., colloidal suspensions), and electrolytic deposition. Other metal deposition techniques are filament evaporation, metal layer evaporation, electron-beam evaporation, flash evaporation, and induction evaporation, and will be apparent to the skilled artisan.

In some embodiments, the detection electrodes are formed by sputter deposition, where an ion beam bombards a block of metal and vaporizes metal atoms, which are then deposited on a wafer material in the form of a thin film. Depending on the lithography method used, the metal films are then etched by means of reactive ion etching or polished using chemical-mechanical polishing. Metal films may be deposited on preformed nanopores or deposited prior to fabrication of the pore.

In some embodiments, the detection electrodes are fabricated by electrodeposition (see, e.g., Xiang et al., 2005, Angew. Chem. Int. Ed. 44:1265-1268; Li et al., Applied Physics Lett. 77(24):3995-3997; and U.S. Publication Application No. 2003/0141189). This fabrication process is suitable for generating a nanopore and corresponding detection electrodes positioned on one face of the solid state film, such as for detecting transverse electron tunneling. Initially, a conventional lithographic process is used to form a pair of facing electrodes on a silicon dioxide layer, which is supported on a silicon wafer. An electrolyte solution covers the electrodes, and metal ions are deposited on one of the electrodes by passing current through the electrode pair. Deposition of metal on the electrodes over time decreases the gap distance between the electrodes, creating not only detection electrodes but a nanometer dimensioned gap for translocation of coded molecules. The gap distance between the electrodes may be controlled by a number of feedback processes.

Where the detection is based on imaging of charge induced field effects, a semiconductor can be fabricated as described in U.S. Pat. No. 6,413,792 and U.S. published application No. 2003/0211502. The methods of fabricating these nanopore devices can use techniques similar to those employed to fabricate other solid state nanopores.

Detection of the tag, such as a polynucleotide, is carried out as further described below. For analysis of the tag, the nanopore may be configured in various formats. In some embodiments, the device comprises a membrane, either biological or solid state, containing the nanopore held between two reservoirs, also referred to as cis and trans chambers (see, e.g., U.S. Pat. No. 6,627,067). A conduit for electron migration between the two chambers allows electrical contact of the two chambers, and a voltage bias between the two chambers drives translocation of the tag through the nanopores. A variation of this configuration is used in analysis of current flow through nanopores, as described in U.S. Pat. Nos. 6,015,714 and 6,428,959; and Kasianowiscz et al., 1996, Proc Natl Acad Sci USA 93:13770-13773, the disclosures of which are incorporated herein by reference.

Variations of above the device are disclosed in U.S. application publication no. 2003/0141189. A pair of nanoelectrodes, fabricated by electrodeposition, is positioned on a substrate surface. The electrodes face each other and have a gap distance sufficient for passage of a single nucleic acid. An insulating material protects the nanoelectrodes, exposing only the tips of the nanoelectrodes for the detection of the nucleic acid. The insulating material and nanoelectrodes separate a chamber serving as a sample reservoir and a chamber to which the polymer is delivered by translocation. Cathode and anode electrodes provide an electrophoresis electric field for driving the tag from the sample chamber to the delivery chamber.

The current bias used to drive the tag through the nanopore can be generated by applying an electric field directed through the nanopore. In some embodiments, the electric field is a constant voltage or constant current bias. In other embodiments, the movement of the tag is controlled through a pulsed operation of the electrophoresis electric field parameters (see, e.g., U.S. Patent Application No. 2003/141189 and U.S. Pat. No. 6,627,067). Pulses of current may provide a method of precisely translocating one or only a few bases of an oligonucleotide tag for a defined time period through the pore and to briefly hold the tag within the pore, and thereby provide greater resolution of the electrical properties of the tag.

The nanopore devices may further comprise an electric or electromagnetic field for restricting the orientation of the oligonucleotide tag as it passes through the nanopore. This holding field can be used to decrease the movement of the oligonucleotide tag within the pore. In some embodiments, an electric field that is orthogonal to the direction of translocation is provided to restrict the movement of the tag molecule within the nanopore. This is illustrated in U.S. Application Publication No. 2003/0141189 through the use of two parallel conductive plates above and beneath the sample plate. These electrodes generate an electric field orthogonal to the direction of translocation of a tag molecule, and thus holding the tag molecule to one of the sample plates. A negatively charged backbone of a DNA, or nucleic acid modified to have negative charges on one strand, will be oriented onto the anodic plate, thereby limiting the motion of the tag molecule.

In still other embodiments, controlling the position of the tag is carried out by the method described in U.S. Application Publication No. 2004/0149580, which employs an electromagnetic field created in the pore via a series of electrodes positions near or on the nanopore. In these embodiments, one set of electrodes applies a direct current voltage and radio frequency potential while a second set of electrodes applies an opposite direct current voltage and a radio frequency potential that is phase shifted by 180 degrees with respect to the radio frequency potential generated by the first set of electrodes. This radio frequency quadrupole holds a charged particle (e.g., nucleic acid) in the center of the field (i.e., center of the pore).

In exemplary embodiments, the nanopore membrane may be a multilayer stack of conducting layers and dielectric layers, where an embedded conducting layer or conducting layer gates provides well-controlled and measurable electric field in and around the nanopore through which the tag translocates. In an aspect, the conducting layer may be graphene. Examples of stacked nanopore membranes are found in US20080187915 and US20140174927, for example.

It is understood that the nanopore may be located in a membrane, layer or other substrate, which terms have been used interchangeably to describe a two-dimensional substrate comprising a nanopore.

In certain embodiments, the nanopore may be formed as part of the assay process for detecting and/or determining concentration of an analyte using the nanopore. Specifically, a device for detecting and/or determining concentration of an analyte using a nanopore may initially be provided without a nanopore formed in a membrane or layer. The device may include a membrane separating two chambers on the opposite sides of the membrane (a cis and a trans chamber). The cis and the trans chambers may include a salt solution and may be connected to a source of electricity. When a nanopore is to be created in the membrane, a voltage is applied to the salt solution in the cis and trans chamber and conductance through the membrane measured. Prior to the creation of a nanopore, there is no or minimal current measured across the membrane. Following creation of a nanopore, the current measured across the membrane increases. The voltage may be applied for an amount of time sufficient to create a nanopore of the desired diameter. Following the creation of a nanopore, an analyte or tag may be translocated through the nanopore and the translocation event detected. In certain embodiments, the same salt solution may be used for nanopore creation as well as for detection of translocation of an analyte or tag through the nanopore. Any suitable salt solution may be utilized for nanopore creation and/or translocation of an analyte or tag through the nanopore. Any salt solution that does not damage the counting label can be used. Exemplary salt solutions include lithium chloride, potassium chloride, sodium chloride, calcium chloride, magnesium chloride and the like. The concentration of the salt solution may be selected based on the desired conductivity of the salt solution. In certain embodiments, the salt solution may have a concentration ranging from 1 mM to 10 M, e.g., 10 mM-10 M, 30 mM-10 M, 100 mM-10 M, 1 M-10 M, 10 mM-5 M, 10 mM-3 M, 10 mM-1 M, 30 mM-5 M, 30 mM-3 M, 30 mM-1 M, 100 mM-5 M, 100 mM-3 M, 100 mM-1 M, 500 mM-5 M, 500 mM-3 M, or 500 mM-1 M, such as, 10 mM, 30 mM, 100 mM, 500 mM, 1 M, 3 M, 5 M, or 10M.

In some embodiments, the nanopore may become blocked, and the blocked nanopore is cleared by modulating the pattern of voltage applied by the electrodes across the nanopore layer or membrane. In some cases, a blocked nanopore is cleared by reversing polarity of the voltage across the nanopore layer or membrane. In some cases, a blocked nanopore is cleared by increasing the magnitude of the voltage applied across the nanopore layer or membrane. The increase in voltage may be transitory increase, lasting 10 seconds (s) or less, e.g., 8 s or less, 6 s or less, 5 s or less, 4 s or less, 3 s or less, 2 s or less, 1 s or less, 0.5 s or less, 0.4 s or less, 0.3 s or less, 0.2 s or less, including 0.1 s or less.

h) Signal Detection

Interrogating the tag/aptamer by translocation through or across a nanopore and detecting the detectable property generates a signal that can be used to count (i.e., determine the quantity or concentration) and/or identify (i.e., determine the presence of) the tag/aptamer. The type of detection method employed may correspond to the property being detected for the tags.

In some embodiments, the detectable property is the effect of the tag on the electrical properties of the nanopore as the tag translocates through the pore. Electrical properties of the nanopore include among others, current amplitude, impedance, duration, and frequency. In certain cases, the tag may be identified by using nanopore force spectroscopy (see e.g., Tropini C. and Marziali A., Biophysical Journal, 2007, Vol. 92, 1632-1637). Devices for detecting the pore's electrical properties may include a nanopore incorporated into a layer such as, a thin film or a membrane, where the film or membrane separates a cis chamber and a trans chamber connected by a conducting bridge. The tag to be analyzed may be present on the cis side of the nanopore in an aqueous solution typically comprising one or more dissolved salts, such as potassium chloride. Application of an electric field across the pore using electrodes positioned in the cis and trans side of the nanopore causes translocation of the tag through the nanopore, which affects the migration of ions through the pore, thereby altering the pore's electrical properties. Current may be measured at a suitable time frequency to obtain sufficient data points to detect a current signal pattern. The generated signal pattern can then be compared to a set of reference patterns in which each reference pattern is obtained from examination of a single population of known tags bound to analyte in a sample with a known analyte concentration. As previously noted, the number of tags of the same type translocating though a nanopore(s) may be counted per unit time, such as, the number of tags of the same type translocating through or across nanopore(s) per 15 min, 13 min, 10 min, 8 min, 6 min, 4 min, 2 min, 1 min, 30 sec, per 20 sec, per 15 sec, per 10 sec, per 5 sec, per 1 sec, per 100 millisec, per 10 millisec, or per 1 millisec. In some cases, the number of tags of the same type translocating though a nanopore(s) may be counted for a certain period of time to determine the amount of time to reach a threshold count. Shifts in current amplitude, current duration, current frequency, and current magnitude may define a signal pattern for the tag and may be used to distinguish different tags from each other. Measurement of current properties of a nanopore, such as by patch clamp techniques, is described in publications discussed above and in various reference works, for example, Hille, B, 2001, Ion Channels of Excitable Membranes, 3rd Ed., Sinauer Associates, Inc., Sunderland, Mass. The number of counts measured over a time period (counts/time) is proportional to the concentration of the molecule (e.g., tag) translocating through or across the nanopore. The concentration of the tag may be determined by generating a standard curve. For example, a series of different concentrations of a standard molecule may be translocated through a nanopore and the counts/time measured to calculate a count rate for each concentration. The count rate of the tag being measured would be compared to the standard curve to calculate the concentration of the tag.

In some embodiments, the detectable property of the tag may be quantum tunneling of electrons. Quantum tunneling is the quantum-mechanical effect of transitioning through a classically-forbidden energy state via a particle's quantum wave properties. Electron tunneling occurs where a potential barrier exists for movement of electrons between a donor and an acceptor. To detect electron tunneling, a microfabricated electrode tip may be positioned about 2 nanometers from the specimen. At an appropriate separation distance, electrons tunnel through the region between the tip and the sample, and if a voltage is applied between the tip and the sample, a net current of electrons (i.e., tunneling current) flows through the gap in the direction of the voltage bias. Where the nanodevice uses detection electrodes for measuring tunneling current, the electrodes are positioned proximately to the translocating tag such that there is electron tunneling between the detection electrodes and tag. As further discussed below, the arrangement of the electrodes relative to the translocating tag may dictate the type of electron transport occurring through the tag.

In some embodiments, analysis of the tag may involve detecting current flow occurring through the nucleic acid chain (i.e., longitudinally along the nucleic acid chain) (Murphy et al., 1994, Proc Natl Acad Sci USA 91(12):5315-9). The exact mechanism of electron transfer is unknown, although electron tunneling is given as one explanation for DNA's transport properties. However, the physics underlying electron transport through a double-stranded nucleic acid is not limiting for the purposes herein, and detection of current flowing through the nucleic acid serves to distinguish one polymer tag from another polymer tag. For detection of electron flow occurring longitudinally through the tag molecule chain, the detection electrodes may be positioned longitudinally to the direction of tag molecule translocation such that there is a gap between the electrodes parallel to the chain of an extended tag molecule. In various embodiments, the detection electrodes may be placed on opposite sides of a layer(s) (e.g., membrane) separating the two sides of the nanopore, while in other embodiments, the detection electrodes may be positioned within the layer(s) that separate the two sides of the nanopore.

Another mode of electron flow in a nucleic acid is that occurring across the nucleic acid, for example, a direction transverse to an extended nucleic acid chain (e.g., across the diameter of a double-stranded nucleic acid). In a double-stranded nucleic acid, electron transport may occur through the paired bases while in a single-stranded nucleic acid, electron transport may occur through a single unpaired base. Furthermore, differences in the chemical compositions, hydration structures, interactions with charged ions, spatial orientation of each base, and different base pairing combinations may alter the transverse electron transport characteristics, and thus provide a basis for distinguishing tag molecules that differ in sequence and/or polymer backbone. For detection of electron flow across a tag molecule (i.e., transverse to an extended nucleic acid chain), the detection electrodes are positioned on one side of the nanopore to interrogate the tag molecule across rather than through the nanopore.

In embodiments of longitudinal or transverse detection, the thickness of the electrodes may determine the total number of bases interrogated by the electrodes. For transverse detection, the tips of the detection electrodes may be dimensioned to interrogate a single nucleobase (as defined herein), and thereby obtain single base resolution. In other embodiments, the dimensions of the detection electrode are arranged to interrogate more than one nucleobase. Thus, in some embodiments, the number of nucleobases interrogated at any one time may be about 2 or more, about 5 or more, about 10 or more, or about 20 or more depending on the resolution required to detect differences in the various polymer sequences of the tag molecule.

In other embodiments, differences in the structure of a tag may be detected as differences in capacitance. This type of measurement is illustrated in US2003/0141189. Capacitance causes a phase shift in an applied ac voltage at a defined applied frequency and impedance. Phase shift characteristics for each nucleobase is determined for nucleic acids of known sequence and structure, and used as reference standards for identifying individual base characteristics. Nearest neighbor analysis may permit capacitance measurements extending to more than a single nucleobase.

In other embodiments, the detection technique may be based on imaging charge-induced fields, as described in U.S. Pat. No. 6,413,792 and U.S. published application No. 2003/0211502, the disclosures of which are incorporated herein by reference. For detecting a tag based on charge induced fields, a semiconductor device described above is used. Application of a voltage between a source region and a drain region results in flow of current from the source to the drain if a channel for current flow forms in the semiconductor. Because each nucleobase has an associated charge, passage of a tag molecule through the semiconductor pore induces a change in the conductivity of the semiconductor material lining the pore, thereby inducing a current of a specified magnitude and waveform. Currents of differing magnitude and waveform are produced by different bases because of differences in charge, charge distribution, and size of the bases. In the embodiments disclosed in U.S. Pat. No. 6,413,792, the polymer passes through a pore formed of a p-type silicon layer. Translocation of the tag molecule is achieved by methods similar to those used to move a polymer through other types of channels, as described above. The magnitude of the current is expected to be on the order of microampere range, which is much higher than the expected picoampere currents detected by electron tunneling. Because the polymer block regions in the tag molecule comprise more than a single nucleobase, these block polymer regions should produce distinctive signals reflective of the charge and charge distribution of the block polymer regions.

It is to be understood that although descriptions above relate to individual detection techniques, in some embodiments, a plurality of different techniques may be used to examine a single tag molecule (see, e.g., Kassies et al., 2005, J Microsc 217:109-16). Examples of multiple detection modes include, among others, current blockade in combination with electron tunneling current, and current blockage in combination with imaging charge induced fields. Concurrent detection with different detection modes may be used to identity a tag molecule by correlating the detection time of the resulting signal between different detection modes.

In some embodiments, measuring the number of tags translocating through the layer or detecting tags translocating through the layer includes observing a current blockade effect of the tags on the nanopores. In some embodiments, an analyte is present in the sample when the current blockade effect is above a threshold level.

3. Device for Analyte Analysis

The present disclosure describes a microfluidics device used in conjunction with a nanopore device and an integrated microfluidics nanopore device. The disclosed microfluidics device used in conjunction with a nanopore device and an integrated microfluidics nanopore device may be used in the method of analyte analysis, as described above. However, in certain cases, the devices described herein may be used for other applications. Likewise, in certain cases, the methods described herein may be used with other devices.

Figure 1A:
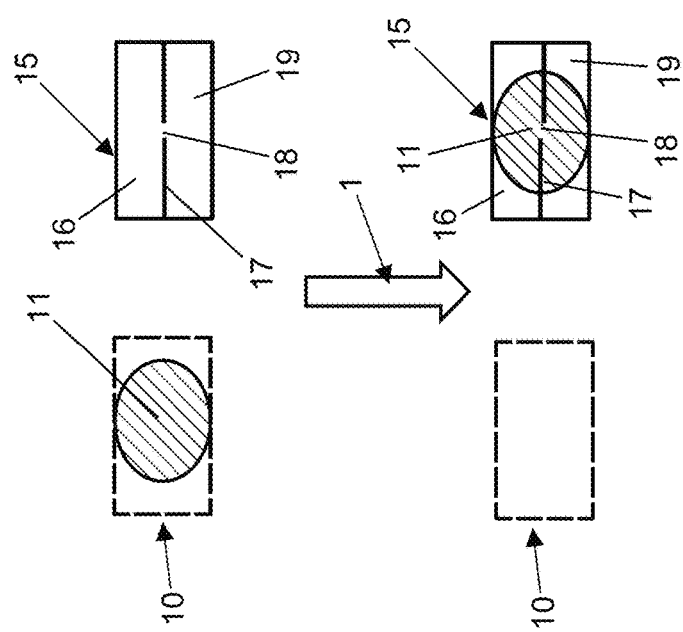

A microfluidics device used in conjunction with a nanopore device is depicted in FIGS. 1A and 1B. The microfluidics device 10 is depicted with a fluid droplet 11 which is to be analyzed in the nanopore device 15. The fluid droplet may include a tag (e.g., a cleaved tag or an aptamer) that is to be counted using the nanopore device. The nanopore device 15 includes a first chamber 16, a layer 17 with a nanopore 18, and a second chamber 19. FIGS. 1A and 1B depict a liquid transfer step 1 in which the fluid droplet 11 is removed from the microfluidics device 10 and placed into the nanopore device 15. As depicted in FIG. 1A, the fluid droplet 11 is deposited over the layer 17 in a manner that results in the droplet being split apart across the layer 17 and positioned at the nanopore 18. The fluid droplet may be introduced into the nanopore device 15 via an entry port (not shown). The entry port may be positioned over a section of the layer 17. For example, the entry port may be located in an opening in a wall of a chamber in which the layer containing nanopore is positioned. In FIG. 1B, the liquid droplet 11 is deposited in the first chamber 16. A buffer addition step 2, introduces a buffer in the second chamber 19. In other embodiments, buffer may be added to the second chamber 19 prior to the introduction of the liquid droplet 11 into the first chamber 16. In yet other embodiments, the liquid droplet 11 may be deposited in the second chamber 19 before or after buffer is added to the first chamber 16. In FIG. 1A, a step of addition of a buffer to either chamber is not needed.

In another embodiment, the device may be an integrated device. The integrated device may include a microfluidics module and a nanopore module that may be built separately and then combined to form the integrated device or the microfluidics module and the nanopore module may be built-in together in a single device.

Figure 2B:
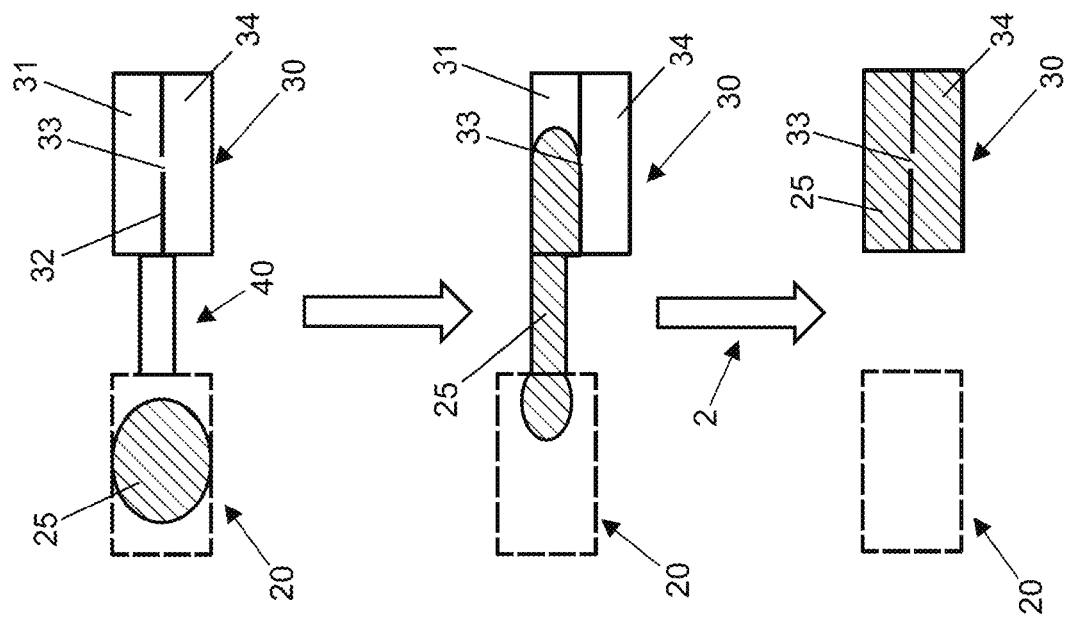
FIG. 2A and FIG. 2B depict a schematic of a reversibly integrated device having a microfluidics module 20 combined with a nanopore module 30 via a channel 40.
Figure 2A:
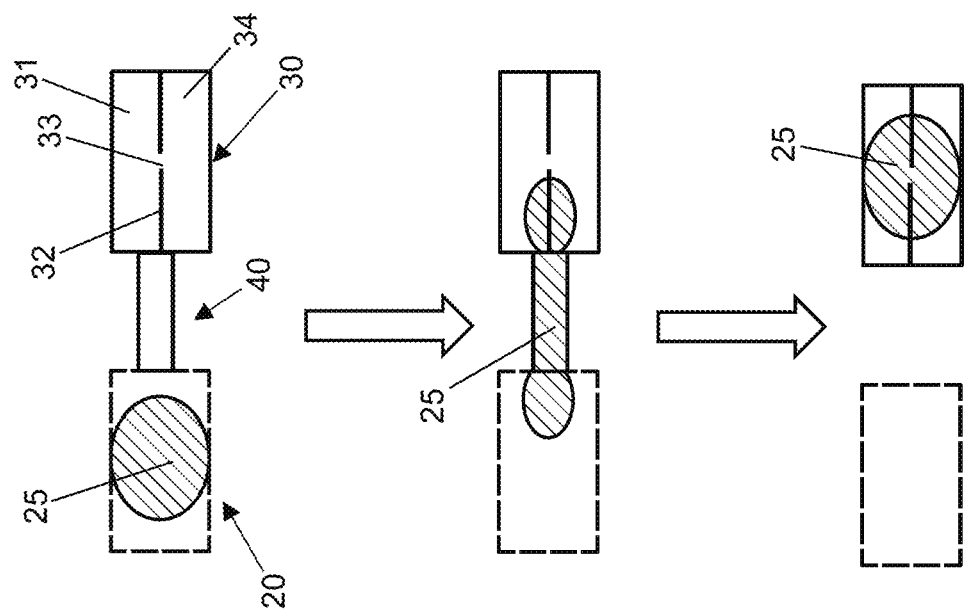

FIGS. 2A and 2B depict a schematic of an integrated device that has a microfluidics module combined with a nanopore module and the two modules are integrated by connecting them using a channel. Although FIGS. 2A and 2B depict a device that includes individual modules that are combined to generate an integrated device, it is understood that the device of FIGS. 2A and 2B can also be manufactured as a unitary device in which the two modules are connected.

In FIGS. 2A and 2B, top panel, a microfluidics module 20 is depicted with a fluid droplet 25 which is to be analyzed in the nanopore device 30. The nanopore module 30 includes a first chamber 31, a layer 32 with a nanopore 33, and a second chamber 34. The microfluidics module 20 is integrated with the nanopore module 30 via a channel 40. The channel fluidically connects the two modules and facilitates the movement of the droplet 25 from the microfluidics module 20 to the nanopore module 30. The middle panel illustrates the movement of the droplet 25 from the microfluidics module 20 to the nanopore module 30 via the channel 40. As shown in FIG. 2A, the channel may connect the microfluidics module 20 to an entry port in the nanopore module 30. The entry port (not shown) may be positioned such that the fluid droplet 25 is deposited over the layer 32 in a manner that results in the droplet being split apart across the layer 32 and positioned at the nanopore 33. At the end of the transfer process, the fluid droplet is positioned across the nanopore 33 (FIG. 2A, bottom panel). In other embodiments, the channel 40 may connect the microfluidics module 20 to an entry port in a first or second chamber of the nanopore module 30. Such an embodiment is shown in FIG. 2B, where the channel 40 connects the microfluidics module 20 to an entry port in a first chamber 31 of the nanopore module 30. Following or prior to the transfer of the liquid droplet 25 into the first chamber 31, a buffer may be added to the second chamber. In step 2 of FIG. 2B, buffer is added to the second chamber 34 following the transfer of the droplet 25 to the first chamber 31. Optionally, after the transfer is completed, the channel 40 may be removed and the two modules separated. The microfluidics and nanopore devices and modules shown in FIGS. 1A, 1B, 2A and 2B, respectively, are each individually functional.

Figure 2C:
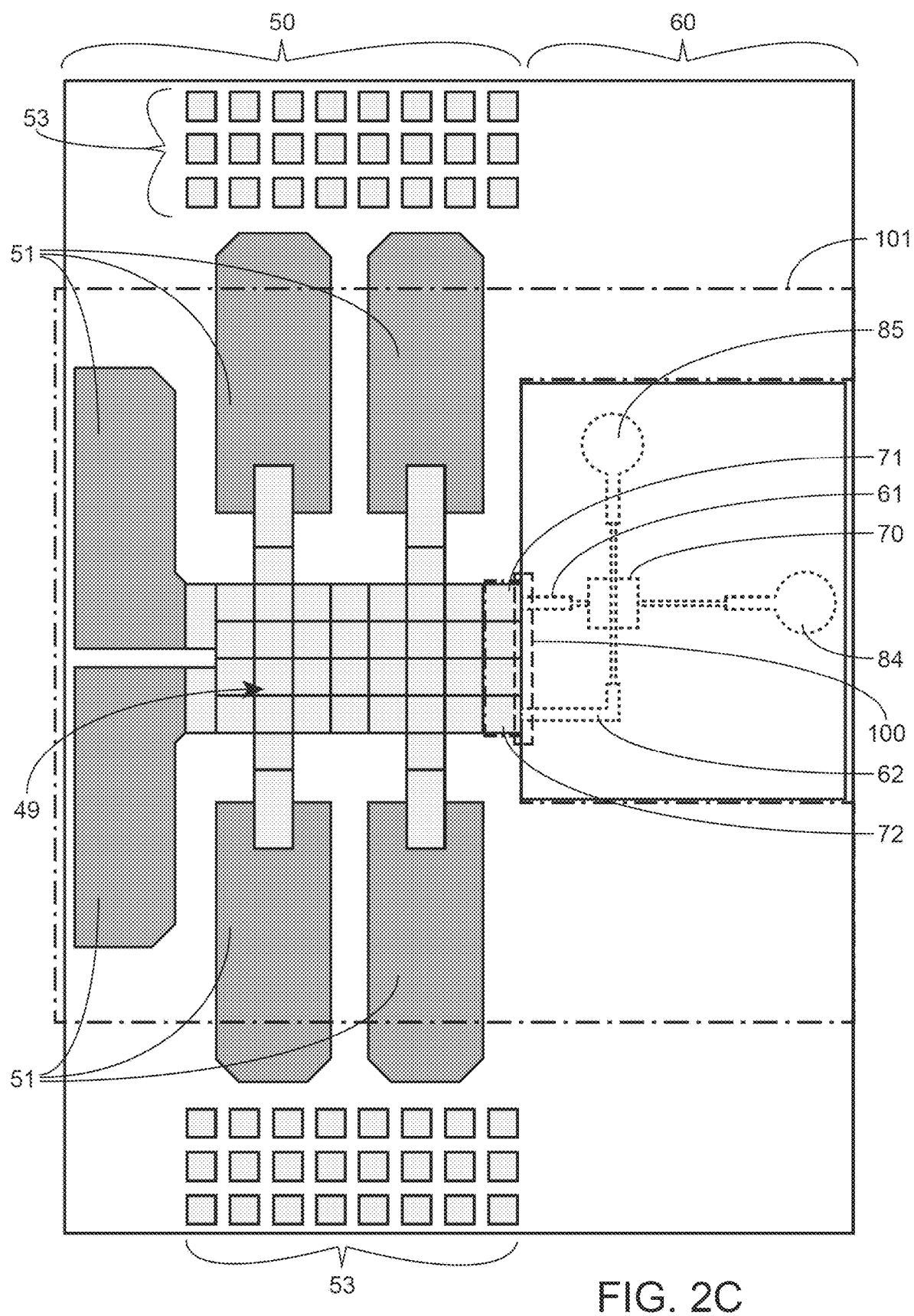

FIGS. 2C-2H depicts an embodiment of an integrated device which includes a digital microfluidics module 50 and a nanopore module 60. The digital microfluidics module is depicted with an array of electrodes 49 that are operatively connected to a plurality of reagent reservoirs 51 used for generation of droplets to be transported to the nanopore module. One or more of the reservoirs 51 may contain a reagent or a sample. Different reagents may be present in different reservoirs. Also depicted in the microfluidics module 50 are contact pads 53 that connect the array of electrodes 49 to a power source (not shown). Trace lines connecting the array of electrodes 49 to the contact pads are not depicted. The array of electrodes 49 transport one or more droplets (such as buffer droplet or a droplet containing buffer and/or tag (e.g., cleaved tag or dissociated aptamer)) to one or both of the transfer electrodes 71 and 72 located at the interface 100 between the digital microfluidics module 50 and a nanopore module 60. The digital microfluidics module 50 and the nanopore module 60 are operatively connected at the interface 100. The nanopore module 60 includes at least two microfluidic capillary channels 61 and 62 that intersect with each other at the location at which a nanopore layer 70 is disposed. The two microfluidic capillary channels 61 and 62 are located in two different substrates in the nanopore module (depicted in FIG. 2D). Thus, the nanopore module includes a first substrate 63 (e.g., bottom substrate) that includes a microfluidic capillary channel 61 in a top surface of the first substrate 63 and further includes a second substrate 64 (e.g., top substrate) with a microfluidic capillary channel 62 in the first surface of the second substrate. The second substrate 64 overlays the microfluidic capillary channel 61 and the first substrate 63 underlays the microfluidic capillary channel 62. The capillary channel 62 overlays capillary channel 61 at the point of intersection of the two channels at the location of the nanopore layer 70 (see also FIG. 2D, bottom panel). The two capillary channels are physically separated at the intersection by the nanopore layer 70 placed at the intersection. The nanopore layer 70 includes at least one nanopore (not shown) that is positioned at the intersection of the capillary channels and allows transport of molecules from one capillary channel to the other through the nanopore. The capillary channels 61 and 62 open at the interface 100 at a first ends of the capillary channels and open to a reservoir/vent (84 and 85, as seen in FIG. 2C) at the second ends of the capillary channels. Also depicted in FIG. 2C is a cover substrate 101 that is positioned over the array of electrodes 49. The cover substrate 101 defines a gap in the microfluidics module in which droplets are manipulated. The cover substrate 101 may optionally include an electrode 55 (e.g., a reference electrode) disposed on a bottom surface of the cover substrate 101 providing a bi-planar electrode configuration for manipulating droplets in the microfluidics module 50. In absence of a bi-planar electrode configuration, droplets may be manipulated in the microfluidics module 50 by using coplanar electrode actuation, for example using the array of electrode 49 or another coplanar electrode configuration. For example, the coplanar electrodes described in U.S. Pat. No. 6,911,132 may be used for manipulating droplets in the microfluidics module 50.

Figure 2D:
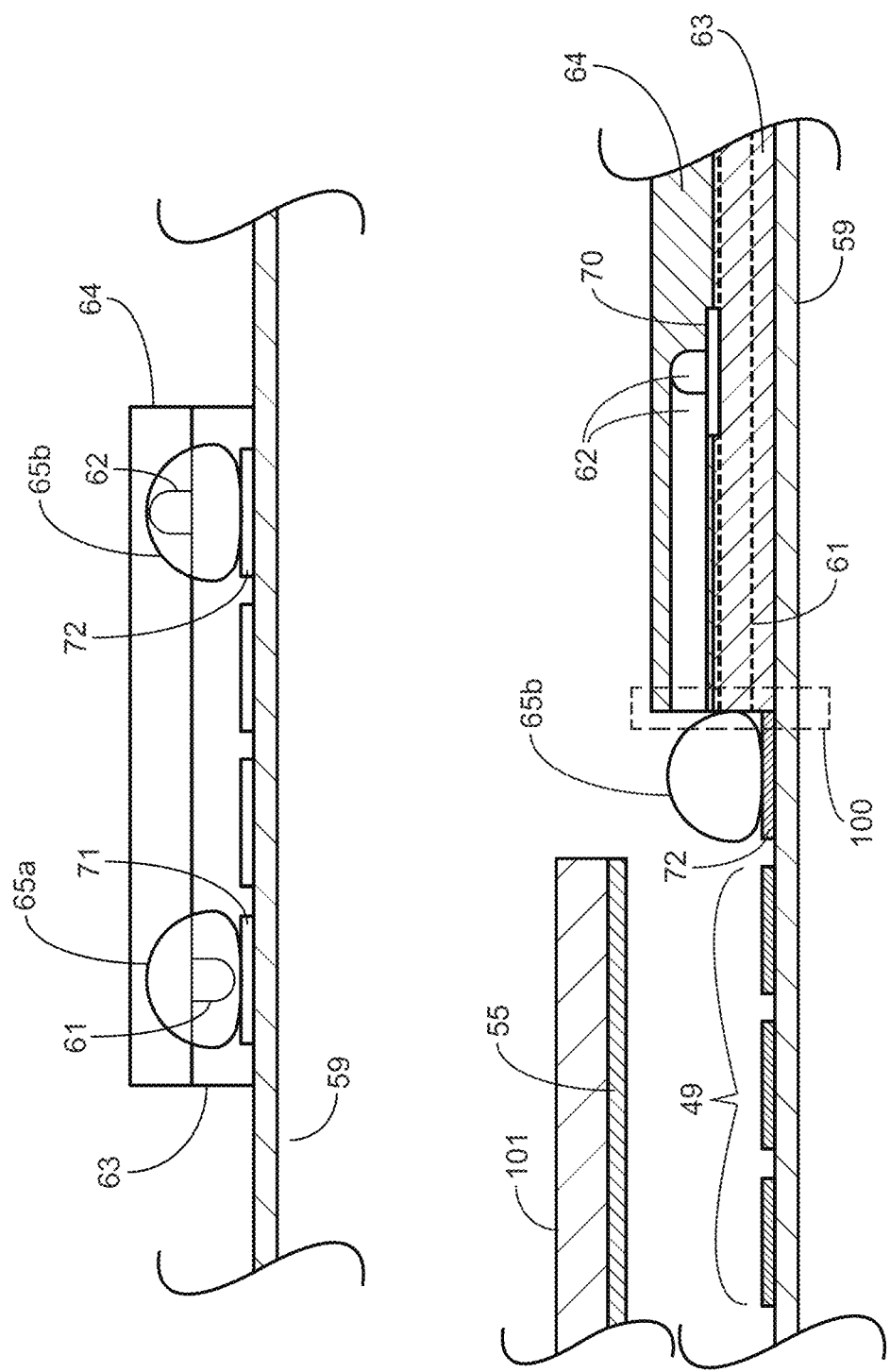

FIG. 2D, top panel, shows a schematic of a front view of a cross-section of the interface 100 at which the digital microfluidics module 50 and a nanopore module 60 are operatively connected. A schematic of a side view of a cross-section of the device at the transfer electrode 72 is depicted in the bottom panel of FIG. 2D. FIG. 2D, top panel shows two droplets (65a and 65b) positioned on two transfer electrodes 71 and 72 that are located at the interface 100 between microfluidics module 50 and a nanopore module 60. As illustrated in FIG. 2D, top panel, the droplet 65a positioned at electrode 71 is aligned with the opening in the capillary channel 61 while the droplet 65b positioned at electrode 72 is aligned with the opening in capillary channel 62. FIG. 2D, bottom panel illustrates a side view of a cross-section of the integrated device showing placement of droplet 65b on transfer electrode 72. The droplet 65b is positioned to move into the capillary channel 62 Capillary channel 61 is also shown; however, the capillary channel is at a distance from the transfer electrode 72 and is aligned with transfer electrode 71 (not shown). The cover substrate 101 with an electrode 55 disposed on the bottom surface of the cover substrate 101 is also depicted. In the embodiments of the integrated devices depicted in FIG. 2D-2H, the nanopore module is disposed on the same substrate as the electrode array of the microfluidics module.

The vertical distance between the top surface of the transfer electrodes and the entrance to the capillary channels may be determined by the thickness of the substrates forming the lower part of the microfluidics module and the nanopore module. The vertical distance may be set based on the volume of the droplets to be transferred to the nanopore module. The vertical distance may be adjusted by varying the thickness of the substrates. For example, the substrates (e.g., substrate 63) of the nanopore module may kept relatively thin or the thickness of the substrate on which the transfer electrodes are disposed can be increased (for example by using a thicker substrate) to ensure that the droplet is aligned with the entrance of the capillary channel. An exemplary device in which the droplets are brought into alignment with the entrance to the capillary channels by using a microfluidics module having a thicker bottom substrate is depicted in FIG. 2E. The device shown in FIG. 2E has the same configuration as described for FIGS. 2C-2D. However, the thickness of the substrate 59a on which the electrode array is positioned is increased relative to the thickness of the part of the substrate on which the nanopore module is disposed. FIG. 2E, top panel depicts a front view of a cross section at the interface 100 between the microfluidics module and the nanopore module. FIG. 2E, bottom panel depicts a side view of a cross section at the position of the transfer electrode 72 and capillary channel 62. As illustrated in FIG. 2E, the substrate 59a on which the electrode array 49 and the transfer electrodes 71 and 72 are disposed is thicker than the substrate 59b on which the nanopore module is disposed. As shown in FIG. 2E, bottom panel, substrate 59a has a first height H1 while substrate 59b has a second height H2, where H1 is greater than H2. The difference in height between the substrates 59a and 59b results in alignment of the capillary channels 61 and 62 in the nanopore module with the droplets positioned on electrodes 71 and 72, respectively. Also depicted in the bottom panel of FIG. 2E is the channel 61. As evident from FIG. 2C, capillary channel 62 is perpendicular to the capillary channel 61 at the location of the nanopore layer 70. Channel 61 is aligned with the transfer electrode 71 and is configured to receive droplet 65a positioned on transfer electrode 71. While the two capillary channels are depicted to be perpendicular to each other at the point of intersection, other configurations are also envisioned where the two channels intersect at an angle other than 90 degrees.

Upon contact with the capillary channel, the droplets move into the capillary channel via any suitable means, such as, capillary action. The movement of a droplet into the capillary channel may be facilitated by additional methods/materials. For example, the droplets may move into the capillary channel via diffusion, Brownian motion, convection, pumping, applied pressure, gravity-driven flow, density gradients, temperature gradients, chemical gradients, pressure gradients (positive or negative), pneumatic pressure, gas-producing chemical reactions, centrifugal flow, capillary pressure, wicking, electric field-mediated, electrode-mediated, electrophoresis, dielectrophoresis, magnetophoresis, magnetic fields, magnetically driven flow, optical force, chemotaxis, phototaxis, surface tension gradient driven flow, Marangoni stresses, thermo-capillary convection, surface energy gradients, acoustophoresis, surface acoustic waves, electroosmotic flow, thermophoresis, electrowetting, opto-electrowetting, or combinations thereof. In addition or alternatively, movement of a droplet into the capillary channel may be facilitated by using for example, an actuation force, such as those disclosed herein; using hydrophilic coating in the capillary; varying size (e.g. width and/or height and/or diameter and/or length) of the capillary channel).

In the embodiments depicted in FIGS. 2C-2H, the flow of a fluid across capillaries channels 61 and 62 is controlled at least in part by changing the cross-section of the capillaries-the fluid initially moves relatively quickly till it enters a narrower portion of the capillaries. One or both droplets may be droplets containing analyte to be detected or counted (or cleaved tag or dissociated aptamer) or conductive solution (e.g., buffer not containing an analyte) for analysis via the nanopore. In certain cases, one droplet 65a may be a droplet containing an analyte/tag/aptamer while the other droplet 65b may be a buffer droplet. While a single droplet is depicted for each channel, in practice, multiple droplets may be transported to the nanopore module. For example, the multiple droplets may be transported to the nanopore module in a sequential manner. In some cases, multiple droplets may be gathered at one or both transfer electrodes to generate a larger droplet which is transported to the nanopore module.

Figure 2F:
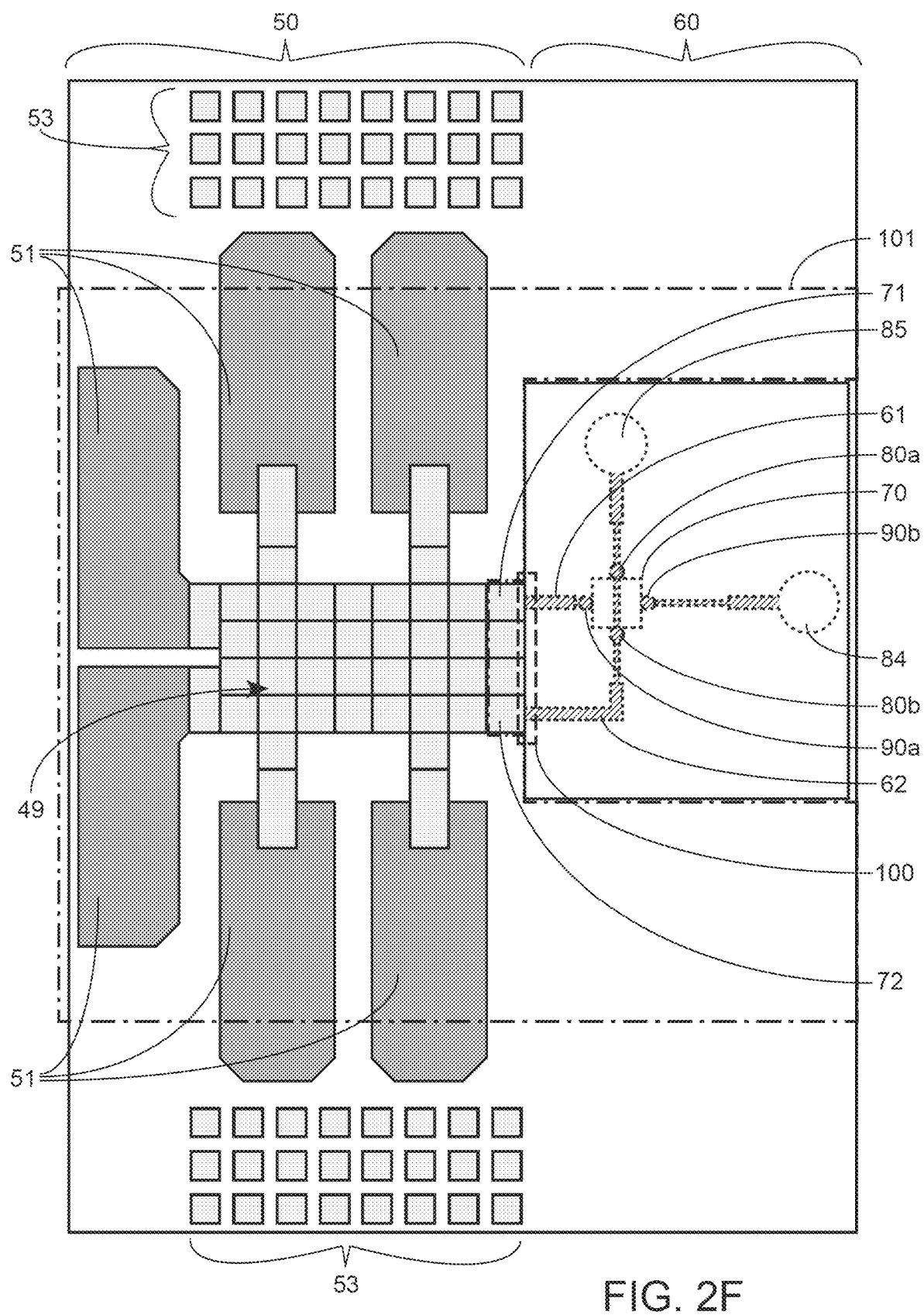
Figure 2G:
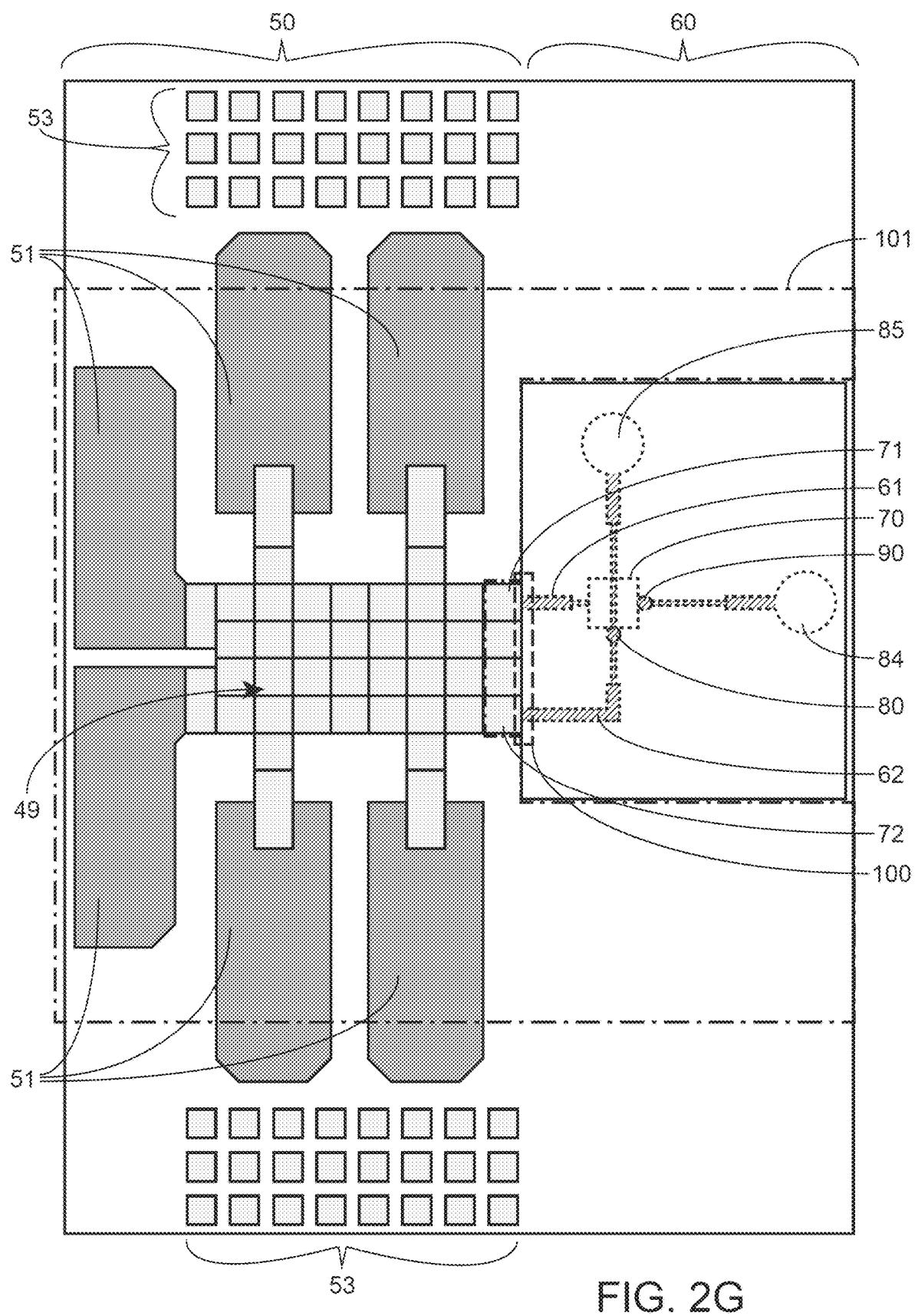

FIG. 2F illustrates an exemplary configuration of the various electrodes used in the integrated device. As noted above, a single continuous electrode 55 (not shown in FIG. 2F) is positioned in a spaced apart manner from the array of electrodes 49 in the microfluidics module 60. The array of electrodes includes a series of individually controllable electrodes. The electrode 55 is disposed on a lower surface of the cover substrate 101. Electrode 55 and the array of electrodes move the droplets over to the transfer electrodes. While it is depicted that electrode 55 does not cover the transfer electrodes 71 and 72, in certain exemplary devices, the cover substrate 101 and the electrode 55 may extend over the transfer electrodes. In embodiments where the electrode 55 does not cover the transfer electrodes, co-planar electrodes may be used to move droplets to the transfer electrode (e.g., coplanar actuation as described in U.S. Pat. No. 6,911,132). As described herein, the single electrode 55 may serve as a reference or a grounding electrode, while the array of electrodes 49 may be individually controllable (for example, the array of electrodes may be actuation electrodes that can be actuated independently). Electrode pairs: pair 80a and 80b and pair 90a and 90b are positioned in the nanopore module. Electrode pairs 80a, 80b and 90a, 90b are used to establish opposite polarity across the nanopore layer 70 for driving charged molecules through the nanopore(s) in the nanopore layer 70. In some embodiments, the electrode pair 80a and 80b may be positive electrodes and the electrode pair 90a and 90b may be negative electrodes. FIG. 2G illustrates an alternative electrode configuration for the nanopore module where two electrodes 80 and 90 (instead of four) are used for establishing a polarity difference across the nanopore layer 70. These examples demonstrate the use of either symmetrical (four electrodes) or asymmetrical (two electrodes) electrode configurations that generate an electric potential gradient across the nanopore layer for translocating charged molecules through the nanopore.

Figure 2H:
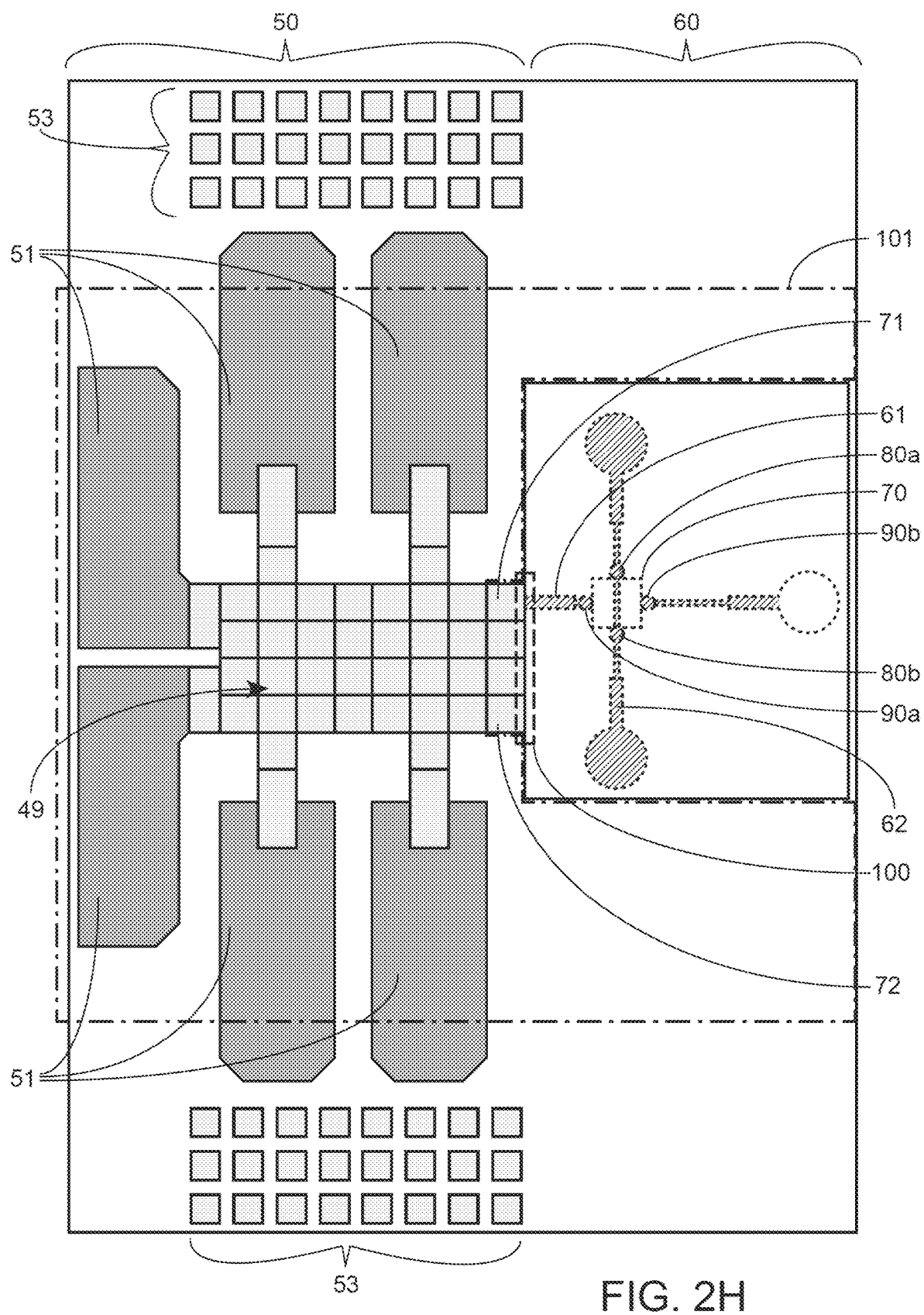

FIG. 2H illustrates an alternative configuration of the capillary channels where only one channel 61 is connected to the microfluidics module at the interface 100. The other channel 62 is connected to two reservoirs that may be filled with a conductive liquid to facilitate transfer of charged molecules across the nanopore.

In certain cases, the integrated devices provided herein may be fabricated by forming reservoirs and array of electrodes for the digital microfluidics module portion on a first area of a top surface of a first substrate. A second substrate may be prepared by disposing a single electrode (e.g., electrode 55) on the bottom surface of the second substrate and positioned over the array of individually controllable electrodes in a spaced apart manner to provide facing orientation between the single electrode and the array of electrodes for bi-planar droplet actuation. As used herein, "droplet actuation" refers to manipulation of droplets using a microfluidics device as disclosed herein or using a droplet actuator as disclosed in U.S. Pat. Nos. 6,911,132, 6,773,566, or U.S. Pat. No. 6,565,727, the disclosures of which are incorporated herein by reference. Thus, the configuration of the bi-planar electrodes or the array of electrodes of the devices disclosed herein may be similar to those disclosed in U.S. Pat. Nos. 6,911,132, 6,773,566, or U.S. Pat. No. 6,565,727. The electrode 55 on the second substrate may also be referred to as a reference electrode. The electrodes in the microfluidics module may optionally be coated with a dielectric material. A hydrophobic coating may also be provided on the dielectric.

In certain embodiments, a microchannel may be formed on a third substrate which may be disposed on a second area of the first substrate on which the array of electrodes 49 is disposed. For example, a third substrate may be bonded onto a second area on the first substrate in which the microfluidics electrode array is disposed in the first area. The substrate may have a pre-formed microchannel or a microchannel may be formed after the bonding step. A fourth substrate with a second microchannel may be disposed on top of the substrate containing the microchannel to provide an integrated device as depicted in FIG. 2C-2H. The nanopore layer may be disposed on either microchannel at the location of the intersection of the two microchannels. Thus, the substrates forming the nanopore module may include microchannels that are open at either ends and on one side. The placement of the fourth substrate over the third substrates closes the microchannels thereby forming capillary channels (e.g., 61 and 62).

In certain embodiments, a microchannel may be formed on a separate substrate which may be disposed on to the first substrate on which the microfluidics array of electrodes is disposed. For example, another substrate may be bonded onto the second area on the first substrate in which the microfluidics electrode array is disposed in the first area. The substrate may have a pre-formed microchannel or a microchannel may be formed after the bonding step. Another substrate with a second microchannel may be disposed on top of the substrate containing the microchannel to provide an integrated device as depicted in FIG. 2C-2H. The nanopore layer may be disposed on either microchannel at the location of intersection of the two microchannels 61 and 62.

In some embodiments, a microchannel may be introduced in the second area adjacent the first area on the first substrate on which the microfluidics array of electrodes is disposed. For example, the microchannel may be etched on the top surface in the second area. A nanopore layer may be placed at a location on the microchannel. The nanopore layer may include preformed nanopore(s). In alternative embodiments, nanopore(s) may be formed after positioning the layer at a location on the microchannel. A third substrate may be prepared by introducing a microchannel on a bottom surface of third substrate. The third substrate may be positioned over the second area on the first substrate such that the top surface of the second area of the first substrate is in contact across its top surface with the bottom surface of the third substrate thereby creating closed capillary channels 61 and 62.

Figure 2I:
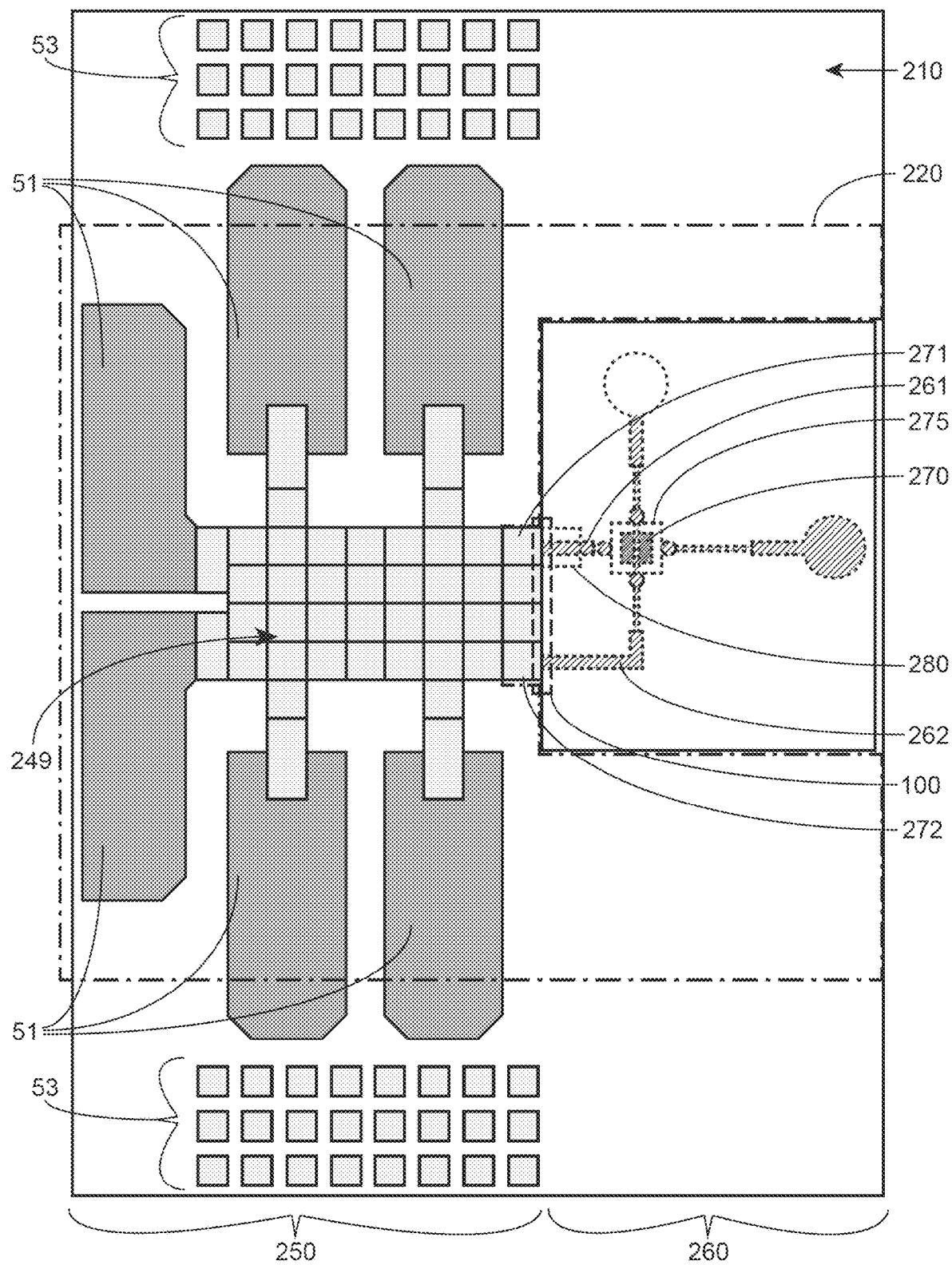

FIGS. 2I-2K depict devices in which the digital microfluidics module 250 and nanopore module 260 share a common bottom (first) substrate 210 on which the array of electrodes 249 (a series of individually controllable electrodes) for the microfluidics module is disposed on a first area and a microfluidic channel 261 is formed in a second area. The microfluidic channel 261 in the first substrate is aligned with the transfer electrode 271. A second substrate 220 having a single continuous electrode 255 (e.g., a reference electrode) is disposed in a spaced apart manner from the array of electrodes 249 in the digital microfluidics module 250. A third substrate 230 comprising a microfluidic channel 262 formed in a lower surface of the third substrate is placed over the second area of the first surface 210 thereby covering the top surface of the first substrate in which the microfluidic channel 261 is formed. The first substrate and the third substrate in the nanopore module enclose the microfluidic channels 261 and 262 thereby providing capillary channels 261 and 262. It is understood that "microfluidic channel(s)" and "microchannel(s)" are used herein interchangeably to refer to a passage or a cut out in a surface of a substrate. Upon placement of a substrate over the passage, the passage is enclosed forming a capillary channel. Similar to the FIG. 2C, the capillary channels may be fluidically connected to the microfluidics module at one end at the interface 100 between the microfluidics module 250 and the nanopore module 260 and with a reservoir or vent on the other end. In other embodiments, the second capillary channel 262 may be configured similarly to the capillary channel 62 in FIG. 2H, i.e., the second capillary channel 262 may not be connected to the microfluidics module at either end and may be connected to a reservoir/vent at both ends. A top view of the device is depicted in FIG. 2I and a front view of a cross-section of the device at the interface between the modules is depicted in FIG. 2I (continued). As is evident from the front view, the droplet 265a is on a plane higher than the entrance to the capillary channel 261. In order to allow the droplet 265a to flow into the capillary channel 261, a notch 280 is created in a side edge of the third substrate 230 to provide space for movement of the droplet down into the microchannel 261. Thus, the fluidic connection between the microfluidics module and the nanopore module is provided by a vertical port formed by the notch 280 providing an opening in a top part of the first capillary channel 261 at one end of the first capillary channel 261 at the interface 100. It is understood that the notch 280 is FIG. 2I is not drawn to size and may be of any suitable size that allows for fluid communication between the transfer electrode 271 and the first capillary channel 261 at the interface 100. Further, the notch may be varied in size. For example, the notch may be a cut-out that extends along a length of the side edge of the third substrate 230 at interface 100 and may be proportioned to match the width of the transfer electrode 271 or the width of the capillary channel 261 or a length in between. The cut-out may be extended nominally along the width of third substrate 230 such that a relatively minor region of the capillary channel 261 is uncovered. In other embodiments, the cut-out may extend over a substantial length of the capillary channel 261. A layer 270 containing a nanopore is positioned across the first capillary channel 261 at the position at which the two capillary channels intersect. The layer 270 is positioned in a support substrate 275. In certain cases, the first substrate 210 may be a glass substrate and the support substrate 275 may be a PDMS gasket.

A side view of a cross-section of the device shown in FIG. 2I is depicted in FIG. 2J. The cross-section is at the region of the device where the first capillary channel 261 is aligned with the first transfer electrode 271. Also depicted is a portion of the microfluidics module 250 with the array of electrodes 249, the second substrate 220 with a single electrode 255 (e.g., reference electrode) positioned in a spaced apart manner from the array of electrodes 249. As shown in FIG. 2J, the single electrode 255 does not cover the transfer electrodes. While not illustrated in these Figures, the second substrate 220 and the single electrode 255 (which may be a reference electrode) may cover the transfer electrodes 271 and 272, providing a bi-planar electrode configuration. In this embodiment, droplets can be moved to the transfer electrodes 271 and 272 using the bi-planar electrodes. The first capillary 261 is located in the first substrate 210 and is located in a plane lower than the plane on which the droplet 265a is present. The third substrate 230 which includes the second microchannel (which is enclosed by the top surface of first substrate 210 to provide the capillary channel 262) is disposed over the first substrate. The third substrate 230 includes the notch 280 (or cut out) at the side edge adjacent to the microfluidics module at the interface 100. The notch 280 opens the capillary 261 on a top portion at the end of the capillary channel 261 providing a vertical port for entrance to the capillary channel 261. As shown by the direction of the arrow, the droplet travels down to the capillary 261 and then proceeds to flow towards the intersection of the first and the second capillary channels. The second capillary channel 262 intersects with the first capillary 261 at the location of the nanopore layer 270. A support substrate 275 positioned over the first capillary channel 261 (and under the second capillary channel 262) is depicted. The support substrate 275 includes the nanopore layer 270. As shown in a top view of the nanopore layer is shown in the inset, the support substrate 275 surrounds the nanopore layer. In some embodiments, the support substrate may be a first layer with a cut out in the center and a second layer with a cut out in the center. The nanopore layer may be disposed at the cut out in between the first and the second layers. A nanopore layer in a support substrate may be used in devices where the bottom substrate 210 is made of glass.

FIG. 2K shows an additional side view of a cross-section of the device shown in FIG. 2I. In FIG. 2J, the cross section is at the location of the first transfer electrode 271. In FIG. 2K, the cross section is at the location of the second transfer electrode 272. As shown in FIG. 2K, the entrance to the second capillary channel 262 is aligned with the position of the droplet 265b present on the second transfer electrode 272. Also depicted in FIG. 2K is the first capillary channel 261 which intersects with the second capillary channel 262 at the location of the nanopore layer 270.

Figure 2L:
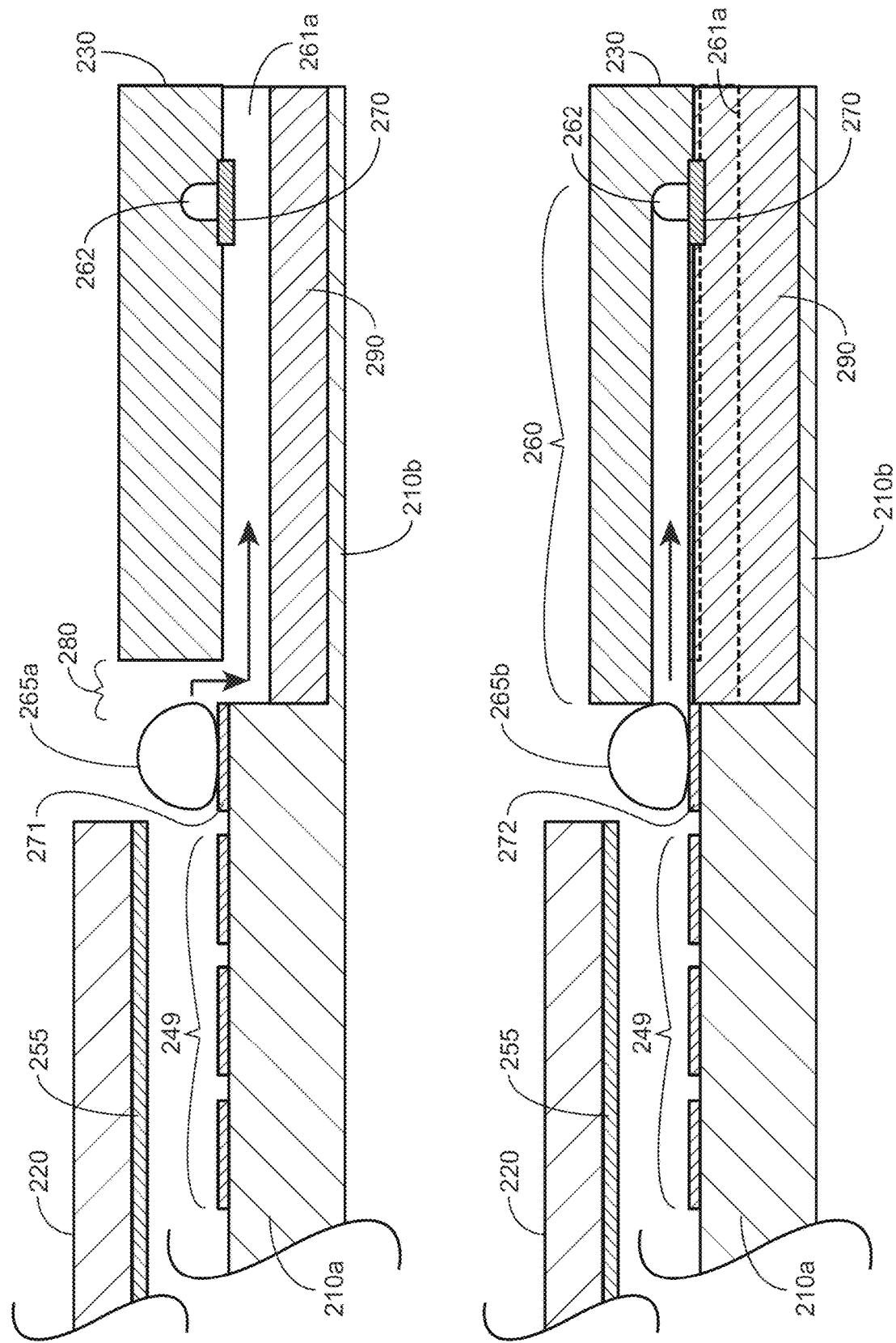

In another embodiment, as shown in FIG. 2L, the first substrate 210 may be include a first portion 210a on which the array of electrodes 249 and transfer electrodes 271 and 272 are disposed and a second portion 210b on which a substrate 290 containing capillary channel 261a is disposed. Similar to the device shown in FIG. 2I-2K, the capillary channel 261a is below the plane on which the transfer electrodes are located. Capillary channel 262 is located in substrate 230 where the entrance to the capillary channel 262 is at the same plane as the transfer electrodes in the microfluidics module 250. Further, similar to FIGS. 2I-2K, entrance to the capillary channel 262 is aligned with the transfer electrode 272. Thus, a droplet positioned on electrode 272 can travel substantially horizontally to the capillary channel 262. Similar to the device shown in FIGS. 2I-2K, the substrate 230 includes a notch 280 in a side edge of substrate 230 to provide space for a droplet positioned on transfer electrode 271 to travel down to capillary 261a which is located in substrate 290. Also depicted in FIG. 2L is the nanopore layer 270. In this embodiment, the nanopore layer is directly disposed on the substrate 290 in absence of the support layer 275. For example, in embodiments where both substrates containing the channels are formed from PDMS, the nanopore layer may be directly disposed in between the substrates in absence of a support substrate. FIG. 2L, top panel depicts a side view of a cross section through the device at the location at which the transfer electrode 271 and capillary channel 261a are located. FIG. 2L, bottom panel depicts a side view of a cross section through the device at the location at which the transfer electrode 272 and the capillary channel 262 are located. From the top, the device looks same as the device shown in FIG. 2I. Thus, the transfer electrodes 271 and 272 are spaced apart same as the transfer electrodes 71 and 72 in the device shown in FIG. 2I.

The electrodes in the nanopore module for the transport of molecules across the nanopore layer via nanopore(s) may be fabricated after positioning of the nanopore layer in the device. For example, the electrodes may be disposed in openings introduced into the substrates and positioned in the capillary channels such that they are exposed in the capillary channels and will be in contact with the fluid present in the capillary channels. The distance of the electrodes from the nanopore may be determined empirically based on resistance, width, diameter, and/or length of the capillary channel (s).

The nanopore layer may be disposed on either channel. The nanopore layer may be adhered to the surface of the substrate containing the microchannel by plasma bonding or via a compressible element, such as a gasket. In certain cases, the substrate containing the first channel may be a glass substrate. In this embodiment, a support substrate, such as, a PDMS layer may be used for positioning the nanopore layer. For example, the nanopore layer may be provided with a PDMS gasket.

Any suitable method may be employed to form the channels on the substrate. In certain cases, lithography or embossing may be used to create the channels for the nanopore module. In other embodiments, the channels may be etched into the substrates. In certain embodiments, a combination of suitable methods may be used to form channels in the substrates. For example, a channel may be formed in a glass substrate using an etching process and another channel may be formed in a PDMS substrate using an appropriate method, such as, soft lithography, nanoimprint lithography, laser ablation or embossing (e.g., soft embossing). The height/width/diameter of the microchannels may be determined empirically. The height/width/diameter of the microchannels may be in the range of 0.5 μm to about 50 μm, e.g., 0.5 μm-40 μm, 1 μm-30 μm, 2 μm-20 μm, 3 μm-10 μm, 5 μm-10 μm, such as, 0.5 μm, 1 μm, 2 μm, 3 μm, 4 μm, 5 μm, 6 μm, 7 μm, 8 μm, 9 μm, 10 μm, 15 μm, 20 μm, 30 μm, 40 μm, or 50 μm. As noted herein, the height/width/diameter of the channels may vary along the length of the channels.

In certain embodiments, the nanopore layer (e.g., 70 or 270) may include a coating of insulating material on one or both sides of the nanopore layer. The insulating material may reduce contact capacitance and decrease noise associated with detection of translocation of a molecule through the nanopore(s) in the nanopore layer. In another embodiment, the surface area of the nanopore layer exposed to a fluid in the capillary channels in fluid contact with the nanopore layer (e.g., capillary channels 61 and 62 or 261 and 262) may be reduced. Reducing the surface area of the nanopore layer that is in contact with a fluid containing the molecules to be detected or counted by the nanopore(s) may minimize contact capacitance and reduce background noise. The surface area of the nanopore layer in contact with a fluid in the capillary channels may be reduced by reducing the size of the capillary channel at the location of the nanopore layer. For example, the height or width or both (e.g., diameter) of the capillary channels at the location of the nanopore layer may be reduced. In another embodiment, the surface area of the nanopore layer may be reduced. In certain devices, a combination of these embodiments for reducing contact capacitance may be included. For example, in certain embodiments, an integrated device as disclosed herein may include capillary channels that have a decreased dimension at the location of the nanopore layer and/or may include a nanopore layer that is coated with an insulating material (e/.g., PDMS) on one or both sides of the nanopore layer and/or may include a nanopore layer having a minimal surface area.

Figure 3:
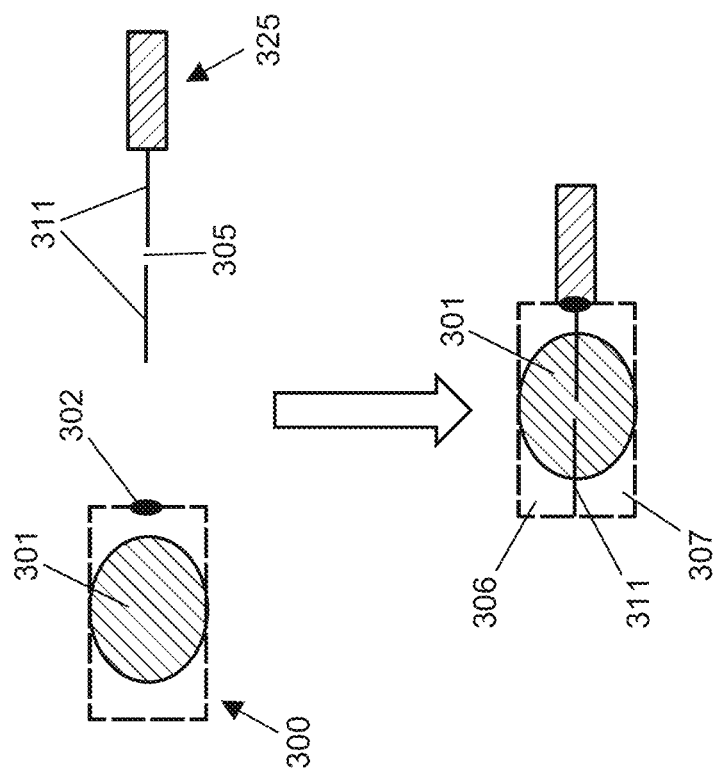
FIG. 3 illustrates an exemplary integrated device which includes a microfluidics module 300 and a nanopore module 325.

FIG. 3 illustrates another exemplary integrated device which includes a microfluidics module 300 and a nanopore module 325. In contrast to the nanopore module in FIGS. 1A, 1B, 2A and 2B, the nanopore module 325 is not functional as a standalone device but functions as a nanopore once integrated with the microfluidics module 300. The microfluidics module 300 includes an opening 302 sized to allow insertion of the nanopore module 325. As depicted in FIG. 3, the microfluidics module includes a fluidic droplet 301 that is to be analyzed using the nanopore module 325, which contains a layer 311 with a nanopore 305. Upon insertion of the nanopore module 325 into the microfluidics module 300, a first chamber 306 and a second chamber 307 separated by the layer 311 are created. The layer 311 also splits the fluid droplet 301 across the nanopore 305.

Figure 4:
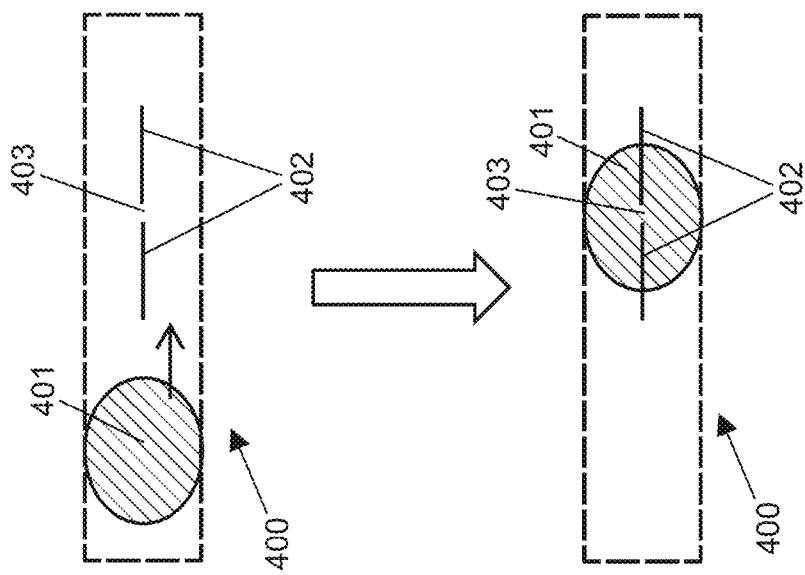
FIG. 4 provides an integrated device 400 in which the digital microfluidics modules includes a built-in nanopore module.

FIG. 4 provides an integrated device 400 in which the digital microfluidics modules includes a built-in nanopore module. In FIG. 4, the nanopore module is positioned downstream from the area in the microfluidics module where a fluidic droplet 401 is generated. The microfluidics module moves the droplet 401 to the nanopore module such that the droplet 401 is split across the layer 402 and is positioned at the nanopore 403. FIG. 4 shows a top view of the device. The top substrate has not been shown for clarity. The nanopore 403 in the nanopore layer 402 has been depicted, although from the top view, nanopore 403 will not be visible. The nanopore layer 402 can be attached to either the bottom substrate or the top substrate.

In FIGS. 1A, 1B, 2A, 2B, 3 and 4, although a single nanopore is shown, it is understood that the layer may include one or more nanopores. In addition, more than one droplet may be positioned in the nanopore module or device. The droplet(s) may be analyzed by applying a voltage across the nanopore(s). Applying the voltage may result in movement of charged molecules across the nanopore(s). When a tag translocates through the nanopore(s), a decrease in electrical current across the nanopore provides an indication of the translocation. In certain embodiments, the chambers of the nanopore module may not be filled with a conductive solution (e.g., buffer)—the conductive solution may be provided by the fluid droplet once it is positioned across the nanopore layer. In certain cases, the first and second chambers, across which voltage is applied for measuring translocation of a tag/aptamer present in the fluid droplet, may be defined by the walls of the nanopore device and the nanopore layer (e.g., see FIGS. 1B and 2B). The first and second chambers may be empty prior to the introduction of the fluid droplet or may contain a conductive fluid. In other cases, the first and second chambers may be defined walls of the microfluidics module and the nanopore layer (e.g., see FIG. 3). In other cases, the first and second chambers may be defined by the fluidic droplet split across the nanopore layer (e.g., see FIGS. 1A, 2A, and 4). In certain cases, the voltage for conducting charged molecules across the nanopore(s) may be applied to the fluid droplet, for example, in embodiments where a conductive solution is not present in the chambers. Voltage may be applied to the fluid droplet via electrodes that are in direct or indirect contact with the fluid droplet. It is understood that the dimension of the nanopore layer is larger than that of the droplet such that droplet is split across the layer and connected only via the nanopore(s).

Figure 5A:
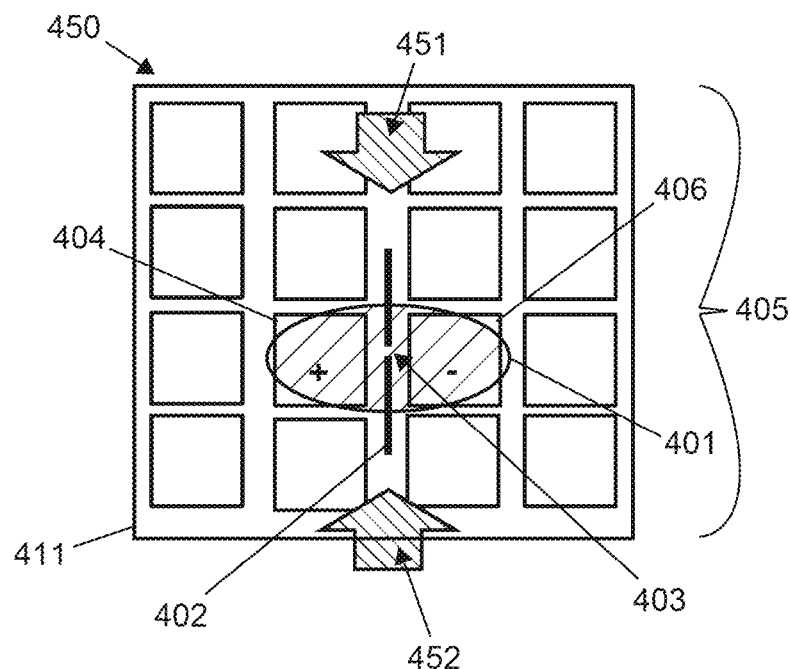
FIG. 5A shows a top view of an integrated device.

FIGS. 5A, 5B, 6 and 7 illustrate movement of droplets in devices that have a digital microfluidics module and a nanopore layer. In FIG. 5A, components of an integrated digital microfluidics/nanopore device 450 are depicted. A top view shows that a droplet 401 that is to be analyzed using the nanopore 403 in the nanopore layer 402 is positioned across the nanopore layer 402. The nanopore 403 is shown here for illustration purposes, although from a top view, the nanopore is not visible. The device 450 includes a substrate 411 on which an array of electrodes 405 is disposed. The array of electrodes is used to position a droplet 401 by splitting the droplet across nanopore layer 402. Arrows 451 and 452 depict the direction in which the droplet 401 may be moved across the array of electrodes to the nanopore layer 402. Upon positioning of the droplet 401 across the nanopore layer 402, the electrodes 404 and 406 positioned below the droplet 401 may be activated to provide a differential voltage across the nanopore layer 402, thereby facilitating movement of molecules (e.g., cleaved tag or aptamer) in the droplet 401 across the nanopore 403. The electrodes 404 and 406 are dual function electrodes, they serve to move the droplet to the nanopore layer and to drive the tag/aptamer across the nanopore 403.

Figure 5B:
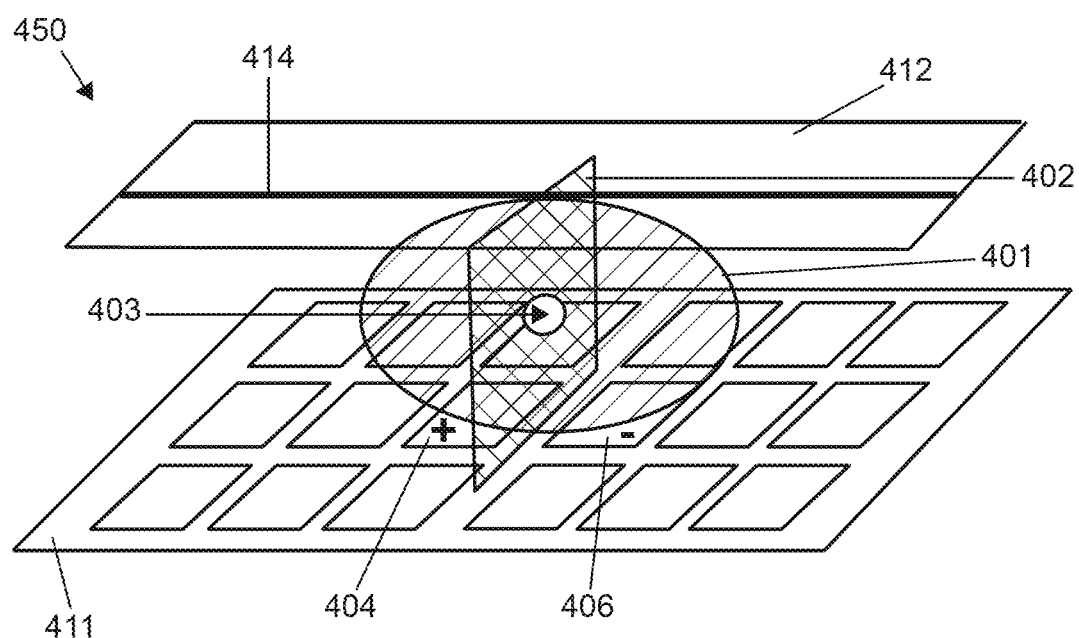
FIG. 5B shows a side view of the integrated device of FIG. 5A.

FIG. 5B depicts a side view of the device 450, a top substrate 412 omitted in the top view shown in FIG. 5A is depicted here. The top substrate 412 is shown to include an electrode 414. Electrode 414 may be a single electrode or an electrode array. The nanopore layer extends from the top substrate to the bottom substrate. The droplet 401 is split across the nanopore layer 402. Although bi-planar electrodes are depicted in FIG. 5B, the device may not include electrodes in both substrates; rather the top or the bottom substrate may include co-planar electrodes. The electrodes 404 and 406 in the vicinity of the droplet 401 have opposite polarity and drive the tag/aptamer across the nanopore 403.

Figure 6:
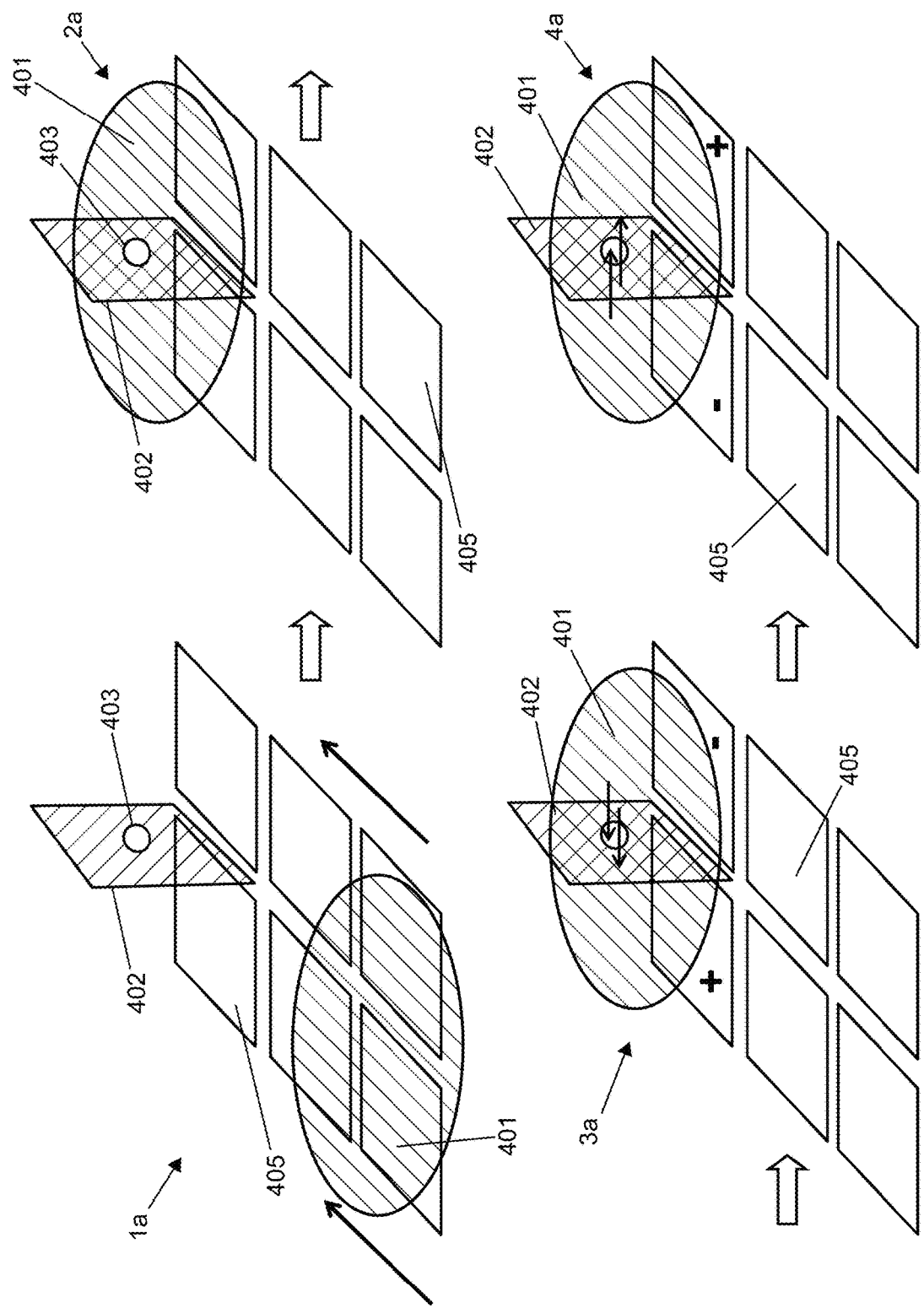
FIG. 6 depicts an exemplary device and method of the present disclosure.

FIG. 6 shows the splitting of droplet 401 across nanopore layer 402 having a nanopore 403. 1a depicts the droplet being moved by the electrodes 405 in the direction indicated by the arrows towards the nanopore layer 402. In 2a, the droplet 401 has been split by the nanopore layer 402 and positioned such that the droplet is connected via the nanopore 403. In 3a, the electrodes positioned across the nanopore layer 402 below the droplet 401, are activated to provide an anode (−) and cathode (+). The activated electrodes drive the negatively charged molecules (including the tags/aptamers being counted) present in the droplet 401 through the nanopore 403. As the tags/aptamers translocate through the nanopore 403, the number of tags/aptamers may be counted as explained herein. Step 3a serves to collect all the tags/aptamers that were divided across the nanopore layer, when the droplet was split, in one side of the droplet.

Once substantially all the tags/aptamers have been translocated to one side of the nanopore membrane, the polarity of the electrodes may be reversed, as shown in 4a, and the tags/aptamers translocated to the other side of the nanopore layer 402 and counted. The number of tags counted in step 3a should be approximately half of the count obtained in step 4a. The steps of reversing polarity of electrodes and counting the tags/aptamers may be repeated any number of times to obtain multiple readings of the number of tags/aptamers in the droplet.

Figure 7:
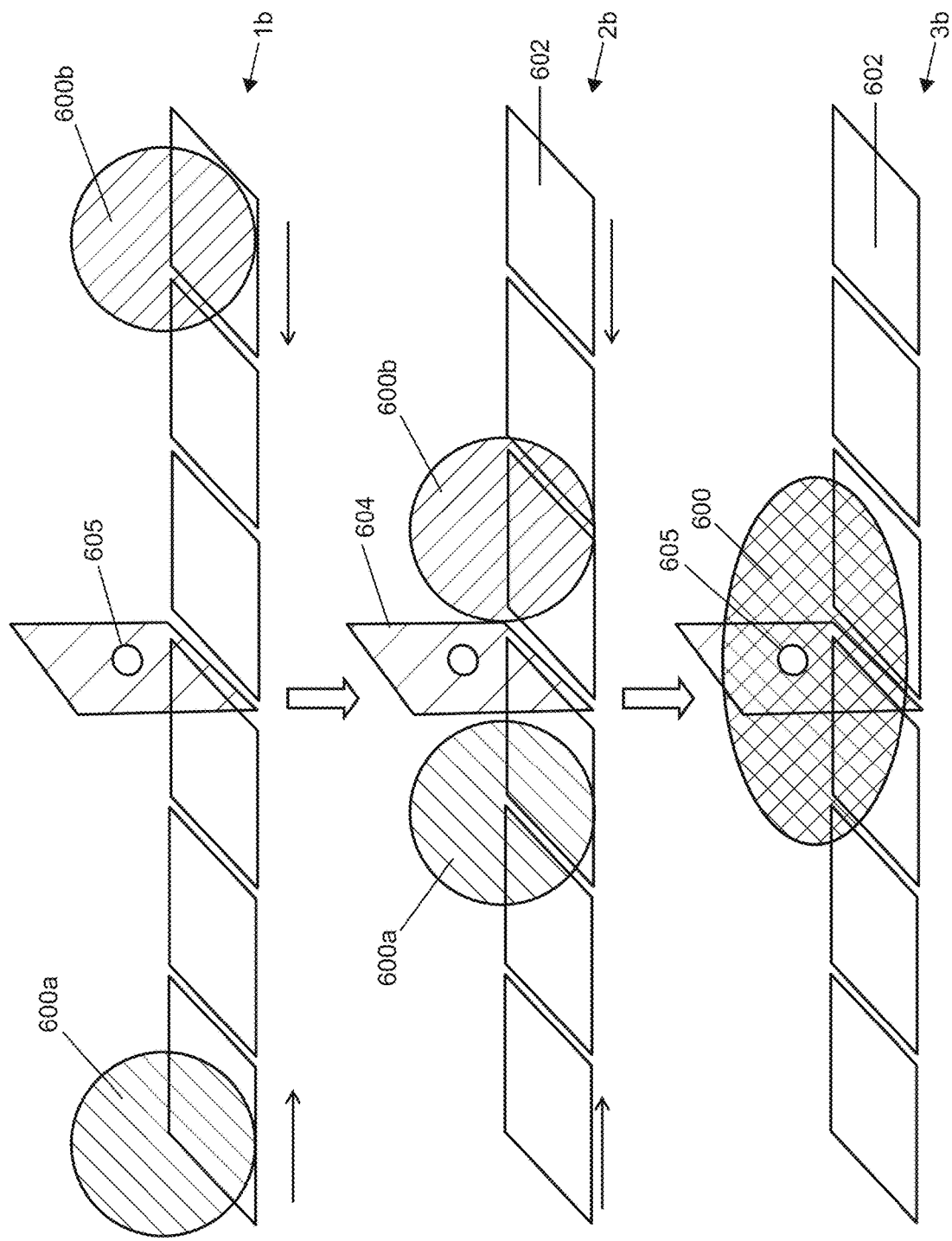
FIG. 7 depicts an exemplary device and method of the present disclosure.
Figure 7:
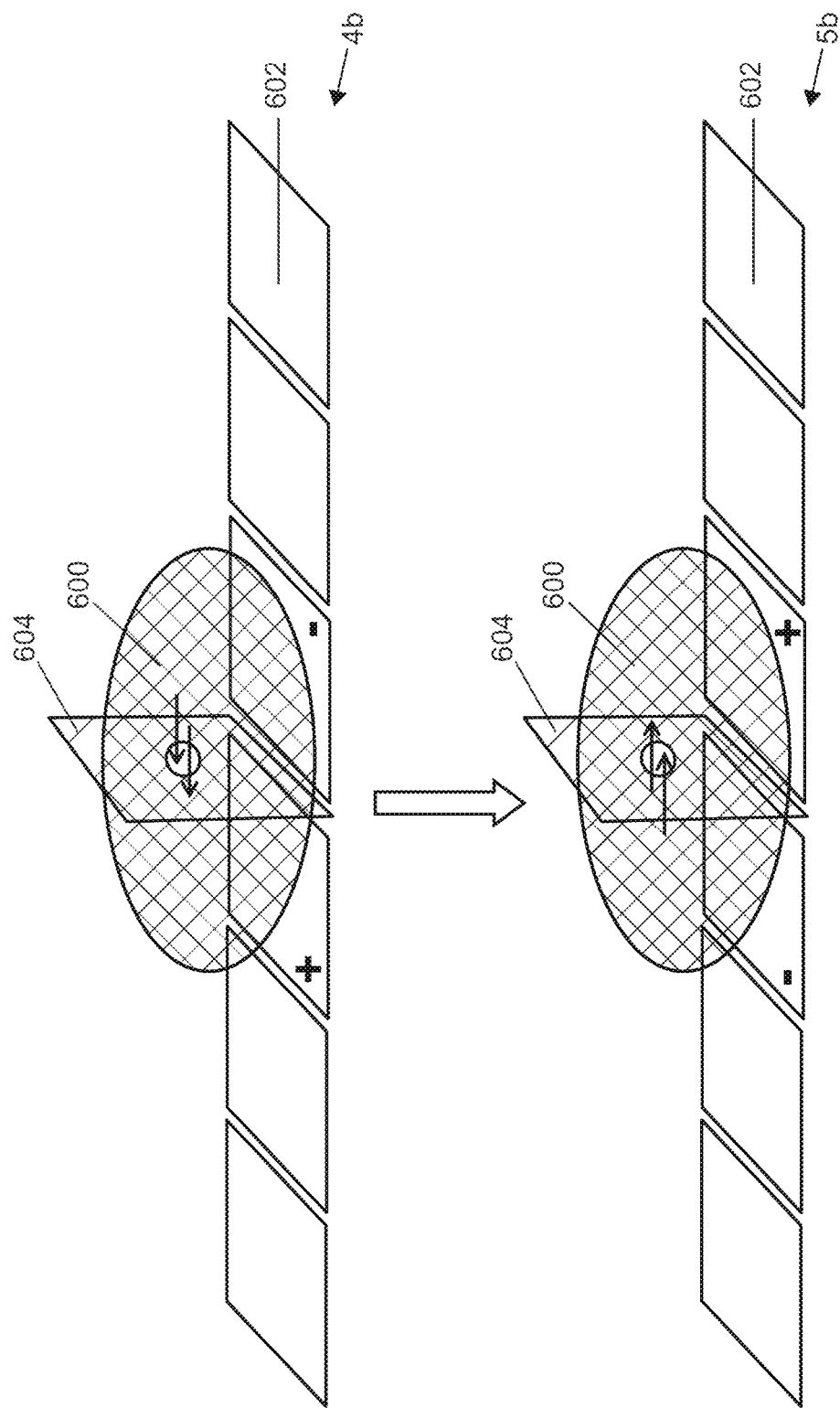

FIGS. 7, 1b and 2b show two droplets 600a and 600b being moved to the nanopore layer 604 in the directions indicated by the arrows. Once at the nanopore layer 604, the droplets wet the nanopore layer and are fluidically connected via the nanopore 605 (3b). In step 4b, an electrode positioned below the droplet 600a is activated to serve as a cathode and an electrode positioned below the droplet 600b is activated to serve as an anode and the negatively charged cleaved tags/dissociated aptamers are driven to the droplet 600a and counted. In step 5b, the polarity of the electrodes is reversed and the negatively charged cleaved tags/dissociated aptamers present in droplet 600a are driven to droplet 600b and counted. The steps of reversing polarity of electrodes and counting the cleaved tags/dissociated aptamers may be repeated any number of times to obtain multiple readings of the number of cleaved tags/dissociated aptamers in the droplet. The two droplets 600a and 600b may both be sample droplets (e.g., droplets containing molecules to be counted) or buffer droplets (e.g., for wetting the nanolayer, prior to positioning a sample droplet(s) at the nanopore. In some embodiments, one of the droplets may be a buffer droplet while the other droplet may be the sample droplet. The tags/aptamers may be counted once or multiple times.

Figure 8:
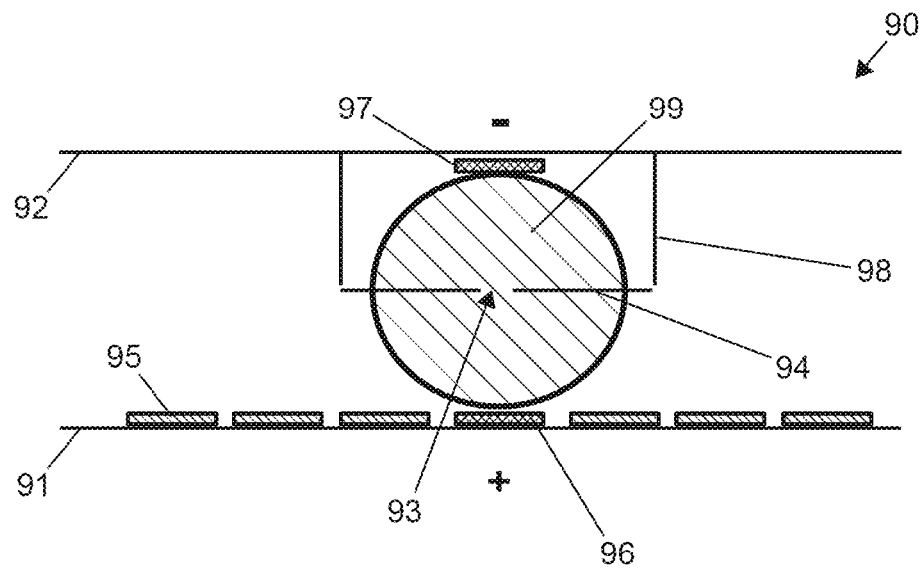
FIG. 8 depicts a side view of an exemplary integrated device of the present disclosure.

FIG. 8 illustrates an integrated digital microfluidics and nanopore device from a side view. Substrates 91 and 92 are positioned in a spaced apart manner. Substrate 92 includes an electrode 97 and substrate 91 includes an electrode array 95. Support structure 98 attaches the nanopore layer 94 to substrate 92. In other embodiments, support structure 98 may be attached to the bottom substrate 91. Electrode array 95 is used for moving the droplet 99 to the nanopore layer 94, where the nanopore layer splits the droplet and fluidically connects the two sides of the droplet via the nanopore 93. Electrodes 96 and 97 serve to drive tags/aptamers in the droplet 99 through the nanopore 93. As noted above, the polarity of electrodes 96 and 97 may be reversed to translocate the tags/aptamers through the nanopore a number of times.

Although the figures depict a single nanopore, it is understood that more than one nanopore may be present in the nanopore layer. The electrodes that flank the nanopore layer and are used to provide a voltage difference across the nanopore layer may or may not be in direct contact with a droplet positioned at the nanopore layer.

The movement of fluidic droplet in the microfluidics and nanopore devices, modules, and the integrated devices may be carried out via any suitable means. The means for moving a fluidic droplet in different devices/modules and channels, if applicable, may be same or different. For example, fluidic droplets may be moved in the microfluidics device or module using fluidic manipulation force, such as, electrowetting, dielectrophoresis, opto-electrowetting, electrode-mediated, electric-field mediated, electrostatic actuation, and the like or a combination thereof. Movement of a fluidic droplet from a microfluidics module to a nanopore module through a fluidic connection, such as, a channel, may be via diffusion, Brownian motion, convection, pumping, applied pressure, gravity-driven flow, density gradients, temperature gradients, chemical gradients, pressure gradients (positive or negative), pneumatic pressure, gas-producing chemical reactions, centrifugal flow, capillary pressure, wicking, electric field-mediated, electrode-mediated, electrophoresis, dielectrophoresis, magnetophoresis, magnetic fields, magnetically driven flow, optical force, chemotaxis, phototaxis, surface tension gradient driven flow, Marangoni stresses, thermo-capillary convection, surface energy gradients, acoustophoresis, surface acoustic waves, electroosmotic flow, thermophoresis, electrowetting, opto-electrowetting, or combinations thereof. A fluidic droplet may be moved in the nanopore module and positioned across the nanopore layer via fluidic manipulation force, such as, electrowetting, dielectrophoresis, opto-electrowetting, electrode-mediated, electric-field mediated, electrostatic actuation, and the like or a combination thereof. The tag/aptamer in the droplet may be translocated through the nanopore(s) using electric potential, electrostatic potential, electrokinetic flow, electroosmotic flow, pressure-induced flow, electrophoresis, electrophoretic transport, electroosmotic transport, diffusion transport, electric-field mediated flow, dielectrophoretic mediated transport of the tag/aptamer, and other methods known to skill in the art or combinations thereof.

Exemplary embodiments of the present disclosure include counting the number of tags present in the droplet positioned across the nanopore layer by first translocating substantially all tags to the same side of the nanopore layer to collect all the tags in a cis or trans chamber, followed by translocating the tags to the other side of the nanopore layer and counting the number of tags traversing through the nanopore(s) in the nanopore layer. As used herein, "cis" and "trans" in the context of a nanopore layer refers to the opposite sides of the nanopore layer. These terms are used to in context of a side of the nanopore layer and also in the context of a chamber on a side of the nanopore layer. As is understood from the description of the devices, the cis and trans chambers may be defined by physical structures defined by walls, substrates, etc. In some cases, the cis and trans chambers may be defined by a droplet placed across a nanopore layer. The droplet may be in contact with a wall or substrate on one or more sides of the droplet. In certain cases, cis and trans chambers may be defined by the droplet, the cis chamber may extend from the cis side of the nanopore layer to the periphery of the portion of the droplet on the cis side and the trans chamber may extend from the trans side of the nanopore layer to the periphery of the portion of the droplet on the trans side. A portion of the droplet on each of cis and trans side may be in contact with a substrate. Thus, the cis and trans chamber may be defined by a combination of the periphery of the droplet, a portion of the substrates and the nanopore layer.

In certain cases, the microfluidics device and/or the microfluidics module may include an inert fluid that is immiscible with the sample droplet and the reagent droplets. For example, the inert fluid may be a heavy fluid that is denser than water, such as oil that is immiscible with the fluidic droplets being generated and processed in the microfluidics module. The inert fluid may facilitate formation of the fluidic droplets as well as increase stability of the shape of the fluid droplets and may further be useful for keeping the different droplets spatially separated from one another. Exemplary inert fluids include polar liquids, silicone oil, fluorosilicone oil, hydrocarbons, alkanes, mineral oil, and paraffin oil. In certain cases, the microfluidics device or module and the inert fluid may be as disclosed in US20070242105, which is herein incorporated by reference in its entirety. In other embodiments, an immiscible fluid is not included in the device. In these embodiments, the ambient air fills the spaces in the device.

As used herein, "droplet(s)" and "fluidic droplet(s)" are used interchangeably to refer to a discreet volume of liquid that is roughly spherical in shape and is bounded on at least two sides by a wall or substrate of the microfluidics device, the nanopore device, microfluidics module, or the nanopore module. Roughly spherical in the context of the droplet refers to shapes such as spherical, partially flattened sphere, e.g., disc shaped, slug shaped, truncated sphere, ellipsoid, hemispherical, or ovoid. The volume of the droplet in the microfluidics and nanopore modules and devices disclosed herein may range from about 10 µL to about 5 µL, such as, 10 µL-1 µL, 7.5 µL-10 µL, 5 µL −1 nL, 2.5 µL-10 nL, or 1 µL-100 nL, e.g., 10 µL, 1 µL, 800 nL, 400 nL, 100 nL, 10 nL, or lesser.

In certain embodiments, the integrated device may include a microfluidics module with a built-in nanopore module. The integrated device may include a first substrate and a second substrate with a gap separating the first and second substrates, the gap (which may be filled with air or an immiscible liquid) providing the space in which a sample droplet is contacted with the first binding member (either immobilized on a magnetic bead or on one of the two substrates); optionally a washing step is performed; followed by contacting the analyte bound to the first binding member with the second binding member; optional mixing and wash step may be performed; and the tag attached to the second binding member is cleaved to generate a droplet containing the cleaved tag. The droplet containing the cleaved tag may then be positioned across a nanopore layer located in the gap between the first and second substrates.

As noted herein, the droplets may be moved in the integrated device via numerous ways, such as, using a programmable fluidic manipulation force (e.g., electrowetting, dielectrophoresis, electrostatic actuation, electric field-mediated, electrode-mediated force, SAW, etc.). In certain cases, the microfluidics device and module may move droplets of sample and reagents for conducting analyte analysis by using electrodes. The electrodes may be co-planar, i.e., present on the same substrate or in a facing orientation (bi-planar), i.e., present in the first and second substrates. In certain cases, the microfluidics device or module may have the electrode configurations as described in U.S. Pat. No. 6,911,132, which is herein incorporated by reference in its entirety. In certain cases, the device may include a first substrate separated from a second substrate by a gap; the first substrate may include a series of electrodes positioned on an upper surface; a dielectric layer may be disposed on the upper surface of the first substrate and covering the series of electrodes to provide a substantially planar surface for movement of the droplets. Optionally, a layer of hydrophobic material may be placed on the upper surface of the dielectric layer to provide a substantially planar surface. In certain cases, the first substrate may include co-planar electrodes—e.g., drive/control and reference electrodes present on a single substrate. In other cases, the second substrate that is positioned over the first substrate may include an electrode on lower surface of the second substrate, where the lower surface of the second substrate is facing the upper surface of the first substrate. The electrode on the second substrates may be covered with an insulating material. The series of electrodes may be arranged in a longitudinal direction along a length of the microfluidics module or in a lateral direction along a width of the microfluidics module or both (e.g., a two-dimensional array or grid). In certain cases, the array of electrodes may be activated (e.g., turned on and off) by a processor of a computer operably coupled to the device for moving the droplets in a programmable manner. Devices and methods for actuating droplets in a microfluidics device are known. In exemplary cases, the microfluidics module may be similar to a droplet actuator known in the field. For example, the first (bottom) substrate may contain a patterned array of individually controllable electrodes, and the second (top) substrate may include a continuous grounding electrode. A dielectric insulator coated with a hydrophobic may be coated over the electrodes to decrease the wettability of the surface and to add capacitance between the droplet and the control electrodes (the patterned array of electrodes). In order to move a droplet, a control voltage may be applied to an electrode (in the array of electrodes) adjacent to the droplet, and at the same time, the electrode just under the droplet is deactivated. By varying the electric potential along a linear array of electrodes, electrowetting can be used to move droplets along this line of electrodes.

The first and second substrates may be made from any suitable material. Suitable materials without limitation include paper, thin film polymer, silica, silicon, processed silicon, glass (rigid or flexible), polymers (rigid, flexible, opaque, or transparent) (e.g., polymethylmethacrylate (PMMA) and cyclic olefin copolymer (COC), polystyrene (PS), polycarbonate (PC), printed circuit board, and polydimethylsiloxane (PDMS). In certain cases, at least the first or the second substrate may be substantially transparent. Substantially transparent substrate may be used in devices where photocleavage of tag attached to a second binding member is performed. In embodiments, where co-planar electrodes are present in one of the substrates, the electrodes may or may not be transparent. In other embodiments, such as, where electrodes are in facing orientation, (present in both substrates) the electrodes on at least one of the substrates may be substantially transparent, for example, the electrodes may be made from indium tin oxide. The electrodes may be made of any suitable material. The electrodes may be made of any conductive material such as pure metals or alloys, or other conductive materials. Examples include aluminum, carbon (such as graphite), chromium, cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, vanadium, zinc, zirconium, mixtures thereof, and alloys or metallic compounds of these elements. In certain embodiments, the conductive material includes carbon, gold, platinum, palladium, iridium, or alloys of these metals, since such noble metals and their alloys are unreactive in aqueous environment.

In certain cases, the first substrate or the second substrate may have a first binding member immobilized thereon in the gap. For example, a surface of the first substrate that is in facing relationship to a surface of the second substrate may include an area on which a first binding member is disposed. As noted herein, the first binding member (e.g., a polypeptide, for example, a receptor, an antibody or a functional fragment thereof) may be immobilized on the surface of a solid substrate using any conventional method. In certain cases, a first position on the surface of the first or the second substrate in the gap may only include one type of binding member (e.g., a single type of antibody). In other embodiments, a first position on the surface of the first or the second substrate in the gap may only include a plurality of different binding members, for analysis of multiple analytes. Alternatively, the device may include a plurality of locations on the surface of the first or second substrates where each location may include a different first binding member immobilized thereupon.

In embodiments where a surface of the first substrate or the second substrate in the gap has a plurality of locations at which different first binding members are immobilized, the locations may be arranged linearly along a length of the device. A sample droplet may be moved linearly to sequentially contact each of the plurality of the locations. In another embodiment, a sample may be split into multiple droplets and each of the droplets may independently contact the each of the plurality of the locations. As noted herein, the first binding member may not be attached to the first or the second substrate and may be attached to a bead that may be introduced in the microfluidics device as, e.g., a droplet.

As noted herein, a sample and any reagents for assaying the sample may be manipulated as discrete volumes of fluid that may be moved in between the first and second substrates using a programmable fluidic manipulation force (e.g., electrowetting, dielectrophoresis, electrostatic actuation, electric field-mediated, electrode-mediated force, etc.). For example, at least one of the first and second substrates may include an array of electrodes for manipulating discrete volumes of fluid, e.g., moving droplets from one location to another in between the first and second substrates, mixing, merging splitting, diluting, etc. In another example, surface acoustic waves may be used to move droplets for the analyte analysis method.

In another embodiment, the microfluidics module may move droplets of sample and reagents for conducting analyte analysis by using surface acoustics waves. In these embodiments the first substrate may a thin planar material conducive to propagation of surface acoustic waves. The first substrate may be a piezoelectric crystal layer, such a lithium niobate ($LiNbO_3$), quartz, $LiTaO_3$ wafer. In certain cases, the piezoelectric wafer may be removably coupled to a supersubstrate, where surface acoustic waves (SAWs) generated from a transducer is transmitted to the supersubstrate via a coupling medium disposed between the piezoelectric crystal layer and the supersubstrate. The upper surface of the supersubstrate may be overlayed by a second substrate and a droplet may be moved in a space between the second substrate and upper surface of the supersubstrate via SAWs generated by an interdigitated transducer connected to the piezoelectric crystal layer. In certain cases, the microfluidics module may be a SAW microfluidics device described in WO2011/023949, which is herein incorporated by reference.

In an alternate embodiment, the microfluidics module may include a first surface separated from a second surface with a space between the first surface and the second surface, where sample and reagent droplets are manipulated for performing the sample analysis disclosed herein. The microfluidics device may further include a layer of surface acoustic wave (SAW) generation material coupled to the first surface; and a transducer electrode structure arranged at the SAW generation material layer to provide surface acoustic waves (SAWs) at the first surface for transmission to droplets on the first surface, where the first surface has at least one SAW scattering element for affecting the transmission, distribution and/or behavior of SAWs at the first surface, and where the SAW generation material is selected from the group consisting of: polycrystalline material, textured polycrystalline material, biaxially textured polycrystalline material, microcrystalline material, nanocrystalline material, amorphous material and composite material. In certain cases, the SAW generation material may be ferroelectric material, pyroelectric material, piezoelectric material or magnetostrictive material. The arrangement of the SAW scattering elements may provide, in effect, a phononic crystal structure that interacts with or affects the acoustic field at the first surface to affect movement of droplet on the first surface. In certain cases, the microfluidics module may be a SAW microfluidics device described in US20130330247, which is herein incorporated by reference. The SAW microfluidics device may be used in conjunction with a nanopore device or may have a nanopore module integrated therewith.

The devices described herein may be used in conjunction with another device or devices, such as, a power source, an acoustic wave generator, and the like.

The device that may be used for carrying out the method steps described herein may also include means for supplying reagent and collecting waste materials. Such means may include chambers, absorption pads, reservoirs, etc. These means may be fluidically connected to the device.

The microfluidics module may be fluidically connected to reservoirs for supplying sample analysis reagents, such as, first binding member, second binding member, wash buffer, cleavage inducing reagent and the like. The nanopore module may be fluidically connected to a reservoir for collecting waste materials, reservoirs for supplying conductive solution to the cis and trans chambers and the like.

The integrated device may be automatic or semi-automatic and may be removably coupled to a housing comprising a source of electricity for supplying voltage to the electrodes and a random access memory for storing instructions for contacting the sample with a first binding member, wherein the first binding member is immobilized on a solid support and wherein the first binding member specifically binds to the analyte; contacting the analyte with a second binding member, wherein the second binding member specifically binds to the analyte and wherein the second binding member comprises a cleavable tag attached thereto; removing second binding member not bound to the analyte bound to the first binding member; cleaving the tag attached to the second binding member bound to the analyte bound to the first binding member; translocating the tag through or across nanopores in a layer; determining the number of tags translocating through the layer; measuring the analyte in the sample based on the numbers of tags translocating through the layer or the time to translocate a known number of tags for a fixed interval of time. As noted herein, the analyte analysis method may be executed using a processor that controls the device. For example, the device may be programed to perform analyte analysis as disclosed herein, including any optional mixing, incubating, and washing steps as disclosed herein. The housing may further include a processor for executing the instructions stored in the memory. The devices described herein may include a data acquisition module (DAQ) for processing electrical signals from the nanopore device or module. In certain cases, a patch-clamp amplifier for processing electrical signals and achieving optimal signal to noise ratio may also be included.

Figure 9:
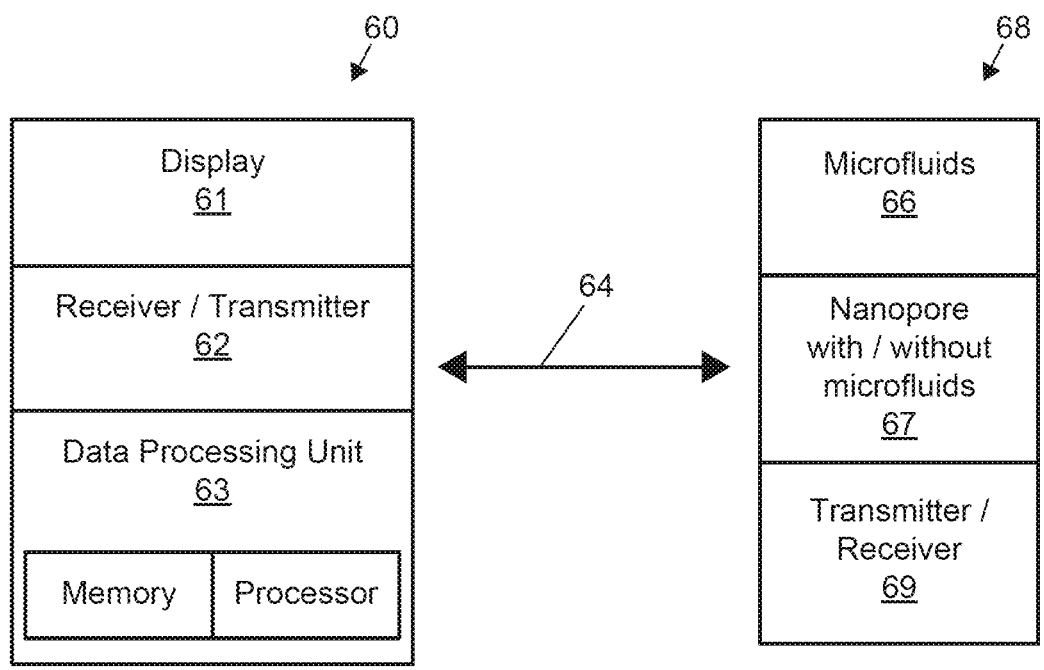
FIG. 9 depicts an exemplary system of the present disclosure.

In certain cases, the devices described herein may be associated with a system for automatically performing at least some steps of the analyte analysis methods. An example of such a system is shown in FIG. 9. The Exemplary system includes a processing component 60 including a data processing unit 63 having a processor and memory, operatively coupled to display 61 and a transmitter/receiver unit 62 that is in communication 64 with a receiver/transmitter unit 69 of a device 68 of the present disclosure. The device 68 is controlled by the processing component 60 that executes instructions (steps of a program) to perform at least some steps of the analyte analysis methods disclosed herein. In certain cases, the processing component 60 may be a computer, a meter with an opening for insertion of the integrated device (the opening may be a slot sized and shaped to accommodate the device and operably connect to the device), or a combination thereof. The communication 64 between the processing component 60 and the device 68 may be wired or wireless. The device 68 may be any device described herein with microfluidics 66 and nanopore 67 functionality. In certain cases, the movement of a droplet in the devices disclosed herein may be programmed as disclosed in U.S. Pat. No. 6,294,063, which is herein incorporated by reference in its entirety.

The various illustrative processes described in connection with the embodiments herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computing system that also has a user interface port that communicates with a user interface, and which receives commands entered by a user, has at least one memory (e.g., hard drive or other comparable storage, and random access memory) that stores electronic information including a program that operates under control of the processor and with communication via the user interface port, and a video output that produces its output via any kind of video output format, e.g., VGA, DVI, HDMI, DisplayPort, or any other form.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein. The camera may be a camera based on phototubes, photodiodes, active pixel sensors (CMOS), CCD, photoresistors, photovoltaic cells or other digital image capture technology.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, a cloud, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more example embodiments, the functions described may be implemented in hardware, software, firmware, or any combination thereof. If implemented in software, the functions may be stored on, transmitted over or resulting analysis/calculation data output as one or more instructions, code or other information on a computer-readable medium. Computer-readable media includes both computer storage media and communication media including any medium that facilitates transfer of a computer program from one place to another. A storage media may be any available non-transitory media that can be accessed by a computer. By way of example, such computer-readable media can include RAM, ROM, EEPROM, CD-ROM or other optical disk storage, magnetic disk storage or other magnetic storage devices, or any other medium that can be used to carry or store desired program code in the form of instructions or data structures and that can be accessed by a computer. The memory storage can also be rotating magnetic hard disk drives, optical disk drives, or flash memory based storage drives or other such solid state, magnetic, or optical storage devices. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

In certain cases, the device may be a microfluidic device, such as a lab-on-chip device, continuous-flow microfluidic device, or droplet-based microfluidic device, where analyte analysis may be carried out in a droplet of the sample containing or suspected of containing an analyte. Exemplary microfluidic devices that may be used in the present methods include those described in WO2007136386, U.S. Pat. No. 8,287,808, WO2009111431, WO2010040227, WO2011137533, WO2013066441, WO2014062551, or WO2014066704. In certain cases, the device may be digital microfluidics device (DMF), a surface acoustic wave based microfluidic device (SAW), a fully integrated DMF and nanopore device, or a fully integrated SAW and nanopore device. In some embodiments, the DMF element and a nanopore element are operatively coupled in the fully integrated DMF and nanopore device, or a SAW element and a nanopore element are operatively coupled in the fully integrated SAW and nanopore device. In some embodiments, the DMF device or the SAW device is fabricated by roll to roll based printed electronics method. In some embodiments, the DMF element or the SAW element is fabricated by roll to roll based printed electronic methods. In some embodiments, the fully integrated DMF and nanopore device or the fully integrated SAW and nanopore device comprise a microfluidic conduit. In some embodiments, the microfluidic conduit couples the DMF element to the nanopore element, and the microfluidic conduit comprises a fluidic flow that is induced by passive forces or active forces.

Exemplary electrowetting techniques can be found in U.S. Pat. No. 8,637,242. Electrophoresis on a microscale such as that described in WO2011057197 may be also utilized. An exemplary dielectrophoresis technique is described in U.S. Pat. No. 6,294,063.

The devices of the present disclosure are generally free of external pumps and valves and are thus economical to manufacture and use. The devices and associated systems disclosed herein, as well as all the methods disclosed herein, are useful for applications in the field, such as, for analysis of a sample at the source of the sample, such as, at point-of-care (e.g., in the clinics, hospitals, physician's office, core laboratory facility, in home, and the like). In some cases, a device or system of the present disclosure (e.g., also as used in the methods disclosed herein) includes a heat source or a light source configured to induce, when the heat source or light source is activated, cleavage of a thermally cleavable or a photocleavable linker linking the tag to the analyte, as described herein.

The present disclosure also describes a microfluidics device used in conjunction with a nanopore-enabled device and an integrated microfluidics nanopore-enabled device. A nanopore-enabled device refers to a device which includes a layer or membrane in which a nanopore can be created. A nanopore-enabled device of the present disclosure includes two chambers separated by the layer or membrane, where the two chambers include an ionic liquid, (e.g., a salt solution, with or without an analyte of interest) for conducting current. A nanopore may be created in the layer of the nanopore-enable device by applying a voltage across the layer using the ionic liquid (e.g., salt solution, with or without an analyte of interest) in the chambers. As will be understood any of the nanopore devices (used in conjunction with a microfluidics device or integrated with a microfluidics module) described herein may initially be provided as a nanopore-enabled device that includes a layer in which a nanopore can be formed but is devoid of a nanopore. A nanopore may be created in the nanopore-enabled device during use, such as, prior to using the nanopore for detecting translocation of a tag. In certain embodiments, an ionic liquid, e.g., salt solution, containing the tag to be detected by the nanopore may be used for both creating the nanopore and for translocating a tag across the created nanopore.

In some embodiments, a quality of the nanopore that is created by applying voltage across the layer, as described above, is assessed by the level of noise in a current measured when a baseline voltage is applied across the nanopore layer or membrane.

In some cases, the nanopore created by applying voltage across the layer, as described above, may be conditioned to physically alter the nanopore and to obtain a desired electroosmotic property, e.g., increase the pore size and/or to reduce noise in the measured current across the nanopore when a voltage is applied across the nanopore layer or membrane. Thus, in some embodiments, a method of generating a nanopore in an integrated digital microfluidics nanopore-enabled device may include conditioning the nanopore. Conditioning may include: alternately applying a first voltage having a first polarity and a second voltage having a second polarity opposite the first polarity across the nanopore layer or membrane, wherein the first and second voltages are each applied at least once; and measuring an electroosmotic property related to a size of the nanopore. In some cases, the electroosmotic property related to a size of the nanopore is measured before the conditioning, to obtain an initial estimate of the size of the nanopore.

The electroosmotic property may be any suitable property that provides an estimate for the size of the nanopore. In some cases, the electroosmotic property is represented by a current-voltage curve obtained over a range of voltages (a range of −1 V to 1 V, e.g., −500 mV to 500 mV, −250 mV to 250 mV, −200 mV to 200 mV, 10 mV to 500 mV, 10 mV to 250 mV, 10 mV to 200 mV, including 15 mV to 200 mV). In some cases, the electroosmotic property is a conductance or resistance measured across the nanopore layer or membrane.

The first and second voltage may have any suitable magnitude for modifying the nanopore and to obtain the desired electroosmotic properties. In some cases, the first and second voltages have a magnitude or 100 mV or more, e.g., 200 mV or more, 500 mV or more, 750 mV or more, 1.0 V or more, 2.0 V or more, 3.0 V or more, including 4.0 V or more, and in some cases has a magnitude of 10 V or less, e.g., 9.0 V or less, 8.0 V or less, 6.0 V or less, including 4.0 V or less. In some embodiments, the first and second voltages have a magnitude in the range of 100 mV to 10 V, e.g., 200 mV to 9.0 V, 250 mV to 9.0 V, 500 mV to 9.0 V, 1.0 V to 8.0 V, including 2.0 V to 6.0 V.

The first and second voltages may each be applied for any suitable length of time for modifying the nanopore and to obtain the desired electroosmotic properties. In some cases, the first and second voltages are each applied for 10 milliseconds (ms) or more, e.g., 100 ms or more, 200 ms or more, 500 ms or more, 1 second (s) or more, 2 s or more, including 3 s or more, and in some cases, is applied for 10 s or less, e.g, 5 s or less, 4 s or less, 3 s or less, 2 s or less, 1 s or less, 500 ms or less, 200 ms or less, including 100 ms or less. In some cases, the first and second voltages are each applied for a duration in the range of 10 ms to 100 ms, 100 ms to 200 ms, 200 ms to 500 ms, 500 ms to 1 s, 1 s to 2 s, 2 s to 3 s, 3 s to 4 s, 3 s to 5 s, or 3 s to 10 s.

The first and second voltages may each be applied any suitable number of times for modifying the nanopore and to obtain the desired electroosmotic properties. In some cases, the first and second voltages are each applied twice or more, three times or more, 4 times or more, 5 times or more, 7 times or more 10 times or more, 20 times or more, 30 times or more, 50 times or more, 100 times or more, 200 times or more, including 500 times or more, and in some embodiments, is applied for 10,000 time or less, e.g., 5,000 times or less, 1,000 times or less, 500 times or less, 400 times or less, 200 times or less, 100 times or less, including 50 times or less. In some embodiments, the first and second voltages are each applied from two to 50 times, 10 to 50 times, 30 to 50 times, 50 to 100 times, 100 to 200 times, 100 to 500 times, 500 to 1,000 times, 500 to 1,000 times, or 500 to 10,000 times.

4. Integration of a Nanopore Module on One Side of a DMF Module

Figure 40:
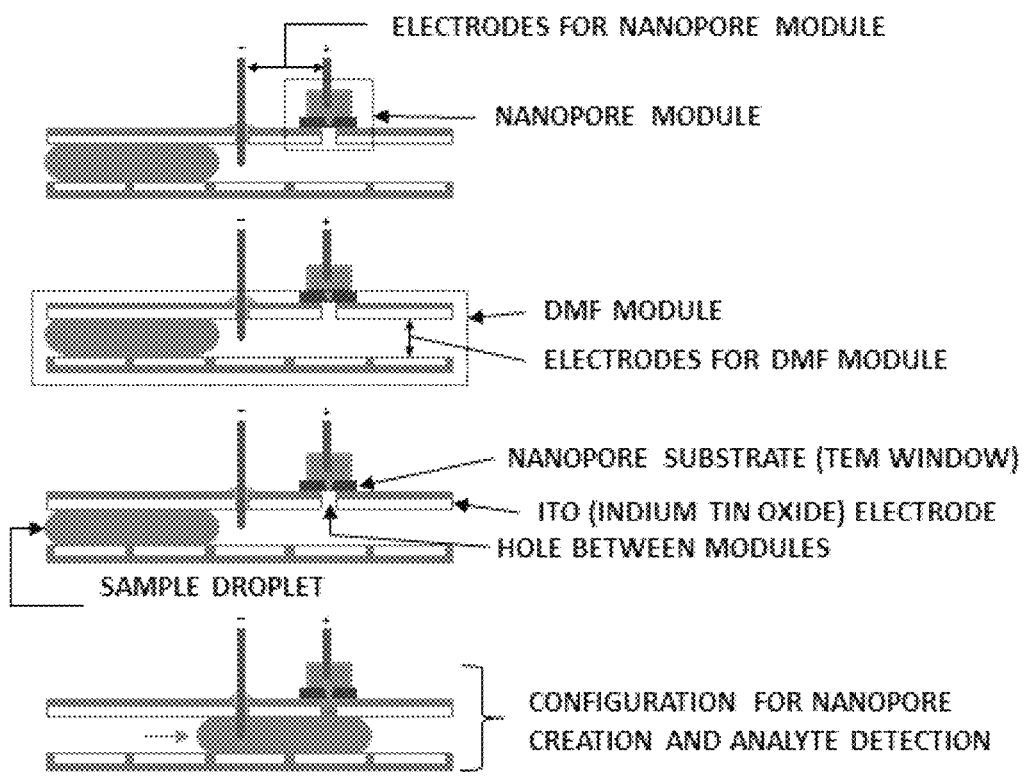
FIG. 40 shows a schematic diagram of an integrated DMF-nanopore module device with the nanopore module positioned on one side of the DMF module, according to embodiments of the present disclosure.

An aspect of the present disclosure includes an integrated device that includes a digital microfluidics (DMF) module and a nanopore layer positioned on one exterior side of the DMF module (FIG. 40). The nanopore of the nanopore layer may be accessed by a droplet in an internal space of the DMF module through a hole (also referred to as an "opening") that is present in the first (e.g., top) or second (e.g., bottom) substrate of the DMF module or through a side of the DMF module between the first and second substrate. As described above, the nanopore layer may include a nanopore membrane or substrate, which in some cases may be a commercially available silicon nitride ($SiN_x$) membrane in a transmission electron microscope (TEM) window. The nanopore layer forms a seal over the hole such that, in the absence of a nanopore (i.e. prior to fabrication of a nanopore, as described herein), a volume of liquid in the DMF module is physically isolated from any volume of liquid on or around the outside of the nanopore layer. In some cases, the nanopore layer is part of a nanopore module, where the nanopore layer separates a compartment within the nanopore module from a volume of liquid in the DMF module (e.g., a liquid droplet in the hole of the substrate, as described above). The nanopore layer or module is sealed to the outer surface of the substrate such that a volume of liquid (e.g., a liquid droplet in the hole of the substrate) is physically isolated from the outside environment.

The hole in the substrate through which a liquid droplet in the DMF has access to the nanopore layer may be dimensioned to be suitable for a liquid droplet to move through the hole by capillary action. Thus, the hole in the substrate may be a capillary channel. The hole may have any suitable cross-sectional shape and dimensions to support movement of a liquid droplet through the hole passively, e.g., by capillary action. In some cases, the diameter of the hole is wider on the side of the DMF than the diameter of the hole on the external side (i.e., the side facing the nanopore layer). In some cases, the angle between the bottom surface of the substrate and the wall of the hole is right angle or obtuse (e.g., 90° or greater, e.g., 95° or greater, including 100° or greater).

The integrated DMF-nanopore module device may include a pair of electrodes, which may find use in fabricating the nanopore in the nanopore layer and/or for detecting an analyte of interest that has been processed by the DMF module, as described elsewhere herein. The pair of electrodes may be made of any suitable material, including, but not limited to, indium tin oxide (ITO). The pair electrodes may be configured in any suitable manner. In some embodiments, one electrode is positioned in a compartment in the nanopore module, and a second electrode is positioned in the DMF module, by physically penetrating the substrate to access the volume of liquid on the other side of the nanopore layer (FIG. 40).

Figure 43:
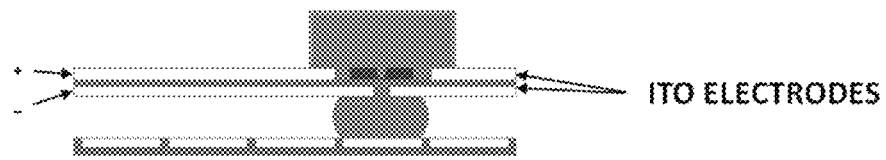
FIG. 43 is a schematic diagram of an integrated DMF-nanopore module device with the nanopore module positioned on one side of the DMF module, according to embodiments of the present disclosure.

In some embodiments, the first electrode may be the same electrode as the single continuous electrode (e.g., the reference electrode) used in the DMF module, and the second electrode may be disposed on the top surface (i.e., outer surface) of the substrate opposite the bottom surface on which the first electrode is positioned (FIG. 43). In such cases, the top surface may be treated in a similar manner as the bottom surface (e.g., coating with an electrode material, such as indium tin oxide, and a polymer, such as polytetrafluoroethylene (including Teflon®). Thus, in some cases, where the second electrode is an electrode on the top surface of the substrate to which the nanopore layer/module is attached, the volume of liquid on the outside surface of the nanopore layer relative to the DMF module is in electrical contact with the second electrode. The electrical path for the nanopore fabrication may be represented as: second electrode→liquid (external)→nanopore membrane (without a nanopore)→liquid (internal to DMF module)→first electrode (same as the single continuous electrode of the DMF). The second electrode may also be absent from the area where the nanopore layer/module is attached so as to force current into the liquid on the outside of the nanopore membrane, which in some cases may be contained within the nanopore module.

Figure 44:
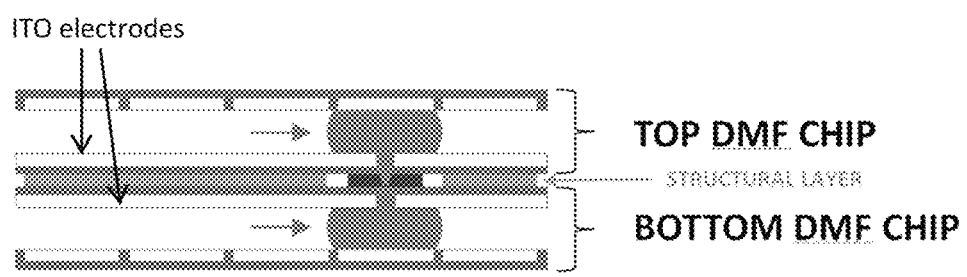
FIG. 44 is a schematic diagram of an integrated DMF-nanopore module device with the nanopore module positioned between two DMF modules, according to embodiments of the present disclosure.

In some embodiments, as shown in FIG. 44, the first electrode is the same electrode as the single continuous electrode (e.g., the reference electrode) used in a first DMF module (e.g., "bottom DMF chip" in FIG. 44), and the second electrode may be provided by a second DMF module (e.g., "top DMF chip" in FIG. 44) having a hole in a corresponding top substrate associated with the single continuous electrode of the second DMF module, and the nanopore layer is interposed between the two DMF modules between the holes in the respective substrates. Thus, the first and second DMF modules may be reversed in orientation relative to each other such that the top substrate associated with the single continuous electrode of the first DMF module is proximal to and faces the top substrate associated with the single continuous electrode of the second DMF module. The two DMF modules may be positioned relative to each other such that, when there is a nanopore in the nanopore layer, the two DMF modules are fluidically and electrically coupled together through the nanopore membrane. Prior to formation of the nanopore, the two volumes of fluid in the two DMF modules may be isolated from each other. In some cases, a structural layer is interposed between the two DMF modules to provide structural support and reduce bending.

Also provided herein is a method of making a nanopore in a nanopore-enabled layer, in an integrated DMF-nanopore module device, as described above. An implementation of the method may include positioning an ionic liquid, e.g., a salt solution (e.g., LiCl, KCl, etc.) to the hole in the DMF module using any suitable method, as described herein, and allowing capillary action to move the liquid through the hole (see, e.g., FIG. 40). An ionic liquid, e.g., a salt solution, may be positioned on the other side of the nanopore-enabled layer (i.e., the nanopore membrane before making a nanopore) The nanopore module is sealed from the DMF module, using any suitable method, such as, but not limited to PDMS, pressure, wax, adhesive, etc., such that the liquid volume in the hole is isolated from a liquid volume on the other side of the nanopore membrane. Application of an electric field, such as a voltage across the nanopore-enabled layer leads to the eventual formation of a nanopore, which can be readily detected, e.g., as a dielectric breakdown in a current trace.

After creation of a nanopore in the nanopore layer, in some cases, a conditioning process may be carried out to physically modify the nanopore and clean the signal. In some cases, the conditioning includes varying the voltage applied across the nanopore over time.

After nanopore fabrication, the DMF module may be re-activated to complete any liquid pre-processing steps for translocation (e.g. replace solution in the DMF, such as replacing KCl with LiCl). After pre-processing, the DMF liquid volume, e.g., a liquid sample containing an analyte of interest, may be positioned in the hole. The DMF system may then be de-activated and the nanopore module may be enabled to allow and detect translocation events.

5. Variations on Methods and on Use of the Device

The disclosed methods of determining the presence or amount of analyte of interest present in a sample, and the use of the microfluidics device, may be as described above. The methods and use of the disclosed microfluidics device may also be adapted in view of other methods for analyzing analytes. Examples of well-known variations include, but are not limited to, immunoassay, such as sandwich immunoassay (e.g., monoclonal-polyclonal sandwich immunoassays, including enzyme detection (enzyme immunoassay (EIA) or enzyme-linked immunosorbent assay (ELISA), competitive inhibition immunoassay (e.g., forward and reverse), enzyme multiplied immunoassay technique (EMIT), a competitive binding assay, bioluminescence resonance energy transfer (BRET), one-step antibody detection assay, homogeneous assay, heterogeneous assay, capture on the fly assay, etc. In some instances, the descriptions below may overlap the method described above; in others, the descriptions below may provide alternates.

a) Immunoassay

The analyte of interest, and/or peptides or fragments thereof, may be analyzed using an immunoassay. The presence or amount of analyte of interest can be determined using the herein-described antibodies and detecting specific binding to analyte of interest. Any immunoassay may be utilized. The immunoassay may be an enzyme-linked immunoassay (ELISA), a competitive inhibition assay, such as forward or reverse competitive inhibition assays, or a competitive binding assay, for example. In some embodiments, one tag is attached to the capture antibody and the detection antibody. Alternately, a microparticle or nanoparticle employed for capture, also can function for detection (e.g., where it is attached or associated by some means to a cleavable linker).

A heterogeneous format may be used. For example, after the test sample is obtained from a subject, a first mixture is prepared. The mixture contains the test sample being assessed for analyte of interest and a first specific binding partner, wherein the first specific binding partner and any analyte of interest contained in the test sample form a first specific binding partner-analyte of interest complex. Preferably, the first specific binding partner is an anti-analyte of interest antibody or a fragment thereof. The order in which the test sample and the first specific binding partner are added to form the mixture is not critical. Preferably, the first specific binding partner is immobilized on a solid phase. The solid phase used in the immunoassay (for the first specific binding partner and, optionally, the second specific binding partner) can be any solid phase known in the art, such as, but not limited to, a magnetic particle, a bead a nanobead, a microbead, a nanoparticle, a microparticle, a membrane, a scaffolding molecule, a film, a filter paper, a disc, or a chip (e.g., a microfluidic chip).

After the mixture containing the first specific binding partner-analyte of interest complex is formed, any unbound analyte of interest is removed from the complex using any technique known in the art. For example, the unbound analyte of interest can be removed by washing. Desirably, however, the first specific binding partner is present in excess of any analyte of interest present in the test sample, such that all analyte of interest that is present in the test sample is bound by the first specific binding partner.

After any unbound analyte of interest is removed, a second specific binding partner is added to the mixture to form a first specific binding partner-analyte of interest-second specific binding partner complex. The second specific binding partner is preferably an anti-analyte of interest antibody that binds to an epitope on analyte of interest that differs from the epitope on analyte of interest bound by the first specific binding partner. Moreover, also preferably, the second specific binding partner is labeled with or contains a detectable label (e.g., tag attached by a cleavable linker, as described above).

The use of immobilized antibodies or fragments thereof may be incorporated into the immunoassay. The antibodies may be immobilized onto a variety of supports, such as magnetic or chromatographic matrix particles, latex particles or modified surface latex particles, polymer or polymer film, plastic or plastic film, planar substrate, a microfluidic surface, pieces of a solid substrate material, and the like.

b) Sandwich Immunoassay

The sandwich immunoassay measures the amount of antigen between two layers of antibodies (i.e., a capture antibody (i.e., at least one capture antibody) and a detection antibody (i.e. at least one detection antibody). The capture antibody and the detection antibody bind to different epitopes on the antigen, e.g., analyte of interest. Desirably, binding of the capture antibody to an epitope does not interfere with binding of the detection antibody to an epitope. Either monoclonal or polyclonal antibodies may be used as the capture and detection antibodies in the sandwich immunoassay.

Generally, at least two antibodies are employed to separate and quantify analyte of interest in a test sample. More specifically, the at least two antibodies bind to certain epitopes of analyte of interest or an analyte of interest fragment forming an immune complex which is referred to as a "sandwich". One or more antibodies can be used to capture the analyte of interest in the test sample (these antibodies are frequently referred to as a "capture" antibody or "capture" antibodies), and one or more antibodies with a detectable label (e.g., tag attached by a cleavable linker) that also bind the analyte of interest (these antibodies are frequently referred to as the "detection" antibody or "detection" antibodies) can be used to complete the sandwich. In some embodiments, an aptamer may be used as the second binding member and may serve as the detectable tag. In a sandwich assay, the binding of an antibody to its epitope desirably is not diminished by the binding of any other antibody in the assay to its respective epitope. In other words, antibodies are selected so that the one or more first antibodies brought into contact with a test sample suspected of containing analyte of interest do not bind to all or part of an epitope recognized by the second or subsequent antibodies, thereby interfering with the ability of the one or more second detection antibodies to bind to the analyte of interest.

In a preferred embodiment, a test sample suspected of containing analyte of interest can be contacted with at least one capture antibody (or antibodies) and at least one detection antibodies either simultaneously or sequentially. In the sandwich assay format, a test sample suspected of containing analyte of interest (membrane-associated analyte of interest, soluble analyte of interest, fragments of membrane-associated analyte of interest, fragments of soluble analyte of interest, variants of analyte of interest (membrane-associated or soluble analyte of interest) or any combinations thereof) is first brought into contact with the at least one capture antibody that specifically binds to a particular epitope under conditions which allow the formation of an antibody-analyte of interest complex. If more than one capture antibody is used, a multiple capture antibody-analyte of interest complex is formed. In a sandwich assay, the antibodies, preferably, the at least one capture antibody, are used in molar excess amounts of the maximum amount of analyte of interest or the analyte of interest fragment expected in the test sample.

Optionally, prior to contacting the test sample with the at least one first capture antibody, the at least one capture antibody can be bound to a solid support which facilitates the separation the antibody-analyte of interest complex from the test sample. Any solid support known in the art can be used, including but not limited to, solid supports made out of polymeric materials in the form of planar substrates or beads, and the like. The antibody (or antibodies) can be bound to the solid support by adsorption, by covalent bonding using a chemical coupling agent or by other means known in the art, provided that such binding does not interfere with the ability of the antibody to bind analyte of interest or analyte of interest fragment. Moreover, if necessary, the solid support can be derivatized to allow reactivity with various functional groups on the antibody. Such derivatization requires the use of certain coupling agents such as, but not limited to, maleic anhydride, N-hydroxysuccinimide, azido, alkynyl, and 1-ethyl-3-(3-dimethylaminopropyl)carbodiimide.

After the test sample suspected of containing analyte of interest is brought into contact with the at least one capture antibody, the test sample is incubated in order to allow for the formation of a capture antibody (or capture antibodies)-analyte of interest complex. The incubation can be carried out at a pH of from about 4.5 to about 10.0, at a temperature of from about 2° C. to about 45° C., and for a period from at least about one (1) minute to about eighteen (18) hours, from about 2-6 minutes, or from about 3-4 minutes.

After formation of the capture antibody (antibodies)-analyte of interest complex, the complex is then contacted with at least one detection antibody (under conditions which allow for the formation of a capture antibody (antibodies)-analyte of interest-detection antibody (antibodies) complex). If the capture antibody-analyte of interest complex is contacted with more than one detection antibody, then a capture antibody (antibodies)-analyte of interest-detection antibody (antibodies) detection complex is formed. As with the capture antibody, when the at least one detection (and subsequent) antibody is brought into contact with the capture antibody-analyte of interest complex, a period of incubation under conditions similar to those described above is required for the formation of the capture antibody (antibodies)-analyte of interest-detection antibody (antibodies) complex. Preferably, at least one detection antibody contains a detectable label (e.g., tag attached by a cleavable linker). The detectable label can be bound to the at least one detection antibody prior to, simultaneously with or after the formation of the capture antibody (antibodies)-analyte of interest-detection antibody (antibodies) complex. Any detectable label known in the art can be used, e.g., a cleavable linker as discussed herein, and others known in the art.

The order in which the test sample and the specific binding partner(s) are added to form the mixture for assay is not critical. If the first specific binding partner is detectably labeled (e.g., tag attached with a cleavable linker), then detectably-labeled first specific binding partner-analyte of interest complexes form. Alternatively, if a second specific binding partner is used and the second specific binding partner is detectably labeled (e.g., tag attached with a cleavable linker), then detectably-labeled complexes of first specific binding partner-analyte of interest-second specific binding partner form. Any unbound specific binding partner, whether labeled or unlabeled, can be removed from the mixture using any technique known in the art, such as washing.

Next, signal, indicative of the presence of analyte of interest or a fragment thereof is generated. Based on the parameters of the signal generated, the amount of analyte of interest in the sample can be quantified. Optionally, a standard curve can be generated using serial dilutions or solutions of known concentrations of analyte of interest by mass spectroscopy, gravimetric methods, and other techniques known in the art.

c) Forward Competitive Inhibition

In a forward competitive format, an aliquot of labeled analyte of interest (e.g., analyte having tag attached with a cleavable linker) of a known concentration is used to compete with analyte of interest in a test sample for binding to analyte of interest antibody.

In a forward competition assay, an immobilized specific binding partner (such as an antibody) can either be sequentially or simultaneously contacted with the test sample and a labeled analyte of interest, analyte of interest fragment or analyte of interest variant thereof. The analyte of interest peptide, analyte of interest fragment or analyte of interest variant can be labeled with any detectable label, including a detectable label comprised of tag attached with a cleavable linker. In this assay, the antibody can be immobilized on to a solid support. Alternatively, the antibody can be coupled to an antibody, such as an antispecies antibody, that has been immobilized on a solid support, such as a microparticle or planar substrate.

Provided herein are methods for measuring or detecting an analyte present in a biological sample. The method includes contacting the sample with a binding member, wherein the binding member is immobilized on a solid support and wherein the binding member specifically binds to the analyte; contacting the sample, which may contain analyte bound to the binding member, with a labeled analyte, wherein the labeled analyte is labeled with a cleavable tag; removing labeled analyte not bound to the binding member; cleaving the tag attached to the labeled analyte bound to the binding member; translocating the cleaved tag through or across one or more nanopores in a layer; and assessing the tag translocating through the layer, wherein measuring the number of tags translocating through the layer measures the amount of analyte present in the sample, or detecting tags translocating through the layer detects that the analyte is present in the sample. In some embodiments, measuring the tags translocating through the layer is assessed, wherein the number of tags translocating through the layer measures the amount of analyte present in the sample. In some embodiments, detecting the tags translocating through the layer is assessed, wherein detecting tags translocating through the layer detects that the analyte is present in the sample.

Provided herein are methods for measuring or detecting an analyte present in a biological sample. The method includes contacting the sample with a binding member, wherein binding member is immobilized on a solid support and wherein binding member specifically binds to the analyte; contacting the sample, which may contain analyte bound to the binding member, with a labeled analyte, wherein the labeled analyte comprises an aptamer; removing labeled analyte not bound to the binding member; dissociating the aptamer bound to the labeled analyte bound to the binding member and translocating the dissociated aptamer through or across one or more nanopores in a layer; and assessing the aptamer translocating through the layer, wherein measuring the number of aptamers translocating through the layer measures the amount of analyte present in the sample, or detecting aptamers translocating through the layer detects that the analyte is present in the sample. In some embodiments, measuring the aptamers translocating through the layer is assessed, wherein the number of aptamers translocating through the layer measures the amount of analyte present in the sample. In some embodiments, detecting the aptamers translocating through the layer is assessed, wherein detecting tags translocating through the layer detects that the analyte is present in the sample.

The labeled analyte of interest, the test sample and the antibody are incubated under conditions similar to those described above in connection with the sandwich assay format. Two different species of antibody-analyte of interest complexes may then be generated. Specifically, one of the antibody-analyte of interest complexes generated contains a detectable label (e.g., tag) while the other antibody-analyte of interest complex does not contain a detectable label. The antibody-analyte of interest complex can be, but does not have to be, separated from the remainder of the test sample prior to quantification of the detectable label. Regardless of whether the antibody-analyte of interest complex is separated from the remainder of the test sample, the amount of detectable label in the antibody-analyte of interest complex is then quantified. The concentration of analyte of interest (such as membrane-associated analyte of interest, soluble analyte of interest, fragments of soluble analyte of interest, variants of analyte of interest (membrane-associated or soluble analyte of interest) or any combinations thereof) in the test sample can then be determined, e.g., as described above. If helpful, determination can be done by comparing the quantity of detectable label in the antibody-analyte of interest complex to a standard curve. The standard curve can be generated using serial dilutions of analyte of interest (such as membrane-associated analyte of interest, soluble analyte of interest, fragments of soluble analyte of interest, variants of analyte of interest (membrane-associated or soluble analyte of interest) or any combinations thereof) of known concentration, where concentration is determined by mass spectroscopy, gravimetrically and by other techniques known in the art.

Optionally, the antibody-analyte of interest complex can be separated from the test sample by binding the antibody to a solid support, such as the solid supports discussed above in connection with the sandwich assay format, and then removing the remainder of the test sample from contact with the solid support.

d) Reverse Competition Assay

In a reverse competition assay, an immobilized analyte of interest can either be sequentially or simultaneously contacted with a test sample and at least one labeled antibody.

Provided herein are methods for measuring or detecting an analyte present in a biological sample. The method includes contacting the sample with a binding member, wherein the binding member specifically binds to the analyte, and the binding member is labeled with a cleavable tag; contacting the sample, which may contain analyte bound to the binding member, with a immobilized analyte, wherein the immobilized analyte is immobilized on a solid support; removing binding member not bound to the immobilized analyte; cleaving the tag attached to the binding member bound to the immobilized analyte; translocating the cleaved tag through or across one or more nanopores in a layer; and assessing the tag translocating through the layer, wherein measuring the number of tags translocating through the layer measures the amount of analyte present in the sample, or detecting tags translocating through the layer detects that the analyte is present in the sample. In some embodiments, measuring the tags translocating through the layer is assessed, wherein the number of tags translocating through the layer measures the amount of analyte present in the sample. In some embodiments, detecting the tags translocating through the layer is assessed, wherein detecting tags translocating through the layer detects that the analyte is present in the sample.

Provided herein are methods for measuring or detecting an analyte present in a biological sample. The method includes contacting the sample with a binding member, wherein the binding member specifically binds to the analyte, and the binding member comprises an aptamer; contacting the sample, which may contain analyte bound to the binding member, with a immobilized analyte, wherein the immobilized analyte is immobilized on a solid support; removing binding member not bound to the immobilized analyte; dissociating the aptamer bound to the binding member that is bound to the immobilized analyte and translocating the dissociated aptamer through or across one or more nanopores in a layer; and assessing the aptamer translocating through the layer, wherein measuring the number of aptamers translocating through the layer measures the amount of analyte present in the sample, or detecting aptamers translocating through the layer detects that the analyte is present in the sample. In some embodiments, measuring the aptamers translocating through the layer is assessed, wherein the number of aptamers translocating through the layer measures the amount of analyte present in the sample. In some embodiments, detecting the aptamers translocating through the layer is assessed, wherein detecting tags translocating through the layer detects that the analyte is present in the sample.

The analyte of interest can be bound to a solid support, such as the solid supports discussed above in connection with the sandwich assay format.

The immobilized analyte of interest, test sample and at least one labeled antibody are incubated under conditions similar to those described above in connection with the sandwich assay format. Two different species analyte of interest-antibody complexes are then generated. Specifically, one of the analyte of interest-antibody complexes generated is immobilized and contains a detectable label (e.g., tag attached with a cleavable linker) while the other analyte of interest-antibody complex is not immobilized and contains a detectable label. The non-immobilized analyte of interest-antibody complex and the remainder of the test sample are removed from the presence of the immobilized analyte of interest-antibody complex through techniques known in the art, such as washing. Once the non-immobilized analyte of interest antibody complex is removed, the amount of detectable label in the immobilized analyte of interest-antibody complex is then quantified following cleavage of the tag. The concentration of analyte of interest in the test sample can then be determined by comparing the quantity of detectable label as described above. If helpful, this can be done with use of a standard curve. The standard curve can be generated using serial dilutions of analyte of interest or analyte of interest fragment of known concentration, where concentration is determined by mass spectroscopy, gravimetrically and by other techniques known in the art.

e) One-Step Immunoassay or Capture on the Fly Assay

In a one-step immunoassay or Capture on the fly assay, a solid substrate is pre-coated with an immobilization agent. The capture agent, the analyte and the detection agent are added to the solid substrate together, followed by a wash step prior to detection. The capture agent can bind the analyte and comprises a ligand for an immobilization agent. The capture agent and the detection agents may be antibodies or any other moiety capable of capture or detection as described herein or known in the art. The ligand may comprise a peptide tag and an immobilization agent may comprise an anti-peptide tag antibody. Alternately, the ligand and the immobilization agent may be any pair of agents capable of binding together so as to be employed for a capture on the fly assay (e.g., specific binding pair, and others such as are known in the art). More than one analyte may be measured. In some embodiments, the solid substrate may be coated with an antigen and the analyte to be analyzed is an antibody.

In some embodiments, a solid support (such as a microparticle) pre-coated with an immobilization agent (such as biotin, streptavidin, etc.) and at least a first specific binding member and a second specific binding member (which function as capture and detection reagents, respectively) are used. The first specific binding member comprises a ligand for the immobilization agent (for example, if the immobilization agent on the solid support is streptavidin, the ligand on the first specific binding member may be biotin) and also binds to the analyte of interest. The second specific binding member comprises a detectable label and binds to an analyte of interest. The solid support and the first and second specific binding members may be added to a test sample (either sequentially or simultaneously). The ligand on the first specific binding member binds to the immobilization agent on the solid support to form a solid support/first specific binding member complex. Any analyte of interest present in the sample binds to the solid support/first specific binding member complex to form a solid support/first specific binding member/analyte complex. The second specific binding member binds to the solid support/first specific binding member/analyte complex and the detectable label is detected. An optional wash step may be employed before the detection. In certain embodiments, in a one-step assay more than one analyte may be measured. In certain other embodiments, more than two specific binding members can be employed. In certain other embodiments, multiple detectable labels can be added. In certain other embodiments, multiple analytes of interest can be detected.

The use of a one step immunoassay or capture on the fly assay can be done in a variety of formats as described herein, and known in the art. For example the format can be a sandwich assay such as described above, but alternately can be a competition assay, can employ a single specific binding member, or use other variations such as are known.

f) Combination Assays (Co-Coating of Microparticles with Ag/Ab)

In a combination assay, a solid substrate, such as a microparticle is co-coated with an antigen and an antibody to capture an antibody and an antigen from a sample, respectively. The solid support may be co-coated with two or more different antigens to capture two or more different antibodies from a sample. The solid support may be co-coated with two or more different antibodies to capture two or more different antigens from a sample.

Additionally, the methods described herein may use blocking agents to prevent either specific or non-specific binding reactions (e.g., HAMA concern) among assay compounds. Once the agent (and optionally, any controls) is immobilized on the support, the remaining binding sites of the agent may be blocked on the support. Any suitable blocking reagent known to those of ordinary skill in the art may be used. For example, bovine serum albumin ("BSA"), phosphate buffered saline ("PBS") solutions of casein in PBS, Tween 20™ (Sigma Chemical Company, St. Louis, Mo.), or other suitable surfactant, as well as other blocking reagents, may be employed.

As is apparent from the present disclosure, the methods and devices disclosed herein, including variations, may be used for diagnosing a disease, disorder or condition in a subject suspected of having the disease, disorder, or condition. For example, the sample analysis may be useful for detecting a disease marker, such as, a cancer marker, a marker for a cardiac condition, a toxin, a pathogen, such as, a virus, a bacteria, or a portion thereof. The methods and devices also may be used for measuring analyte present in a biological sample. The methods and devices also may be used in blood screening assays to detect a target analyte. The blood screening assays may be used to screen a blood supply.

6. Counting and Data Analysis

The number of translocation events can be determined qualitatively or quantitatively using any routine techniques known in the art. In some embodiments, the number of translocation events can be determined by first calculating the anticipated current change found in a double stranded DNA translocation event under experimental test conditions using the equation:

$$\Delta G = \frac{\sigma \pi d_{DNA}^2}{4L}, \tag{S1}$$

as referenced in Kwok et al., "Nanopore Fabrication by controlled Dielectric Breakdown" Supplementary Information Section 8 and Kwok, H.; Briggs, K.; and Tabard-Cossa, V.; *"Nanopore Fabrication by Controlled Dielectric Breakdown"*—PLoS ONE 9(3): e92880 (2014). Using this anticipated current blockage value, the binary file data of the experimental nanopore output can be visually or manually scanned for acceptable anticipated current blockage events. Using these events, the Threshold and Hysteresis parameters required for the CUSUM nanopore software can be applied and executed. The output from this software can be further analyzed using the cusumtools readevents.py software and filtering blockage events greater than 1000 pA (as determined from the first calculation). The flux events, time between events and other calculations can be determined from the readevents.py analysis tool. Additional calculations can be made on the CUSUM generated data using JMP software (SAS Institute, Cary, N.C.). Other methods of threshold settings for data analysis known in the art can be used.

7. Qualitative Analysis

Figure 25:
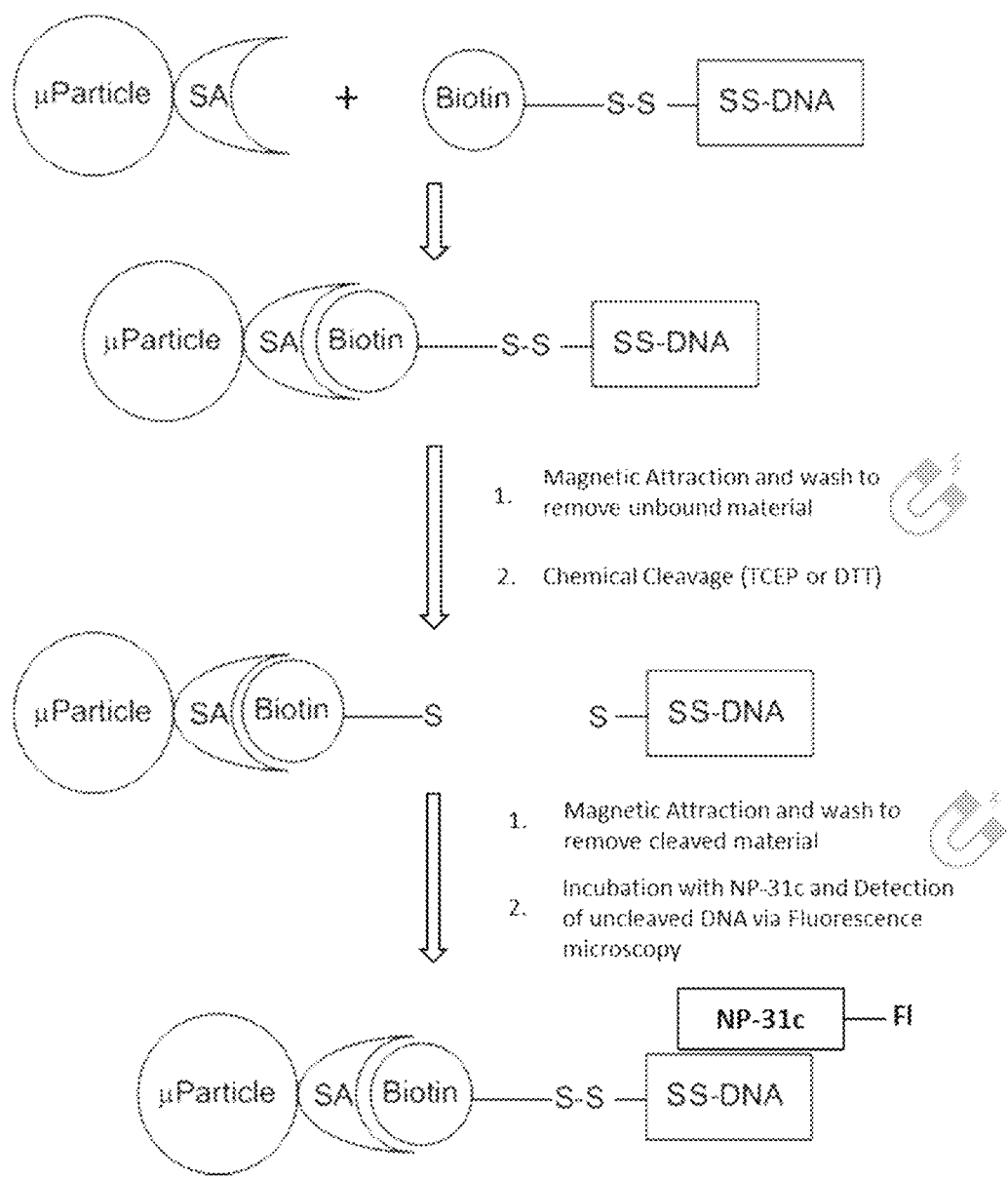
FIG. 25 shows a schematic of the thiol-mediated chemical cleavage.

A qualitative assay can be conducted using the methods and process of steps as described herein. A direct assay can be conducted using the cleavable linker conjugate, as described in Example 17, with a thiol based cleavage step, as shown in FIG. 25. It is understood that other cleavable linker approaches to conducting such an assay may also include, but are not limited to, various other methods of cleavage of a linker so as to allow for the counting of various tags, as described herein. Additionally, aptamers can be employed. For example, such other alternative cleavage methods and/or reagents in addition to the method described in Example 17 can include those described in Example 16, Example 18, Example 19, Example 20 and Example 21, in addition to other cleavage methods described herein and known to those skilled in the art. It is also understood that while the assay format demonstrated in this Example (Example 24) represents a direct assay, other formats such as sandwich immunoassay formats and/or various competitive assay formats, and including capture on the fly formats, such as are known to those skilled in the art, can be implemented as well to conduct an assay using the described methods.

For example, the sandwich immunoassay format for the detection of TSH (thyroid stimulating hormone), as described in Example 9, demonstrated the ability to conduct such an assay on a low cost DMF chip. Additionally, a number of various bioconjugation reagents useful for the generation of immunoconjugate or other active specific binding members having cleavable linkers can be synthesized using various heterobifunctional cleavable linkers such as those described in Example 1, Example 2, Example 3, Example 4, Example 5 and Example 6, in addition to other cleavable linkers that are otherwise known to those skilled in the art. Immunoconjugates useful for the practice of the present invention can be synthesized by methods such as those described in Example 3, Example 4, Example 5 and Example 6 as well as by other methods known to those skilled in the art. Additionally, Example 8 shows the functionality of various fluidic droplet manipulations on a low cost chip that can facilitate various steps needed to carry out various assay formats including sandwich and competitive assay formats, and including capture on the fly formats, as well as other variations thereof known to those skilled in the art. Example 11 shows the fabrication of a nanopore that can be used to count cleavable label in an assay but it is understood that other methods for nanopore fabrication known to those skilled in the art can also be used for this purpose. Example 16 also represents another construct useful for the conduct of an assay where a cleavage is effected, thus leading to a countable label being released so as to be countable using the nanopore counting method, as described within this example. This construct and others that would be apparent to those skilled in the art can be used in an assay as described herein.

Figure 28:
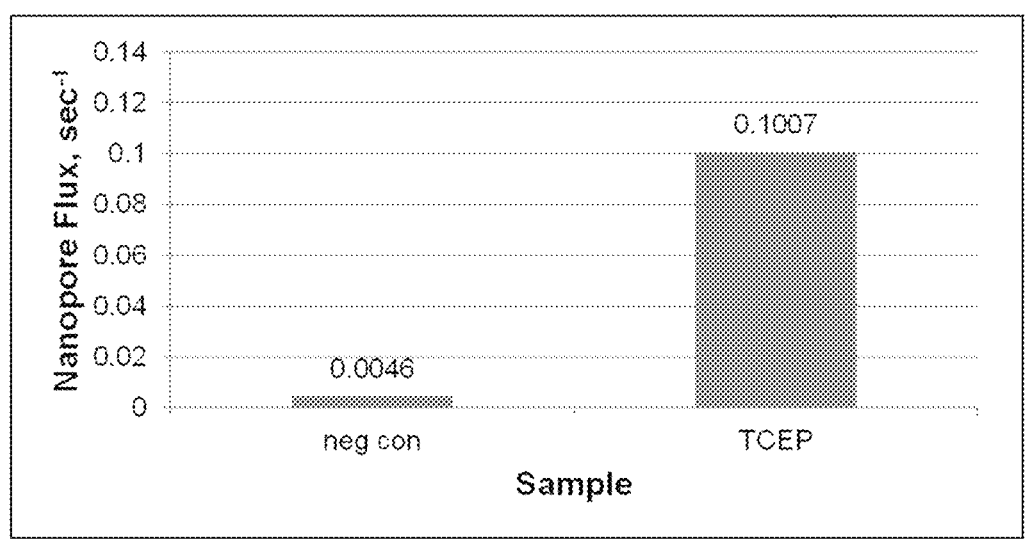
FIG. 28 displays a bar chart of sample versus nanopore flux (DMF cleavage) in $sec^{-1}$.

Example 22 shows generally how counting can be done so as to be able to measure translocation events relating to the presence of a variety of labels traversing the nanopore. FIG. 29 shows the concept of thresholding of the signal so as to be able to manipulate the quality of data in a counting assay. FIG. 28 shows qualitative assay data that is representative of the type of data that can be used to determine the presence of an analyte using such assay methods as described within this example. It is also understood that while dsDNA was used as a label in this particular example, other labels, such as the label described in Example 5 and/or Example 22 can also be utilized, including, but not limited to nanobeads, dendrimers and the like. Moreover, other known labels also can be employed. Such constructs as needed to generate appropriate reagents can be synthesized through various examples described herein in this application, or otherwise via methods known to those skilled in the art.

8. Quantitative Analysis

A quantitative assay can be conducted using the methods and process of steps as described herein. A direct assay can be conducted using the cleavable linker conjugate, as described in Example 17, with a thiol based cleavage step, and as shown in FIG. 25. It is understood that other cleavable linker approaches to conducting such an assay may also include, but are not limited to, various other methods of cleavage of a linker so as to allow for counting of various tags using a nanopore, as described herein.

Additionally, aptamers can be employed. For example, such other cleavage methods in addition to the method described in Example 17 can include, but is not limited to, those described in Example 18, Example 19, Example 20 and Example 21, in addition to other methods described herein and known to those skilled in the art. It is also understood that while the assay format demonstrated in this Example (Example 25) represents a direct assay, other formats such as sandwich immunoassay formats and/or various competitive assay formats, and including capture on the fly formats, such as are known to those skilled in the art, can be implemented as well to conduct an assay.

For example, the sandwich immunoassay format for the detection of TSH (thyroid stimulating hormone), as described in Example 9, demonstrated the ability to conduct such an assay on a low cost DMF chip. Additionally, a number of various bioconjugation reagents useful for the generation of immunoconjugate or other active specific binding members having cleavable linkers can be synthesized by those skilled in the art using various heterobifunctional cleavable linkers and conjugates synthesized by methods such as those described in Example 1, Example 2, Example 3, Example 4, Example 5 and Example 6, in addition to other cleavable linkers or conjugates that could be synthesized by methods that are known to those skilled in the art. Additionally, Example 8 shows the functionality of various fluidic droplet manipulations on a low cost chip that can facilitate various steps needed to carry out various assay formats including sandwich and competitive assay formats, and including capture on the fly formats, as well as other variations thereof known to those skilled in the art. Example 16 also represents another construct useful for the conduct of an assay where a cleavage is effected, thus leading to a countable label being released so as to be countable using the nanopore counting method as described within this example. This construct as well as other that would be apparent to those skilled in the art can be used in an assay as described herein.

Figure 31:
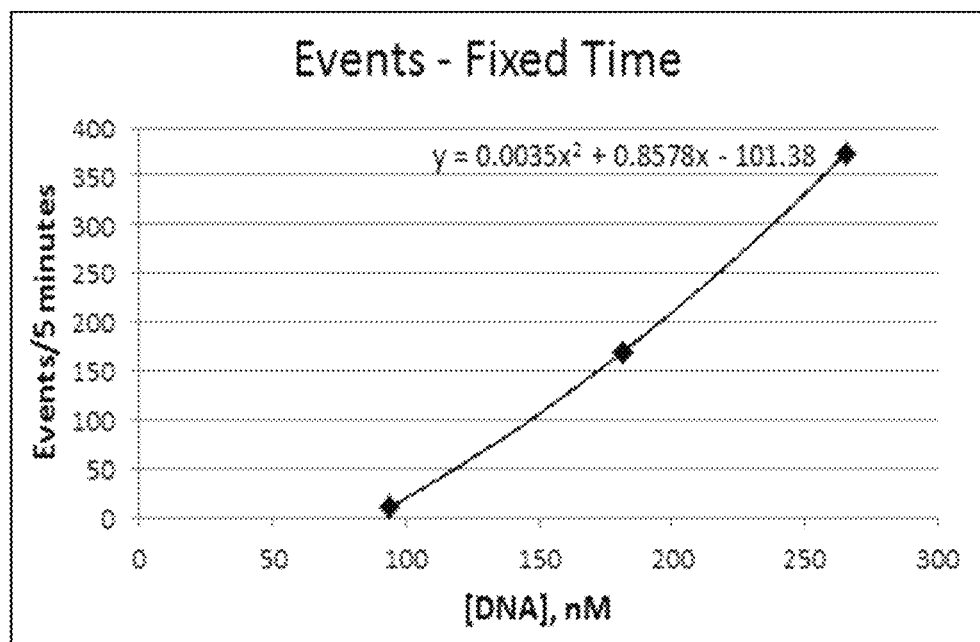
FIG. 31 shows a dose-response curve of number of events over a fixed amount of time (5 min).
Figure 32:
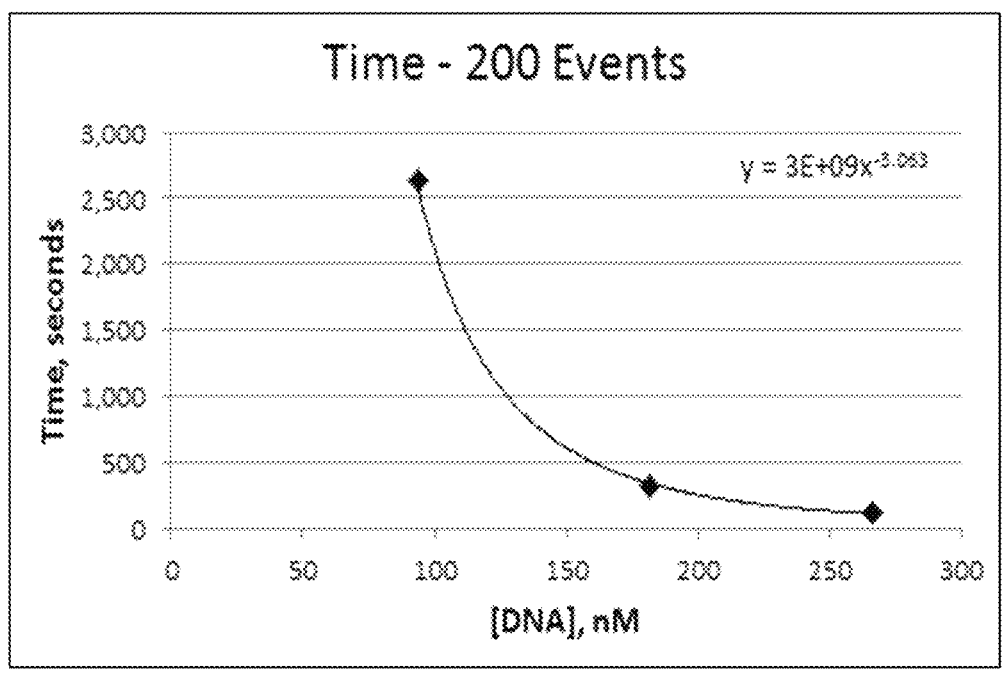
FIG. 32 shows a dose-response curve of time required for fixed number of events.
Figure 33:
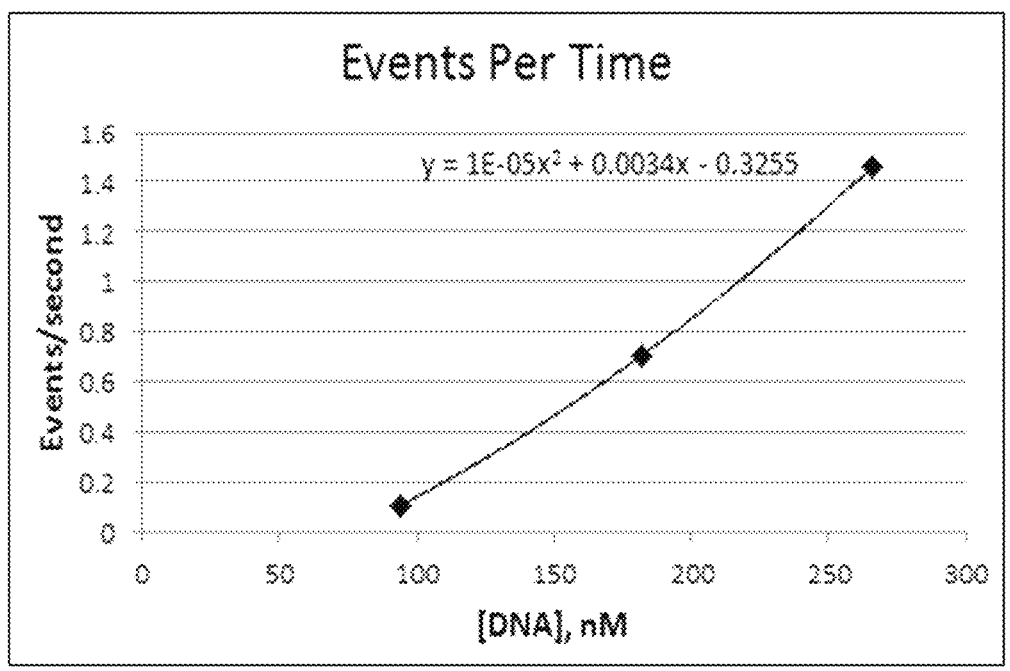
FIG. 33 shows a dose-response curve of events per unit time.
Figure 34:
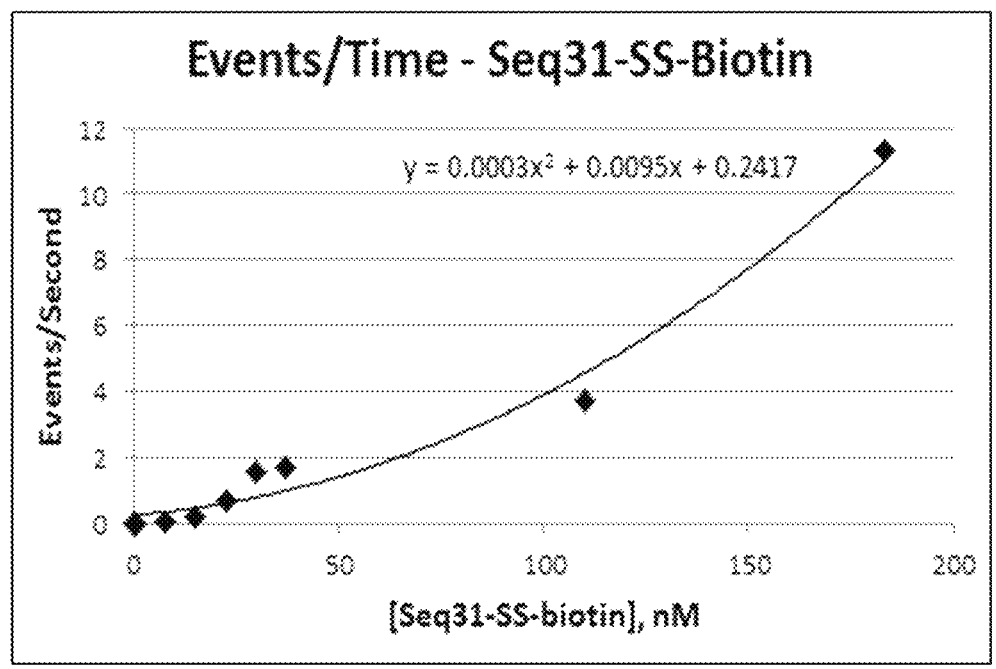
FIG. 34 shows a dose-response curve of events per unit time using Seq31-SS-biotin.

Example 22 shows generally how counting can be performed so as to be able to measure translocation events relating to the presence of a label traversing the nanopore. FIG. 29 shows the concept of thresholding of the signal so as to be able to manipulate the quality of data in a counting assay. FIGS. 31, 32 and 33 show quantitative assay data output that is representative of the type of data that can be used to determine the amount of an analyte using such assay methods as described within this example. FIG. 34 shows a standard curve generated from a construct that has been cleaved using a chemical method. It is also understood that while dsDNA was used as a label in this particular example, other labels, such as the label described in Example 5, can also be utilized, including, but not limited to, nanobeads, dendrimers and the like. Moreover, other known labels also can be employed. Such constructs as needed to generate appropriate reagents can be synthesized as described herein, or via methods known to those skilled in the art.

9. Kits and Cartridges

Also provided herein is a kit for use in performing the above-described methods with or without the disclosed device. The kit may include instructions for analyzing the analyte with the disclosed device. Instructions included in the kit may be affixed to packaging material or may be included as a package insert. The instructions may be written or printed materials, but are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, "instructions" may include the address of an internet site that provides the instructions.

The kit may include a cartridge that includes a microfluidics module with a built-in nanopore module, as described above. In some embodiments, the microfluidics and nanopore modules may be separate components for reversible integration together or may be fully or irreversibly integrated in a cartridge. The cartridge may be disposable. The cartridge may include one or more reagents useful for practicing the methods disclosed above. The cartridge may include one or more containers holding the reagents, as one or more separate compositions, or, optionally, as admixture where the compatibility of the reagents will allow. The cartridge may also include other material(s) that may be desirable from a user standpoint, such as buffer(s), a diluent (s), a standard(s) (e.g., calibrators and controls), and/or any other material useful in sample processing, washing, or conducting any other step of the assay. The cartridge may include one or more of the specific binding members described above.

Alternatively or additionally, the kit may comprise a calibrator or control, e.g., purified, and optionally lyophilized analyte of interest or in liquid, gel or other forms on the cartridge or separately, and/or at least one container (e.g., tube, microtiter plates or strips) for use with the device and methods described above, and/or a buffer, such as an assay buffer or a wash buffer, either one of which can be provided as a concentrated solution. In some embodiments, the kit comprises all components, i.e., reagents, standards, buffers, diluents, etc., which are necessary to perform the assay. The instructions also can include instructions for generating a standard curve.

The kit may further comprise reference standards for quantifying the analyte of interest. The reference standards may be employed to establish standard curves for interpolation and/or extrapolation of the analyte of interest concentrations. The kit may include reference standards that vary in terms of concentration level. For example, the kit may include one or more reference standards with either a high concentration level, a medium concentration level, or a low concentration level. In terms of ranges of concentrations for the reference standard, this can be optimized per the assay. Exemplary concentration ranges for the reference standards include but are not limited to, for example: about 10 fg/mL, about 20 fg/mL, about 50 fg/mL, about 75 fg/mL, about 100 fg/mL, about 150 fg/mL, about 200 fg/mL, about 250 fg/mL, about 500 fg/mL, about 750 fg/mL, about 1000 fg/mL, about 10 pg/mL, about 20 pg/mL, about 50 pg/mL, about 75 pg/mL, about 100 pg/mL, about 150 pg/mL, about 200 pg/mL, about 250 pg/mL, about 500 pg/mL, about 750 pg/mL, about 1 ng/mL, about 5 ng/mL, about 10 ng/mL, about 12.5 ng/mL, about 15 ng/mL, about 20 ng/mL, about 25 ng/mL, about 40 ng/mL, about 45 ng/mL, about 50 ng/mL, about 55 ng/mL, about 60 ng/mL, about 75 ng/mL, about 80 ng/mL, about 85 ng/mL, about 90 ng/mL, about 95 ng/mL, about 100 ng/mL, about 125 ng/mL, about 150 ng/mL, about 165 ng/mL, about 175 ng/mL, about 200 ng/mL, about 225 ng/mL, about 250 ng/mL, about 275 ng/mL, about 300 ng/mL, about 400 ng/mL, about 425 ng/mL, about 450 ng/mL, about 465 ng/mL, about 475 ng/mL, about 500 ng/mL, about 525 ng/mL, about 550 ng/mL, about 575 ng/mL, about 600 ng/mL, about 700 ng/mL, about 725 ng/mL, about 750 ng/mL, about 765 ng/mL, about 775 ng/mL, about 800 ng/mL, about 825 ng/mL, about 850 ng/mL, about 875 ng/mL, about 900 ng/mL, about 925 ng/mL, about 950 ng/mL, about 975 ng/mL, about 1000 ng/mL, about 2 pg/mL, about 3 pg/mL, about 4 pg/mL, about 5 pg/mL, about 6 pg/mL, about 7 pg/mL, about 8 pg/mL, about 9 pg/mL, about 10 pg/mL, about 20 pg/mL, about 30 pg/mL, about 40 pg/mL, about 50 pg/mL, about 60 pg/mL, about 70 pg/mL, about 80 pg/mL, about 90 pg/mL, about 100 pg/mL, about 200 pg/mL, about 300 pg/mL, about 400 pg/mL, about 500 pg/mL, about 600 pg/mL, about 700 pg/mL, about 800 pg/mL, about 900 pg/mL, about 1000 pg/mL, about 2000 pg/mL, about 3000 pg/mL, about 4000 pg/mL, about 5000 pg/mL, about 6000 pg/mL, about 7000 pg/mL, about 8000 pg/mL, about 9000 pg/mL, or about 10000 pg/mL.

Any specific binding members, which are provided in the kit may incorporate a tag or label, such as a fluorophore, enzyme, aptamer, dendrimer, bead, nanoparticle, microparticle, polymer, protein, biotin/avidin label, or the like, or the kit can include reagents for labeling the specific binding members or reagents for detecting the specific binding members and/or for labeling the analytes or reagents for detecting the analyte. If desired, the kit can contain one or more different tags or labels. The kit may also include components to elicit cleavage, such as a cleavage mediated reagent. For example, a cleavage mediate reagent may include a reducing agent, such as dithiothreitol (DTT) or tris(2-carboxyethyl)phosphine) TCEP. The specific binding members, calibrators, and/or controls can be provided in separate containers or pre-dispensed into an appropriate assay format or cartridge. The tag may be detected using the disclosed device.

The kit may include one or more specific binding members, for example, to detect one or more target analytes in the sample in a multiplexing assay. The number of different types of specific binding members in the kit may range widely depending on the intended use of the kit. The number of specific binding members in the kit may range from 1 to about 10, or higher. For example, the kit may include 1 to 10 specific binding members, 1 to 9 specific binding members, 1 to 8 specific binding members, 1 to 7 specific binding members, 1 to 6 specific binding members, 1 to 5 specific binding members, 1 to 4 specific binding members, 1 to 3 specific binding members, 1 to 2 specific binding members, 2 to 10 specific binding members, 2 to 9 specific binding members, 2 to 8 specific binding members, 2 to 7 specific binding members, 2 to 6 specific binding members, 2 to 5 specific binding members, 2 to 4 specific binding members, 3 to 10 specific binding members, 3 to 9 specific binding members, 3 to 8 specific binding members, 3 to 7 specific binding members, 3 to 6 specific binding members, 3 to 5 specific binding members, 3 to 4 specific binding members, 4 to 10 specific binding members, 4 to 9 specific binding members, 4 to 8 specific binding members, 4 to 7 specific binding members, 4 to 6 specific binding members, 5 to 10 specific binding members, 5 to 9 specific binding members, 5 to 8 specific binding members, 5 to 7 specific binding members, 5 to 6 specific binding members, 6 to 10 specific binding members, 6 to 9 specific binding members, 6 to 8 specific binding members, 6 to 7 specific binding members, 7 to 10 specific binding members, 7 to 9 specific binding members, 7 to 8 specific binding members, 8 to 10 specific binding members, 8 to 9 specific binding members, or 9 to 10 specific binding members. Each of the one or more specific binding members may bind to a different target analyte and each specific binding member may be labeled with a different tag and/or aptamer. For example, the kit may include a first specific binding member that binds to a first target analyte, a second specific binding member that binds to a second target analyte, a third specific binding member that binds to a third target analyte, etc. and the first specific binding member is labeled with a first tag and/or aptamer, the second specific binding member is labeled with a second tag and/or aptamer, the third specific binding member is labeled with a third tag and/or aptamer, etc. In addition to the one or more specific binding members, the kits may further comprise one or more additional assay components, such as suitable buffer media, and the like. The kits may also include a device for detecting and measuring the tag and/or an aptamer, such as those described supra. Finally, the kits may comprise instructions for using the specific binding members in methods of analyte detection according to the subject invention, where these instructions for use may be present on the kit packaging and/or on a package insert.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components. One or more of the components may be in liquid form.

The various components of the kit optionally are provided in suitable containers as necessary. The kit further can include containers for holding or storing a sample (e.g., a container or cartridge for a urine, saliva, plasma, cerebrospinal fluid, or serum sample, or appropriate container for storing, transporting or processing tissue so as to create a tissue aspirate). Where appropriate, the kit optionally also can contain reaction vessels, mixing vessels, and other components that facilitate the preparation of reagents or the test sample. The kit can also include one or more sample collection/acquisition instruments for assisting with obtaining a test sample, such as various blood collection/transfer devices such as microsampling devices, micro-needles, or other minimally invasive pain-free blood collection methods; blood collection tube(s); lancets; capillary blood collection tubes; other single fingertip-prick blood collection methods; buccal swabs, nasal/throat swabs; 16-gauge or other size needle, circular blade for punch biopsy (e.g., 1-8 mm, or other appropriate size), surgical knife or laser (e.g., particularly hand-held), syringes, sterile container, or canula, for obtaining, storing or aspirating tissue samples; or the like. The kit can include one or more instruments for assisting with joint aspiration, cone biopsies, punch biopsies, fine-needle aspiration biopsies, image-guided percutaneous needle aspiration biopsy, bronchoaveolar lavage, endoscopic biopsies, and laproscopic biopsies.

If the tag or detectable label is or includes at least one acridinium compound, the kit can comprise at least one acridinium-9-carboxamide, at least one acridinium-9-carboxylate aryl ester, or any combination thereof. If the tag or detectable label is or includes at least one acridinium compound, the kit also can comprise a source of hydrogen peroxide, such as a buffer, solution, and/or at least one basic solution. If desired, the kit can contain a solid phase, such as a magnetic particle, bead, membrane, scaffolding molecule, film, filter paper, disc, or chip.

If desired, the kit can further comprise one or more components, alone or in further combination with instructions, for assaying the test sample for another analyte, which can be a biomarker, such as a biomarker of a disease state or disorder, such as infectious disease, cardiac disease, metabolic disease, thyroid disease, etc.

The present invention has multiple aspects, illustrated by the following non-limiting examples.

10. Examples

Example 1

Synthesis of Photocleavable 2-Nitrobenzyl Succinimidyl/Maleimidyl Bifunctional Linker Synthesis of Compound 2.

Synthesis of the photocleavable sulfosuccinimidyl/maleimidyl linker is derived from Agasti, et al., *J. Am. Chem. Soc.*, 134(45), 18499-18502, 2012. Briefly, starting material 4-[4-(1-hydroxyethyl)-2-methoxy-5-nitrophenoxy]butyric acid (0.334 mmol) is dissolved in dry dichloromethane (DCM) under argon atmosphere. The flask is cooled to 0° C. by placing it in an ice bath. Compound 2-(1H-benzotriazole-1-yl)-1,1,3,3-tetramethyluronium hexafluorophosphate (HBTU) (0.368 mmol) and trimethylamine (TEA) (0.835 mmol) are added to the solution. The reaction mixture is stirred at 0° C. for 5 min and subsequently N-(2-aminoethyl) maleimide trifluoroacetate salt (0.368 mmol) is added. After stirring at 0° C. for 15 min, the reaction mixture is allowed to rise to room temperature (RT) and further stirred for 18 h. After dilution of the reaction mixture with DCM (45 ml), the organic phase is washed with water (2×), saturated NaCl solution (1×) and dried over sodium sulfate. The organic layer is concentrated under reduced pressure and purified by flash chromatography using a $SiO_2$ column (eluent: 100% DCM to 3% methanol in DCM, v/v). Compound 1 (0.024 mmol) is dissolved in anhydrous dimethylformamide (1 ml).

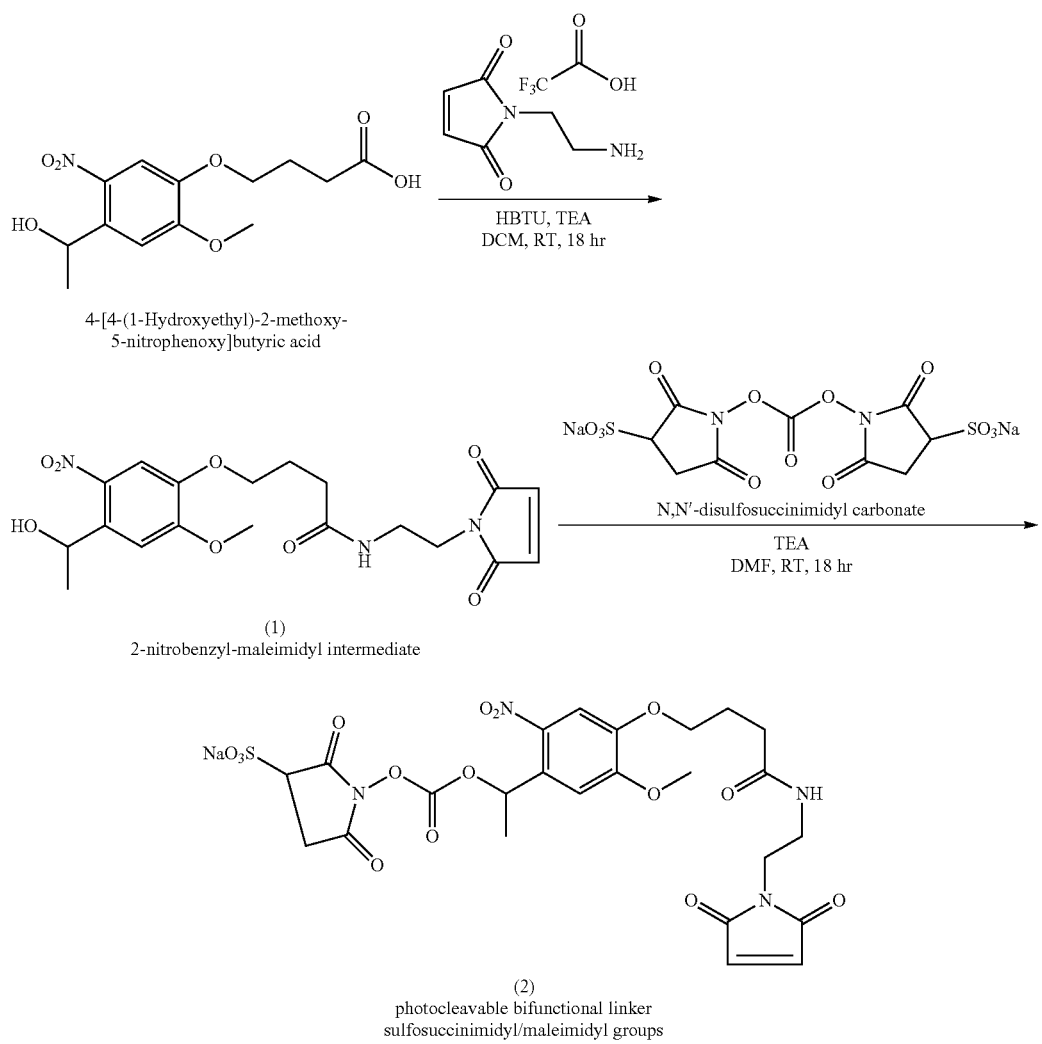

*In the above synthesis DMF is dimethylformamide.

N,N'-disulfosuccinimidyl carbonate (DSC) (0.071 mmol) and TEA (0.096 mmol) are successively added to the solution. The reaction mixture is stirred at RT for 18 h. The reaction mixture is purified by directly loading onto a C18 reverse phase column (eluent: 5% acetonitrile in water to 95% acetonitrile in water, v/v). Starting material and other chemicals used for the synthesis may be purchased from Sigma-Aldrich.

Example 2

Synthesis of Photocleavable Sulfosuccinimidyl/DBCO 2-Nitrobenzyl Bifunctional Linker by placing it in an ice bath. Compound 2-(1H-benzotriazole-1-yl)-1,1,3,3-tetramethyluronium hexafluorophosphate (HBTU) (0.368 mmol) and trimethylamine (TEA) (0.835 mmol) are added to the solution. The reaction mixture is stirred at 0° C. for 5 min and subsequently DBCO-amine (0.368 mmol) is added. After stirring at 0° C. for 15 min, the reaction mixture is allowed to rise to RT and further stirred for 18 h. After dilution of the reaction mixture with DCM (45 ml), the organic phase is washed with water (2×), saturated NaCl solution (1×) and dried over sodium sulfate. The organic layer is concentrated under reduced pressure and purified by flash chromatography using a SiO$_2$ column (eluent: 100% DCM to 3% methanol in DCM, v/v). Compound 3 (0.024 mmol) is dissolved in anhydrous dimethylformamide (1 ml). N,N'-disulfosuccinimidyl carbonate

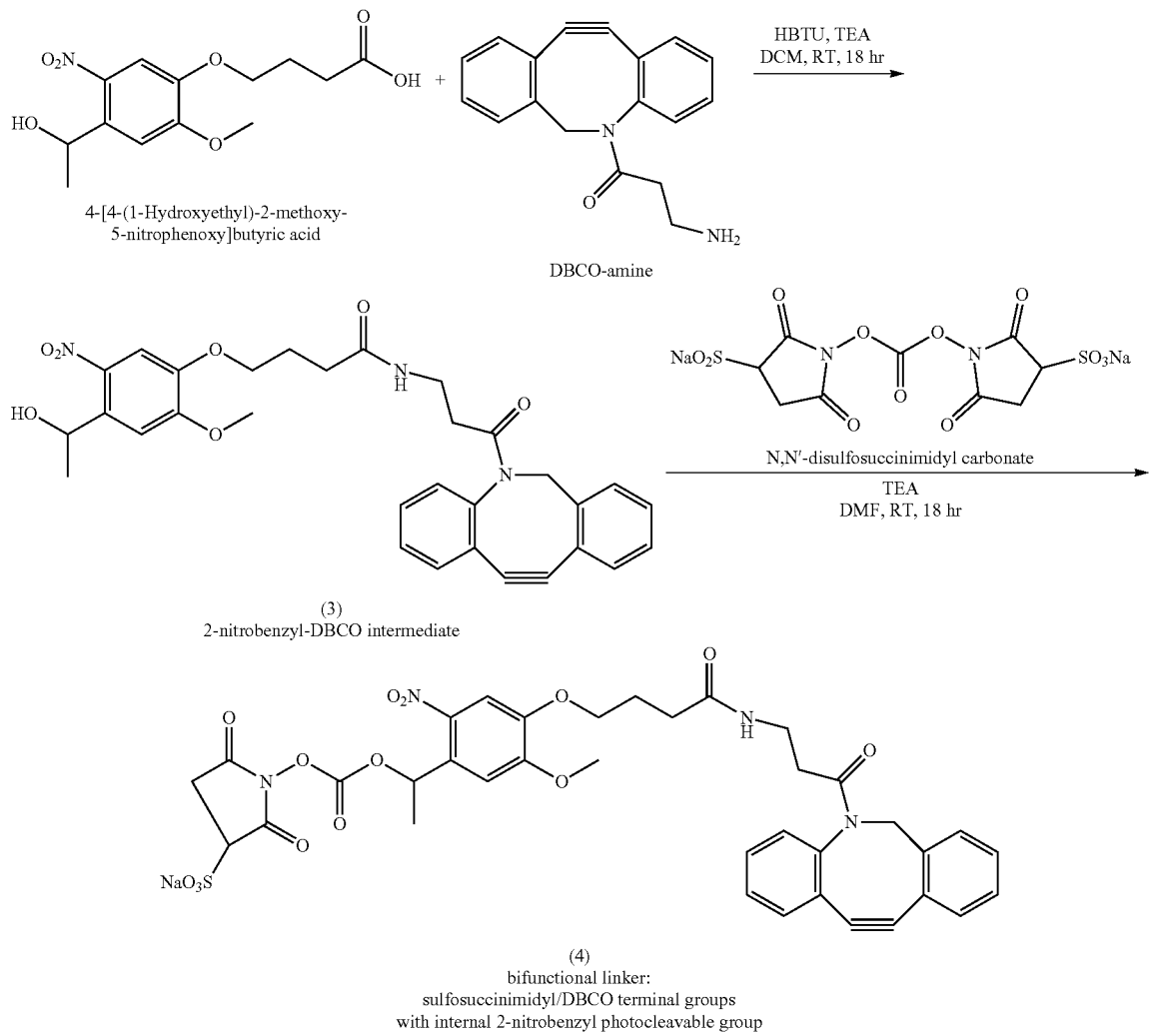

*In the above synthesis DMF is dimethylformamide.

Synthesis of Compound 4.

Synthesis of the photocleavable sulfosuccinimidyl/dibenzocyclooctyl (DBCO) alkynyl linker is derived from a similar procedure described in Agasti, et al., *J. Am. Chem. Soc.*, 134(45), 18499-18502, 2012. Briefly, starting material 4-[4-(1-hydroxyethyl)-2-methoxy-5-nitrophenoxy]butyric acid (0.334 mmol) is dissolved in dry dichloromethane (DCM) under argon atmosphere. The flask is cooled to 0° C. (DSC) (0.071 mmol) and TEA (0.096 mmol) are successively added to the solution. The reaction mixture is stirred at RT for 18 h. The reaction mixture is purified by directly loading onto a C18 reverse phase column (eluent: 5% acetonitrile in water to 95% acetonitrile in water, v/v). Starting material and other chemicals used for the synthesis may be purchased from Sigma-Aldrich.

Example 3

Coupling and Photochemical Cleavage of Antibody-DNA Conjugate Using Sulfosuccinimidyl/Maleimidyl 2-Nitrobenzyl Bifunctional Linker Bioconjugation and Cleavage of Antibody and DNA.

DNA molecules may be conjugated to antibodies using the following scheme. DNA may be thiolated at the 5' terminus by replicating a DNA sequence in a PCR reaction using two PCR primers where one or both primers are labeled with a 5'-thiol group. Labeled DNA (100 μM final concentration) is dissolved in 50 mM HEPES (pH=7.0) with stirring. Compound 2 (2 mM) is added and the reaction is allowed to proceed at RT for 2 hours. After coupling, excess unreacted maleimide groups are quenched with excess dithiothreitol (DTT). The conjugate is purified on a gel filtration column (Sephadex G-25) or by extensive dialysis at 4° C. in an appropriate conjugate storage buffer. Purified DNA-succinimidyl linker (50 μM final concentration) is dissolved in 100 mM PBS (pH=7.5) with stirring. Native antibody (50 μM final concentration) is added and the reaction is allowed to proceed at RT for 2 hours. The Ab-DNA conjugate is purified using a Sephadex column (Sephadex G25) operated with 100 mM PBS, pH 7.5, or BioGel P-30 gel filtration media.

The conjugate may be cleaved prior to nanopore detection by illuminating with a UV lamp at 365 nm. This example may also be used on DNA dendrimers using the same bioconjugation chemistry.

Example 4

Coupling and Photochemical Cleavage of Antibody-DNA Conjugate Using Sulfosuccinimidyl/DBCO 2-Nitrobenzyl Bifunctional Linker Bioconjugation and Cleavage of Antibody and DNA.

DNA molecules may be conjugated to antibodies using the following scheme. DNA may be aminated at the 5' terminus by replicating a DNA sequence in a PCR reaction using two PCR primers where one or both primers are labeled with a 5'-amine group. Labeled DNA (100 μM final concentration) is dissolved in 100 mM PBS (pH=7.5) with stirring. Compound 4 (2 mM final concentration) is added and the reaction is allowed to proceed at RT for 2 hours. The DNA-DBCO linker is purified on a gel filtration column (Sephadex G-25) or by extensive dialysis at 4° C. in an appropriate conjugate storage buffer. Purified DNA-DBCO linker (50 μM final concentration) is dissolved in 50 mM Tris (pH=7.0) with stirring. Copper-free Click chemistry is used to couple the DNA-DBCO linker to the antibody. Azido-labeled antibody (Kazane et al., *Proc. Natl. Acad. Sci.*, 109(10), 3731-3736, 2012) (25 μM final concentration) is added and the reaction is allowed to proceed at RT for 6-12 hours. The Ab-DNA conjugate is purified using a Sephadex column (Sephadex G25) operated with 100 mM PBS, pH 7.5, or BioGel P-30 gel filtration media.

The conjugate may be cleaved prior to nanopore detection by illuminating with a UV lamp at 365 nm. This example may also be used on DNA dendrimers using the same bioconjugation chemistry.

Example 5

Nanoparticle-Antibody Conjugates for Digital Immunoassays (Nanopore Counting)

This example describes covalent conjugation of an antibody to 26 nm carboxylated polystyrene nanoparticles (NP, PC02N), such as those which can be obtained from Bangs Labs (Fishers, Ind., USA). The 26 nm NPs have a surface charge of 528.7 μeq/g and a parking area of 68.4 sq·Å/group (per manufacturer information).

Activation of Carboxyl-Polystyrene Nanoparticles:

1.0 mL (100 mg/mL) of 26 nm carboxylated-NP is washed with 10 mL of 0.1M MES (2-[N-morpholino]ethane sulfonic acid, pH 4.5-5.0. After the wash, the pellets are resuspended in 100 mL of 0.1M MES pH 4.5-5.0 for a 1.0 mg/mL NP concentration (0.1% solids). 10.0 mL nanoparticle suspension (10 mg NP, 5.28 μeq carboxyl) is transferred to a vial and reacted with 10 μL (5.28 μmoles, 1.0 equiv/ $CO_2H$ eq) of a freshly prepared 10 mg/mL EDC solution in water (1-Ethyl-3-[3-dimethylaminopropyl]carbodiimide hydrochloride) and 17 μL (7.93 μmoles, 1.5 equiv/1 equiv EDC) of a 10 mg/mL solution of sulfo-NHS solution in water (N-hydroxysulfosuccinimide, Sigma, Cat #56485) at room temperature for 15 min with continuous mixing. The reacted suspension is centrifuged at 6,500 g and the solution is discarded. The pellet is washed with 20 mL of 20 mM PBS/5 mM EDTA pH 7.5 and spun down by centrifugation at 6,500 g. The supernatant is removed. The succinimide-activated carboxyl-NP pellet is resuspended in 50 mM PBS pH 7.5 and 9.8 μL (52.8 nmoles, 0.01 equiv/1 $CO_2H$ eq) of a 1.0 mg/mL pyridine dithioethylarine solution in water is immediately added and allowed to react with continuous stirring for 2-4 h at room temperature. The pyridyl-derivatized carboxyl-NP is washed with 10 mL of 20 mM PBS/5 mM EDTA pH 7.5 and resuspended in 10.0 mL of the same buffer. The nanoparticle concentration is determined using UV-Vis spectroscopy (600 nm, scatter) using a carboxyl-NP calibration curve. Pyridyl-ligand loading on the NP is determined by reducing a defined amount of NP with 10 mM TCEP or DTT, removing the reducing agent by centrifugation, resuspending the pyridyl-activated NP pellet in PBS/EDTA pH 7.2 and reacting with the Ellman reagent (measure A412 of the supemrnatant). The activated NP is stored at 4° C. if not used on the same day for antibody conjugation.

A range of EDC/NHS and pyridine dithioethyl amine molar inputs are evaluated to determine the desired stoichiometry for preparing distinct antibody-nanoparticle conjugates. Reaction parameters (pH, temperature, time) are assessed to achieve the desired NP activation outcome.

Antibody Reduction:

1.0 mL of a 10 mg/mL antibody solution (10 mg) is mixed well with 38 μL of a freshly prepared 30 mg/mL 2-MEA solution (10 mM reaction concentration) (2-mercaptoethylamine hydrochloride), then capped and placed at 37° C. for 90 min. The solution is brought to room temperature and the excess 2-MEA is removed with a desalting column, pre-equilibrated in 20 mM PBS/5 mM EDTA pH 7.5. The concentration of the reduced antibody is determine using UV-Vis absorbance at A280 (protein absorbance) and A320 (scatter correction). The number of free thiols is determined using the Ellman test. The conditions are optimized as needed to generate 2 or 4 free thiols (Cys in the antibody hinge region). The reduced antibody is used immediately for coupling to pyridyl-derivatized carboxyl-NP.

Coupling of reduced antibody to activated-nanoparticle:

Assumptions made: (1) antibody parking area is 45 nm$^2$; (2) 26 nm nanoparticle surface area is 2,120 nmn$^2$; (3) 47 antibody molecules theoretically fit on the surface of a 26 nm NP.

Procedure:

To 10 mL (10 mg) of a 0.1% solution of pyridyl-activated carboxy-nanoparticles in 20 nmM PBSi5 mM EDTA (pH 7.5), 0.10 mg (0.66 nmoles, 0.10 mL) of the reduced antibody is added at 1.0 mg/mL in the same EDTA containing buffer. The mixture is allowed to react at room temperature with mixing for 2 h, centrifuged to remove unbound molecules, and aspirated. The pellet is washed with 10 mL of PBS pH 7.2, centrifuged, and aspirated. The antibody-NP conjugate is suspended in 10.0 mL of PBS pH 7.2. The conjugate NP concentration (% solids) is determined using UV-Vis spectroscopy (600 nm). The particle conjugate is examined by SEM and the size/charge distribution is determined using the ZetaSizer. Size exclusion chromatography can be used to isolate distinct conjugates from a potential distribution of conjugate population. Antibody-to-NP incorporation ratio can be determined by flow cytometry using fluorescently labelled antigen conjugate or using a Micro BCA (uBCA) assay. A range of antibody-to-NP molar inputs can be evaluated, along with conjugation temperature and pH to generate a homogenous population of distinct conjugates (i.e., NP incorporation ratio of 2 or 4).

Nanopore Counting Immunoassay

The scheme above illustrates the nanopore counting assay utilizing the reduced antibody-activated nanoparticle conjugate whose preparation is described above. The immune complex formed in the course of the immunoassay can be cleaved by reduction of the disulfide bond linker to form the free antibody-analyte-antibody complex and free nanoparticle tag, which permits the nanoparticle tag to be counted upon passage through the nanopore.

Example 6

Synthesis of CPSP Conjugates

A. CPSP Antibody Conjugate.

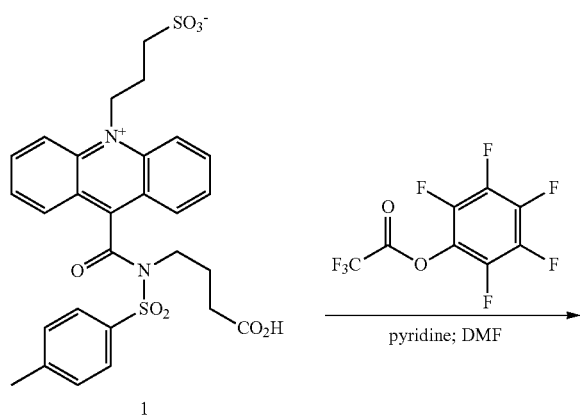

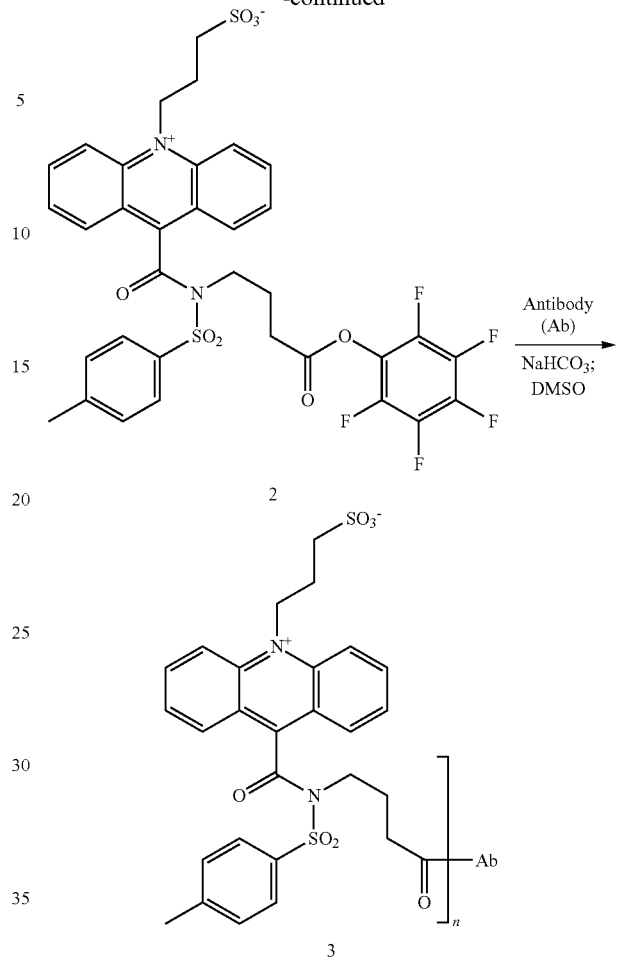

*In the above synthesis DMF is dimethylformamide.

3-(9-((4-Oxo-4-(perfluorophenoxy)butyl)(tosyl)carbamoyl)acridin-10-ium-10-yl)propane-1-sulfonate (2)

A 25 mL round bottom flask equipped with a magnetic stirrer and a nitrogen inlet was charged with 3-(9-((3-carboxypropyl)(tosyl)carbamoyl)acridin-10-ium-10-yl)propane-1-sulfonate (CPSP) (1) (1 mmol), pyridine (5 mmol) and dimethylformamide (10 mL). The solution was cooled in an ice bath and pentafluorophenyl trifluoroacetate (1.3 mmol) was added dropwise. The ice bath was removed and the reaction was stirred at room temperature for 3 hours. The volatile components were removed from the reaction in vacuo and the residue was taken up in methanol and purified by reverse phase HPLC to give the title compound.

CPSP Antibody Conjugate (3):

A solution of 2 (1 µL of a 10 mM solution in DMSO) was added to an antibody solution (100 µL of a 10 µM solution in water) and aqueous sodium bicarbonate (10 µL of a 1M solution). The resulting mixture was stirred at room temperature for 4 hours. Purification of the product was achieved on a spin column to give the CPSP antibody conjugate 3. The value of "n" varies in an antibody-dependent fashion. The incorporation can be controlled to some extent by raising or lowering the active ester concentration (i.e., compounds 2, 5, 9 and 13) and/or by raising or lowering the pH during the reaction, but always results in a distribution of incorporation values. The average incorporation ration ("I.R.") is determined experimentally after the reaction. Typically, "n" is any value between 1 and 10.

B. CPSP Antibody Conjugate with Spacer.
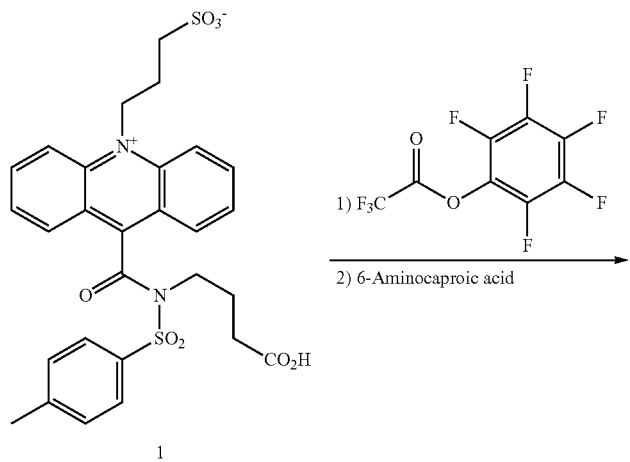
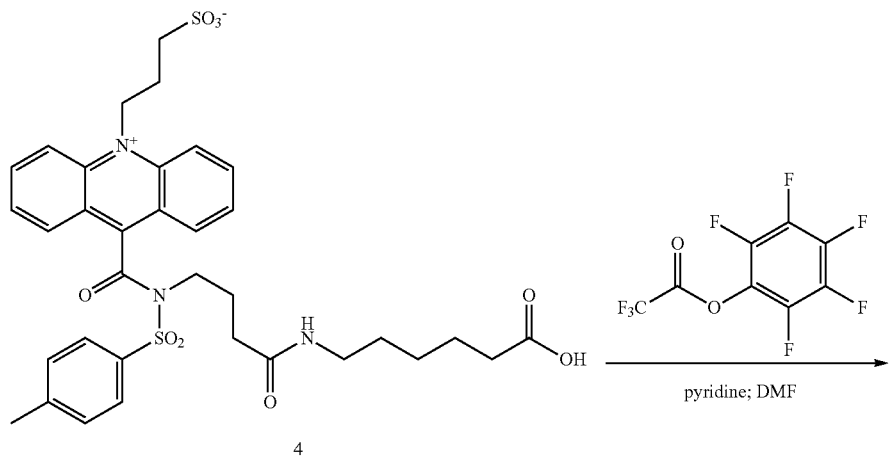
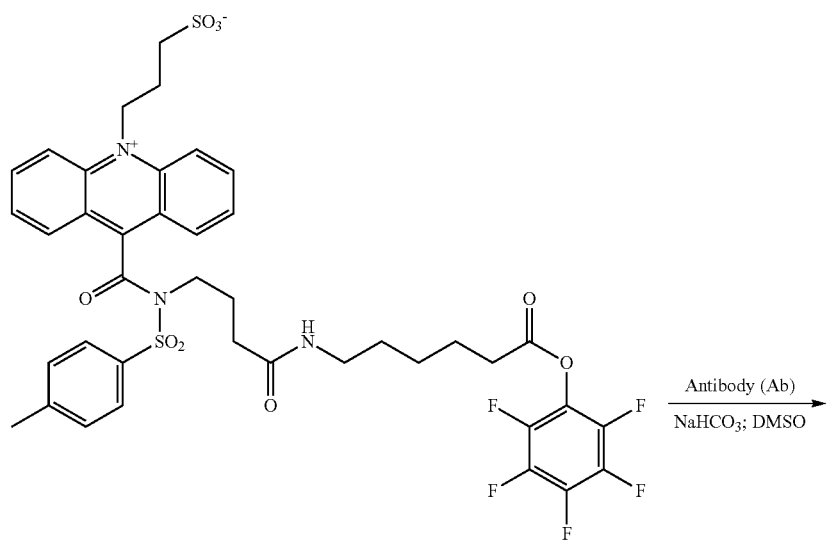

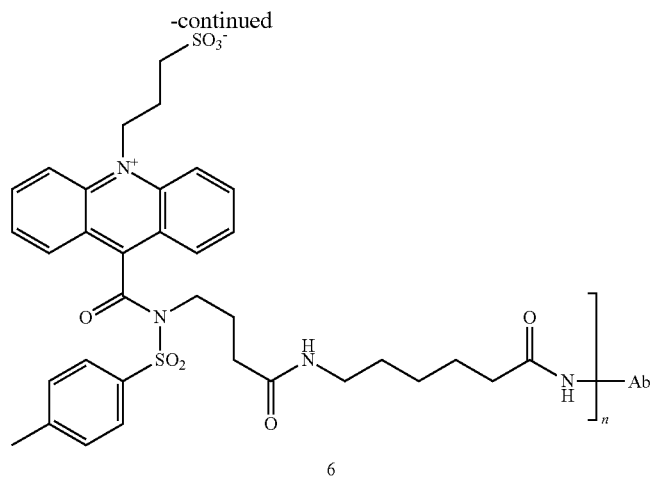

6

*In the above synthesis DMF is dimethylformamide.

3-(9-((4-((5-Carboxypentyl)amino)-4-oxobutyl)(tosyl)carbamoyl)acridin-10-ium-10-yl)propane-1-sulfonate (4)

A 25 mL round bottom flask equipped with a magnetic stirrer and a nitrogen inlet was charged with 3-(9-((3-carboxypropyl)(tosyl)carbamoyl)acridin-10-ium-10-yl)propane-1-sulfonate CPSP (1) (1 mmol), pyridine (5 mmol) and dimethylformamide (10 mL). The solution was cooled in an ice bath and pentafluorophenyl trifluoroacetate (1.3 mmol) was added dropwise. The ice bath was removed and the reaction was stirred at room temperature for 3 hours. 6-Aminocaproic acid (1.3 mmol) was then added to the reaction in small portions followed by N,N-diisopropylethylamine (5 mmol), and the reaction was stirred for 1 hour at room temperature. After this time, the volatile components were removed from the reaction in vacuo and the residue was purified by reverse phase HPLC to give the title compound.

3-(9-((4-Oxo-4-((6-oxo-6-(perfluorophenoxy)hexyl)amino)butyl)(tosyl)carbamoyl) acridin-10-ium-10-yl)propane-1-sulfonate (5)

A 25 mL round bottom flask equipped with a magnetic stirrer and a nitrogen inlet was charged with 4 (1 mmol), pyridine (5 mmol) and dimethylformamide (10 mL). The solution was cooled in an ice bath and pentafluorophenyl trifluoroacetate (1.3 mmol) was added dropwise. The ice bath was removed and the reaction was stirred at room temperature for 3 hours. After this time, the volatile components were removed from the reaction under a stream of nitrogen and the residue was purified by reverse phase HPLC to give the title compound.

CPSP Antibody Conjugate with Spacer (6):

A solution of 5 (1 μL of a 10 mM solution in DMSO) was added to an antibody solution (100 μL of a 10 μM solution in water) and aqueous sodium bicarbonate (10 μL of a 1M solution). The resulting mixture was stirred at room temperature for 4 hours. Purification of the product was achieved on a spin column to give the CPSP antibody conjugate with spacer 6. Typically, "n" is any value between 1 and 10.

C. CPSP Oligonucleotide-Antibody Conjugate.

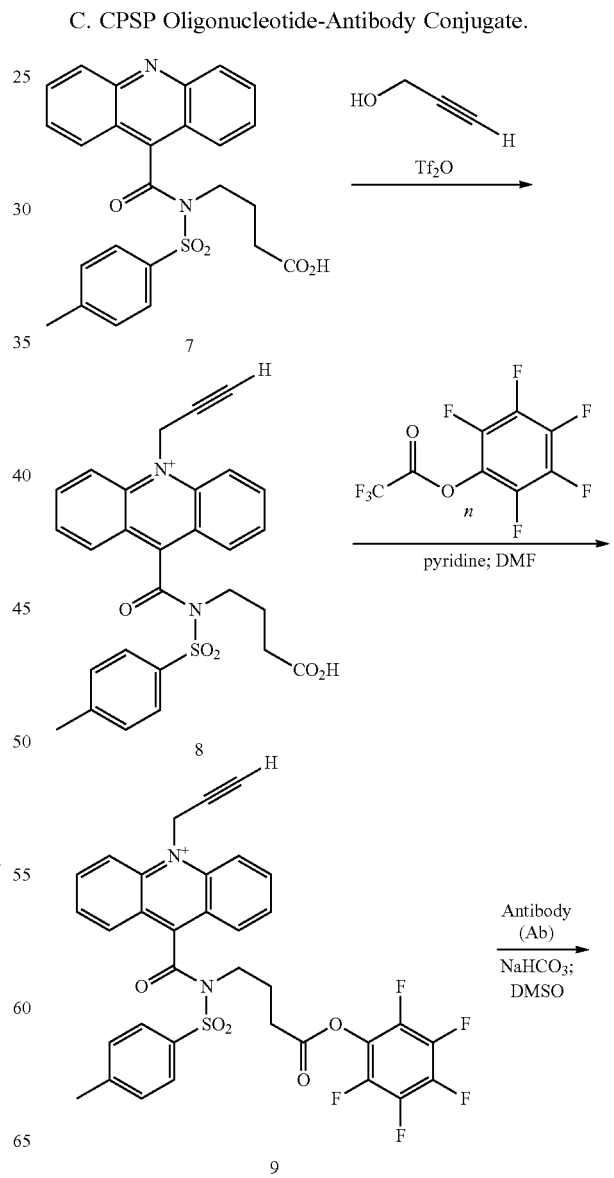

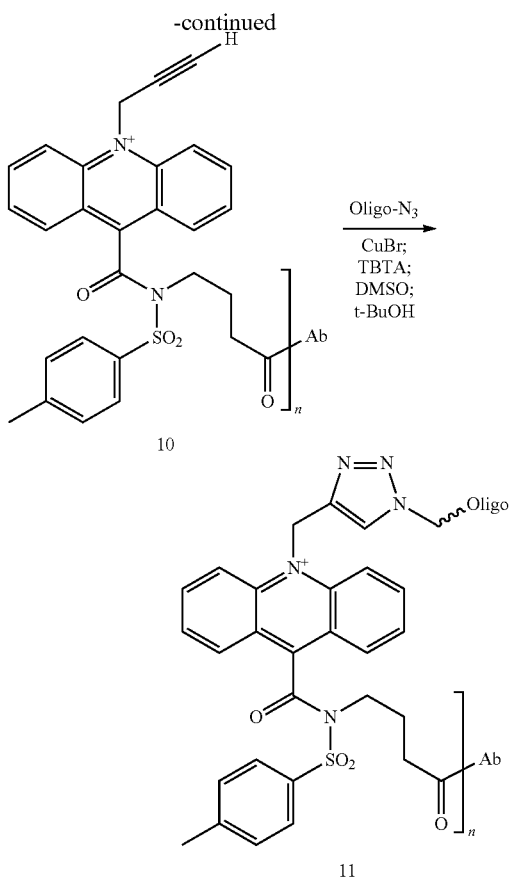

*In the above synthesis DMF is dimethylformamide.

9-((3-Carboxypropyl)(tosyl)carbamoyl)-10-(prop-2-yn-1-yl)acridin-10-ium (8)

A 100 mL round bottom flask equipped with a magnetic stirrer and a nitrogen inlet was charged with propargyl alcohol (10 mmol), 2,6-di-tert-butylpyridine (10 mmol) and methylene chloride (50 mL) and cooled to −20° C. Triflic anhydride was then added dropwise to the solution and the reaction was stirred for 2 hours at −20° C. Pentane (25 mL) was added to the reaction and the resulting precipitated salts were separated by filtration. The volatile components were evaporated in vacuo and the residue was redissolved in methylene chloride (25 mL) in a 100 mL round bottom flask. 4-(N-Tosylacridine-9-carboxamido)butanoic acid (CP-acridine) (7) (1 mmol) was added in small portions and the reaction was stirred at room temperature for 18 hours. The volatile components were evaporated in vacuo and the residue was taken up in methanol (5 mL) and purified by reverse phase HPLC to give the title compound.

9-((4-oxo-4-(perfluorophenoxy)butyl)(tosyl)carbamoyl)-10-(prop-2-yn-1-yl)acridin-10-ium (9)

A 25 mL round bottom flask equipped with a magnetic stirrer and a nitrogen inlet was charged with 8 (1 mmol), pyridine (5 mmol) and dimethylformamide (10 mL). The solution was cooled in an ice bath and pentafluorophenyl trifluoroacetate (1.3 mmol) was added dropwise. The ice bath was removed and the reaction was stirred at room temperature for 3 hours. The volatile components were removed from the reaction in vacuo and the residue was taken up in methanol and purified by reverse phase HPLC to give the title compound.

CPSP Antibody Conjugate (10):

A solution of 9 (1 μL of a 10 mM solution in DMSO) was added to an antibody solution (100 μL of a 10 μM solution in water) and aqueous sodium bicarbonate (10 μL of a 1M solution). The resulting mixture was stirred at room temperature for 4 hours. Purification of the product was achieved on a spin column to give the CPSP antibody conjugate 10. Typically, "n" is any value between 1 and 10.

CPSP Oligonucleotide-Antibody Conjugate (11):

A mixture of an oligoazide (10 nmol in 5 μL water), CPSP antibody conjugate 10 (10 nmol in 10 μL water) and a freshly prepared 0.1 M "click solution" (3 μL-see below) was shaken at room temperature for 4 hours. The reaction was diluted with 0.3M sodium acetate (100 μL) and the DNA conjugate was precipitated by adding EtOH (1 mL). The supernatant was removed and the residue was washed 2×with cold EtOH (2×1 mL). The residue was taken up in water (20 μL) and the solution of the CPSP oligonucleotide-antibody conjugate 11 was used without further purification. Typically, "n" is any value between 1 and 10.

"Click Solution":

CuBr (1 mg) was dissolved in 70 μL DMSO/t-BuOH 3:1 to form a 0.1 M solution. (This solution must be freshly prepared and cannot be stored.) Tris(benzyltriazolylmethyl)amine (TBTA) (54 mg) was dissolved in 1 mL DMSO/t-BuOH 3:1 to form a 0.1 M solution. (This solution can be stored at −20° C.) 1 volume of the 0.1 M CuBr solution was added to 2 volumes of the 0.1 M TBTA solution to provide a "click solution."

D. CPSP Oligonucleotide-Antibody Conjugate with Spacer.

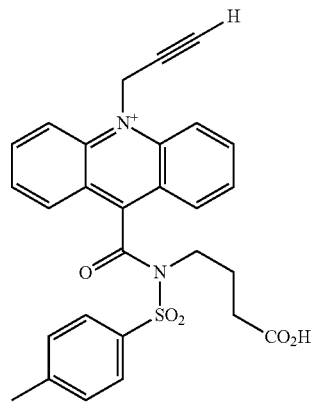

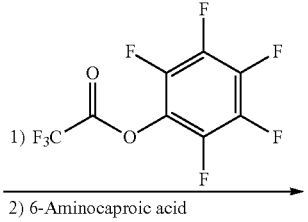

1) $F_3C\overset{O}{-}O\text{-}C_6F_5$ 2) 6-Aminocaproic acid

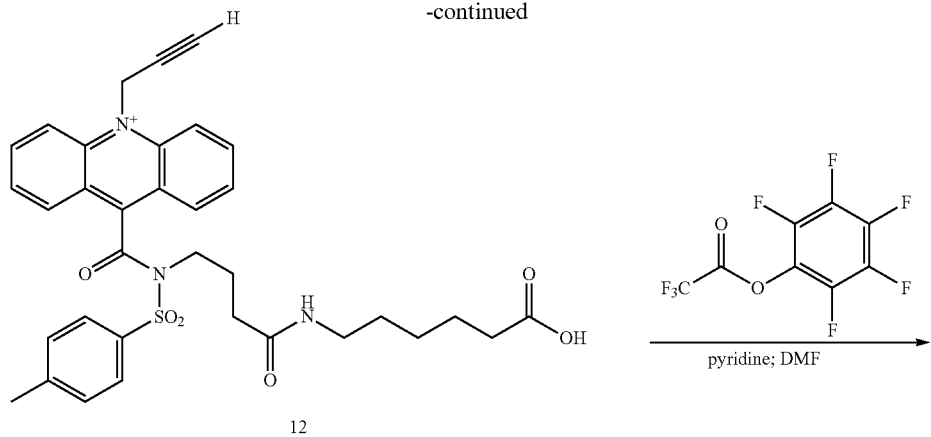
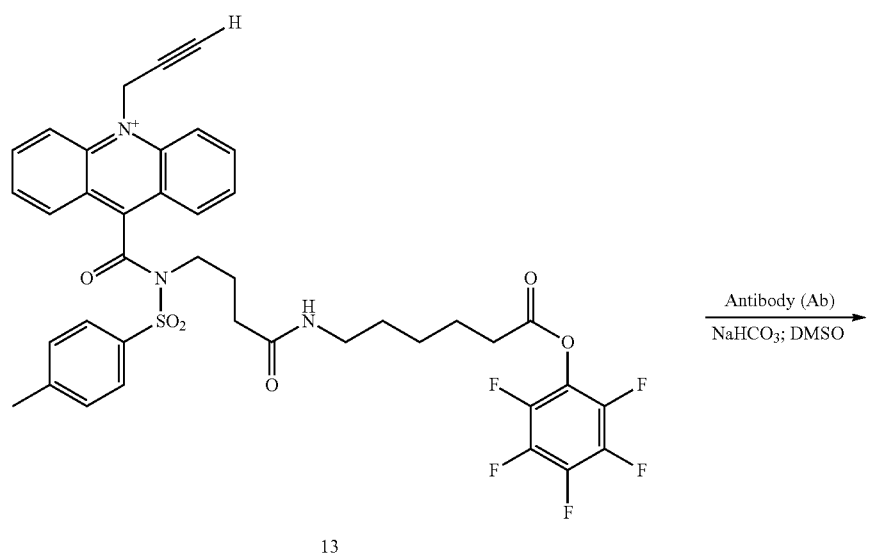
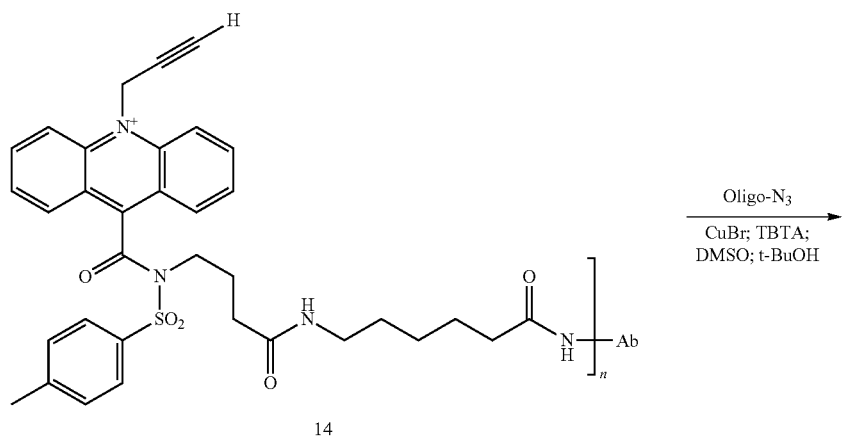

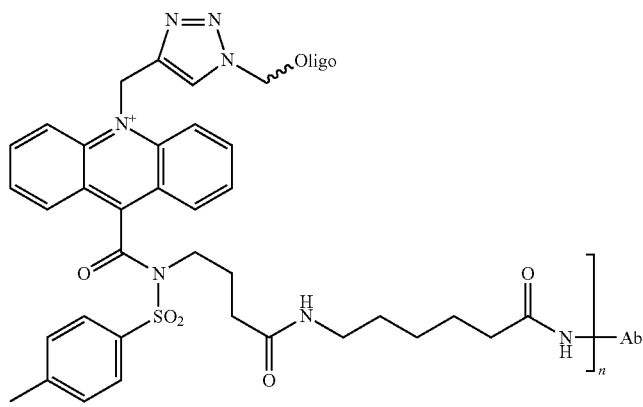

15

*In the above synthesis DMF is dimethylformamide.

9-((4-((5-carboxypentyl)amino)-4-oxobutyl)(tosyl)carbamoyl)-10-(prop-2-yn-1-yl)acridin-10-ium (12)

A 25 mL round bottom flask equipped with a magnetic stirrer and a nitrogen inlet was charged with 8 (1 mmol), pyridine (5 mmol) and dimethylformamide (10 mL). The solution was cooled in an ice bath and pentafluorophenyl trifluoroacetate (1.3 mmol) was added dropwise. The ice bath was removed and the reaction was stirred at room temperature for 3 hours. 6-Aminocaproic acid (1.3 mmol) was then added to the reaction in small portions followed by N,N-diisopropylethylamine (5 mmol), and the reaction was stirred for 1 hour at room temperature. After this time, the volatile components were removed from the reaction in vacuo and the residue was purified by reverse phase HPLC to give the title compound.

9-((4-oxo-4-((6-oxo-6-(perfluorophenoxy)hexyl)amino)butyl)(tosyl)carbamoyl)-10-(prop-2-yn-1-yl)acridin-10-ium (13)

A 25 mL round bottom flask equipped with a magnetic stirrer and a nitrogen inlet was charged with 12 (1 mmol), pyridine (5 mmol) and dimethylformamide (10 mL). The solution was cooled in an ice bath and pentafluorophenyl trifluoroacetate (1.3 mmol) was added dropwise. The ice bath was removed and the reaction was stirred at room temperature for 3 hours. After this time, the volatile components were removed from the reaction under a stream of nitrogen and the residue was purified by reverse phase HPLC to give the title compound.

CPSP Antibody Conjugate with Spacer (14):

A solution of 13 (1 μL of a 10 mM solution in DMSO) was added to an antibody solution (100 μL of a 10 μM solution in water) and aqueous sodium bicarbonate (10 μL of a 1M solution). This was stirred at room temperature for 4 hours. Purification of the product was achieved on a spin column to give the CPSP antibody conjugate with spacer 14. Typically, "n" is any value between 1 and 10.

CPSP Oligonucleotide-Antibody Conjugate (15):

A mixture of an oligoazide (e.g., such as is commercially available) (10 nmol in 5 μL water), CPSP antibody conjugate with spacer 14 (10 nmol in 10 μL water) and a freshly prepared 0.1 M "click solution" (3 μL-see Example 6.C) was shaken at room temperature for 4 hours. Typically, "n" is any value between 1 and 10. The reaction was diluted with 0.3M sodium acetate (100 μL) and the DNA conjugate was precipitated by adding EtOH (1 mL). The supernatant was removed and the residue was washed 2× with cold EtOH (2×1 mL). The residue was taken up in water (20 L) and the solution of the CPSP oligonucleotide-antibody conjugate with spacer 15 was used without further purification.

Cleavage of CPSP Antibody Conjugates with or without Spacer and CPSP Oligonucleotide-Antibody Conjugate with or without Spacer.

The CPSP antibody conjugates with or without spacer and CPSP oligonucleotide-antibody conjugate with or without spacer, as described, are cleaved or "triggered" using a basic hydrogen peroxide solution. In the ARCHITECT® system, the excited state acridone intermediate produces a photon, which is measured. In addition, the cleavage products are an acridone and a sulfonamide. The conjugates of Examples 6.A-D are used with the disclosed device by counting the acridone and/or sulfonamide molecules.

E. CPSP Oligonucleotide Conjugate with no Antibody.

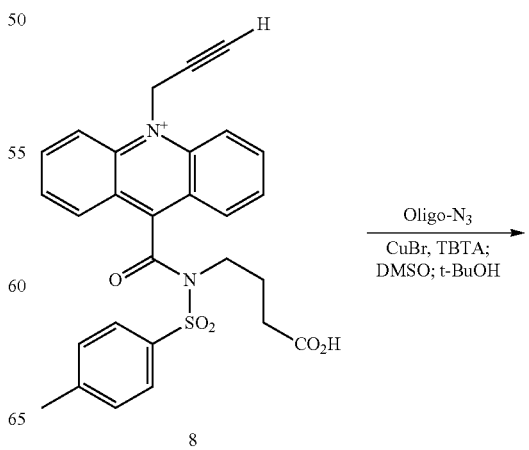

8

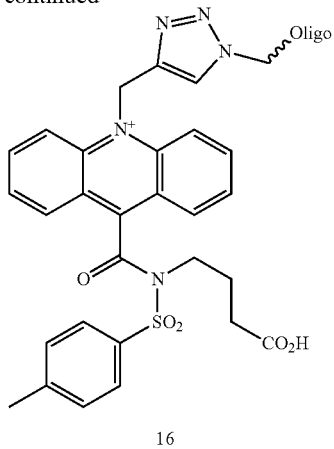

16

CPSP Oligonucleotide Conjugate with No Antibody (16):

A mixture of an oligoazide (e.g., such as is commercially available) (10 nmol in 5 μL water), propargyl-CPSP 8 (10 nmol in 10 μL water) and a freshly prepared 0.1 M "click solution" (3 μL—see Example 6.C) can be shaken at room temperature for 4 hours. The reaction can be diluted with 0.3M sodium acetate (100 μL) and the DNA conjugate precipitated by adding EtOH (1 mL). The supernatant can be removed and the residue washed 2× with cold EtOH (2×1 mL). The residue can be taken up in water (20 μL) and the solution of the CPSP oligonucleotide-antibody conjugate with spacer 16 can be used without further purification.

Example 7

Fabrication of Low-Cost DMF Bottom Chip

Figure 10:
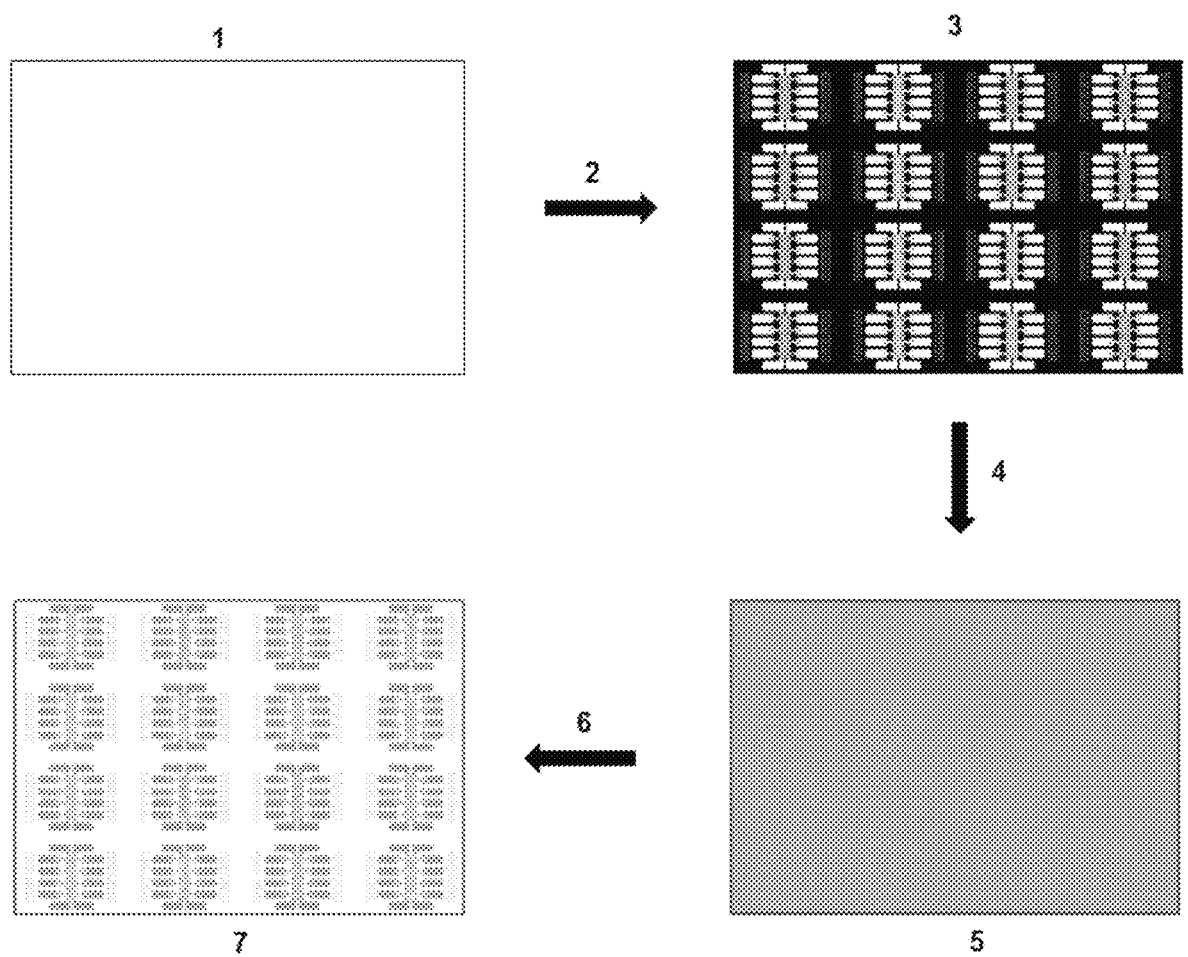
FIG. 10 depicts a schematic of a fabrication process of a low-cost DMF chip.
Figure 11:
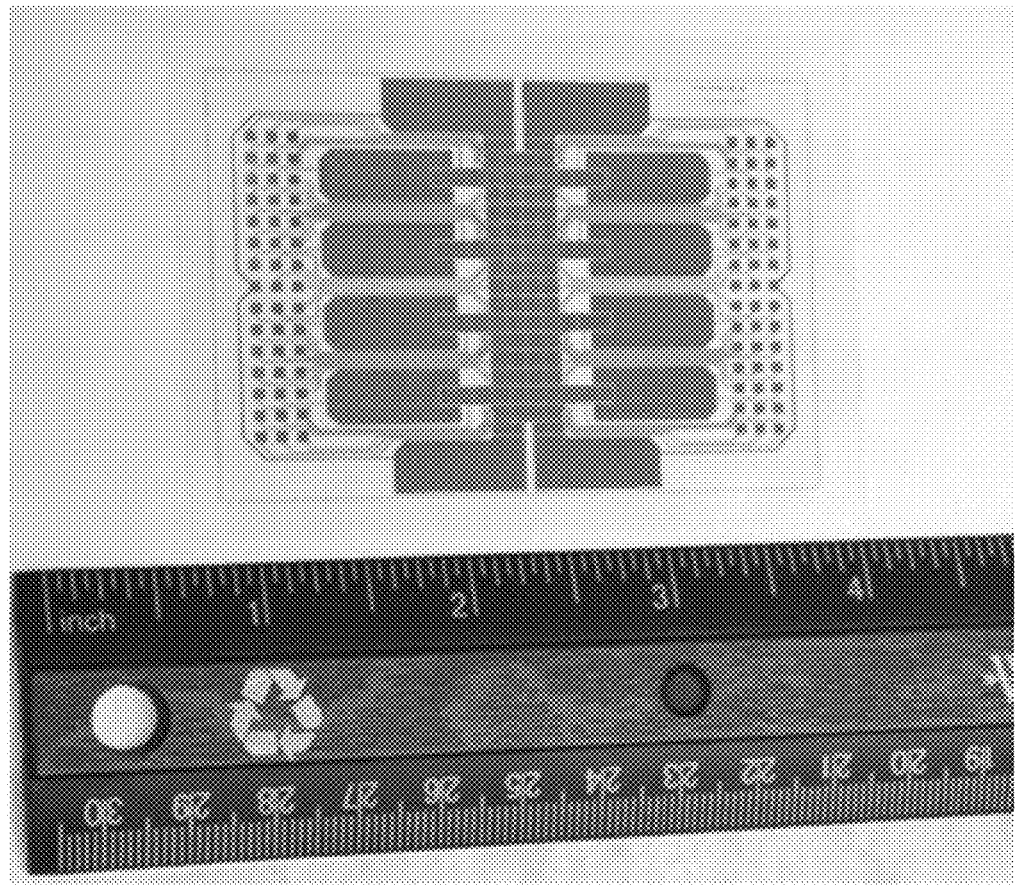
FIG. 11 depicts a single flexible DMF chip fabricated according to the schematic in FIG. 10.

Low-cost flexible DMF chips were fabricated using roll-to-roll (R2R) flexographic printing combined with a wet lift-off process for electrode patterning by using the process described in Lo C-Y et al., Microelectronic Engineering 86 (2009) 979-983 with some modifications. A schematic of the fabrication process is depicted in FIG. 10. A roll of MELINEXR ST506 polyethylene terephthalate (PET) 5.0 mil substrate (1) was used as the starting material for DMF electrode printing. A layer of yellow ink (Sun Chemical) was flexo-printed (2) on the PET substrate using a 1.14 mm thick printing plate (Flint MCO3) at a rate of 10 m/minute using an ink transfer volume of 3.8 ml/m$^2$ on an Anilox roller assembly. A negative image of the DMF electrode pattern results from the flexo printing step (3). Prior to metal deposition, the ink was dried two times in a hot air oven (2×100° C.). An EVA R2R Metal Evaporator was used to deposit a layer of silver metal onto the printed PET substrate to form a uniform coating of silver at a thickness of 80 nm (4). The metalized ink-film substrate (5) was subjected to a wet lift-off process using a combination of acetone plus ultrasound in a sonication bath at a speed of 1 m/minute (6). This chemical/physical treatment allows the silver-ink layer to dissolve, while keeping the silver-only layer intact. Removal of the ink-silver layer resulted in a DMF printed electrode pattern consisting of 80 actuation electrodes (2.25×2.25 mm) with either 50 or 140 μm electrode gap spacing (7). As a QC check, a total of 80-90 random chips from a single roll were visually inspected for electrode gap spacing and connector lead width variation. Typical yields of chips, determined to have acceptable gap specifications, were close to 100%. A single fabricated flexible chip is depicted in FIG. 11. The fabricated flexible chip measures 3"×2" and includes electrodes, reservoirs, contact pads and leads.

A dielectric coating was applied to the electrodes and reservoirs by using either rotary screen printing or Gravure printing. For rotary screen printing, Henkel EDAC PF-455B was used as a dielectric coating by printing with a Gallus NF (400 L) screen at a printing speed of 2 m/minute and a UV curing rate of 50%. Typical dielectric thickness was 10-15 μm. For Gravure printing, cylinders were designed to print a high-viscosity dielectric ink, such as IPD-350 (Inkron), at a speed of 2 m/minute using an ink volume of 50 ml/m$^2$. Typical dielectric thickness for Gravure printing was 7-8 μm. A final hydrophobic layer was printed using either Millidyne Avalon 87 or Cytonix Fluoropel PFC 804 UC coating with Gravure cylinders (140-180 L) and a printing speed of 8 m/minute, followed by four successive oven drying steps (4×140° C.). Typical hydrophobic thickness was 40-100 nm.

Alternatively, for small batches of individual chips, the dielectric and hydrophobic coatings may be applied using chemical vapor deposition (CVD) and spin coating, respectively.

Example 8

Functional Testing of Low-Cost DMF Chip

Figure 12:
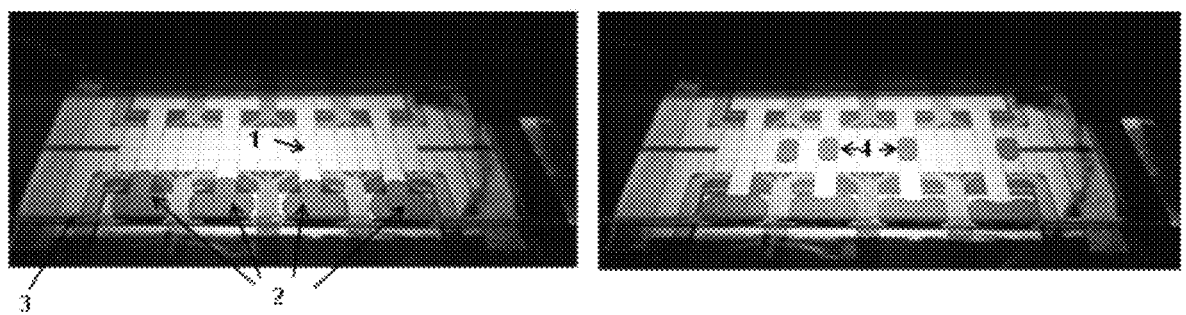
FIG. 12 depicts actuation of droplets in a DMF chip, according to embodiments of the present disclosure.

A 3"×2" PET-based DMF bottom chip manufactured as outlined in Example 7 above was tested for actuation capability. FIG. 12 depicts a 3"×2" PET-based DMF chip (1) over which a 0.7 mm thick glass substrate (3) is positioned. The glass substrate (3) includes a transparent indium tin oxide (ITO) electrode on a lower surface of the glass substrate and a Teflon coating over the ITO electrode. The DMF chip includes 80 silver actuation electrodes with a straight edge electrode design and a 50 μm gap between electrodes, along with 8 buffer reservoirs (see Example 7 above).

The bottom electrodes were coated with a layer of dielectric Parylene-C(6-7 μm thick) and a final coating of Teflon (50 nm thick) by CVD and spin-coating, respectively. Approximately 50 μL of PBS buffer with 0.1% surfactant (2) was pipetted into four adjacent reservoirs on the bottom DMF chip. Droplet sizes ranged from 700-1,500 nL (one or two droplets) and were checked for both vertical and horizontal lateral movement (4), in addition to circular sweep patterns necessary for mixing. Droplet actuation was achieved using a voltage of 90 V$_{rms}$. Approximately 90% of the actuation electrodes on the chip were tested and found to be fully functional.

Example 9

TSH Immunoassay on Low-Cost DMF Chip

Figure 13A:
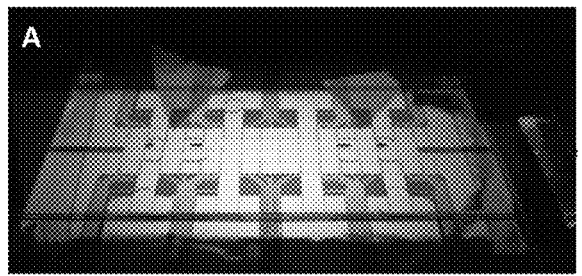
FIGS. 13A-13E depict performance of an immunoassay in a DMF chip, according to embodiments of the present disclosure.
Figure 13B:
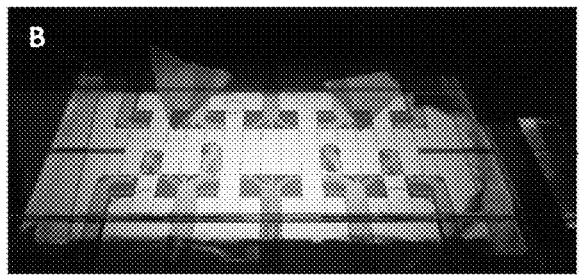
Figure 13C:
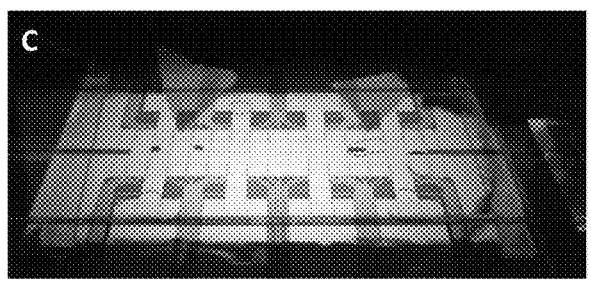
Figure 13D:
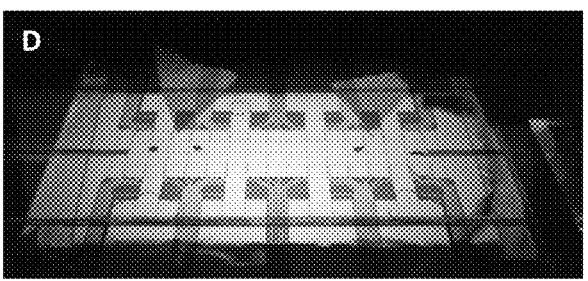
Figure 13E:
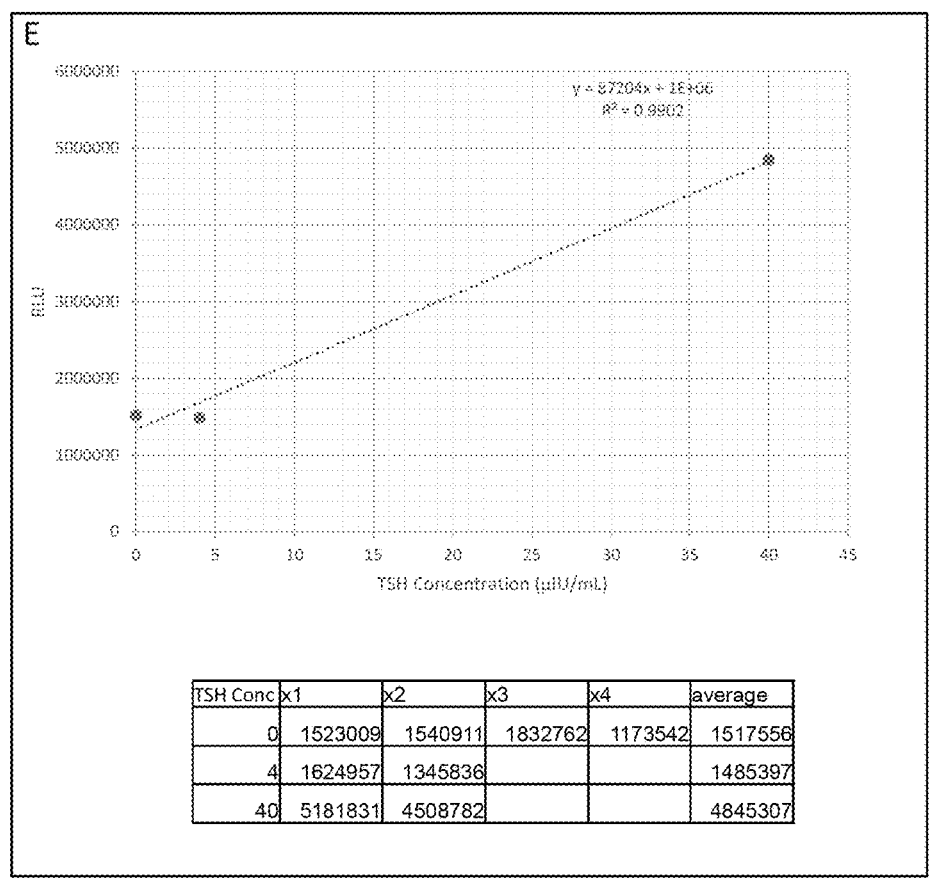

The 3'×2" PET-based DMF chip overlayed with the glass substrate as described in Example 8 above, was tested for its ability to carry out a thyroid stimulating hormone (TSH) immunoassay, using chemiluminescence detection. Mock samples included TSH calibrator material spiked into tris buffered saline (TBS) buffer containing a blocking agent and a surfactant. Three samples were tested—0, 4, 40 μIU/ml. 2 μL of anti-beta TSH capture antibody, coated on 5 μm magnetic microparticles (3×10$^8$ particles/ml), was dispensed from the microparticle reservoir into the middle of the DMF electrode array. The magnetic microparticles were separated from the buffer by engaging a neodymium magnet bar (3 in.×½ in.×¼ in. thick, relative permeability $\mu_r$=1.05, remnant field strength $B_r$=1.32 T) under the DMF chip (FIG. 13A). 5 µL of sample was moved to the microparticle slug, followed by mixing the microparticle suspension (FIG. 13B) over a four-electrode square configuration for 5 minutes. The microparticles were separated from the sample by the magnet, and the supernatant was moved to a waste reservoir (FIGS. 13C and 13D). 2 µL of 1 µg/mL anti-TSH detection antibody conjugated to horseradish peroxidase (HRP) was moved to the microparticle slug and mixed for 2 minutes. The microparticles were separated by the magnet, and the supernatant was moved to the waste reservoir. The microparticles containing the immunoassay sandwich complex were washed a total of four times with 4×2 µL of PBS wash buffer containing 0.1% surfactant. Wash buffer from each wash step was moved to waste after the step was completed. Chemiluminescent substrate consisted of 1 µL of SuperSignal $H_2O_2$ and 1 µL luminol (ThermoFisher Scientific), which was moved to the microparticle slug, followed by mixing for 6 minutes. Chemiluminescent signal was measured at 427 nm emission (347 nm excitation) using an integrated Hamamatsu H10682-110 PMT with a 5 V DC source. A dose-response curve was plotted against relative luminescence (see FIG. 13E).

Example 10

Nanopore Module Fabrication

A nanopore module was fabricated using standard soft lithography fabrication methods coupled with integration of a commercially available silicon nitride ($SiN_x$) membrane embedded in a TEM window (Norcada). The module consisted of four separate layers of PDMS—a top and bottom PDMS substrate containing the transfer microchannels, and two optional intermediate PDMS layers to seal the TEM window.

SU8 Master Mold Fabrication:

A clean, dry glass substrate was spincoated with photoresist (SU8-50) to a desired thickness. Areas of the coated substrate were then selectively exposed to near-UV light using a photomask. The mask exposes photoresist to UV light only in regions where the transfer microchannel and reservoir shapes are to remain. Exposure was followed by a bake to cross-link regions of photoresist that were exposed. An SU8 developer was then used to remove remaining, unexposed photoresist from the substrate. The final product is a master mold—a glass substrate with patterned transfer microchannels and reservoirs of hard photoresist.

Intermediate PDMS Layer Fabrication:

For fabricating the intermediate PDMS layers, a solution containing PDMS monomer and its curing agent (Sylgard 184 silicone elastomer) in the ratio of 7:1 PDMS monomer: curing agent was spincoated on a glass slide, followed by heating on a hot plate for 30 minutes at 70° C. The PDMS layers were peeled off the glass substrate and 1.25 mm cut-out was punched through the PDMS layers to provide an opening allowing access to the TEM window. Surface of the PDMS layers was made hydrophilic by plasma treating for 30 seconds using a corona treater at a distance of 8 mm. A second plasma treatment (5 seconds) was used to treat the surface of the PDMS layers and TEM window before bonding the $SiN_x$ TEM window between the two intermediate PDMS layers.

Figure 14A:
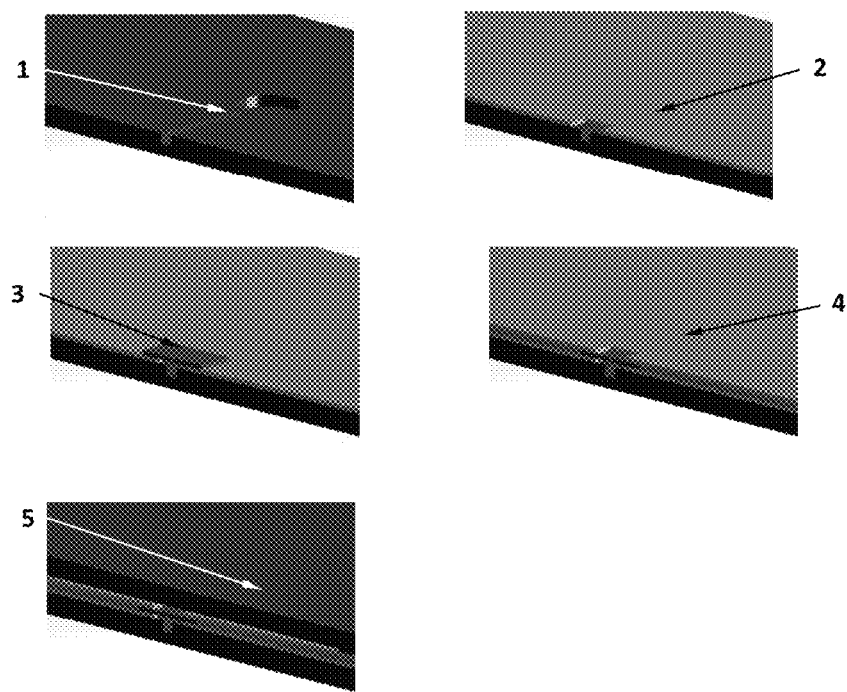
Figure 14B:
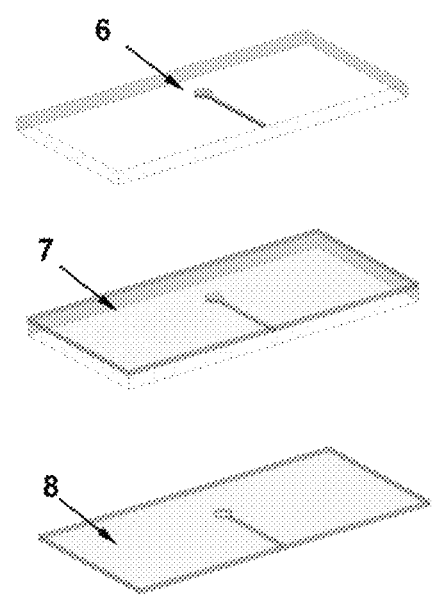

Top and Bottom PDMS Fabrication:

The top and bottom PDMS substrates containing microchannels were fabricated, as shown in FIG. 14B, by mixing PDMS monomer and curing agent in a ratio of 7:1 PDMS monomer: curing agent and pouring over glass containing the SU8 patterned mold (6) patterned with the transfer microchannels and reservoirs (see SU8 Master Mold Fabrication described above). The microchannels measured approximately 110 to 135 µm in width and 50 µm in depth. After degassing for 15 minutes, the SU8 mold was heated on a hot plate for 60 minutes at 70° C. (7). After curing, the PDMS substrates were peeled off the SU8 mold (8) and cut to yield rectangular PDMS substrates having an approximate dimension of 30 mm length×20 mm width×3 mm depth. Access holes (1.25 mm in diameter) were punched through the PDMS substrates to allow subsequent insertion of electrodes into the microchannels. The final assembly is shown in FIG. 14A and includes from bottom to top, bottom PDMS substrate containing one microchannel (1), a first intermediate PDMS layer (2) containing a cut-out positioned over the microchannel, the $SiN_x$ membrane in TEM window (3), a second intermediate PDMS layer (4) also containing a cut-out, and a top PDMS substrate (5) containing a second microchannel.

Alignment of Top and Bottom PDMS Substrates:

A PDMS bottom substrate (prepared as outlined in "Top and Bottom PDMS Fabrication," above) was plasma treated for 30 seconds, followed by bonding of a first intermediate PDMS layer (prepared as outlined in "Intermediate PDMS Layer Fabrication," above) onto the PDMS bottom substrate. Similarly, a PDMS top substrate was plasma treated for 30 seconds, followed by bonding of a second intermediate PDMS layer onto the PDMS top substrate. The cut-outs in the intermediate layers were aligned with the microchannels. Both top and bottom PDMS pieces were oxygen plasma treated for 30 seconds, followed by placement of the $SiN_x$ membrane window in between the top and bottom pieces and aligned with the cut-outs in the intermediate PDMS layers. The top piece aligned with the $SiN_x$ membrane aligned with the bottom piece were pressed together until all air bubbles were released. The final nanopore PDMS assembly was heated on a hot plate for at 100° C. for 30 minutes and plasma treated for 5 minutes. The final module assembly, shown in FIG. 14C, (9a) contained two channels (one straight and one "L-shaped" channel), each ending in a reservoir for a solution (e.g., a buffer). The TEM window containing the $SiN_x$ membrane is positioned at the intersection of the two perpendicular microchannels (FIG. 14C, 9b).

Example 11

Nanopore Fabrication

Nanopore fabrication was accomplished by subjecting a $SiN_x$ TEM window, housed between two PDMS layers, to a potential bias until dielectric breakdown occurred, thereby opening up a small-diameter hole in the membrane. This allows for in situ formation of a pore within the microfluidic device, prior to detection of analytes. Nanopore formation by dielectric breakdown has been previously shown to be useful for rapid fabrication of small diameter pores in solid-state dielectric membranes (H. Kwok, K. Briggs, V. Tabard-Cossa, *PLoS-One,* 9(3), 2014).

$SiN_x$ membrane commercially available as transmission electron microscope (TEM) windows (Norcada) were embedded in the assembled PDMS module as outlined in Example 10 above) and were used to generate the nanopore. The perpendicular microchannel junction exposed a cross sectional area (50 µm×50 µm) of the $SiN_x$ TEM window to a salt solution (1 M KCl) disposed on opposite sides of the membrane (cis and trans). Ag/AgCl electrodes were placed into each microchannel approximately 3 mm from the center of the $SiN_x$ TEM window into holes punched through the PDMS substrate. A syringe containing a blunt needle was used to fill both cis and trans microchannels by adding ethanol to the two reservoirs until liquid was observed emerging from the channel openings on the module edge. The resistance was measured to check for proper sealing and to ensure the TEM-$SiN_x$ membrane was intact. A resistance on the order of MΩ indicated good sealing and a membrane that was intact and undamaged. The ethanol was flushed out of the microchannel with deionized water, and replaced with a 1 M KCl solution by injecting into the two reservoirs. The resistance was measured again to check for proper sealing.

Figure 15A:
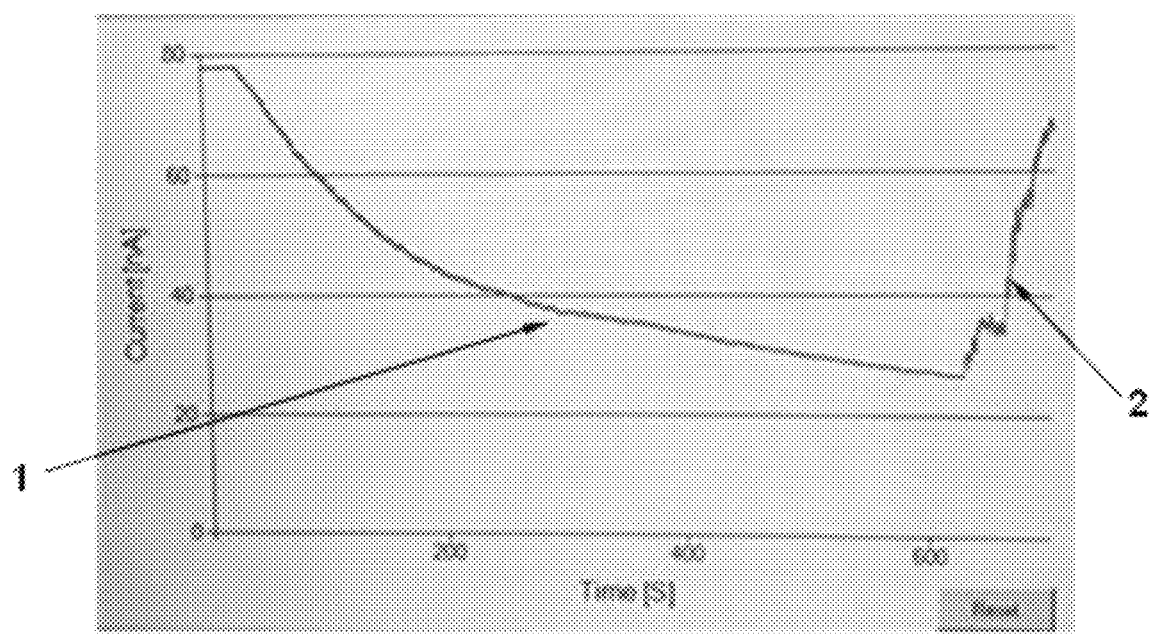
FIG. 15A shows a plot of leakage current measured in real-time.

A constant voltage of 4.4 V was applied to the membrane assembly and the leakage current was monitored in real-time. The leakage current measured in real-time is plotted in FIG. 15A. FIG. 15A shows the leakage current (1) prior to nanopore creation. A threshold value of >5 nA was used as the cut-off value, i.e.—to signify pore creation. After approximately 10 minutes, an increase in leakage current was observed (2). The voltage was turned off immediately following the detection of increase in leakage current. The diameter of the created pore was 6.9 nm, as determined by the following relationship:

$$G = \sigma\left(\frac{4L}{\pi d^2} + \frac{1}{d}\right)^{-1}$$

where G=conductance, σ=bulk conductivity (12.35 S/m measured for KCl), L=thickness of the membrane (10 nm), d=pore diameter (S. Kowalczyk, A. Grosberg, Y. Rabin, C. Dekker, *Nanotech.*, 22, 2011).

Figure 15B:
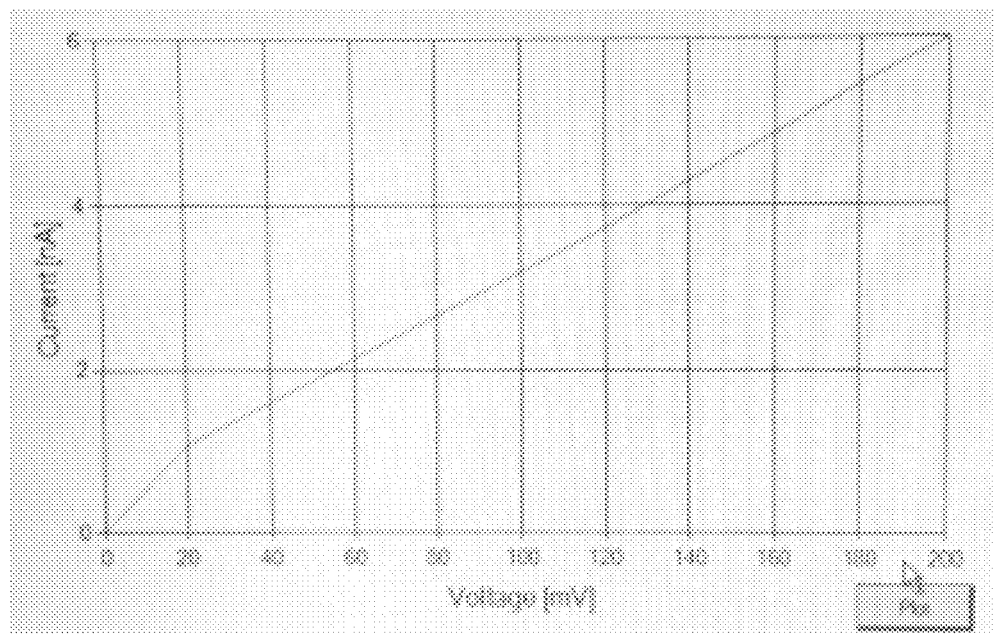
FIG. 15B depicts a current-voltage (I-V) curve for a nanopore.

After pore creation, a current-voltage (I-V) curve (see FIG. 15B) was used to verify that the nanopore displayed ohmic behavior, indicating the nanopore was symmetrical in shape and the resistance was independent of the applied voltage or current. The same 1 M KCl solution was used for both pore fabrication and I-V curves.

Example 12

Dry Microchannel Filling

Figure 16A:
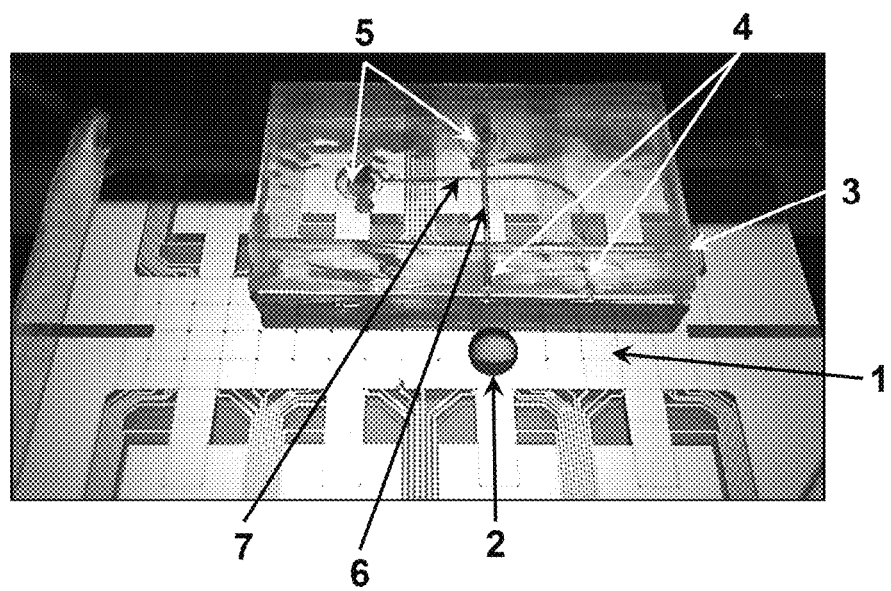
FIGS. 16A-16C show filling of a capillary channel in an integrated DMF-nanopore module device, according to embodiments of the present disclosure.
Figure 16B:
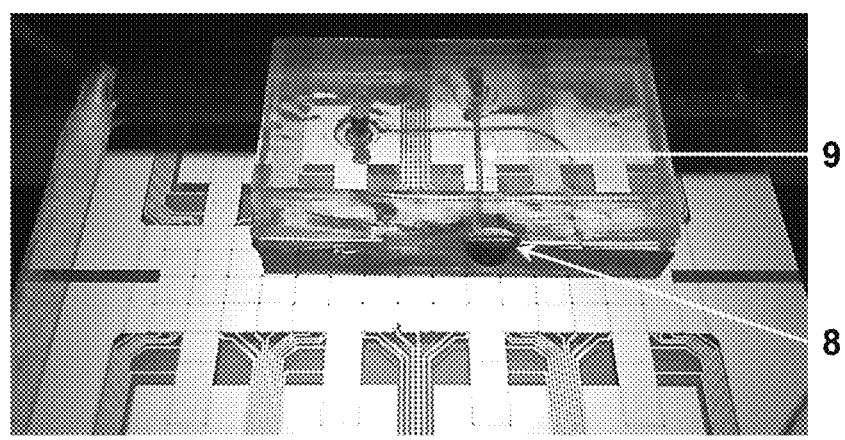
Figure 16C:
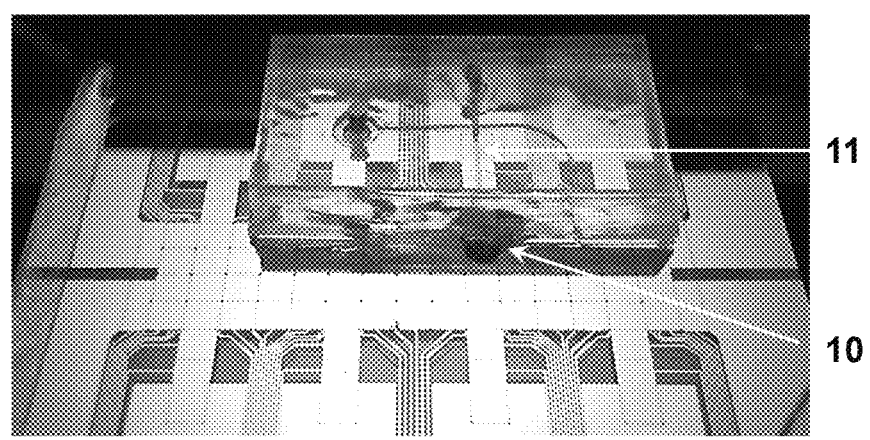

The capillary conduit contained in the assembled PDMS module (i.e., the integrated device including a DMF module and a nanopore module) was tested for its ability to spontaneously fill high-salt solutions from the DMF electrode assembly (FIGS. 16A-16C). Filling was achieved via spontaneous capillary flow (SCF). The nanopore membrane was not included in order to allow for better visualization of the microchannels. With reference to FIG. 16A, a glass DMF chip (3"×2"×0.0276") containing 80 actuation electrodes (1) (2.25 mm×2.25 mm, Cr-200 nm thickness) was used to move a droplet (2) of 3.6 M LiCl, 0.05% Brij 35 and blue dye (to aid with visualization). The PDMS module (3) contained two openings facing the DMF electrode array (4), two reservoirs (5) and two microchannels—one straight channel (6) and one L-shaped channel (7). The module assembly was placed on the DMF glass surface so that the two channel openings faced the interior of the DMF electrode array. Since a top grounding electrode chip was not used, droplet movement was achieved by using co-planar bottom electrodes to generate the driving potential.

A 10 µL droplet of blue-colored LiCl salt solution was placed on an electrode in the middle of the DMF electrode array. A voltage of 100 $V_{rms}$ (10 kHz) was used to move the droplet to the transfer electrode adjacent to the straight microchannel opening. As shown in FIG. 16B, after the droplet contacted the PDMS surface (8), the time required to fill the 130 m diameter straight channel (9) and reach the reservoir was measured. As shown in FIG. 16C, after approximately 30 seconds, the volume of the droplet was visibly smaller (10) and the channel was half filled (11). A total time of 53 seconds was required to fill the entire dry microchannel (130 µm diameter).

Wet Microchannel Filling: A 10 µL droplet of blue-colored LiCl salt solution was placed on an electrode in the middle of the DMF electrode array. A voltage of 100 $V_{rms}$ (10 kHz) was used to move the droplet to the transfer electrode adjacent to the straight microchannel opening. The channel was pre-filled with ethanol to mimic a pre-wetted channel. After the droplet contacted the PDMS surface, a time of <1 second was required to fill the channel up to the reservoir. This was significantly faster than the dry channel, suggesting pre-wetting with a hydrophilic solution enhances microchannel fill rates.

Example 13

DMF Droplet Transfer in Integrated Silicon NP Device

Figure 17:
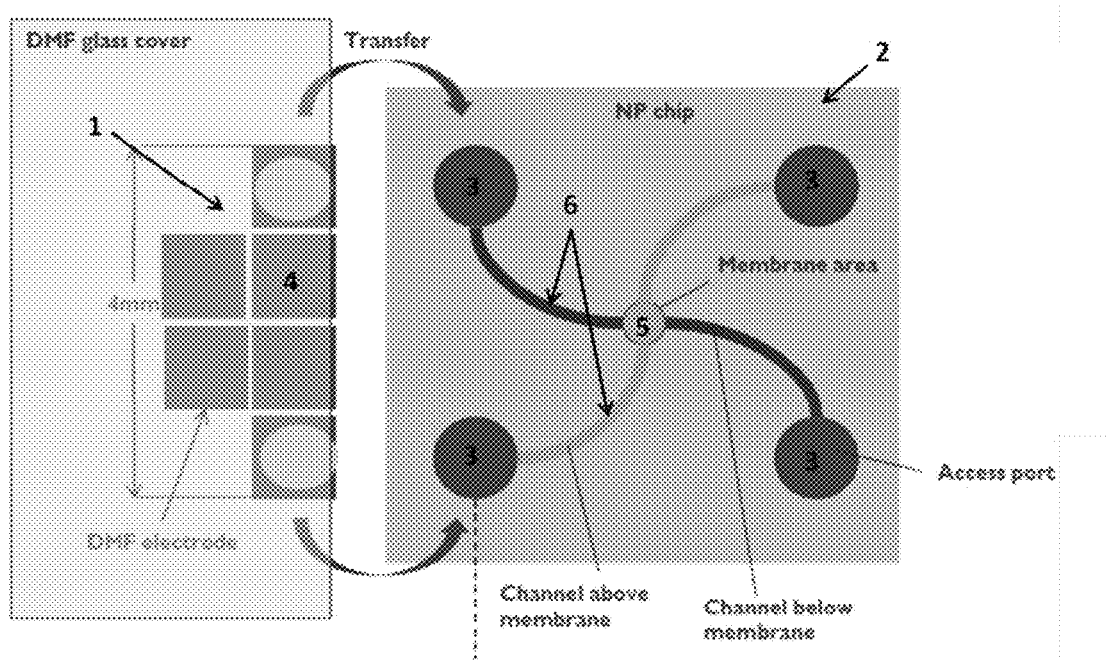
FIG. 17 shows a schematic diagram for droplet transfer between modules in an integrated DMF-nanopore module device, according to embodiments of the present disclosure.
Figure 18:
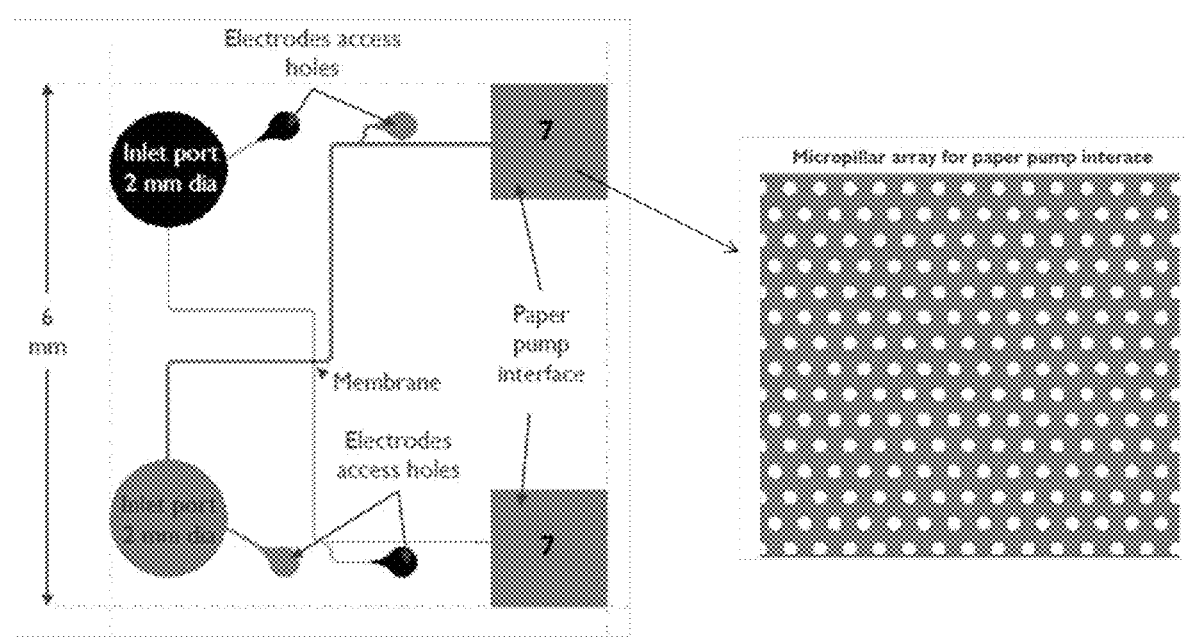
FIG. 18 shows a schematic diagram of a nanopore module design, according to embodiments of the present disclosure.

In addition to flexible substrates, such as PDMS, rigid substrates (e.g. silicon) may be used to fabricate the nanopore module. FIG. 17 shows a digital microfluidics (DMF) chip (1), containing actuation electrodes (4), from which droplets are transferred to a silicon microfluidic chip containing a nanopore sensor (2). Droplets are transferred between the two component chips by access ports (3) in the top surface of the microfluidic chips containing the nanopore sensor. Access ports are connected to the nanopore sensor (5) by microfluidic channels (6). Droplets are moved from the access ports, through the microfluidic channels by capillary forces, and movement may be aided by a passive paper pump fabricated from an array of micropillars (7) (FIG. 18). The passive pumps may also remove fluid from the microchannels, enabling different fluidic solutions to be used sequentially without contamination (for example, between solutions for nanopore formation and nanopore sensing).

Fabrication of the silicon nanopore module may include using standard CMOS photolithography and etching processes. FIG. 18 shows an example of a silicon nanopore module design, where the approximate die size is 10 mm×10 mm, with a frontside channel (cis) and a backside channel (trans) for filling the nanopore buffer(s). The frontside channel has a width and depth of 30 µm, and is 11 mm long. The backside channel has a width of 50 µm, a depth of 200 µm, and is 11 mm long. The micropillar dimensions are 30 µm pillar diameter, spacing of 30 µm and depth of 200 µm.

Figure 19:
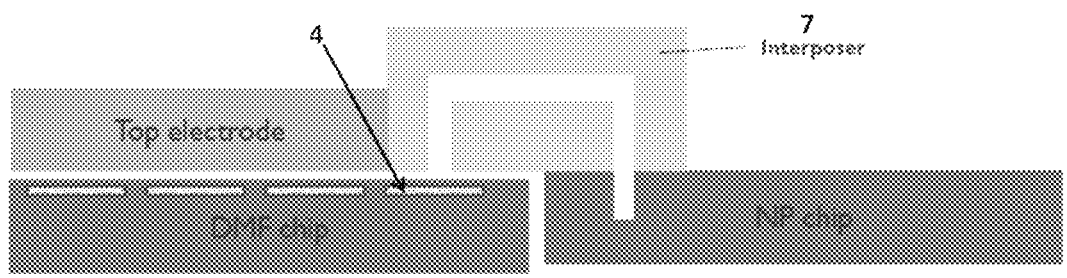
FIG. 19 shows a schematic diagram of an integrated DMF-nanopore module device adapted to perform droplet transfer between the modules by passive transport, according to embodiments of the present disclosure.
Figure 20:
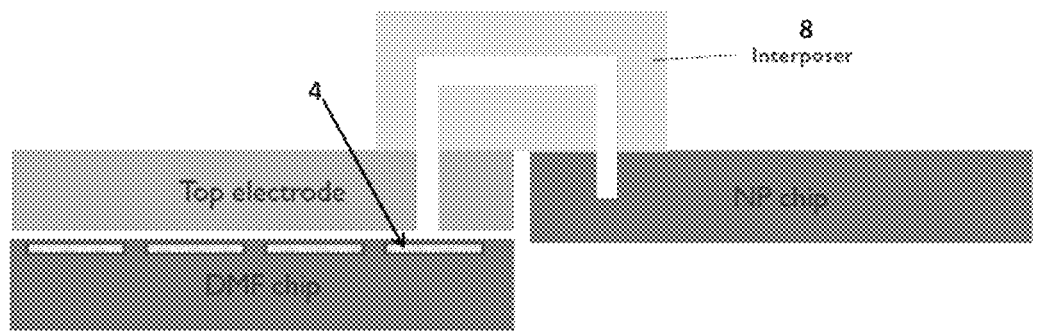
FIG. 20 shows a schematic diagram of an integrated DMF-nanopore module device adapted to perform droplet transfer between the modules by passive transport, according to embodiments of the present disclosure.
Figure 21:
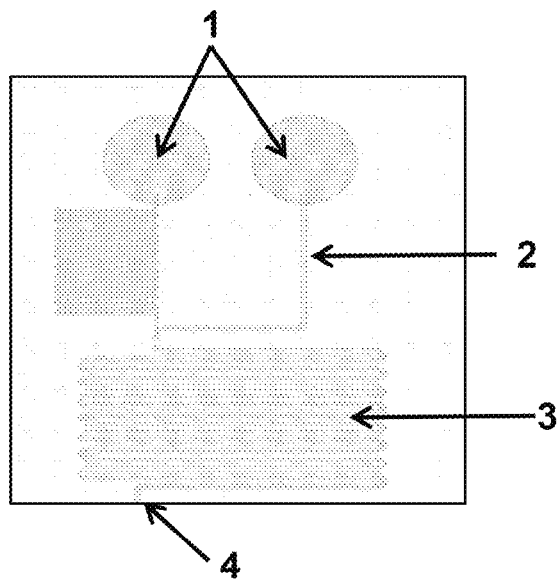

The DMF and nanopore module may be joined using an interface fabricated from molded plastic or by direct bonding (FIGS. 19 and 20). A droplet positioned on an electrode (4) within the DMF chip aligned with an access port is transferred by capillary forces, facilitated by the interposer (7). Alternatively, the top electrode (8) the DMF chip may be modified to further facilitate this process by introducing holes connecting the actuation electrodes (4) with the interposer (8) (FIG. 20).

Example 14

Droplet Transfer Between DMF and Nanopore Modules by Capillary Forces

The ability to move high-salt translocation buffer from a DMF chip to a module containing a suitable nanopore membrane was tested in a silicon microfluidic chip. A serpentine microchannel was tested for its ability to passively move a droplet of 1 M KCl (pH=8) using spontaneous capillary flow (SCF) as the sole driving force. The entire microchannel was fabricated in silicon and served as a model for fluidic transfer in a CMOS-based silicon environment. The serpentine microchannel was designed to have two access ports (for fluidic loading). The channel dimensions measured 160 µm in diameter, with an approximate length of 2.5 cm. Droplets of a solution suitable for formation of nanopores by dielectric breakdown were demonstrated to fill the silicon microfluidic structure using passive capillary forces.

Figure 21:
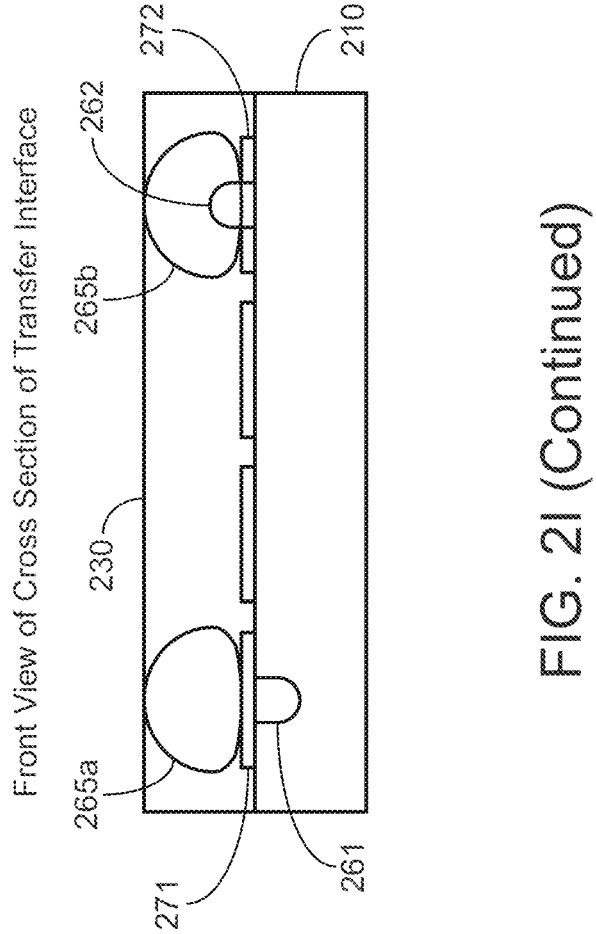
FIG. 21 is a schematic diagram of a silicon microfluidic device containing silicon microchannels that allow passive movement of a liquid droplet by passive transport, according to embodiments of the present disclosure.
Figure 22:
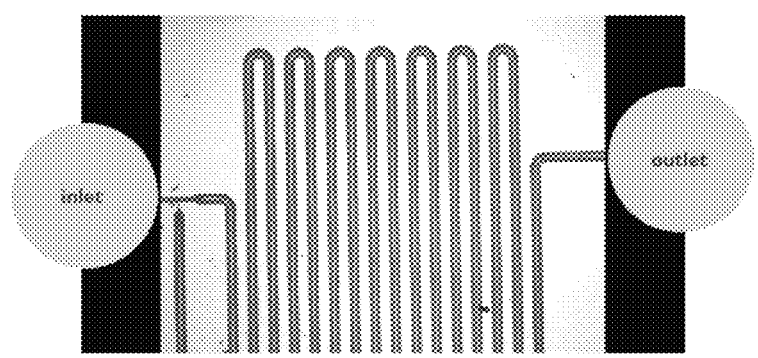
FIG. 22 is an image of a silicon microchannel of a silicon microfluidic device that allows passive movement of a liquid droplet by passive transport, according to embodiments of the present disclosure.

With reference to FIG. 21, individual droplets of 1M KCl solution (pH=8.0) were placed in one of the inlet ports (1) connecting to a transport microfluidic channel (2), leading to a serpentine channel 2.5 cm in length (3). The channel terminated (4) at a port (not shown) exposed to atmospheric pressure. A magnified image of the serpentine channel is shown in FIG. 22. Capillary filling was monitored using a sCMOS camera fitted to an optical microscope. Deposition of the salt solution into the inlet port resulted in spontaneous filling of the microchannel by passive capillary forces at a rate of several mm/second, thereby demonstrating the capability to transfer fluid in the microchannel to a nanopore membrane.

As a further test of transfer rate, the channel was emptied of the KCl solution and dried under a stream of nitrogen. Further droplets of 1M KCl solution (pH=8.0) were placed in the inlet port of the dried microchannel and capillary filling was monitored using and optical microscope. Faster fill rates were observed, compared to the "dry" channel (i.e., compared to the first time the KCl solution was introduced into the channel), thereby showing that pre-filling of the silicon microchannel with a hydrophilic solution enhanced subsequent fluidic filling.

Example 15

Fabrication of Integrated Nanopore Sensor with Fluidic Microchannels

Figure 23A:
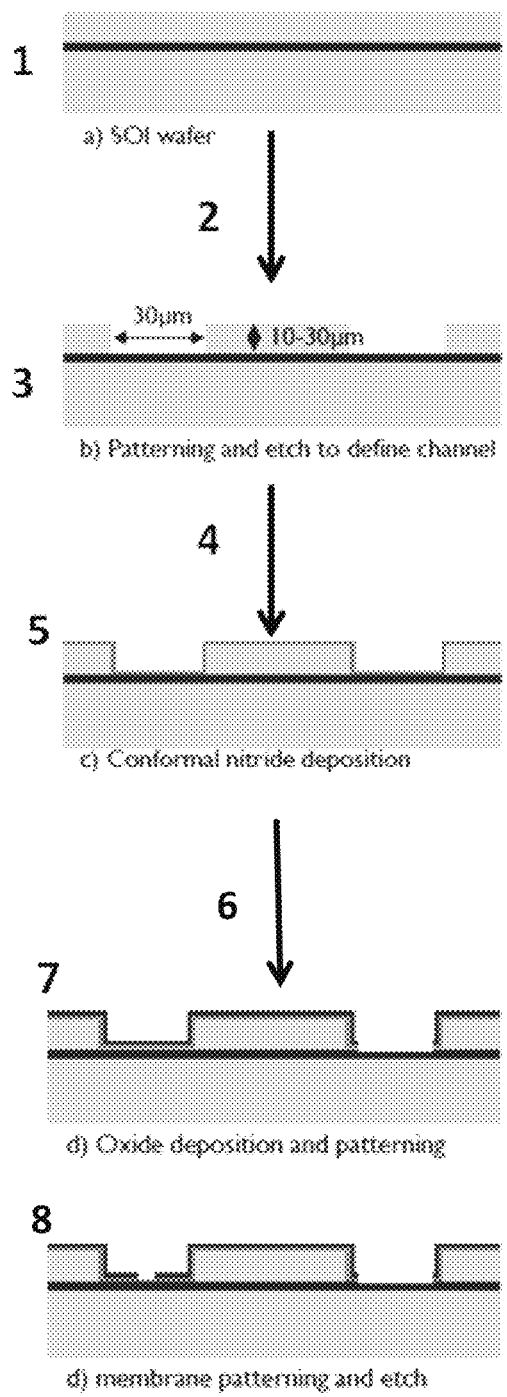
FIG. 23A and FIG. 23B show a schematic of a fabrication method for an integrated nanopore sensor, according to embodiments of the present disclosure.
Figure 23B:
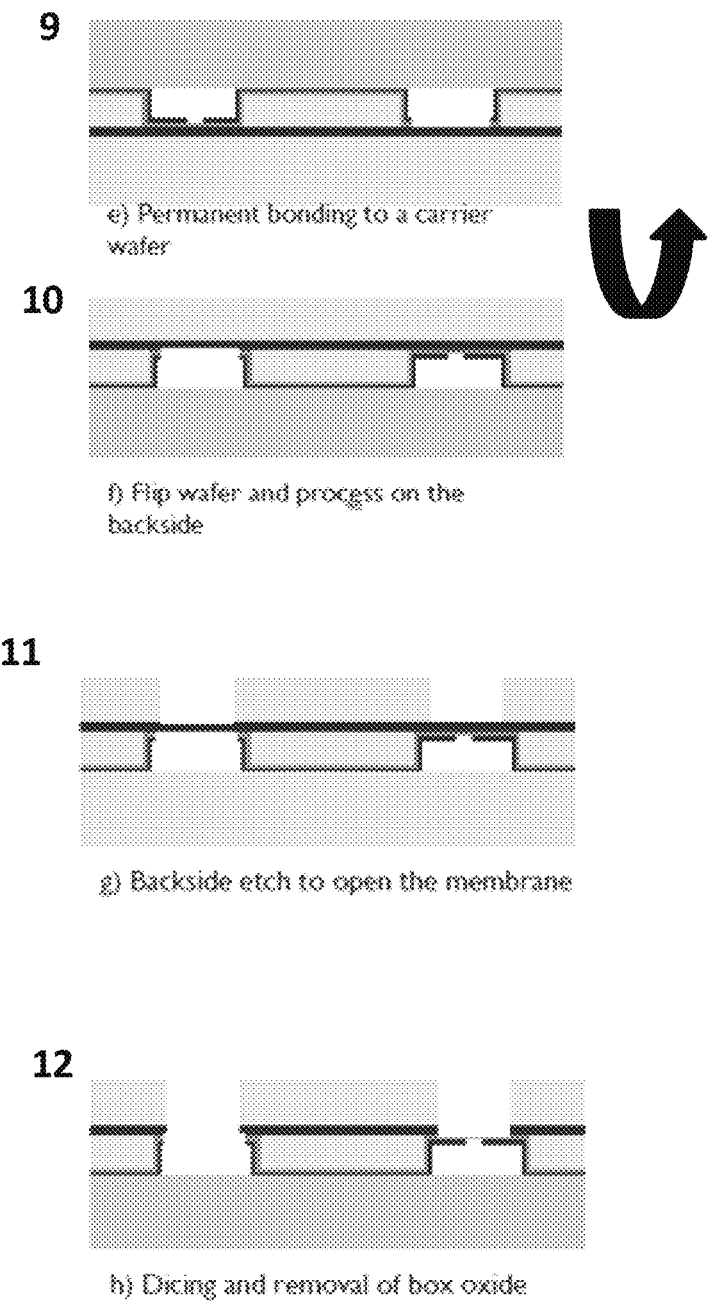

An integrated nanopore sensor within fluidic microchannels is fabricated using photolithography and etching processes to modify a silicon-on-oxide (SOI) wafer (FIGS. 23A-23B).

The SOI wafer (1) is subjected to photolithography and etching (2) to produce a structure suitable for the movement of small fluidic volumes (3) with dimensions of 30 µm width and 10-30 µm channel depth.

A silicon nitride (SiN) material (5) is deposited onto the patterned SOI wafer by evaporation (4).

A layer of oxide material (7) is deposited over the silicon nitride (5) by evaporation (6). The underlying silicon (1) is exposed by selectively removing the overlying oxide and nitride materials covering one of the microstructures using a combination of photolithography and etching (6). This structure will form a microchannel for actuating small volumes of fluid.

The underlying silicon nitride within a second microstructure is selectively exposed by removing the overlying oxide layer only using a combination of photolithography and etching (8).

The exposed microstructures are permanently bonded to a carrier wafer (9) and the structure is inverted for further processing (10). The oxide material on the inverse side of the SOI wafer is selectively patterned using a combination of photolithography and etching to expose the back side of each microstructure (11).

Example 16

Synthesis of Cleavable DNA-Biotin Construct

Synthesis of Non-Biotinylated Double-Stranded DNA (NP1):

Two single-stranded 50-mers were synthesized using standard phosphoramidite chemistry (Integrated DNA Technologies). Oligo NPT-1S consisted of a 50 nucleotide DNA sequence containing an amino group on the 5'-terminus, separated from the DNA by a C-12 carbon spacer (SEQ ID NO: 1) (1, MW=15,522.3 g/mole, ε=502,100 $M^{-1}cm^{-1}$). Oligo NP1-2AS consisted of a 50 nucleotide DNA sequence complementary to NPT-1S (SEQ ID NO: 2) (2, MW=15,507.1 g/mole, ε=487,900 $M^{-1}$ $cm^{-1}$). Both oligonucleotides were quantitated and lyophilized prior to subsequent manipulation.

1
NP1-1S:
H₂N-AGTCATACGAGTCACAAGTCATCCTAAGATACCATACACATACCAA
GTTC

2
NP1-2AS:
GAACTTGGTATGTGTATGGTATCTTAGGATGACTTGTGACTCGTATGACT

3
Final ds-DNA Design-NP1:
H₂N-AGTCATACGAGTCACAAGTCATCCTAAGATACCATACACATACCAA
GTTCTCAGTATGCTCAGTGTTCAGTAGGATTCTATGGTATGTGTATGGTT
CAAG Synthesis of Non-Biotinylated Double-Stranded 50-bp DNA Construct:

NP1-2AS (1.44 mg, 93.4 nmoles) was reconstituted in 0.5 mL distilled water to give a 187 µM solution. NP1-1S (1.32 mg, 85.3 nmoles) was reconstituted in 0.5 mL of 50 mM phosphate, 75 mM sodium chloride buffer pH 7.5 to give a 171 µM solution. The double-stranded construct (3) (SEQ ID NO: 1—forward strand (top); SEQ ID NO: 2—reverse strand (bottom)) was made by annealing 60 µL of NP1-1S solution (10.2 µmoles) with 40 µL of NP1-2AS solution (7.47 µmoles). The mixture was placed in a heating block at 85° C. for 30 min, followed by slow cooling to room temperature over 2 hours. Double-stranded material was purified by injecting the total annealing volume (100 µL) over a TosoH G3000SW column (7.8 mm×300 mm) equilibrated with 10 mM PBS buffer, pH 7.2. The column eluent was monitored at 260 and 280 nm. The double-stranded material (3) eluted at 7.9 minutes (approx. 20 minutes). The DNA was concentrated to 150 µL using a 0.5 mL Amicon filter concentrator (MW cut-off 10,000 Da). The final DNA concentration was calculated to be 40.5 µM, as determined by $A_{260}$ absorbance.

nylating the 5'-amino-DNA. Approx. 100 µL of ssDNA (1, 171 µM, 17.1 µmoles, 0.265 mg) (SEQ ID NO: 1) solution in 50 mM PBS, pH 7.5 was mixed with 3.4 L of 0.1 mM

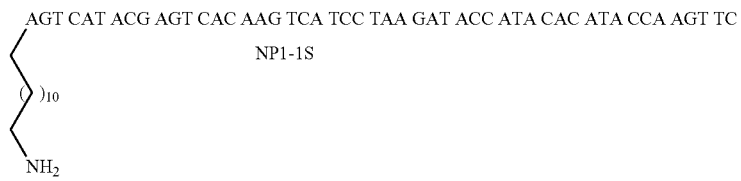

1

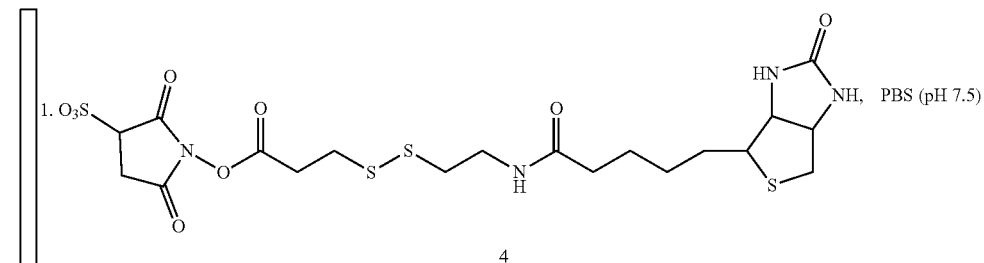

4

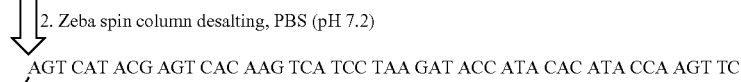

5
NP1-1S-disulfide-biotin

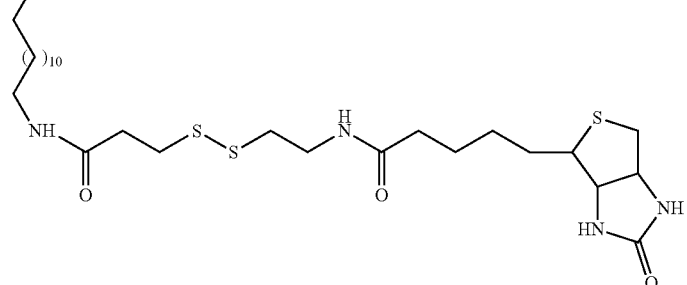

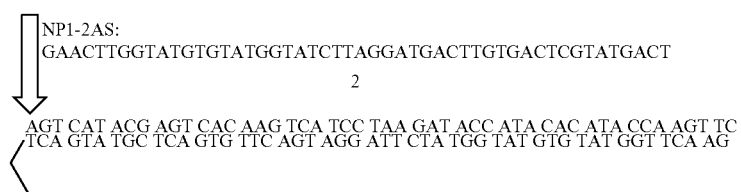

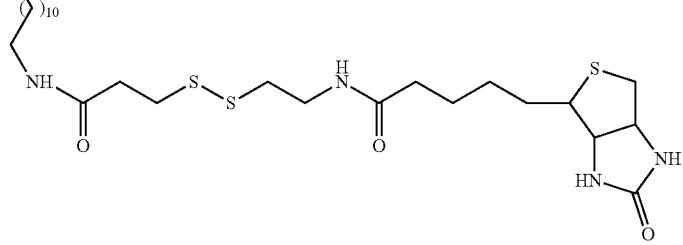

6
NP1-disulfide-biotin

Biotinylation of Single-Stranded 5'-Amino Oligo:

A 100 mM solution of sulfo-NHS—SS-Biotin (4, ThermoFisher Scientific) was made by dissolving 6 mg of powder in 0.099 mL of anhydrous DMSO (Sigma Aldrich). The solution was vortexed and used immediately for biotinylating reagent in DMSO (34.1 µmoles, 20-fold molar excess over the ssDNA). The mixture was mixed and allowed to react at room temperature for 2 hours. Two 0.5 mL Zeba spin desalting columns (MW cut-off 7,000 Da, ThermoFisher Scientific) were equilibrated in 10 mM PBS, pH 7.2. The crude biotinylated ssDNA solution was added to one Zeba column and eluted at 4,600 rpm for 1.3 minutes. The eluent was transferred to a second Zeba column and eluted as described. The concentration of the purified NP1-1S—SS-Biotin (5) (SEQ ID NO: 1 was determined by measuring the $A_{260}$ absorbance (2.03 mg/ml, 131 µM).

Formation of Biotinylated Double-Stranded DNA:

Approximately 60 µL of NP1-1S—SS-Biotin solution (5, 7.85 µmoles, 131 µM, 2.03 mg/mL) was mixed with 42 µL of NP1-2AS solution (2, 7.85 µmoles, 187 µmol/L) (SEQ ID NO: 2). The solution was placed in a heating block at 85° C. for 30 minutes, followed by slow cooling to room temperature over 2 hours. The double-stranded product was purified over a TosoH G3000SW column (7.8 mm×300 mm) using 10 mM PBS, pH 7.2 by injecting the entire annealing volume (approx. 100 µL). The double-stranded biotinylated material eluted at 7.9 minutes (20 minutes run time), as monitored by $A_{260}$ absorbance. The eluent volume was reduced to 480 µL using a 0.5 mL Amicon filter concentrator (MW cut-off 10,000 Da). The final NP1-dithio-biotin (6) (SEQ ID NO: 1—forward strand (top); SEQ ID NO:2—reverse strand (bottom)) concentration was calculated to be 16.3 µM, as determined by $A_{260}$ absorbance.

Example 17

Alternate Synthesis of Cleavable DNA-Biotin Construct

Complementary DNA Sequences (NP-31a and NP-31b):

Two single-stranded 60-mers were synthesized using standard phosphoramidite chemistry (Integrated DNA Technologies). Oligo NP-31a consisted of a 60 nucleotide DNA sequence containing an amino group on the 5'-terminus, separated from the DNA by a C-6 carbon spacer (SEQ ID NO: 3) (1, MW=18,841.2 g/mole, 1.7 µM/OD). Oligo NP-31b consisted of a 60 nucleotide DNA sequence complementary to NP-31a (SEQ ID NO: 4) (2, MW=18292.8 g/mole, 1.8 µM/OD). Both oligonucleotides were quantitated and lyophilized prior to subsequent manipulation.

```
                                                    1
NP-31a:
H2N-5'GCC CAG TGT CTT TGT AGG AGG AGC AGC GCG TCA

ATG TGG CTG ACG GAC CAT GGC AGA TAG3'
                                                    2
NP-31b:
5'CTA TCT GCC ATG GTC CGT CAG CCA CAT TGA CGC GCT

GCT CCT CCT ACA AAG ACA CTG GGC3'
                                                    3
ds-DNA Design-NP-31:
H2N-5'GCC CAG TGT CTT TGT AGG AGG AGC AGC GCG TCA

ATG TGG CTG ACG GAC CAT GGC AGA TAG3'

3'CGG GTC ACA GAA ACA TCC TCC TCG TCG CGC TGA TAC

ACC GAC TGC CTG GTA CCG TCT ATC5'
```

Biotinylation of Single-Stranded 5'-Amino Oligo NP-31a:

A 10 mM solution of NHS—S-S-dPEG$_4$-Biotin (4, MW=751.94 g/mole, Quanta BioDesign, Ltd) was prepared by dissolving 15.04 mg of powder in 2.0 mL of dimethylformamide (Sigma Aldrich). The solution was vortexed and used immediately for biotinylating the 5'-amino-DNA. Approx. 100 µL of ssDNA (1, 100 µM, 0.01 µmoles, 0.188 mg) (SEQ ID NO: 3) solution in 10 mM phosphate buffered saline (PBS), pH 7.4 was mixed with 10 µL of 10 mM biotinylating reagent in DMF (0.1 µmoles, 10-fold molar excess versus the ssDNA). The mixture was mixed and allowed to react at room temperature for 2 hours. Two 0.5 mL Zeba spin desalting columns (MW cut-off 7,000 Da, ThermoFisher Scientific) were equilibrated in 10 mM PBS, pH 7.2. The crude biotinylated ssDNA solution was added to one Zeba column and eluted at 4,600 rpm for 2 minutes. The eluent was transferred to a second Zeba column and eluted as described. The concentration of the purified NP-31-SS-Biotin (5) (SEQ ID NO: 3) was determined by measuring the $A_{260}$ absorbance (1.45 mg/mL, 77 µM).

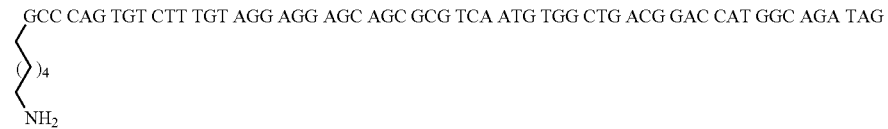

1 NP-31a

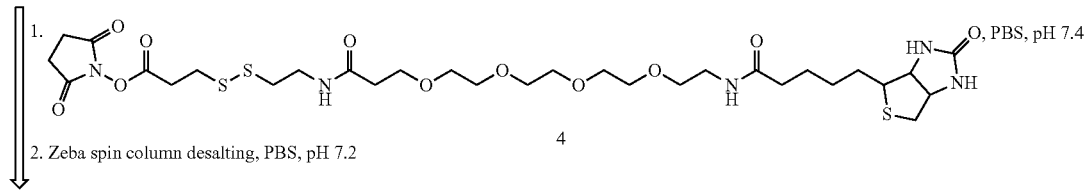

4

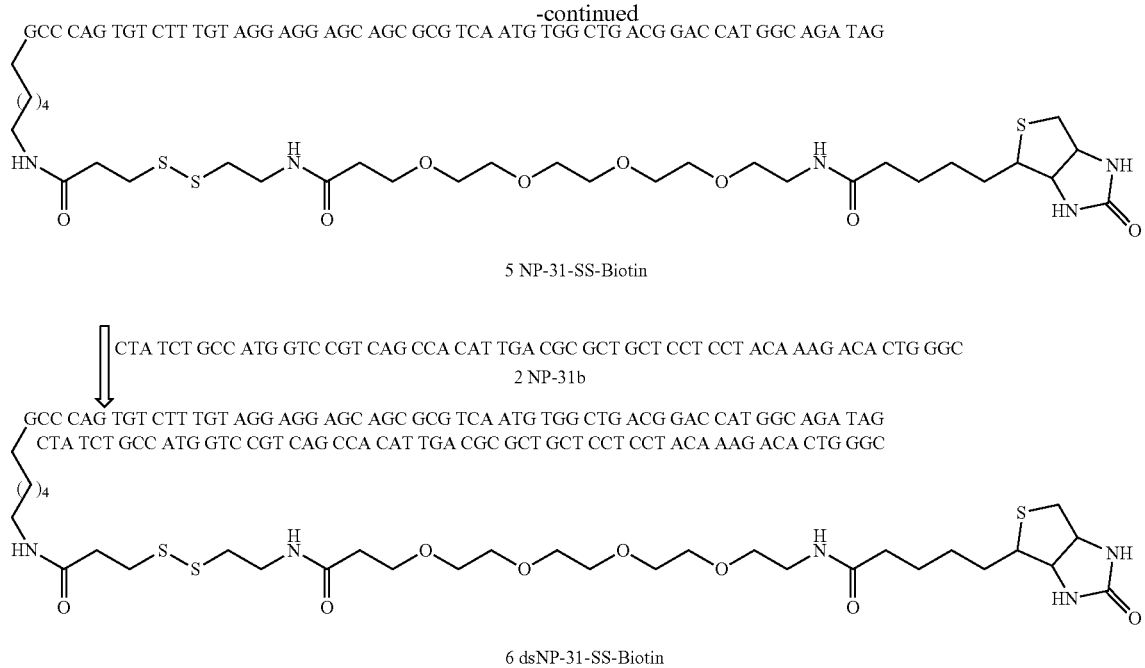

5 NP-31-SS-Biotin 6 dsNP-31-SS-Biotin

Formation of Biotinylated Double-Stranded DNA:

Approximately 60 μL of NP-31-SS-Biotin solution (5, 77 μM) (SEQ ID NO: 3) was mixed with 50 μL of NP-31b solution (2, 100 μM). The solution was placed in a heating block at 85° C. for 30 minutes, followed by slow cooling to room temperature over 2 hours. The double-stranded product (SEQ ID NO:3—forward strand (top); SEQ ID NO:4—reverse strand (bottom)) was purified over a TosoH G3000SW column (7.8 mm×300 mm) using 10 mM PBS, pH 7.2 by injecting the entire annealing volume (approximately 100 μL). The double-stranded biotinylated material eluted at 7.57 minutes as monitored by $A_{260}$ absorbance. The eluent volume was reduced using a 0.5 mL Amicon filter concentrator (MW cut-off 10,000 Da). The final dsNP-31-SS-Biotin (6) (SEQ ID NO: 3—forward strand (top); SEQ ID NO: 4—reverse strand (bottom)) concentration was calculated to be 11 μM, as determined by $A_{260}$ absorbance.

Example 18

Synthesis of Cleavable DNA-biotin—Thiol-Mediated Cleavage Construct

Binding ofssNP-31-SS-Biotin to Streptavidin Coated Magnetic Microparticles (SA-MP) and Chemical Cleavage (TCEP or DTT):

Chemical cleavage experiments were performed on magnetic microparticles via the following method (see FIG. 25). 100 μL of the modified oligonucleotide ssNP-31-SS-Biotin solution at 77 μM in PBS, pH 7.2 was incubated with 1 μL 0.1% Streptavidin paramagnetic microparticles for 30 minutes at room temperature. Excess oligo was removed by attracting the particles to a magnet and washing 10 times with PBST buffer, pH 7.4. The oligo-bound particles were incubated with varying concentrations of either DTT or TCEP in PBS, pH 7.4 for 15 minutes. Microparticles were washed 10 times with PBST buffer, pH 7.4 to remove any cleaved oligonucleotide. Complementary sequence NP-31c (SEQ ID NO: 5) (7, MW=7494.6 g/mole, 5.2 μM/OD) containing a fluorophore was incubated with the microparticles for 30 minutes in PBS, pH 7.4 to bind with any uncleaved ssNP-31-SS-Biotin remaining intact on the particle. The microparticles were attracted to a magnet and washed 10 times with PBST buffer, pH 7.4 to remove any excess NP-31c segments. Coated microparticles prepared as above that were washed but not subjected to chemical cleavage served as a control. The fluorescent signal on the particles was measured by fluorescence microscopy. Maximum cleavage efficiency was measured at 79% and 93% for DTT and TCEP, respectively as shown in Table 1.

7

NP-31c:

AlexaFluor® 546-5'CTA TCT GCC ATG GTC CGT CAG3'

TABLE 1

| | Fluorescent Signal on Microparticles (Relative Light Units) | Cleavage Efficiency |
|---|---|---|
| DTT (mM) | | |
| 50 | 3579 | 79% |
| 25 | 7417 | 57% |
| 12.5 | 11642 | 32% |
| 0.78125 | 17052 | 0% |
| 0 | 17059 | (Control) |
| TCEP (mM) | | |
| 250 | 460 | 93% |
| 222 | 448 | 94% |
| 187 | 474 | 93% |
| 142 | 512 | 92% |
| 83 | 477 | 93% |
| 45 | 453 | 93% |
| 19 | 452 | 93% |
| 0 | 5023 | (Control) |

Example 19

Synthesis of Cleavable DNA-Biotin—Photocleavage Construct

Evaluation of a Photocleavable DNA Sequence and Efficiency of Cleavage on Microparticles:

A photocleavable sequence of single-stranded DNA was synthesized using standard phosphoramidite chemistry (Integrated DNA Technologies). The oligonucleotide consisted of 48 nucleotides composing two Oligo segments (Oligo 8-1 (SEQ ID NO: 6) and Oligo 8-2 (SEQ ID NO: 7)) separated by two photocleavable moieties (8, MW=15,430.1 g/mole, 441800 L mol$^{-1}$ cm$^{-1}$). The 5'-terminus contained an amino group separated from the DNA by a C-6 carbon spacer. A complementary strand to Oligo 8-2 was synthesized containing a fluorescent tag (9, MW=7738.8 g/mole, 212700 L mol$^{-1}$ cm$^{-1}$) (SEQ ID NO: 8). Both oligonucleotides were quantitated and lyophilized prior to subsequent manipulation.

```
Oligo 8-1 (SEQ ID NO: 6):
5'AAA AAA GGT CCG CAT CGA CTG CAT TCA3'

Oligo 8-2 (SEQ ID NO: 7):
5'CCC TCG TCC CCA GCT ACG CCT3'

NP-8 (8) (Oligo 8-1 (SEQ ID NO: 6) and Oligo 8-2
(SEQ ID NO: 7) joined by two photocleavable
moieties ("PC")):
H2N-5'AAAAAAGGTCCGCATCGACTGCATTCA-PC-PC-

CCCTCGTCCCCAGCTACGCCT3'

NP-9 (9) (SEQ ID NO: 8):
AlexaFluor546-5' AGG CGT AGC TGG GGA CGA GGG3'
```

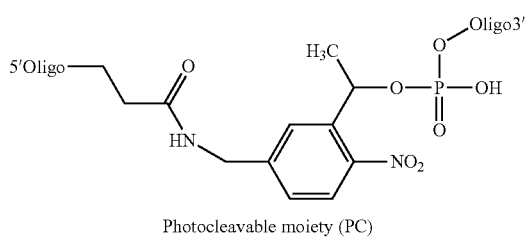

Photocleavable moiety (PC)

Figure 26A:
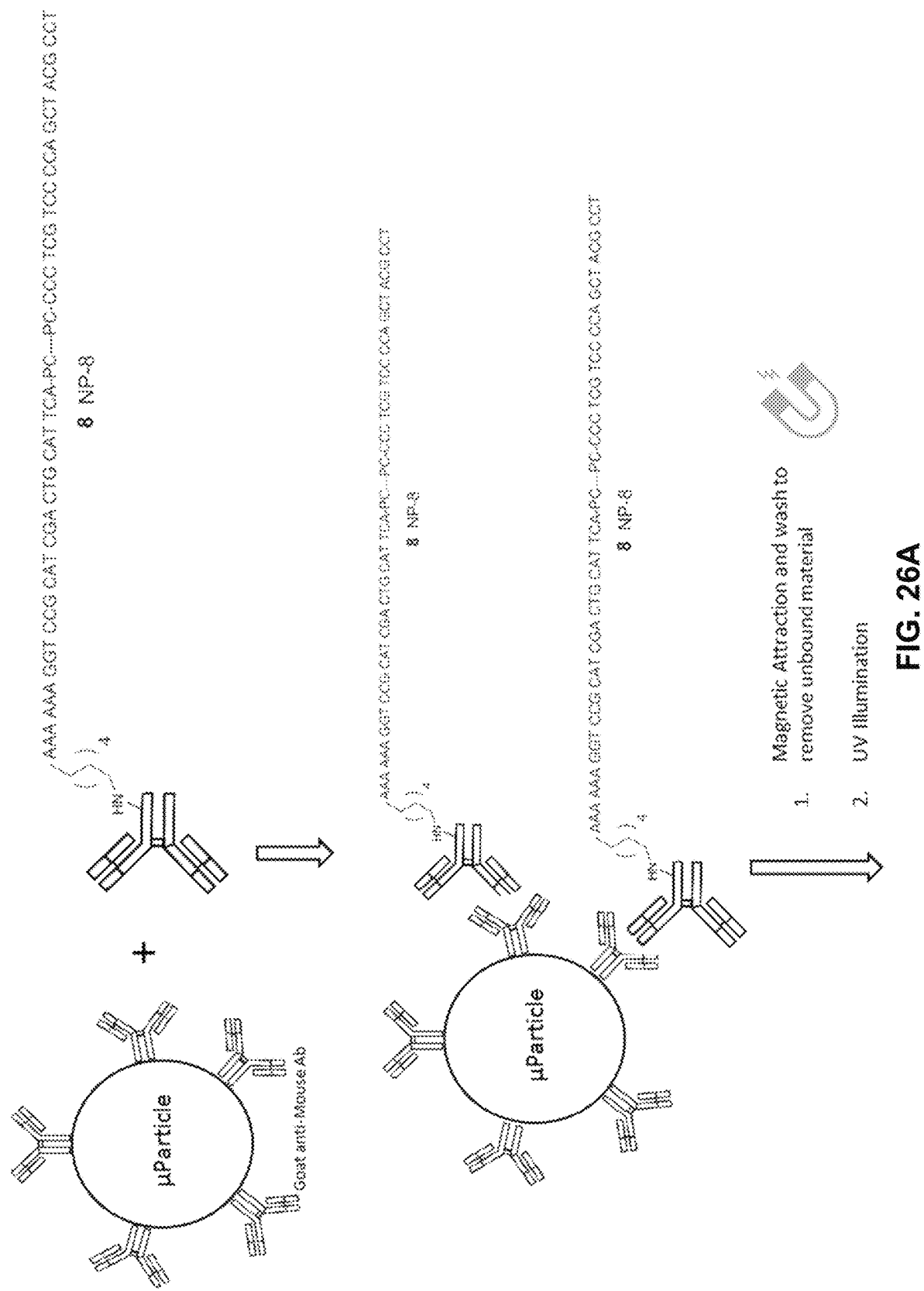
FIG. 26A and FIG. 26B show a schematic of photocleavage experiments performed on magnetic microparticles.
Figure 26B:
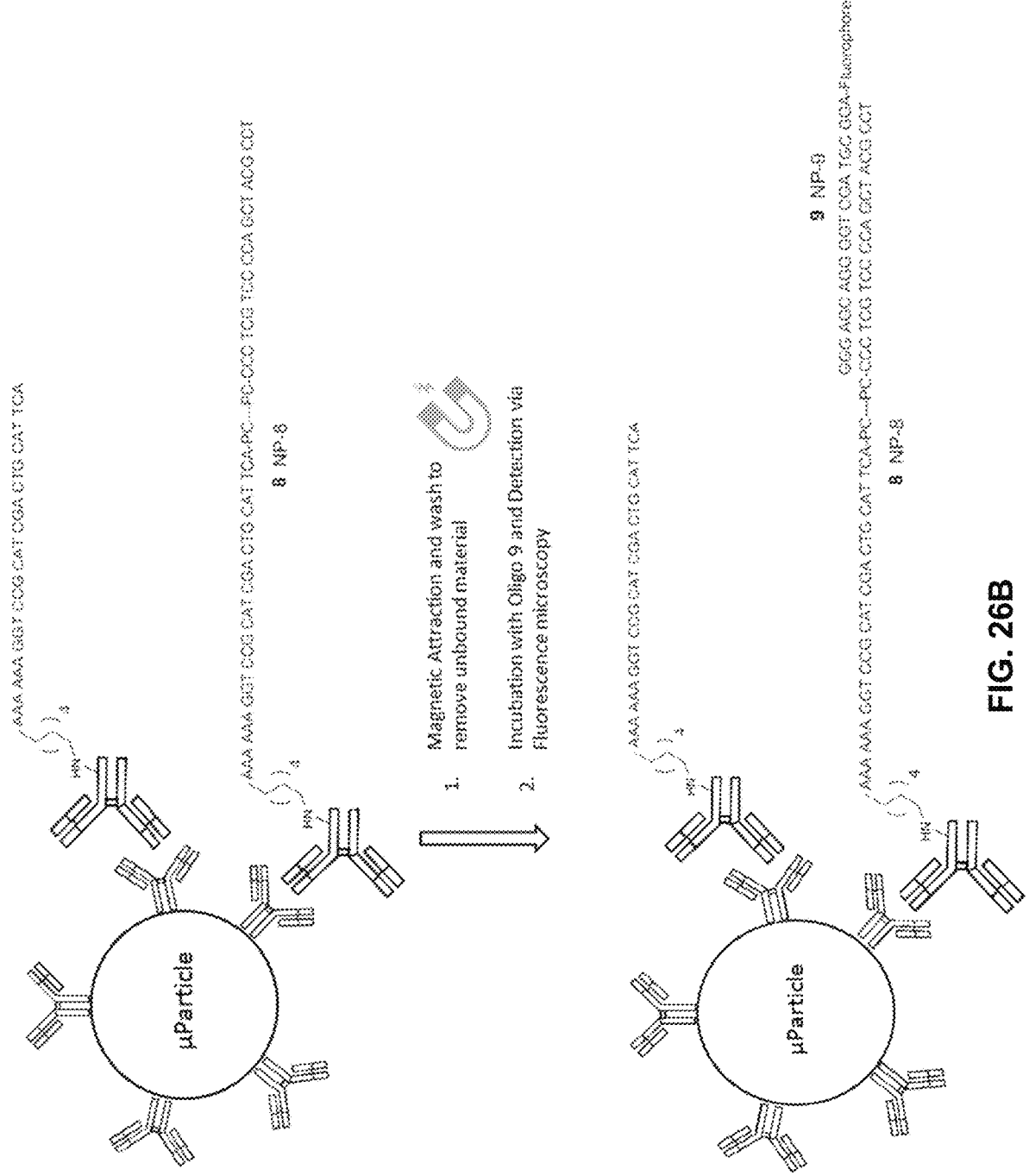

Photocleavage experiments were performed on magnetic microparticles via the following method (see FIGS. 26A and 26B). NP-8 was covalently attached to an antibody to generate an Ab-oligo complex (prepared by Biosynthesis Inc.). 100 µL of 33 nM antibody-oligo complex was incubated with 1 µL 0.1% solids of goat anti-mouse microparticles for 30 minutes at room temperature. Excess antibody-oligo complex was removed by attracting the particles to a magnet and washing 10 times with PBST buffer, pH 7.4. The microparticle complex solution was illuminated under UV light (300-350 nm wavelength) for 5 minutes. The microparticles were attracted to a magnet and washed 10 times with PBST buffer, pH 7.4 to remove any cleaved Oligo segments. Following particle resuspension in PBST buffer, pH 7.4, fluorescently labeled Oligo 9 (SEQ ID NO: 8) was added to the irradiated microparticles and incubated for 30 minutes at room temperature. Coated microparticles prepared as above that were washed but not subjected to UV illumination (uncleaved Oligo 8-2) served as a control. The fluorescent signal (AlexaFluor 546) on the particles was imaged by a fluorescence microscope. Cleavage efficiency when bound to paramagnetic microparticles was measured at 74% as shown in Table 2.

TABLE 2

| | Fluorescent Signal on Microparticles (Relative Light Units) |
|---|---|
| Illumination | 3660 |
| No Illumination (Control) | 13928 |
| Cleavage Efficiency | 74% |

Example 20

Thermal Cleavable Linkers

This Example describes thermal cleavable linkers and their cleavage. Such thermal cleavable linkers can be employed, for example, in a DMF chip, droplet-based microfluidic chip, SAW chip, or the like, as described herein.

Thermal cleavable linkers are cleaved by elevating the temperature above a threshold, such as in the thermal separation of double-stranded DNA. Temperature elevation in the DMF chip can be achieved photothermally by transferring energy from light to an absorbing target. In one method, a source of light, such as a laser, having a wavelength of about 980 nm (range about 930 nm to about 1040 nm) can be applied to the DMF chip in the region of the fluid sample. The light can be absorbed by the water molecules in the fluid, resulting in an increase in temperature and cleavage of the linker. The level and duration of heating can be controlled by pulse length, pulse energy, pulse number, and pulse repetition rate. For example, photothermal heating using the absorbance band of water is described, e.g., U.S. Pat. No. 6,027,496.

Photothermal heating also can be achieved by coupling the light source with a dye, or pigment containing target. In this case, a target area of the DMF chip is printed with an absorbing dye or pigment, e.g. carbon black. When the fluid is in contact with the target, the light source, e.g. a commercially available laser diode, is directed at the light-absorbing target, resulting in a localized increase in temperature and cleavage of the linker. The level and duration of heating can be controlled by the absorbance properties of the target, light wavelength, pulse length, pulse energy, pulse number, and pulse repetition rate. For example, photothermal heating using a light source in combination with a light absorbing target is described in U.S. Pat. No. 6,679,841.

In a third method of photothermal heating, an absorbing dye or pigment can be introduced into the fluid in the DMF chip. The light is then transmitted through the DMF chip and the energy transferred to the dissolved or suspended absorbing material, resulting in a localized increase in temperature and cleavage of the linker. The level and duration of heating is controlled by absorbance properties of the target material, light wavelength, pulse length, pulse energy, pulse number, and pulse repetition rate. In one embodiment of this method, the light absorbing target is the magnetic microparticle suspension used in the device. For example, photothermal heating using suspended nanoparticles in a fluid droplet is described in Walsh et al., Analyst, 140(5), 1535-42 (2015). The reference of Walsh et al. also demonstrates some of the control that can be achieved in photothermal applications.

Example 21

Thermal Cleavage Accomplished Via Microwave-Induced Particle Hyperthermia

This Example describes the use of microwave-induced particle hyperthermia to facilitate thermal denaturation (such as dsDNA denaturation, retro-Michael reactions, retro-Diels-Alder, and other eliminations) to release a countable moiety via a thermal sensitive cleavable linker, as immunoassay detection can be accelerated with the use of low powered microwave radiation. Such thermal sensitive cleavable linkers can be employed, for example, in a DMF chip, as described herein.

In this example, formation of an orthogonally functionalized short dsDNA segment such as a 15 bp sequence with a double stranded $T_m$ in the range of 40-55° C. serves as the thermal release agent. The dsDNA segment can be reacted with antibody via attachment chemistry such as sulfhydryl-maleimide interaction and 26 nm carboxylated polystyrene nanoparticles (NP), such as those which can be obtained from Bangs Labs (Fishers, Ind., USA) via attachment chemistry such as amine-activated carboxylic acid chemistry. The 26 nm NPs have a surface charge of 528.7 µeq/g and a parking area of 68.4 sq·Å/group (per manufacturer information). The antibody and nanoparticle are associated through the dsDNA segment which forms a thermally triggered releasable linker. The thermal linker can be cleaved using a technique such as microwave irradiation to trigger particle hyperthermia and a localized temperature gradient.

```
DNA Sequence 1 (10) (SEQ ID NO: 9):
H2N-5' CAA GCC CGG TCG TAA3'

DNA Sequence 1b (11) (SEQ ID NO: 10):
Maleimide-5' TTA CGA CCG GGC TTG3' dsDNA Sequence (12) (SEQ ID NO: 9 - forward strand
(top); SEQ ID NO: 10 - reverse strand (bottom)):

H2N-5' CAA GCC CGG TCG TAA3'

3' GTT CGG GCC AGC ATT5'-Maleimide.
```

Annealing of the Orthogonally Functionalized Complementary D1VA Sequences Complex A solution of approximately 100 µM DNA Sequence I (SEQ ID NO: 9) in PBS pH 7.5 can be mixed with 1.0 molar equivalents of DNA Sequence 1b (theoretical $T_m$ 51.6° C. per Integrated DNA Technologies oligo analyzer tool) (SEQ ID NO: 10) in PBS pH 7.5 and placed in a heating block at 60° C. for 30 minutes, followed by slow cooling to room temperature over 2 hours. The resulting dsDNA product is purified over a Tosol-I G3000SW column (7.8 mm×300 mm) using 10 mM PBS, pH 7.2 by injecting the entire annealing volume. The eluent volume is reduced using a 0.5 mL Amicon filter concentrator. The final dsDNA concentration is determined by A260 absorbance. The reaction scheme is depicted below ("Mal" is maleimide).

Activation of Carboxyl-Polystyrene Nanoparticles and Addition of Double Stranded DNA:

Carboxy nanoparticles are preactivated as described in Example 5 under section "Activation of carboxyl-polystyrene nanoparticles." The DNA loading on the NP is determined by thermal denaturation of the bound DNA strands, particle washing, annealing of a fluorescently labelled complementary DNA sequence (such as AlexaFluor546-5'-TTA CGA CCG GGC TTG3' (SEQ ID NO: 11)) and quantified using a fluorescence microscope.

Antibody Reduction and Conjugation to a NP-dsDNA Complex:

The antibody is reduced as described in Example 5 under section "Antibody reduction." The reduced antibody can be used immediately for coupling to the NP-dsDNA complex. The resulting conjugate is centrifuged at 6,500 g and the supernatant is removed via decanting. The wash procedure is repeated 5 times with PBS pH 7.5 to remove any free antibody from the nanoparticle. The active antibody to nanoparticle incorporation ratio may be quantified using a fluorescently labeled antigen to the given antibody. The conjugate NP concentration (% solids) is determined using UV-Vis spectroscopy (600 nm). The particle conjugate is examined by SEM and the size/charge distribution is determined using the ZetaSizer.

Microwave-Induced Particle Hyperthermia and Nanopore Counting Immunoassay:

The scheme above illustrates the nanopore counting assay utilizing the thermally denatured antibody-nanoparticle conjugate whose preparation is described above. A sandwich type immunoassay can be prepared using magnetic microparticles coated with an analyte capture agent in which blood analyte is incubated with magnetic microparticles, washed, and incubated with the antibody-nanoparticle conjugate described. Particle hyperthermia can be induced using microwave irradiation to create a local temperature gradient near the particle surface. Particle hyperthermia methods such as those reviewed in Dutz and Hergt (Nanotechnology, 25:452001 (2014)) may be used. The adaptation of these techniques to local thermal denaturation in an immunoassay setting can provide a method to release a counting moiety (such as a nanoparticle). Following removal of the magnetic microparticles, the counting moiety (nanoparticle) is counted upon passage through the nanopore.

Example 22

Nanopore Counting Data

This Example describes nanopore counting data for a variety of tags, e.g., ssDNA hybrid molecules with polyethyleneglycols (DNA-STAR), dsDNA, dsDNA labeled with DBCO, and PAMAM succinamic acid dendrimers. Use of these different tags along with different size nanopores was done to provide for nanopore optimization. Different molecular polymer labels were suspended in an appropriate salt buffer and detected using a standard fluidic cell cassette.

Current-voltage (i-V) recordings (voltammetric data) and current-time (i-t) recordings were recorded using in-house instrumentation. A computer software program called CUSUM was employed to run through the acquired data and detect events based on the threshold input by the user. Any impact of subjectivity in the assessment was minimized by detection of as many events as possible and filtering afterwards for specific purposes.

Initial experiments were performed with the tags added to the cis side of the membrane. An electric bias of 200 mV was applied to the label solution and current blockades were monitored using the Axopatch 200B amplifier and CUSUM software.

It is known that small molecules can go through nanopores quite fast unless the pore size restricts their passage. The current blockages of fast events can be deformed due to the limited bandwidth of a system. Faster molecules can even be completely undetected by a particular system.

In our studies, only larger polymers and molecules labeled with large group modifiers were detected. Experimental conditions and number of detectable events are shown in Table 3.

TABLE 3

| Polymer | Cconc (nM) | Background Elecrolyte | Electrolyte concentration (M) | pH | Membrane Thickness (nm) | Nanopore Diameter (nm) | Detection voltage (mV) | Events detected by CUSUM |
|---|---|---|---|---|---|---|---|---|
| 50 bp dsDNA control | 60 | LiCl | 3.6 | 8.0 | 10 | 3.9 | 200 | 414 |
| DBCO backbone | 96 | LiCl | 3.6 | 8.0 | 10 | 3.9 | 200 | 594 |
| dsDNa star | 20 | LiCl | 3.6 | 8.0 | 10 | 3.9 | 200 | 5589 |
| PAMAM ($6^{th}$ gen)-succinamic acid | 100 | KCl | 1.0 | 10 | 10 | 7.8 | 100 | 264 |
|  |  |  |  |  |  |  | 150 | 1122 |
|  |  |  |  |  |  |  | 200 | 1322 |

These data confirm that DNA dendrimers, polymers, and PAMAM dendrimers can be used as detection labels for solid-state nanopore sensors.

Example 23

Nanopore Differentiation of Biomolecules

In this Example, the nanopore was used to differentiate biomolecules (e.g., dsDNA stars, DBCO-modified dsDNA and regular dsDNA). This methodology can be used for multiplexing using different label types.

This Example employed a 50 bp oligonucleotide containing a branch point in the middle (bp #25), where a single-stranded oligonucleotide was covalently linked (DNA-Star); a double-stranded 50 bp oligonucleotide containing a dibenzylcyclooctyne (DBCO) modification in the middle (base #25); and a 5'-thiol modified double-stranded DNA oligonucleotide.

Figure 24A:
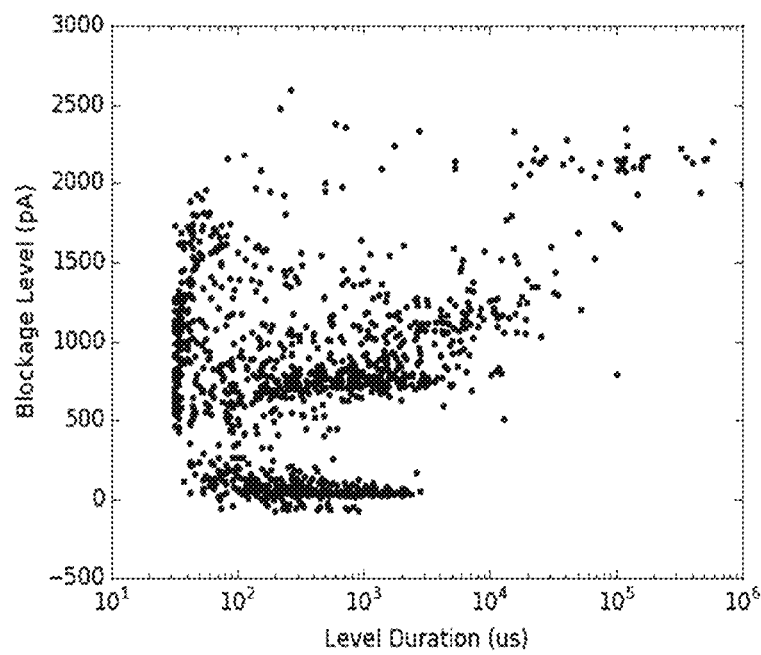
Figure 24B:
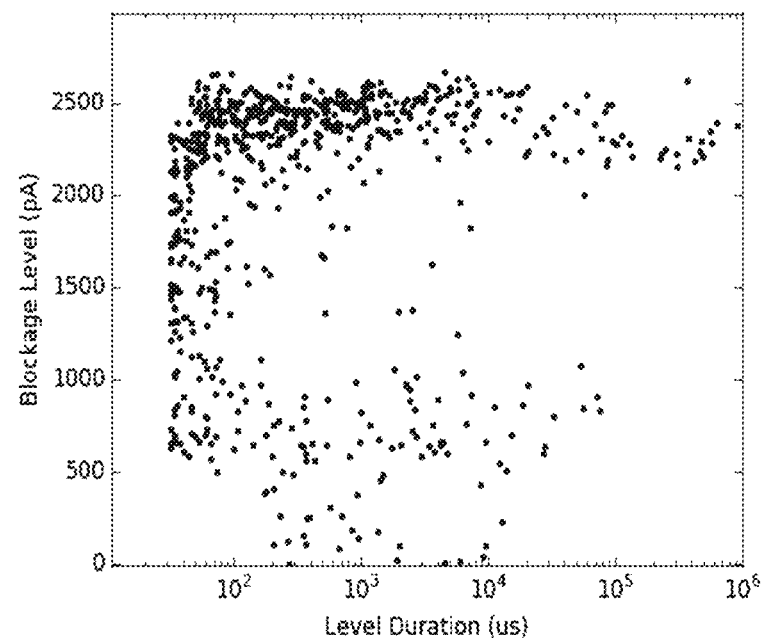
Figure 24C:
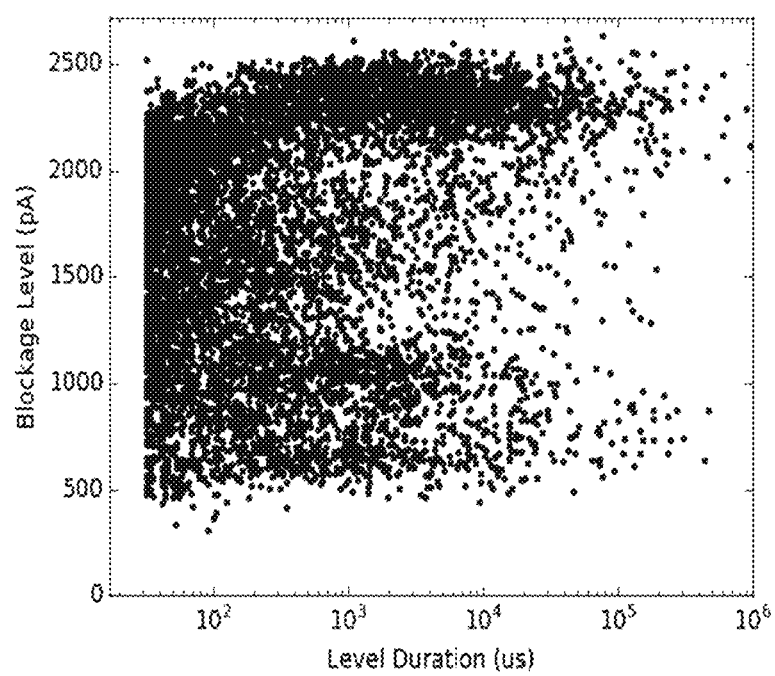

These various modified DNA molecules were analyzed using three different $SiN_x$ nanopores in 3.6 M LiCl buffer. DNA-star molecules were analyzed with a 4.0 nm diameter pore; DBCO-modified DNA was analyzed with a 3.7 nm diameter pore; thiol-modified DNA was analyzed with a 4.2 nm diameter pore. Current blockade levels (pA) were plotted against nanopore duration times (sec), in order to show the ability of the nanopores to differentiate the three different biomolecules. At a population level, the three different labels appear to be distinguishable, as demonstrated by the distinct pattern differences in the scatter plots (FIGS. 24A-24C). Identification of individual events in real-time requires additional levels of blockade level and time information as a way to distinguish signals from noise. The ability to differentiate different nanopore labels demonstrate that nanopores can be employed for multiplexing in various assays.

Example 24

Qualitative Analysis

The following example describes a method for conducting a qualitative assay. Basically, in this example, a construct was used to demonstrate the principle of the assay on a DMF chip and the contruct was cleaved and the label was released and then counted using a nanopore so as to generate a signal as it translocates the nanopore, thus indicating that the binding of two specific binding member pairs (streptavidin and biotin) wherein this cleavage and subsequent counting of a dsDNA label is correlated to the specific binding having occurred during the assay. Furthermore, appropriate control experiments were conducted to confirm that the signal generated from the label that was counted during the nanopore translocation measurement was due to the specific binding event having occurred during the assay process rather than being correlated to the presence of thiol cleavage reagent being introduced into the assay process flow. The details of the experiments conducted follow.

Figure 27:
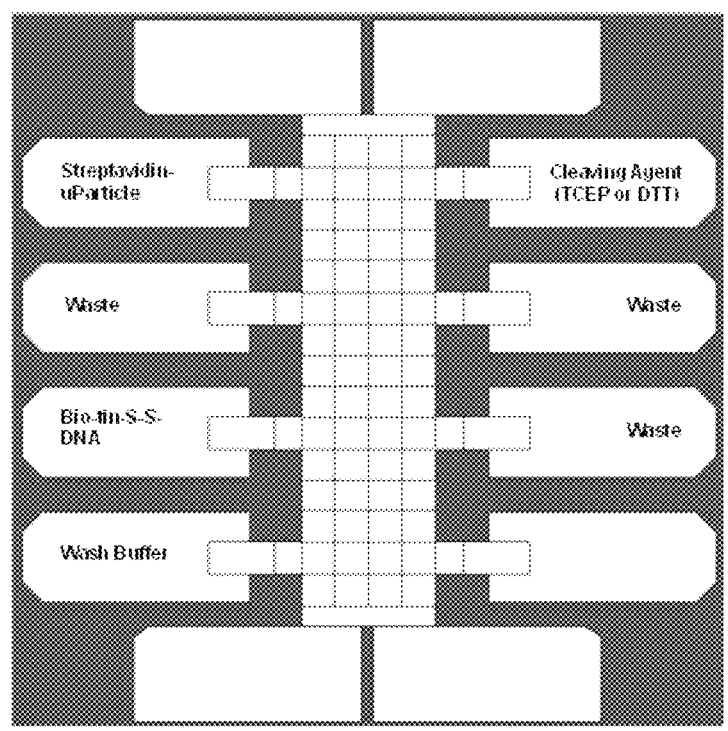
FIG. 27 shows a schematic of the reagent placement on the DMF chip.

Thiol-Mediated Cleavage Using DMF:

A biotin-labeled double-stranded DNA containing a cleavable disulfide bond ((6) of Example 17) was used as a target for nanopore detection/counting. The binding assay consisted of binding the biotin DNA to streptavidin magnetic microparticles on a DMF chip, followed by a thiol-mediated chemical cleavage step (see FIG. 25). Reagent placement on the DMF chip is shown in FIG. 27. The cleaved DNA target, separated from the species bound to the streptavidin magnet particles, was transferred to a nanopore fluidic cell containing a solid-state silicon nitride ($SiN_x$) membrane with a pre-drilled nanopore created by controlled dielectric breakdown (H. Kwok, et al., *PLoS,* 9(3), 2014). The DNA target material was counted and analyzed using open-source CUSUM software analysis package (NIST).

Appropriate reagents were loaded onto a glass DMF chip (3"×2"×0.0276") containing 8 reagent reservoirs. Except for waste reservoirs, each reservoir contained approx. 5 μL of each reagent. Concentrations of reagents were as follows: 10 μM Biotin-SS-DNA in PBS (pH=7.2); 10 mg/mL (w/v) M-270 2.7 μm streptavidin-coated magnetic microparticles (Life Technologies); PBS wash buffer (pH=7.2)+0.05% ETKT (Ethylene tetra-KIS (ethoxylate-block-propoxylate) tetro), 50 mM tris-(2-carboxyethyl)phosphine (TCEP). Approximate size of a dispensed DMF droplet was 1.5 μL.

One droplet of M-270 streptavidin-coated microparticles was dispensed and mixed with 1 droplet of dsNP-31-SS-biotin for approx. 40 minutes. Mixing was accomplished by combining the 2 droplets and moved in a circular pattern on the DMF chip over 12 electrodes (3×4). The bottom magnet was engaged to collect the microparticles and the supernatant was moved to a waste reservoir. Next, two droplets of PBS/ETKT buffer were dispensed and moved to the microparticle slug, which was then resuspended in solution. The suspension was mixed for 5 minutes before the magnet was again engaged and the supernatant was removed to the waste reservoir. The particle wash step was repeated a total of 11 times, while gradually increasing the mixing time up to 45 minutes. The last wash supernatant was moved to an empty reservoir. An additional 5 droplets of PBS/ETKT was moved to the same reservoir. The wash and PBS/ETKT in the reservoir was removed using a 34-AWG nonmetallic syringe (Microfil 34-AWG) and transferred to a 1.5 mL Eppendorftube, in preparation for nanopore analysis. Cleavage was initiated by moving 2 droplets of TCEP reagent to the microparticle slug and mixing for 45 minutes. The bottom magnet was engaged and the supernatant (containing the cleaved DNA) was moved to an empty reservoir. An additional 5 droplets of PBS/ETKT wash buffer was moved to the same reservoir. The final extract was removed from the DMF chip using the 34 gauge nonmetallic syringe and transferred to a 1.5 mL Eppendorf tube, in preparation for nanopore analysis. The cleavage eluent was microfuged for 30 seconds and placed in a magnetic rack for 1 minute, to remove any trace microparticles.

Nanopore Analysis:

Nanopore fabrication was achieved using controlled dielectric breakdown (CBD) of a 10 nm thick $SiN_x$ membrane embedded in a TEM window (0.05 μm×0.05 μm) (Norcada NT0052, low stress $SiN_x$). This method is capable of producing small diameter solid-state pores with high precision and minimal cost. The TEM-$SiN_x$ membrane was placed in a polytetrafluoroethylene (PTFE) fluidic cell containing two buffer chambers, and sealed using two silicone elastomer gaskets. The fluidic cell contained a 16 μL volume channel in the bottom of the cell, which connected the salt solution in the upper chamber to the nanopore membrane. For nanopore fabrication, the fluidic cell was first filled with degassed ethanol, exchanged with degassed deionized water and then filled with degassed 0.5 M KCl, buffered to pH 10 with sodium bicarbonate in 18 MΩ deionized water. Fabrication was performed using an amplifier using a bias voltage of 8V. The two sides of the fluid cell were connected using silver/silver chloride wires. As described in Kwok et al, while setting a fixed voltage of 8V, the current exhibits a capacitance (reduction of current) in real time. When the current increases, the power is removed from the cell. The sampling rate for the fabrication=25 KHz. An increase of the leakage current indicates formation of a pore, whereby the voltage was turned off. The pore diameter was determined from the following conductance-based equation:

$$G = \sigma\left(\frac{4L}{\pi d^2} + \frac{1}{d}\right)^{-1}$$

where G=conductance, σ=bulk conductivity (12.35 S/m measured for KCl), L=thickness of the membrane (10 nm), d=pore diameter (S. Kowalczyk, A. Grosberg, Y. Rabin, C. Dekker, *Nanotech.*, 22, 2011). The nanopore was checked for ohmic behavior by generating an I-V curve. The measured diameter of the nanopore was determined to be 4.4 nm, and was subsequently used for detection of the cleaved ds-SS-DNA target.

The fabrication salt buffer was replaced with 3.6 M LiCl, which was used as the sensing buffer for detecting translocation events. A headstage was placed between an Axopatch 200B amplifier and the silver/silver chloride connection to the fluidic cell housing the nanopore membrane.

Approx. 0.2 μL of the TCEP-cleaved ds-DNA target was diluted with 1.8 μL PBS buffer (this represented a 10-fold dilution of the TCEP-cleavage eluent), and the entire volume was loaded and mixed into the nanopore cell chamber, which contained approximately 30 μL of 3.6 M LiCl salt solution. The last DMF wash eluent was used as a negative cleavage control (this was not diluted). The number of DNA translocations was measured for 23 and 65 minutes for the TCEP eluent and negative control, respectively and converted to a flux rate ($sec^{-1}$). The results depicted in FIG. 28 demonstrate that the ds-SS-DNA target was successfully cleaved from the M-270 streptavidin particles using DMF and detected using a solid-state nanopore as a detector. SNR was determined to be 21.9, as measured from the nanopore flux rate.

Data Analysis:

The number of translocation events were determined by first calculating the anticipated current change found in a double stranded DNA translocation event under experimental test conditions using the equation $$\Delta G = \frac{\sigma \pi d_{DNA}^2}{4L}, \tag{S1}$$

as referenced in Kwok et al., "Nanopore Fabrication by controlled Dielectric Breakdown" Supplementary Information Section 8 and Kwok, H.; Briggs, K.: and Tabard-Cossa, V.; "*Nanopore Fabrication by Controlled Dielectric Breakdown*"—PLoS ONE 9(3): e92880 (2014). Using this anticipated current blockage value, the binary file data of the experimental nanopore output was visually manually scanned for acceptable anticipated current blockage events. Using these events, the Threshold and Hysteresis parameters required for the CUSUM nanopore software were applied and executed. The output from this software was further analyzed using the cusumtools readevents.py software and filtering blockage events greater than 1000 pA (as determined from the first calculation). The flux events, time between events and other calculations were determined from the readevents.py analysis tool. Additional calculations were made on the CUSUM generated data using JMP software (SAS Institute, Cary, N.C.). It is understood that this method of threshold setting is one approach to data analysis and setting a threshold and that the present invention is not limited to this method and that other such methods as known to those skilled in the art can also be used.

Summary:

This example describes a qualitative assay by conducting the process of steps as described herein. A direct assay was conducted using the cleavable linker conjugate, as described in Example 17, with a thiol based cleavage step, as shown in FIG. 25. It is understood that other cleavable linker approaches to conducting such an assay may also include, but are not limited to, various other methods of cleavage of a linker so as to allow for the counting of various tags, as described herein. For example, such other alternative cleavage methods and/or reagents in addition to the method described in Example 17 can include those described in Example 16, Example 18, Example 19, Example 20 and Example 21, in addition to other cleavage methods described herein and known to those skilled in the art. It is also understood that while the assay format demonstrated in this Example (Example 24) represents a direct assay, other formats such as sandwich immunoassay formats and/or various competitive assay formats, such as are known to those skilled in the art, can be implemented as well to conduct an assay using the described methods.

For example, the sandwich immunoassay format for the detection of TSH (thyroid stimulating hormone), as described in Example 9, demonstrated the ability to conduct such an assay on a low cost DMF chip. Additionally, a number of various bioconjugation reagents useful for the generation of immunoconjugate or other active specific binding members having cleavable linkers can be synthesized using various heterobifunctional cleavable linkers such as those described in Example 1, Example 2, Example 3, Example 4, Example 5 and Example 6, in addition to other cleavable linkers that are otherwise known to those skilled in the art. Immuoconjugates useful for the practice of the present invention can be synthesized by methods such as those described in Example 3, Example 4, Example 5 and Example 6 as well as by methods known to those skilled in the art. Additionally, Example 8 shows the functionality of various fluidic droplet manipulations on a low cost chip that can facilitate various steps needed to carry out various assay formats including sandwich and competitive assay formats as well as other variations thereof known to those skilled in the art. Example 11 shows the fabrication of a nanopore that can be used to count cleavable label in an assay but it is understood that other methods for nanopore fabrication known to those skilled in the art can also be used for this purpose. Example 16 also represents another construct useful for the conduct of an assay where a cleavage is effected, thus leading to a countable label being released so as to be countable using the nanopore counting method, as described within this example.

Example 22 shows generally how counting can be effected so as to be able to measure translocation events relating to the presence of a variety of labels traversing the nanopore. FIG. 29 shows the concept of thresholding of the signal so as to be able to manipulate the quality of data in a counting assay. FIG. 28 shows qualitative assay data that is representative of the type of data that can be used to determine the presence of an analyte using such assay methods as described within this example. It is also understood that while dsDNA was used as a label in this particular example, other labels, such as the label described in Example 5 and/or Example 22 can also be utilized, including, but not limited to nanobeads, dendrimers and the like. Such constructs as needed to generate appropriate reagents can be synthesized through various examples herein this application or otherwise via methods known to those skilled in the art.

Example 25

Quantitative Analysis

The following example describes a method for conducting a quantitative assay. Basically, in this example, and as an extension of Example 24, a standard curve was generated so as to demonstrate that increased amounts of counting label, in this case with the countable label being a dsDNA molecule, correlated on a standard curve to the amount of specific binding agent that has been bound (which it turn correlates to the amount of analyte existing in the original sample) in an assay (binding) step. The standard curve for this particular experiment can be found in FIG. 31, FIG. 32, FIG. 34 based on various different methods of data analysis or FIG. 34 which relies up flux to generate a standard curve. In the latter case, the measurement method shown in FIG. 34 based based upon the events/time (flux of counting events) but it is understood that other measurement methods can also be used to generate a standard curve correlating to the amount of analyte concentration being measured in a given sample. The details of the experiments conducted are as follows.

Nanopore Fabrication:

Nanopore fabrication was achieved using controlled dielectric breakdown (CBD) of a 10 nm thick $SiN_x$ membrane embedded in a TEM window (0.05 μm×0.05 μm) (Norcada NT0052, low stress $SiN_x$) as this method is capable of producing small diameter solid-state pores with high precision and minimal cost. The TEM-$SiN_x$ membrane was placed in a polytetrafluoroethylene (PTFE) fluidic cell containing two buffer chambers, and sealed using two silicone elastomer gaskets. The fluidic cell contained a 16 μl volume channel in the bottom of the cell, which connected the salt solution in the upper chamber to the nanopore membrane. For nanopore fabrication, the fluidic cell was first filled with degassed ethanol, exchanged with degassed deionized water and then filled with degassed 0.5 M KCl, buffered to pH 10 with sodium bicarbonate in 18 MΩ deionized water. Fabrication was performed using an amplifier using a bias voltage of 8V. The two sides of the fluid cell were connected using silver/silver chloride wires. As described in Kwok et al, while setting a fixed voltage of 8V, the current exhibits a capacitance (reduction of current) in real time. When the current increases, the power is removed from the cell. The sampling rate for the fabrication was 25 KHz. An abrupt increase of the leakage current indicated formation of a pore, whereby the voltage was turned off. The 0.5 M KCl buffer was replaced with 3.6 M LiCl (pH=8.3).

The pore diameter was determined from the following conductance-based equation:

$$G = \sigma\left(\frac{4L}{\pi d^2} + \frac{1}{d}\right)^{-1},$$

where G=conductance, σ=bulk conductivity (16.06 S/m measured for LiCl), L=thickness of the membrane (10 nm), and d=pore diameter (S. Kowalczyk, A. Grosberg, Y. Rabin, C. Dekker, Nanotech., 22, 2011). The nanopore was checked for ohmic behavior by generating an I-V curve. The measured diameter of the nanopore was determined to be 4.8 nm, and was subsequently used for detection of the DNA calibration standards.

Figure 30A:
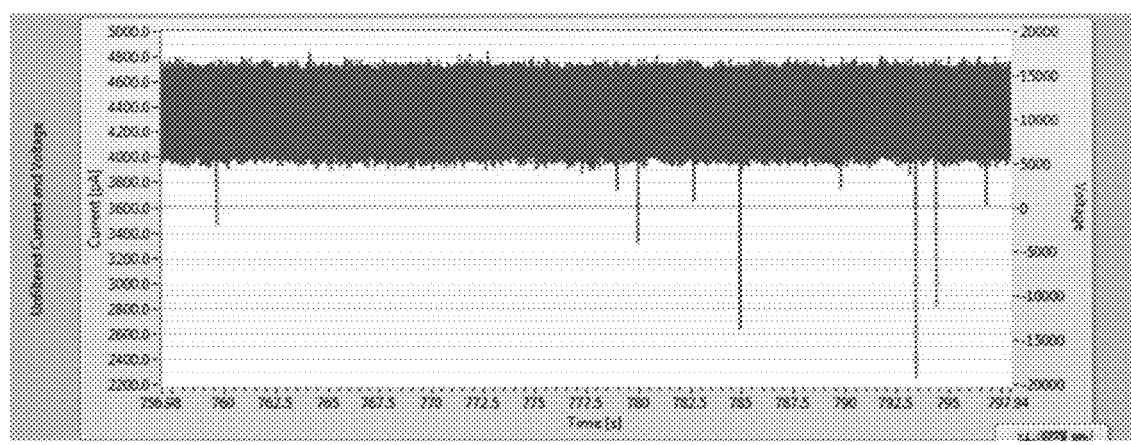
FIGS. 30A-30C show current blockages over different time periods for three standards of 94 nM (FIG. 30A), 182 nM (FIG. 30B), and 266 nM (FIG. 30C).
Figure 30B:
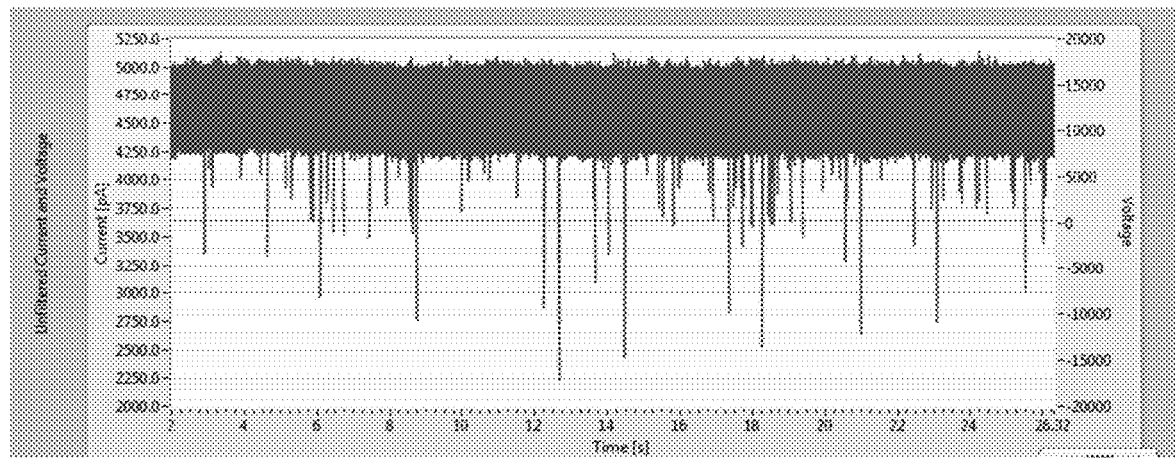
Figure 30C:
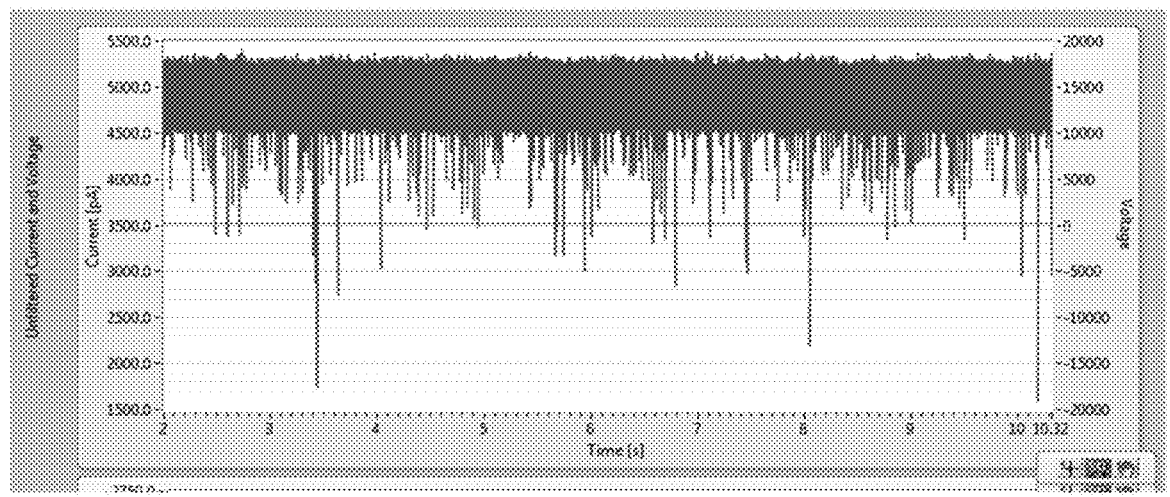

DNA Dose-Response:

DNA standards were used as calibrators to observe a dose-response curve by determining the change in nanopore flux rate with increasing concentrations of DNA. This generated a standard curve, which can be used for quantitation of a cleaved DNA label in an immunoassay. Two μl of a 1.5 μM 100 bp DNA standard (ThermoScientific) was pipetted into the PTFE fluidic cell containing 30 μl of 3.6 M LiCl salt solution, to give a final concentration of 94 nM DNA. The reagent was mixed by pipetting the solution up and down several times prior to nanopore analysis. The cell was subjected to a DC bias of +200 mV and monitored for current blockades over 60 minutes. CUSUM analysis software was used to characterize electrical signals and count rates. This procedure was repeated two times to give two additional points on the standard curve, 182 nM and 266 nM. Current blockades over different time periods are shown for all three standards—41 seconds for 94 nM (FIG. 30A); 24 seconds for 182 nM (FIG. 30B); 8 seconds for 266 nM (FIG. 30C). Baseline noise was empirically estimated to be approximately 900 pA, 900 pA and 1,000 pA for FIG. 30A, FIG. 30B and FIG. 30C, respectively.

Data from the run was used to generate three different types of dose-response curves—number of events over a fixed amount of time (5 minutes) (FIG. 31); time required for fixed number of events (200 events) (FIG. 32); and events per unit time (FIG. 33). Each of these curves may be used as a standard curve for a quantitative nanopore-based immunoassay, using DNA as the label. Similarly, other labels may be used to quantitate various analytes, such as dendrimers, polymers, nanoparticles, and the like.

Figure 47:
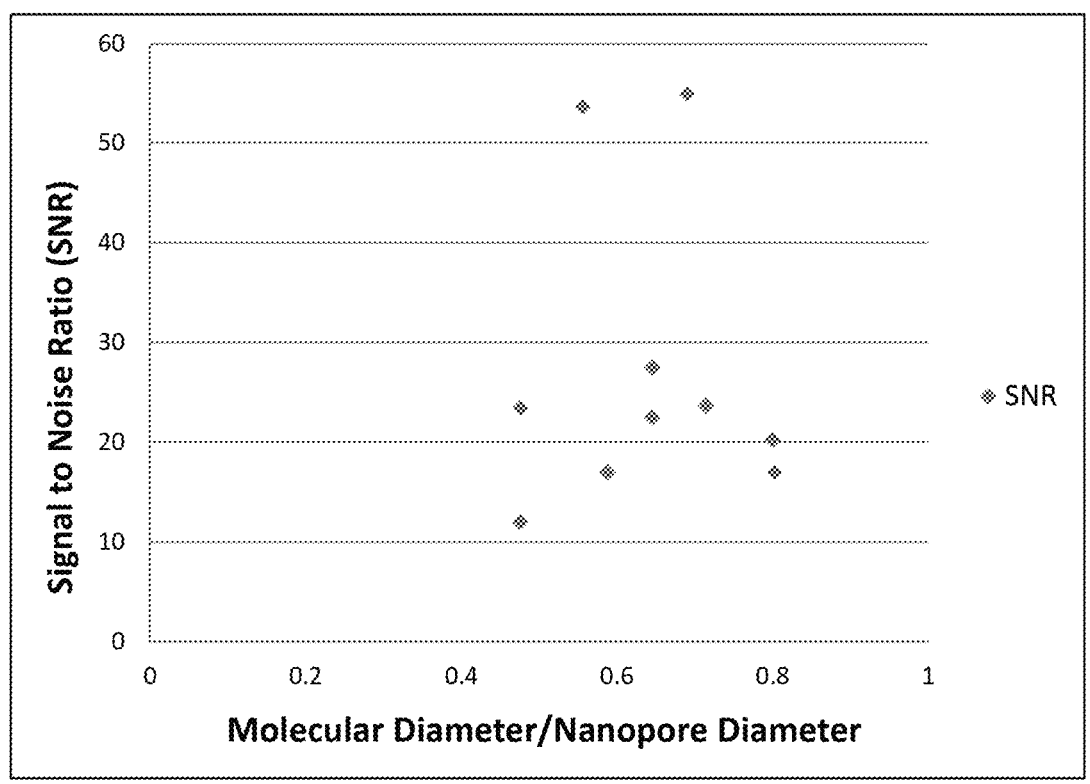
FIG. 47 shows a scatter plot of the averages of ratios plotted between counting label average diameter and nanopore size to the SNR (signal to noise ratio).
Figure 48:
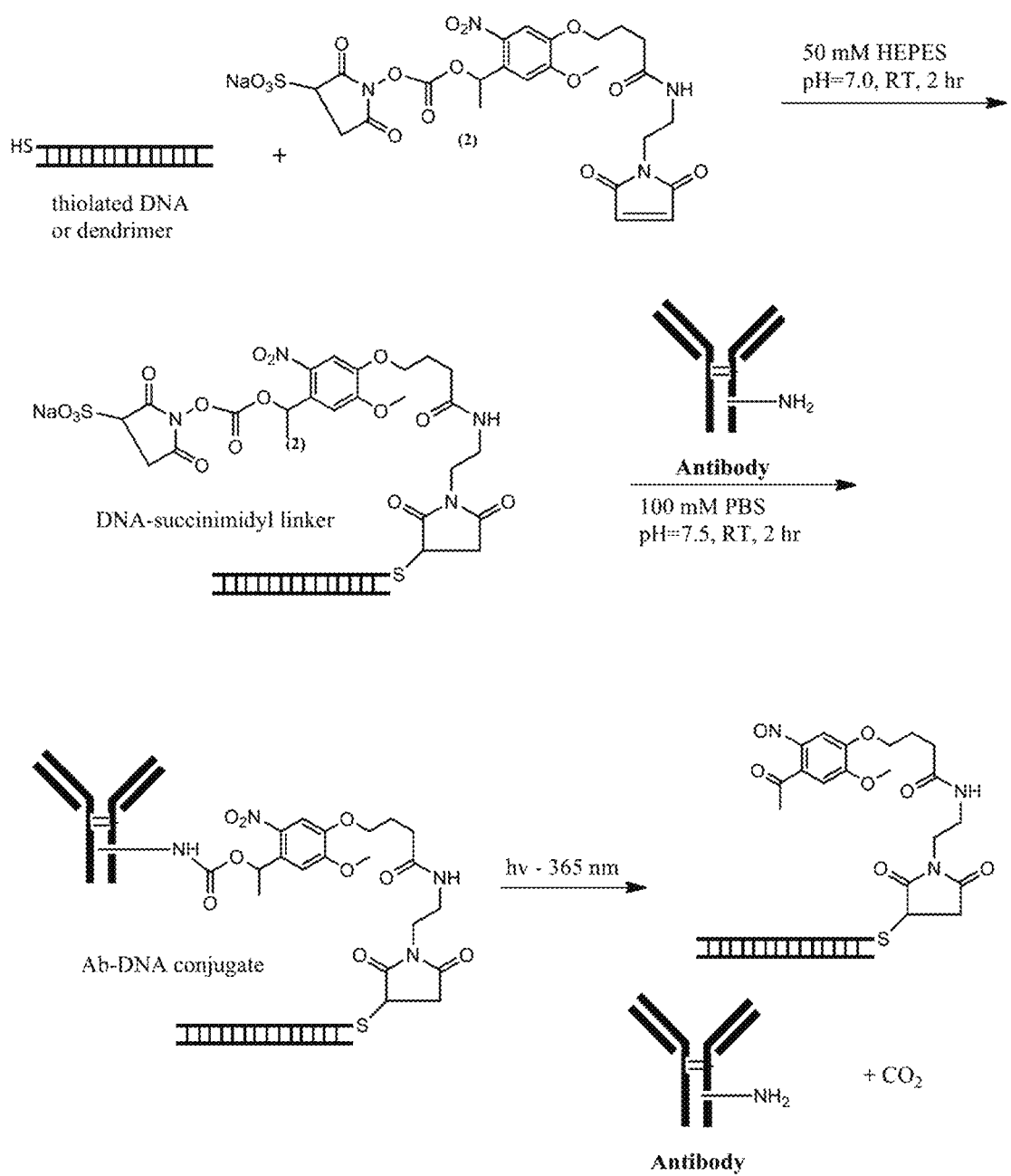
FIG. 48 shows a diagram illustrating an example of coupling and photochemical cleavage of antibody-DNA conjugate using sulfosuccinimidyl/maleimidyl 2-nitrobenzyl bifunctional linker.
Figure 49:
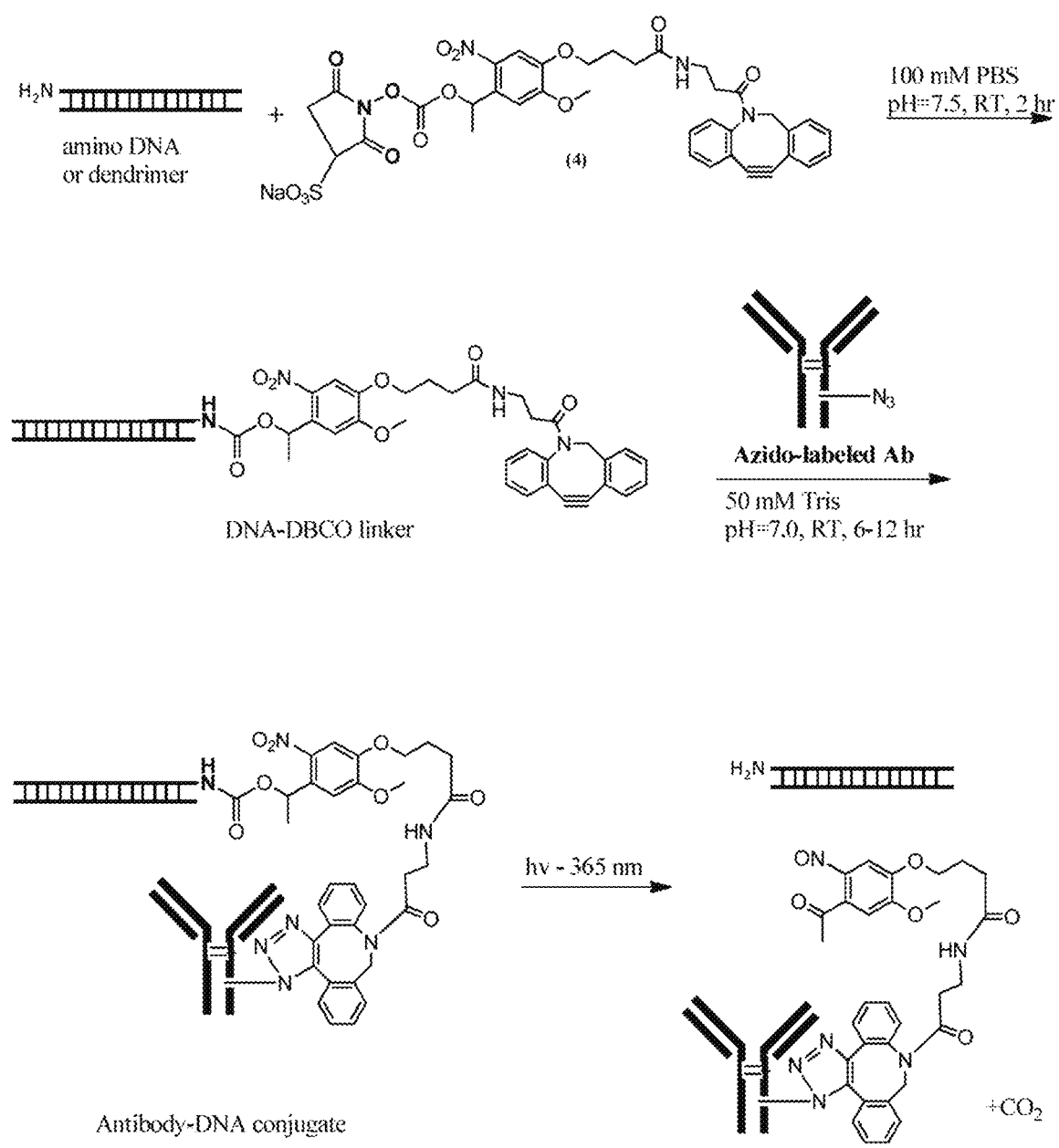
FIG. 49 shows a diagram illustrating an example of coupling and photochemical cleavage of antibody-DNA conjugate using sulfosuccinimidyl/DBCO 2-nitrobenzyl bifunctional linker.
Figure 50:
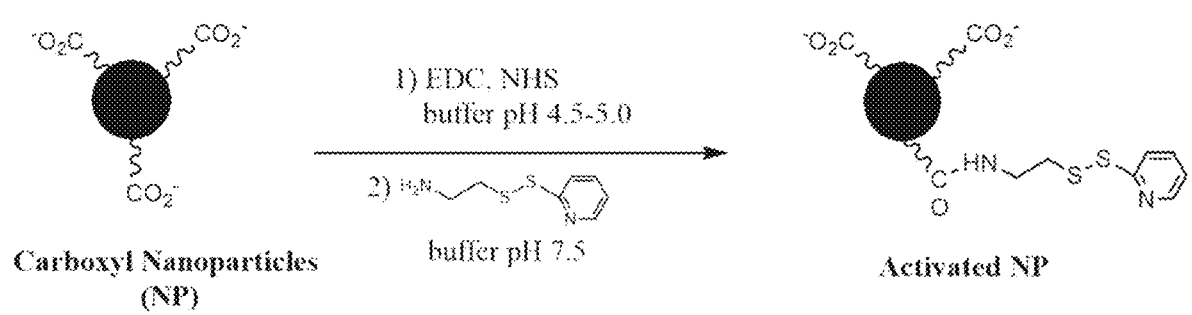
FIG. 50 shows a diagram illustrating an example of activation of carboxylpolystyrene nanoparticles.
Figure 51:
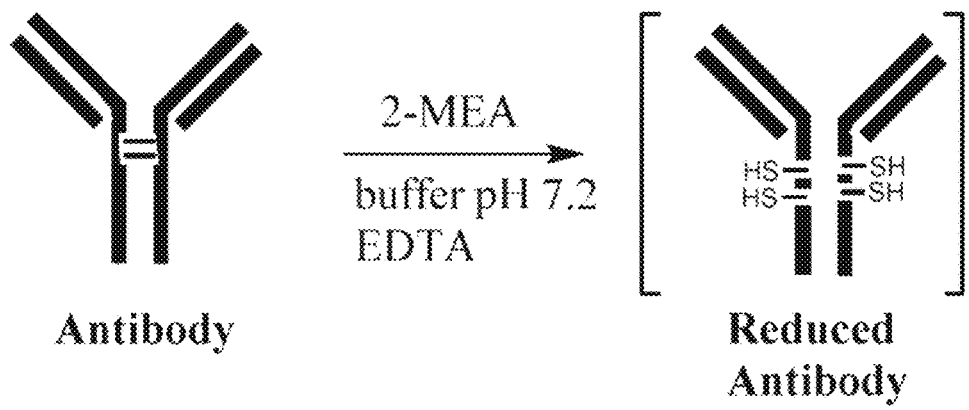
Figure 52:
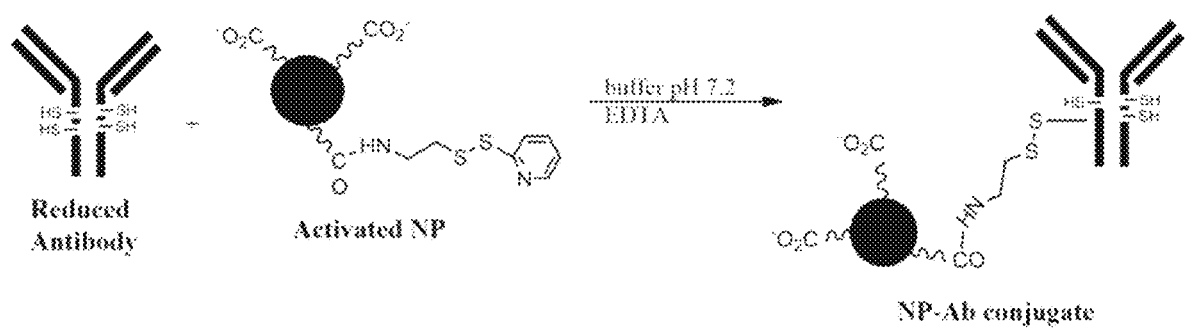
Figure 53:
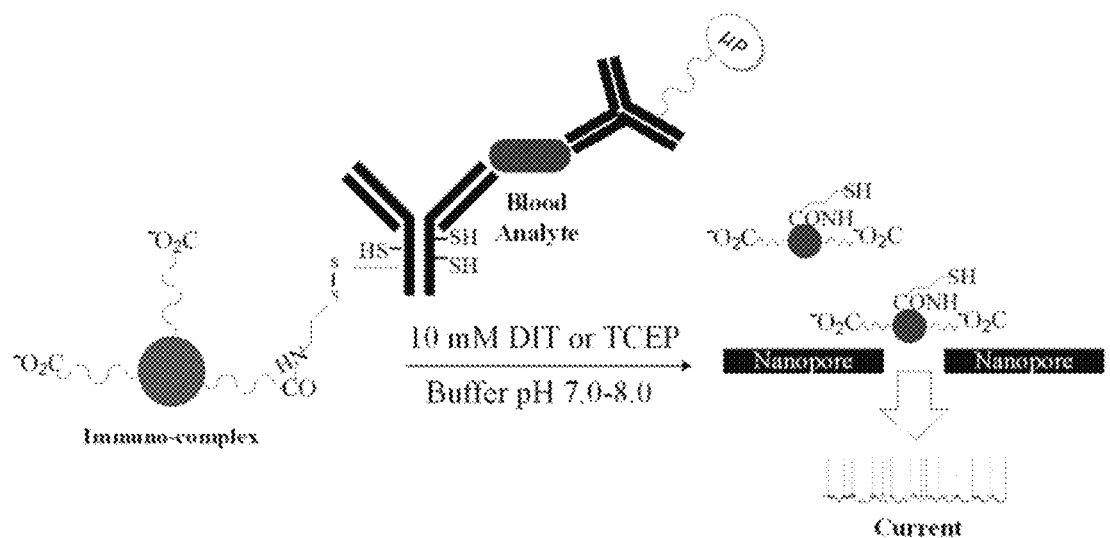
Figure 54:
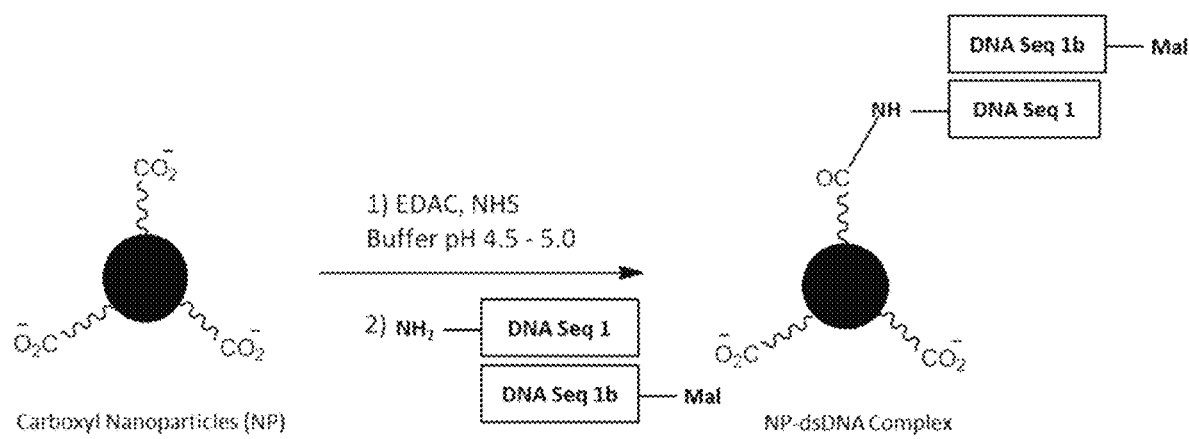
Figure 55:
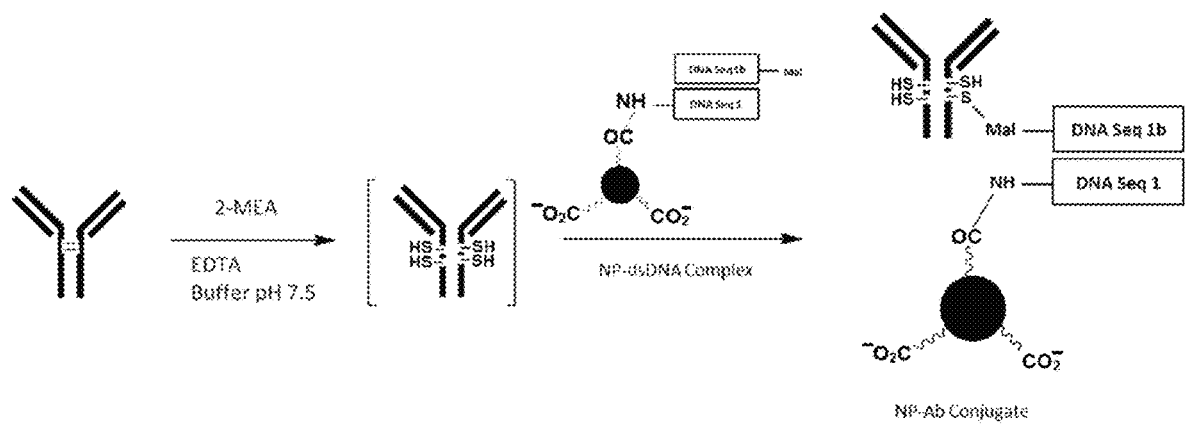
Figure 56:
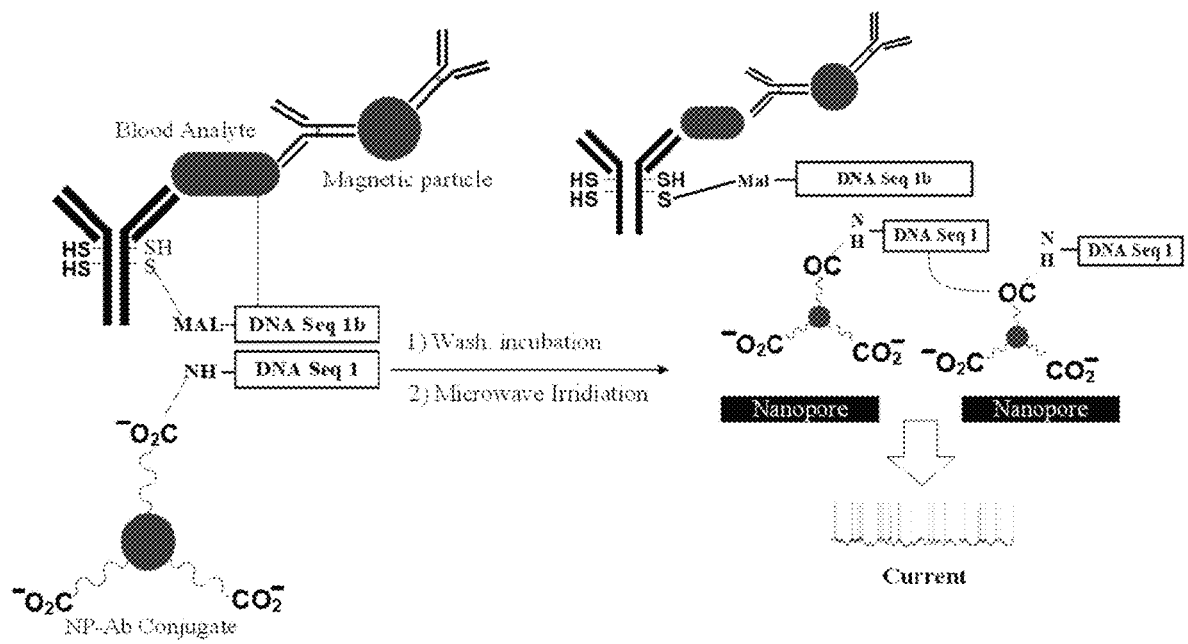

Seq31-SS-Biotin DNA Dose-Response:

The synthetic DNA construct, Seq31-SS-biotin, was used as the source material to generate a dose-response curve (FIG. 47). This target can be used to quantitate the cleaved label NP-Seq31-SS-biotin, which was cleaved from the streptavidin beads in the qualitative assay. Since this material has approximately the same MW and charge density as the cleaved label Seq31-SS-biotin, it may be used in a calibration curve to quantitate the cleaved target from streptavidin microparticles using TCEP and/or DTT.

Data Analysis:

The number of translocation events were determined by first calculating the anticipated current change found in a double stranded DNA translocation event under experimental test conditions using the equation:

$$\Delta G = \frac{\sigma \pi d_{DNA}^2}{4L} \quad (S1)$$

as referenced in Kwok et al., "Nanopore Fabrication by controlled Dielectric Breakdown" Supplementary Information Section 8 and Kwok, H.; Briggs, K.; and Tabard-Cossa, V.; "*Nanopore Fabrication by Controlled Dielectric Breakdown*"—PLoS ONE 9(3): e92880 (2014). Using this anticipated current blockage value, the binary file data of the experimental nanopore output was visually manually scanned for acceptable anticipated current blockage events. Using these events, the Threshold and Hysteresis parameters required for the CUSUM nanopore software were applied and executed. The output from this software was further analyzed using the cusumtools readevents.py software and filtering blockage events greater than 1000 pA (as determined from the first calculation). The flux events, time between events and other calculations were determined from the readevents.py analysis tool. Additional calculations were made on the CUSUM generated data using JMP software (SAS Institute, Cary, N.C.). It is understood that this method of threshold setting is one approach to data analysis and that the present invention is not limited to this method but other such methods as known to those skilled in the art can also be used.

Summary:

This example describes a quantitative assay by conducting the process of steps as described herein. A direct assay was conducted using the cleavable linker conjugate, as described in Example 17, with a thiol based cleavage step, and as shown in FIG. 25. It is understood that other cleavable linker approaches to conducting such an assay may also include, but are not limited to, various other methods of cleavage of a linker so as to allow for counting of various tags using a nanopore, as described herein. For example, such other cleavage methods in addition to the method described in Example 17 can include, but is not limited to, those described in Example 18, Example 19, Example 20 and Example 21, in addition to other methods described herein and known to those skilled in the art. It is also understood that while the assay format demonstrated in this Example (Example 25) represents a direct assay, other formats such as sandwich immunoassay formats and/or various competitive assay formats, such as are known to those skilled in the art, can be implemented as well to conduct an assay.

For example, the sandwich immunoassay format for the detection of TSH (thyroid stimulating hormone), as described in Example 9, demonstrated the ability to conduct such an assay on a low cost DMF chip. Additionally, a number of various bioconjugation reagents useful for the generation of immunoconjugate or other active specific binding members having cleavable linkers can be synthesized by those skilled in the art using various heterobifunctional cleavable linkers and conjugates synthesized by methods such as those described in Example 1, Example 2, Example 3, Example 4, Example 5 and Example 6, in addition to other cleavable linkers or conjugates that could be synthesized by methods that are known to those skilled in the art. Additionally, Example 8 shows the functionality of various fluidic droplet manipulations on a low cost chip that can facilitate various steps needed to carry out various assay formats including sandwich and competitive assay formats as well as other variations thereof known to those skilled in the art. Example 16 also represents another construct useful for the conduct of an assay where a cleavage is effected, thus leading to a countable label being released so as to be countable using the nanopore counting method as described within this example.

Example 22 shows generally how counting can be performed so as to be able to measure translocation events relating to the presence of a label traversing the nanopore. FIG. 29 shows the concept of thresholding of the signal so as to be able to manipulate the quality of data in a counting assay. FIGS. 31, 32 and 33 show quantitative assay data output that is representative of the type of data that can be used to determine the amount of an analyte using such assay methods as described within this example. FIG. 34 shows a standard curve generated from a construct that has been cleaved using a chemical method. It is also understood that while dsDNA was used as a label in this particular example, other labels, such as the label described in Example 5, can also be utilized, including, but not limited to, nanobeads, dendrimers and the like. Such constructs can be synthesized via methods known to those skilled in the art.

Example 26

Nanopore Electrical Field Simulations

A series of COMSOL simulation runs were performed on the proposed nanopore membrane design used in the silicon module, to study the influence of the size of the $SiO_2$ via on the counter ion concentration and electroosmotic flow rate through a theoretical 10 nm diameter nanopore. A top layer of $SiO_2$ served multiple purposes—1) provide an insulating layer to the $SiN_x$ membrane and, thereby, reduce the capacitive noise of the nanopore; 2) to increase the robustness and strength of the $SiN_x$ membrane within the silicon substrate; 3) to decrease the size of the $SiN_x$ area exposed to solution, thereby improving positioning of the pore on the membrane from the controlled dielectric breakdown (CBD) process. Electrical field simulations were used to determine interference of the SiO2 layer on localized counter ion concentration and electroosmotic flow through the pore.

With reference to FIG. 35, the silicon substrate (1) was etched to give cis and trans chambers, situated above and below the $SiN_x$ membrane. The $SiN_x$ membrane (50 μm×50 μm) (2) was layered between a 300 μm thick bottom layer of $SiO_2$ and a 300 μm thick top layer of $SiO_2$ (3). The top layer was fabricated to form a $SiO_2$ via (4), which allowed formation of the nanopore during CBD. The optimal diameter of the SiO2 via was determined by the simulation.

COMSOL Simulation Results:

COMSOL electrical field simulations used physical models based on materials, electrostatics, molecular transport and Laminar flow properties. Electric potential was based on Poisson equation; ionic flux was based on Nernst-Planck equation; fluid velocity was based on Stokes equation. Physical parameters used for the simulation are defined in Table 1, shown in FIG. 36.

Figure 37:
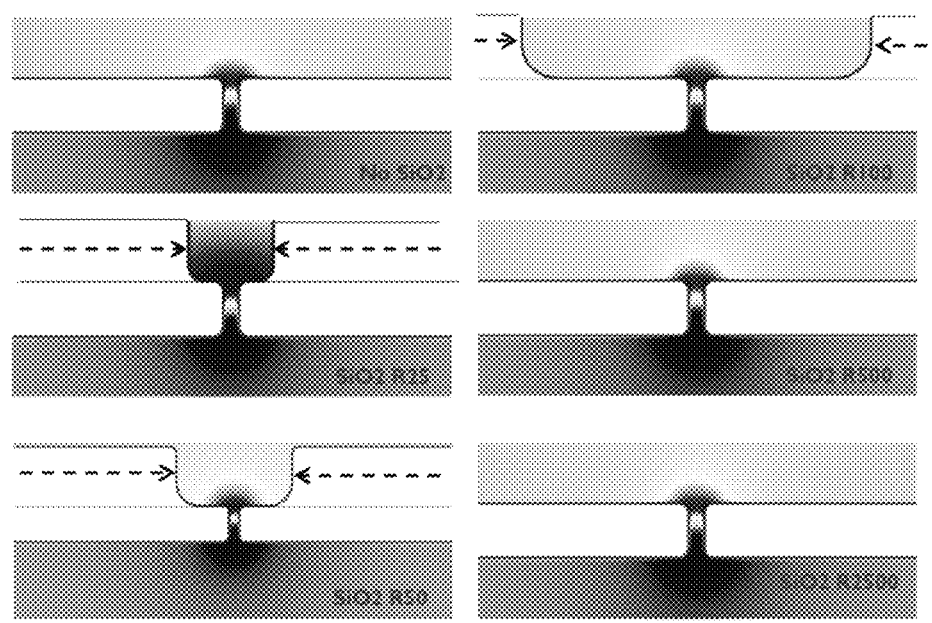
FIG. 37 is a collection of images showing simulation results for counter ion concentration gradients near a nanopore in a silicon nanopore module, according to embodiments of the present disclosure.

COMSOL results for counter ion concentration gradients near the pore are shown in FIG. 37, and show little to no influence of the ionic concentration when the $SiO_2$ via diameter was >50 nm in diameter. Below 50 nm, an accumulation of net charge near the mouth of the pore resulted. The most severe effect was observed at a diameter of 25 nm, where a large ionic gradient formed near the pore. The results showed a fairly large influence of the $SiO_2$ surface when the nanopore was less than 25-50 nm away from the $SiO_2$ wall.

Figure 38:
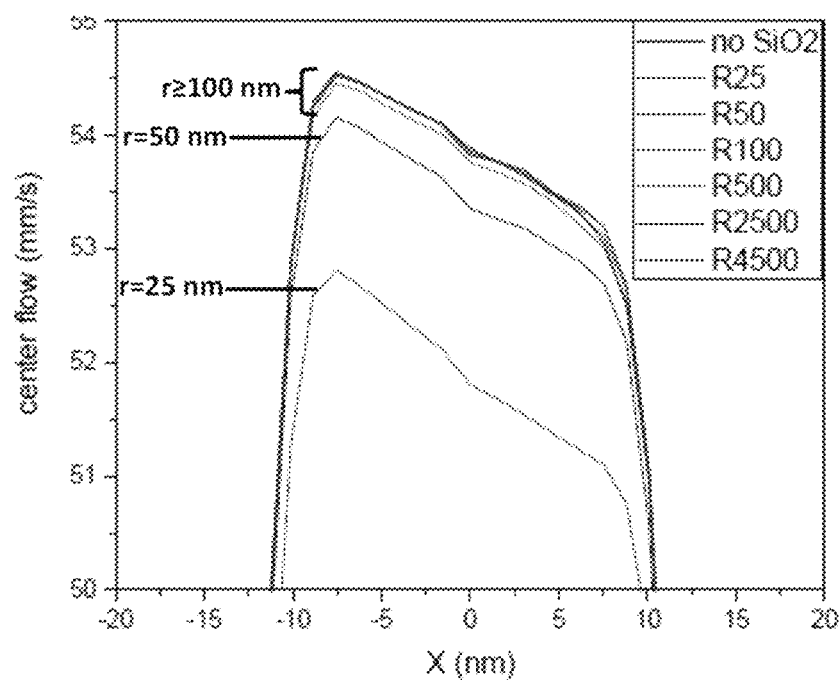
FIG. 38 is a graph showing the effects of the diameter of a $SiO_2$ via made over a nanopore membrane with a nanopore on the electroosmotic flow through the nanopore, according to embodiments of the present disclosure.

Electroosmotic flow rates of counter ions through the pore were simulated as a way to determine any influence the $SiO_2$ layer may have on nanopore sensing (FIG. 38). The highest rate of electroosmotic flow occurred with the larger via diameters (100-4,500 nm). A reduction in flow rate through the pore was observed for a 50 nm $SiO_2$ via, followed by a significant reduction for a 25 nm via.

Figure 39:
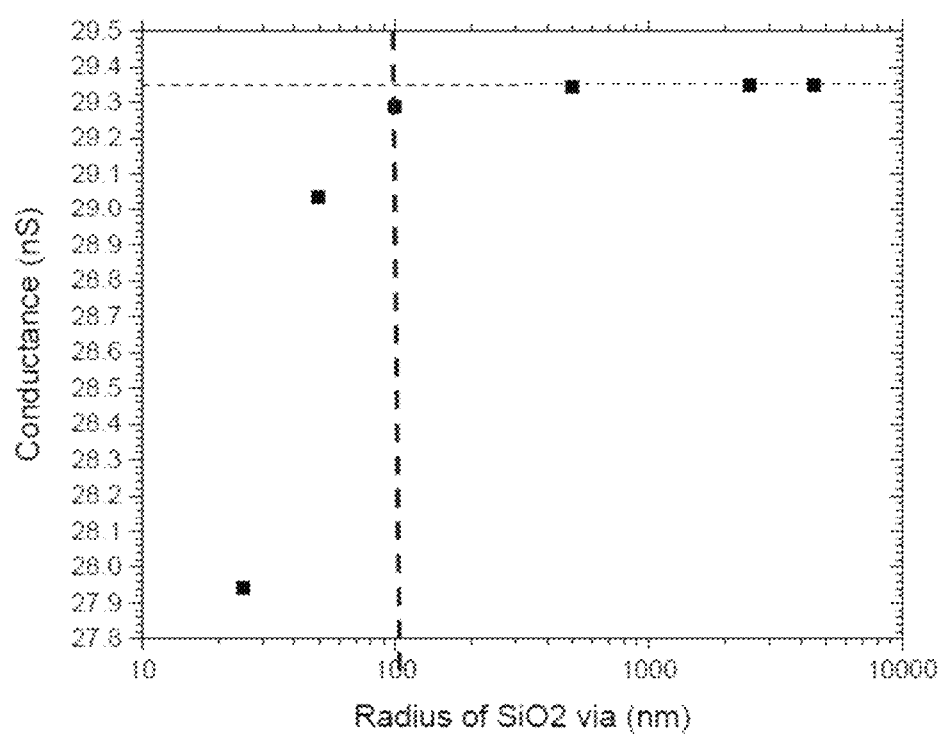
FIG. 39 is a graph showing the effects of the diameter of a $SiO_2$ via made over a nanopore membrane with a nanopore on the conductance through the nanopore, according to embodiments of the present disclosure.

As shown in FIG. 39, measurement of conductance through the pore vs. via diameters showed a saturation curve above 100 nm, with diminishing conductance as the via diameter was reduced in size from 100 nm to 25 nm.

Example 27

Integrating a Nanopore Module into a Digital Microfluidic (DMF) Module

The nanopore module was located on one side of the DMF module. A hole was present in the DMF module to allow liquid transport from the DMF module to the nanopore module for pore creation and analyte detection (e.g., see FIG. 40).

Figure 41:
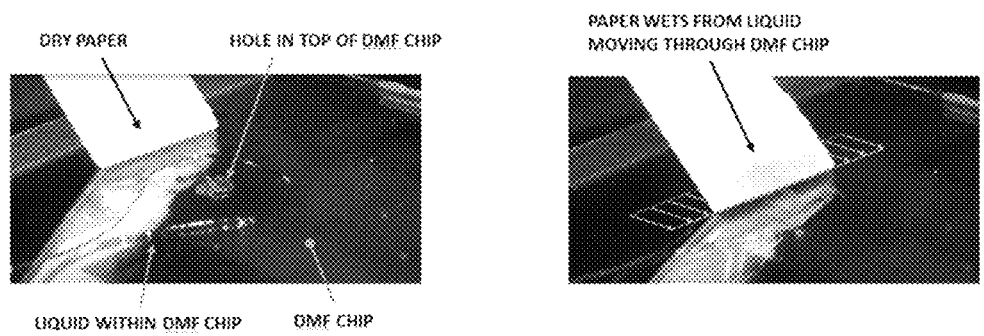
FIG. 41 is a collection of images showing movement of liquid from a DMF module through a hole in a DMF module substrate by capillary force, according to embodiments of the present disclosure.

One electrode from the nanopore module terminated within the fluid volume in the nanopore module. The other electrode terminated within the fluid volume in the DMF module. This electrode was routed through a second hole in the DMF module. To demonstrate that liquid was able to move through the hole within the DMF module, a flat piece of paper was pushed over the exterior surface of the chip after liquid was moved in place. The wetting of this paper showed that the liquid was able to move from the DMF module to another module located above this hole via capillary forces (FIG. 41).

Figure 42:
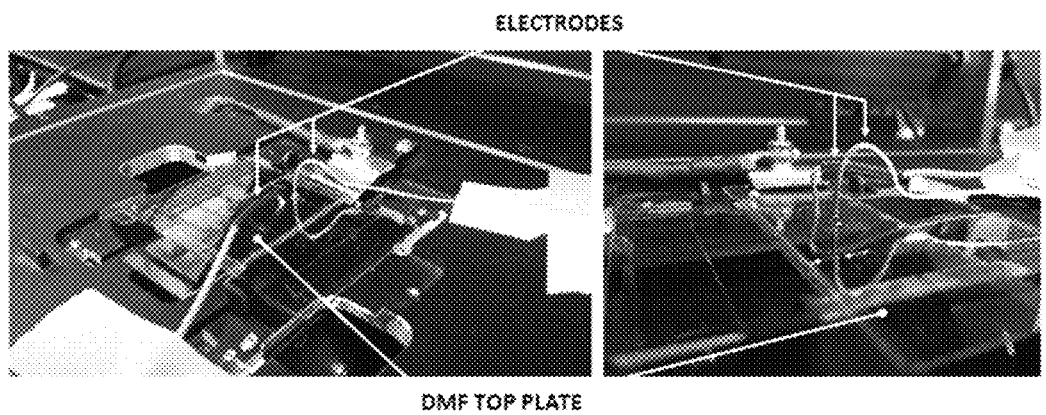
FIG. 42 is a collection of images showing an integrated DMF-nanopore module device with the nanopore module positioned on one side of the DMF module and electrodes configured for nanopore fabrication, according to embodiments of the present disclosure.

With reference to FIG. 42, the DMF module was equipped with Ag/AgCl electrodes for control of the nanopore fabrication. In this setup, the liquid volume on the nanopore module was an open-air droplet of LiCl. This liquid was dispensed directly onto the nanopore module and the electrode terminal was suspended within this droplet.

Figure 45:
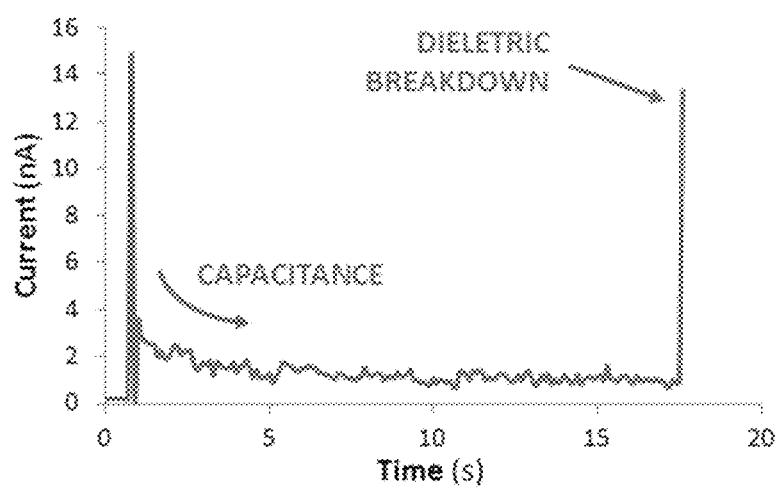
FIG. 45 is a graph showing fabrication of a nanopore in a nanopore membrane (a transmission electron microscope (TEM) window) by applying a voltage across the nanopore membrane, and as evidenced by dielectric breakdown, according to embodiments of the present disclosure.

The sample was moved to the hole in the DMF module using DMF technology. The sample passively migrated through the hole to become exposed to the nanopore module for nanopore creation. The nanopore module is sealed to the DMF module (e.g. using PDMS, pressure, wax, etc.), isolating the liquid volumes held within each module. FIG. 45 shows the current as a function of time during the fabrication of the nanopore.

Figure 46A:
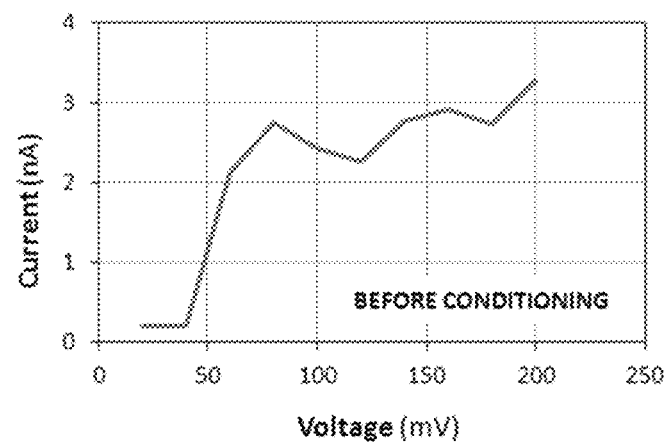
FIG. 46A and FIG. 46B are a collection of graphs showing current-voltage (I-V) curves of a nanopore formed in a membrane, before and after a conditioning process, according to embodiments of the present disclosure.
Figure 46B:
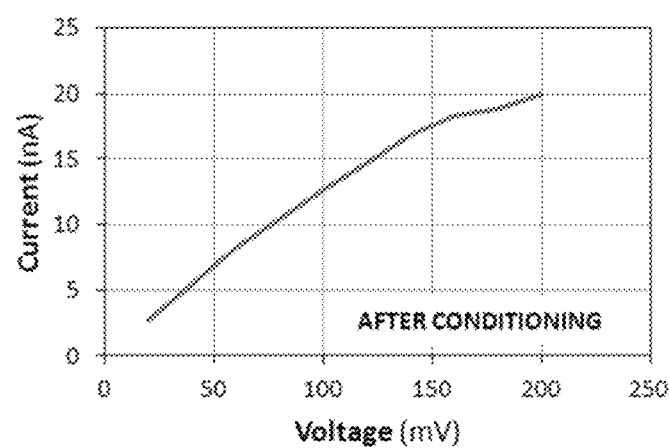

Once the nanopore was created, a conditioning process (varying voltage over time) was used to physically modify the nanopore and clean the signal. This process improved symmetry in the I-V curve. The before and after I-V curves are shown in FIGS. 46A and 46B, respectively.

Example 28

Counting Labels and Pore Size Analysis

A set of experiments were run using double stranded DNA under various sets of conditions to analyze and demonstrate certain attributes relative to pore size and counting label size. In these experiments, various parameters were explored including detection voltage, DNA length, DNA concentration, salt concentration and salt composition, membrane material, membrane thickness, nanopore diameter and other factors.

The data set was then analyzed relative to signal to noise ratio and compared that factor to various pore size relative to counting label size (estimated molecular diameter). Certain factors such as membrane material and thickness, for example, were held constant in this set of experiments, while other factors were varied.

From an aggregate data set analysis, the averages of ratios were plotted between counting label average diameter and nanopore size to the SNR (signal to noise ratio) determined in the experiment (FIG. 47). FIG. 47 demonstrates generally that useful counting data can be obtained from a range of such ratios, in this particular data set from between around 0.4 to 0.8 in such ratio—assuming a molecular diameter of a dsDNA of around 2.0 nm approximately. Linear dsDNA is known from the literature to be about that molecular diameter and the analysis assumes the DNA threads through the pore in its linear conformation. Table 4 shows the calculated data.

TABLE 3

| AVERAGE PORE LABEL MOLECULAR DIAMETER TO PORE RATIO | SNR |
|---|---|
| 0.645 | 27.5 |
| 0.556 | 53.7 |
| 0.476 | 12 |
| 0.714 | 23.7 |
| 0.803 | 17 |
| 0.645 | 22.5 |
| 0.8 | 20.2 |
| 0.588 | 17 |
| 0.69 | 55 |
| 0.476 | 23.5 |

While conditions varied, as previously mentioned in this example, the general range in this data set shows that counting data with reasonable signal to noise can be obtained within this range. Furthermore, it should be noted that one skilled in the art would recognize that other counting label moleculer diameter to nanopore diameter ratios could be utilized to achieve reasonable SNR. Additionally, it would be recognized by one skilled in the art that generally a label should have at least one dimension of its molecular diameter that is less than the size of the nanopore so as to be able to pass through the pore, or in other words, this ratio of label molecular diameter to nanopore diameter should generally be less than one for the label to be able to pass through the pore, except in cases perhaps where conditions such as are described in a technology called nanopore force spectroscopy is used, wherein energy is added to the system to facilitate conformational changes to occur in the label and thus allow it to pass through the pore after deformation to a level that would allow such a translocation event to occur.

It should also be understood to one skilled in the art that other labels can be utilized for counting other than dsDNA as described in this example, and that they may have different behaviors than that shown in this graph. Furthermore, it should also be understood that it is possible to also obtain acceptable SNR from other molecular diameter to nanopore ratios to enable molecular counting of such labels, and that current blockage can be related to molecular diameter of such a counting label as described in the equation below $$\Delta G = \frac{\sigma \pi d_{DNA}^2}{4L} \quad (S1)$$

which can be found in the following references: Kwok et al., "Nanopore Fabrication by controlled Dielectric Breakdown" Supplementary Information Section 8 and/or Kwok H. Briggs, K.; and Tabard-Cossa, V.; "*Nanopore Fabrication by Controlled Dielectric Breakdown*"—PLoS ONE 9(3): e92880 (2014). This equation can be used in order to gate or threshold signal as described in Examples 24 and 25 in this document.

Certain specific conditions varied within this aggregate set of nanopore counting experiments included:
Ionic Strength—either 3 or 3.6 M
DNA length—10 kbp, 50 bp or 1 kbp
Ionic Salt Used—either LiCl or KCl
Membrane Material—$SiN_x$ (constant throughout data set)
Membrane Thickness—10 nm (constant throughout data set)
DNA Concentration(s)—varied between 3 nM and around 306 nM
Voltages—varied including increments between 50 and 600 mV
Nanopore Diameter—a variety of pore sizes including 8.0, 1.1, 3.6, 4.2, 2.8, 2.5, 7.7, 3.1, 2.7, 2.6, 2.9 and 4.2 (all in nanometers).

Conclusions can be drawn that various conditions, including but not limited to these, show that one can obtain in situations where the countable label is smaller than the diameter of the pore can cause a blockage of the flux of ion current across the pore when a voltage is applied as per the amount as calculable but this equation of Kwok et al as referenced in this example [Kwok et al., "Nanopore Fabrication by controlled Dielectric Breakdown" Supplementary Information Section 8 and/or Kwok, H.; Briggs, K.; and Tabard-Cossa, V.; "*Nanopore Fabrication by Controlled Dielectric Breakdown*"—PLoS ONE 9(3): e92880 (2014)].

It is also understood that these conditions can be applied to show counting label molecular diameters to pore diameters that will function with reasonable signal to noise for other labels besides dsDNA, including but not limited to dendrimers, hemi-dendrimers, nanobeads, anionic or cationic polymers, denatured linearized aptamers, negatively or positively charged poly peptides or other charged polymers or countable molecular entities and the like.

Finally, although the various aspects and features of the invention have been described with respect to various embodiments and specific examples herein, all of which may be made or carried out conventionally, it will be understood that the invention is entitled to protection within the full scope of the appended claims.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clause:

Clause 1. A method for measuring or detecting an analyte present in a biological sample, the method comprising: (a) contacting the sample with a first binding member, wherein the first binding member is immobilized on a solid support and wherein the first binding member specifically binds to the analyte; (b) contacting the analyte with a second binding member, wherein the second binding member specifically binds to the analyte and wherein the second binding member comprises a cleavable tag attached thereto; (c) removing second binding member not bound to the analyte bound to the first binding member; (d) cleaving the tag attached to the second binding member bound to the analyte bound to the first binding member; (e) translocating the tag through one or more nanopores in a layer; and (f) assessing the tag translocating through the layer, wherein measuring the number of tags translocating through the layer measures the amount of analyte present in the sample, or wherein detecting tags translocating through the layer detects that the analyte is present in the sample.

Clause 2. The method of clause 1, wherein each tag translocating through the layer is a translocation event and measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference standard comprising a calibration curve, standard addition, or digital polymerase chain reaction.

Clause 3. The method of clauses 2, wherein the standard curve in subsection i) is determined by measuring the number of translocation events for control concentrations of analyte during a set period of time; wherein the standard curve in subsection ii) is determined by measuring the time it takes for a set number of translocation events to occur for control concentrations of analyte; and wherein the standard curve in subsection iii) is determined by measuring the average time between translocation events to occur for control concentrations of analyte.

Clause 4 The method of any one of clauses 1 to 3, wherein the method involves single molecule counting.

Clause 5. The method of any one of clauses 1 to 4, wherein the tag is selected from the group consisting of an anionic polymer, a cationic polymer, a dendrimer, and a nanoparticle.

Clause 6. The method of any one of clauses 1 or 5, wherein the tag is substantially spherical or hemi-spherical.

Clause 7. The method of any one of clauses 1 to 6, wherein the tag is substantially spherical and comprises a nanoparticle.

Clause 8. The method of any one of clauses 1 to 7, wherein the tag is substantially spherical or hemi-spherical and comprises a dendrimer.

Clause 9. The method of clauses 8, wherein the dendrimer is positively or negatively charged.

Clause 10. The method of clauses 5 or 7, wherein the nanoparticle comprises a positively charged nanoparticle.

Clause 11. The method of clauses 10, wherein the nanoparticle comprises a negatively charged nanoparticle.

Clause 12 The method of any one of clauses 1 to 11, wherein the first and the second binding members are antibodies or receptors.

Clause 13. The method of any one of clauses 1 to 12, wherein the first binding member is a receptor and the second binding member is an antibody or wherein the first binding member is an antibody and the second binding member is a receptor.

Clause 14. The method of any one of clauses 1 to 12, wherein the first binding member is a first antibody and the second binding member is a second antibody.

Clause 15. The method of any one of clauses 1 to 14, wherein the tag is negatively charged and the translocating comprises applying a positive potential across the layer thereby translocating the tag through the layer.

Clause 16. The method of any one of clauses 1 to 14, wherein the tag is positively charged and the translocating comprises applying a negative potential across the layer thereby translocating the tag through the layer.

Clause 17. The method of any one of the clauses 1 to 16, wherein at least the steps (a)-(d) are carried out in a microfluidics device, droplet based microfluidic device; digital microfluidics device (DMF), a surface acoustic wave based microfluidic device (SAW), a fully integrated DMF and nanopore device, or a fully integrated SAW and nanopore device.

Clause 18. The method of clauses 17, wherein a DMF element and a nanopore element are operatively coupled in the fully integrated DMF and nanopore device, or a SAW element and a nanopore element are operatively coupled in the fully integrated SAW and nanopore device.

Clause 19. The method of clauses 17, wherein the DMF device or the SAW device is fabricated by roll to roll based printed electronics method.

Clause 20. The method of clauses 18, where the DMF element or the SAW element is fabricated by roll to roll based printed electronic methods.

Clause 21. The method of clauses 17, wherein the fully integrated DMF and nanopore device or the fully integrated SAW and nanopore device comprise a microfluidic conduit.

Clause 22. The method of clauses 21, wherein the microfluidic conduit couples the DMF element to the nanopore element, and the microfluidic conduit comprises a fluidic flow that is induced by passive forces or active forces.

Clause 23. The method of any one of clauses 1 to 22, wherein the nanopore is a solid state nanopore or a biological nanopore.

Clause 24. The method of any one of the clauses 1 to 23, wherein measuring the number of tags translocating through the layer comprises observing a change in current induced by an interaction of the tags with the nanopores.

Clause 25. The method of clauses 24, wherein the analyte is present in the sample when the current change has a magnitude above a threshold level.

Clause 26. The method of clauses 23, wherein the method further comprises transporting a droplet containing the tag obtained in step (d) to a nanopore device and placing the droplet across a nanopore layer present in the nanopore device such that the droplet is split by the nanopore layer and is connected by nanopore(s) present in the nanopore layer, wherein the tag is present in the droplet on both sides of the nanopore layer.

Clause 27. The method of clauses 26, wherein the method comprises translocating the tag present on a first side of the nanopore layer across the nanopore to a second side of the nanopore layer, thereby collecting the tag in the split droplet on the second side of nanopore layer.

Clause 28. The method of clauses 26, further comprising translocating the tag to the first side of the nanopore layer and determining the number of tags present in the droplet.

Clause 29. The method of any one of clauses 1 to 28, wherein the tag comprises a cleavable linker.

Clause 30. A method for measuring or detecting an analyte of interest present in a biological sample, the method comprising (a) contacting the sample with a solid support, a first specific binding member, and a second specific binding member, wherein the solid support comprises an immobilization agent, the first specific binding member comprises a ligand for the immobilization agent and the first specific binding member specifically binds the analyte of interest, the second specific binding member comprises a cleavable tag, and the second specific binding member specifically binds the analyte of interest, wherein a solid support/first specific binding member/analyte of interest/second specific binding member complex is formed; (b) removing second specific binding member not bound to the solid support/first specific binding member/analyte/second specific binding member complex; (c) cleaving the tag attached to the labeled analyte bound to the second specific binding member in the solid support/first specific binding member/analyte of interest/second specific binding member complex; (d) translocating the tag through one or more nanopores in a layer; and (e) assessing the tags translocating through the layer, wherein measuring the number of tags translocating through the layer measures the amount of analyte present in the sample, or wherein detecting tags translocating through the layer detects that the analyte is present in the sample.

Clause 31. A method for measuring or detecting an analyte present in a biological sample, the method comprising: (a) contacting the sample with a first binding member, wherein the first binding member is immobilized on a solid support and wherein the first binding member specifically binds to the analyte; (b) contacting the analyte with a second binding member, wherein the second binding member specifically binds to the analyte and wherein the second binding member comprises an aptamer; (c) removing aptamer not bound to the analyte bound to the solid substrate; (d) dissociating the aptamer bound to the analyte (e) translocating the dissociated aptamer through one or more nanopores in a layer; and (f) assessing the aptamer translocating through the layer, wherein measuring the number of aptamers translocating through the layer measures the amount of analyte present in the sample, or wherein detecting aptamers translocating through the layer detects that the analyte is present in a the sample.

Clause 32. The method of clauses 31, wherein each aptamer translocating through the layer is a translocation event and measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference standard comprising a calibration curve, standard addition, or digital polymerase chain reaction.

Clause 33. The method of clauses 32, wherein the standard curve in subsection i) is determined by measuring the number of translocation events for control concentrations of analyte during a set period of time; wherein the standard curve in subsection ii) is determined by measuring the time it takes for a set number of translocation events to occur for control concentrations of analyte; and wherein the standard curve in subsection iii) is determined by measuring the average time between translocation events to occur for control concentrations of analyte.

Clause 34. The method of any one of clauses 31 to 33, wherein the method involves single molecule counting.

Clause 35. The method of any one of clauses 31 to 34, wherein the aptamer is a DNA aptamer.

Clause 36. The method of any one of clauses 31 to 34, wherein the aptamer is a RNA aptamer.

Clause 37. The method of any one of clauses 31 to 36, wherein the first binding member is an antibody.

Clause 38. The method of any one of clauses 31 to 36, wherein the analyte is a ligand and the first binding member is a receptor.

Clause 39. The method of any one of the clauses 31 to 38, wherein at least the steps (a)-(d) are carried out in a microfluidics device, droplet based microfluidic device, digital microfluidics device (DMF), a surface acoustic wave based microfluidic device (SAW), a fully integrated DMF and nanopore device, or a fully integrated SAW and nanopore device.

Clause 40. The method of clauses 39, wherein a DMF element and a nanopore element are operatively coupled in the fully integrated DMF and nanopore device, or a SAW element and a nanopore element are operatively coupled in the fully integrated SAW and nanopore device.

Clause 41. The method of clauses 39, wherein the DMF device or the SAW device is fabricated by roll to roll based printed electronics method.

Clause 42. The method of clauses 40, where the DMF element or the SAW element is fabricated by roll to roll based printed electronic methods.

Clause 43. The method of clauses 39, wherein the fully integrated DMF and nanopore device or the fully integrated SAW and nanopore device comprise a microfluidic conduit.

Clause 44. The method of clauses 43, wherein the microfluidic conduit couples the DMF element to the nanopore element, and the microfluidic conduit comprises a fluidic flow that is induced by passive forces or active forces.

Clause 45. The method of any one of clauses 31 to 44, wherein the nanopore is a solid state nanopore or a biological nanopore.

Clause 46. An integrated digital microfluidics nanopore device comprising: a first substrate, comprising an array of electrodes; a second substrate spaced apart from the first substrate; and a nanopore layer disposed between the first and second substrates, wherein the array of electrodes are configured to position the droplet across the nanopore layer such that the droplet is split by the nanopore layer into a first portion and a second portion, wherein at least two electrodes of the array of electrodes are positioned across the nanopore layer, where the two electrodes form an anode and a cathode and operate to drive current through a nanopore in the nanopore layer when a liquid droplet is positioned across the nanopore layer.

Clause 47. The device of clauses 46, wherein the nanopore layer is attached to the first and second substrates.

Clause 48. The device of clauses 46, wherein the nanopore layer is attached to the first or the second substrate.

Clause 49. The device of any one of clauses 46 to 48, wherein the electrodes are transparent.

Clause 50. The device of any one of clauses 46 to 49, wherein the electrodes are disposed in a grid pattern.

Clause 51. The device of any one of clauses 46 to 50, wherein the at least two electrodes of the array of electrodes positioned across the nanopore layer flank the nanopore layer and are not positioned across the nanopore layer.

Clause 52. The device of any one of clauses 46 to 51, wherein the electrodes are interdigitated.

Clause 53. The device of any one of clauses 46 to 51, wherein the array of electrodes are configured for activation by a power source, wherein the power source activates the electrodes in a sequential manner.

Clause 54. The device of clauses 53, wherein sequential manner comprises turned one or more electrodes on or off.

Clause 55. The device of any one of clauses 52 to 54, wherein the activation of the array of electrodes by a power source is controlled by a set of instructions executed by a processor that controls the power source.

Clause 56. An integrated digital microfluidics nanopore device comprising: a first substrate, comprising an array of electrodes; a second substrate spaced apart from the first substrate; and a nanopore layer disposed between the first and second substrates, wherein the array of electrodes are configured to position a droplet across the nanopore layer such that the nanopore layer splits the droplet into a first portion and a second portion, wherein at least one electrode of the array of electrodes is in contact with the first portion of a droplet positioned across the nanopore layer and the electrode in the second substrate is positioned to contact the second portion of the droplet positioned across the nanopore layer, where the two electrodes form an anode and a cathode and operate to drive current through a nanopore in the nanopore layer when a liquid droplet is positioned across the nanopore layer.

Clause 57. The device of clauses 56, wherein the nanopore layer is attached to the first substrate.

Clause 58. The device of any one of clauses 56 or 57, wherein the nanopore layer is attached to the second substrate.

Clause 59. The device of any one of clauses 56 to 58, wherein the first and/or second substrates are transparent.

Clause 60. The device of any one of clauses 56 to 59, wherein the array of electrodes are transparent.

Clause 61. A kit comprising the device of any one of clauses 46 to 60, or for use in the method of any one of clauses 1 to 45.

Clause 62. The kit of clauses 61, further comprising additional reagents, wherein at least one reagent comprises a tag than can be detected by translocation through the nanopore layer of the device.

Clause 63. A method of using the device of any one of clauses 46 to 60, or the method of any one of clauses 1 to 45, for measuring or detecting an analyte present in a biological sample or for diagnosing a patient or screening a blood supply.

Clause 64. The method of any one of clauses 1 to 45, wherein at least the steps (a)-(d) are carried out using the device of any one of clauses 46 to 60.

Clause 65. Use of the device of any one of clauses 46 to 60, or the use of the method of any one of clauses 1 to 45, in a method of diagnosing a patient or screening a blood supply or for measuring or detecting an analyte present in a biological sample.

Clause 66. A method for measuring or detecting an analyte present in a biological sample, the method comprising: (a) contacting the sample with a binding member, wherein the binding member is immobilized on a solid support and wherein the binding member specifically binds to the analyte; (b) contacting the sample with a labeled analyte, wherein the labeled analyte is labeled with a cleavable tag; (c) removing labeled analyte not bound to the binding member; (d) cleaving the tag attached to the labeled analyte bound to the binding member; (e) translocating the tag through one or more nanopores in a layer; and (f) assessing the tags translocating through the layer, wherein measuring the number of tags translocating through the layer measures the amount of analyte present in the sample, or wherein detecting tags translocating through the layer detects that the analyte is present in the sample.

Clause 67. A method for measuring or detecting an analyte present in a biological sample, the method comprising: (a) contacting the sample with a binding member, wherein binding member is immobilized on a solid support and wherein binding member specifically binds to the analyte; (b) contacting the sample with a labeled analyte, wherein the labeled analyte comprises an aptamer; (c) removing labeled analyte not bound to the binding member; (d) dissociating the aptamer bound to the labeled analyte and translocating the dissociated aptamer through one or more nanopores in a layer; and (e) assessing the aptamer translocating through the layer, wherein measuring the number of aptamers translocating through the layer measures the amount of analyte present in the sample, or wherein detecting aptamers translocating through the layer detects that the analyte is present in the sample.

Clause 68. A method for measuring or detecting an analyte present in a biological sample, the method comprising: (a) contacting the sample with a binding member, wherein the binding member specifically binds to the analyte, and the binding member is labeled with a cleavable tag; (b) contacting the sample with a immobilized analyte, wherein the immobilized analyte is immobilized on a solid support; (c) removing binding member not bound to the immobilized analyte; (d) cleaving the tag attached to the binding member bound to the immobilized analyte; (e) translocating the tag through one or more nanopores in a layer; and (f) assessing the tag translocating through the layer, wherein measuring the number of tags translocating through the layer measures the amount of analyte present in the sample, or wherein detecting tags translocating through the layer detects that the analyte is present in the sample.

Clause 69. A method for measuring or detecting an analyte present in a biological sample, the method comprising: (a) contacting the sample with a binding member, wherein the binding member specifically binds to the analyte, and the binding member comprises an aptamer; (b) contacting the sample with a immobilized analyte, wherein the immobilized analyte is immobilized on a solid support; (c) removing binding member not bound to the immobilized analyte; (d) dissociating the aptamer bound to the binding member bound to the immobilized analyte and translocating the dissociated aptamer through one or more nanopores in a layer; and (e) assessing the aptamer translocating through the layer, wherein measuring the number of aptamers translocating through the layer measures the amount of analyte present in the sample, or wherein detecting aptamers translocating through the layer detects that the analyte is present in the sample.

Clause 70. The method of clauses 66 or 68, wherein each tag translocating through the layer is a translocation event and measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference standard comprising a calibration curve, standard addition, or digital polymerase chain reaction.

Clause 71. The method of clauses 67 or 69, wherein each aptamer translocating through the layer is a translocation event and measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference standard comprising a calibration curve, standard addition, or digital polymerase chain reaction.

Clause 72. The method of clauses 70 or 71, wherein the standard curve in subsection i) is determined by measuring the number of translocation events for control concentrations of analyte during a set period of time; wherein the standard curve in subsection ii) is determined by measuring the time it takes for a set number of translocation events to occur for control concentrations of analyte; and wherein the standard curve in subsection iii) is determined by measuring the average time between translocation events to occur for control concentrations of analyte.

Clause 73. The method of any one of clauses 66 to 72, wherein the method involves single molecule counting.

Clause 74. The method of any one of clauses 66, 68, 70, 72, or 73, wherein at least the steps (a)-(d) are carried out using the device of any one of clauses 46 to 60.

Clause 75. The method of any one of clauses 67, 69, 71, 72, or 73, wherein at least the steps (a)-(d) are carried out using the device of any one of clauses 46 to 60.

Clause 76. The method of any one of clauses 66, 68, 70, 72, 73, or 74, wherein the tag is selected from the group consisting of an anionic polymer, a cationic polymer, a dendrimer, and a nanoparticle.

Clause 77. The method of any one of clauses 66, 68, 70, 72, 73, or 74, wherein the tag is substantially spherical or hemi-spherical.

Clause 78. The method of any one of clauses 66, 68, 70, 72, 73, or 74, wherein the tag is substantially spherical and comprises a nanoparticle.

Clause 79. The method of any one of clauses 66, 68, 70, 72, 73, or 74, wherein the tag is substantially spherical or hemi-spherical and comprises a dendrimer.

Clause 80. The method of clauses 79, wherein the dendrimer is positively or negatively charged.

Clause 81. The method of clauses 79, wherein the nanoparticle comprises a positively charged nanoparticle.

Clause 82. The method of clauses 76 or 78, wherein the nanoparticle comprises a negatively charged nanoparticle.

Clause 83. The method of any one of clauses 66, 68, 70, 72, 73, 74, or 76 to 82, wherein the binding member is an antibody or receptor.

Clause 84. The method of any one of clauses 66, 68, 70, 72, 73, 74, or 76 to 83, wherein the tag is negatively charged and the translocating comprises applying a positive potential across the layer thereby translocating the tag across the layer.

Clause 85. The method of any one of clauses 66, 68, 70, 72, 73, 74, or 76 to 84, wherein the tag is positively charged and the translocating comprises applying a negative potential across the layer thereby translocating the tag across the layer.

Clause 86. The method of any one of the clauses 66, 68, 70, 72, 73, 74, or 76 to 85, wherein measuring the number of tags translocating through the layer comprises observing a current blockade effect of the tags on the nanopores.

Clause 87. The method of clauses 86, wherein the analyte is present in the sample when the current blockade effect is above a threshold level.

Clause 88. The method of any one of clauses 67, 69, 71, 72, 73, or 75, wherein the aptamer is a DNA aptamer.

Clause 89. The method of any one of clauses 67, 69, 71, 72, 73, or 75, wherein the aptamer is a RNA aptamer.

Clause 90. The method of any one of clauses 67, 69, 71, 72, 73, 75, 88, or 89, wherein the binding member is an antibody.

Clause 91. The method of any one of clauses 67, 69, 71, 72, 73, 75, 88, or 89, wherein the analyte is a ligand and the binding member is a receptor.

Clause 92. The method of any one of clauses 67, 69, 71, 72, 73, 75, or 88 to 91, wherein the method further comprises transporting a droplet containing the tag to a nanopore device and placing the droplet across a nanopore layer present in the nanopore device such that the droplet is split by the nanopore layer and is connected by nanopore(s) present in the nanopore layer, wherein the tag is present in the droplet on both sides of the nanopore layer.

Clause 93. The method of clauses 92, wherein the method comprises translocating the tag present on a first side of the nanopore layer across the nanopore to a second side of the nanopore layer, thereby collecting the tag in the split droplet on the second side of nanopore layer Clause 94. The method of clauses 92, further comprising translocating the tag to the first side of the nanopore layer and determining the number of tags present in the droplet.

Clause 95. The method of any one of clauses 67, 69, 71, 72, 73, 75, or 88 to 94, wherein the method further comprises transporting a droplet containing the aptamer to a nanopore device and placing the droplet across a nanopore layer present in the nanopore device such that the droplet is split by the nanopore layer and is connected by nanopore(s) present in the nanopore layer, wherein the aptamer is present in the droplet on both sides of the nanopore layer.

Clause 96. The method of clauses 95, wherein the method comprises translocating the aptamer present on a first side of the nanopore layer across the nanopore to a second side of the nanopore layer, thereby collecting the aptamer in the split droplet on the second side of nanopore layer Clause 97. The method of clauses 95, further comprising translocating the aptamer to the first side of the nanopore layer and determining the number of aptamers present in the droplet.

Clause 98. The method of any one of clauses 66 to 97, wherein the nanopore is a solid state nanopore or a biological nanopore.

Clause 99. The method of any one of clauses 1 to 45 or 63 to 98, wherein the second binding member further comprises a spacer.

Clause 100. The method of clauses 99, wherein the spacer comprises a nitrobenzyl group, dithioethylamino, 6 carbon spacer, 12 carbon spacer, or 3-(9-((3-carboxypropyl)(tosyl)carbamoyl)acridin-10-ium-10-yl)propane-1-sulfonate.

Clause 101. The method of clauses 100, wherein the spacer comprises a nitrobenzyl group, and the tag is a DNA molecule.

Clause 102. The method of clauses 100, wherein the spacer is dithioethylamino and the tag is a carboxylated nanoparticle.

Clause 103. The method of clauses 100, wherein the spacer is 3-(9-((3-carboxypropyl)(tosyl)carbamoyl)acridin-10-ium-10-yl)propane-1-sulfonate and the tag is an oligonucleotide.

Clause 104. The method of clauses 103, wherein the spacer comprises a 6 carbon spacer or a 12 carbon spacer and the tag is biotin.

Clause 105. The method of clauses 104, wherein the second binding member comprises a nucleic acid comprising a nucleotide sequence set forth in any one of SEQ ID NOs: 1-11.

Clause 106. An integrated digital microfluidics nanopore device comprising a microfluidics module and a nanopore module; the microfluidics module comprising an array of electrodes, wherein the array of electrodes transports at least one droplet of fluid to a first transfer position in the array of electrodes, wherein the first transfer position is at an interface between the microfluidics module and the nanopore module; the nanopore module comprising: a first capillary channel; and a second capillary channel; wherein at least the first capillary channel extends to the interface and is adjacent to the first transfer position, and is positioned to receive a fluid droplet positioned at the first transfer position; wherein the first capillary channel intersects with the second capillary channel, wherein a nanopore layer is positioned in between the first and second capillary channels at the location where the first and the second capillary channels intersect.

Clause 107. The device of clauses 106, wherein the array of electrodes transports at least one droplet of fluid to a second transfer position in the array of electrodes, wherein the second transfer position is at an interface between the microfluidics module and the nanopore module wherein the second capillary channel extends to the interface and is adjacent to the second transfer position, and is positioned to receive a fluid droplet positioned at the second transfer position.

Clause 108. The device of clauses 106, wherein the second capillary channel extends between a vent or a reservoir on one or both ends of the second capillary channel.

Clause 109. The device of clauses 108, wherein the second capillary channel is connected to a first reservoir at one end and a second reservoir at the other end.

Clause 110. The device of clauses 109, wherein the first reservoir and/or the second reservoir comprises a fluid to be positioned within the second capillary channel at the intersection which fluid facilitates operation of the nanopore layer to drive current through a nanopore of the nanopore layer.

Clause 111. The device of clauses 109, wherein the first capillary channel and/or the second capillary channel varies in cross sectional width across a length of the capillary channel such that the width decreases at the intersection compared to the width on either sides of the intersection.

Clause 112. The device of clauses 106, wherein the first capillary channel comprises a first pair of electrodes and the second capillary channel comprises a second pair of electrodes, wherein the first pair of electrodes is positioned in the first capillary channel and flank the nanopore in the nanopore layer and wherein second pair of electrodes is positioned in the second capillary channel and flank the nanopore in the nanopore layer.

Clause 113. The device of any one of clauses 107 to 112, wherein the droplets are droplets comprising a molecule to be counted by transporting through the nanopore in the nanopore layer.

Clause 114. The device of clauses 107, wherein the fluid droplets have different compositions and are a first droplet and a second droplet, the first droplet comprising a molecule to be counted by transporting across the nanopore layer through the nanopore and the second droplet comprising a conductive fluid lacking the molecule, where the conductive fluid facilitates transport of the molecule across the nanopore layer via the nanopore.

Clause 115. The device of any one of clauses 106 to 114, wherein the first capillary channel comprises a first electrode positioned proximal to the nanopore layer and the second capillary channel comprising a second electrode positioned proximal to the nanopore layer, wherein each of the first and second electrodes are exposed in the capillary channels such that they are in contact with a fluid present in the capillary channels and wherein the first and second electrodes operate to drive current through a nanopore in the nanopore layer when a liquid is positioned across the nanopore layer in the first and second capillary channels.

Clause 116. The device of any one of clauses 106 to 115, wherein the first transfer position and the first capillary channel are on substantially the same plane, and wherein the fluid droplet is aligned with an opening of the first capillary channel.

Clause 117. The device of any one of clauses 106 to 115, wherein the first transfer position is at a plane higher than the first capillary channel and wherein the device is configured with a vertical port for transferring the fluid droplet down to an opening of the first capillary channel.

Clause 118. The device of clauses 117, wherein the first surface of the first substrate comprises a first area on which the array of electrodes is disposed and a second area in which the first microchannel is formed, wherein the array of electrodes is on a plane higher than the plane at which the first microchannel is formed.

Clause 119. The device of clauses 117, wherein the second substrate comprises a notch at a side edge located at the interface, wherein the notch is aligned over the first capillary channel and provides a vertical port for transport of a droplet located at the transfer electrode to the opening of the first capillary channel.

Clause 120. The device of any one of clauses 106 to 119, further comprising a single electrode spaced apart from the array of electrodes, wherein the single electrode extends over at least a portion of the array of electrodes at the first transfer position and is in bi-planar configuration with the at least a portion of the array of electrodes at the first transfer position.

Clause 121. The device of any one of clauses 107 to 119, further comprising a single electrode spaced apart from the array of electrodes.

Clause 122. The device of any one of clauses 106 to 119, further comprising a single electrode spaced apart from the array of electrodes, wherein the single electrode does not extend over the first transfer position and is not in bi-planar configuration with the array of electrodes, wherein the fluid droplet is moved to the first transfer position by using coplanar electrodes.

Clause 123. The device of any one of clauses 106 to 119, further comprising a single electrode spaced apart from the array of electrodes wherein the single electrode does not extend over the first transfer position and is not in bi-planar configuration with the array of electrodes, wherein the fluid droplets are moved to the transfer position by using coplanar electrodes.

Clause 124. A method of using the device of any one of clauses 106 to 123, or the method of any one of clauses 66 to 105, for measuring or detecting an analyte present in a biological sample or for diagnosing a patient or screening a blood supply.

Clause 125. The method of any one of clauses 1 to 45 or 66 to 105, wherein at least the steps (a)-(d) are carried out using the device of any one of clauses 106 to 123.

Clause 126. Use of the device of any one of clauses 106 to 123, or the use of the method of any one of clauses 1 to 45, in a method of diagnosing a patient or screening a blood supply or for measuring or detecting an analyte present in a biological sample.

Clause 127. A method for measuring an analyte present in a biological sample, the method comprising: (a) contacting the sample with a first binding member, wherein the first binding member is immobilized on a solid support and wherein the first binding member specifically binds to the analyte; (b) contacting the analyte with a second binding member, wherein the second binding member specifically binds to the analyte and wherein the second binding member comprises a cleavable tag attached thereto; (c) removing second binding member not bound to the analyte bound to the first binding member; (d) cleaving the tag attached to the second binding member bound to the analyte bound to the first binding member; (e) translocating the tag through one or more nanopores in a layer; and (f) assessing the tag translocating through the layer, wherein each tag translocating through the layer is a translocation event, wherein measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference standard comprising a calibration curve, standard addition, or digital polymerase chain reaction, wherein the standard curve in subsection i) is determined by measuring the number of translocation events for control concentrations of analyte during a set period of time; wherein the standard curve in subsection ii) is determined by measuring the time it takes for a set number of translocation events to occur for control concentrations of analyte; and wherein the standard curve in subsection iii) is determined by measuring the average time between translocation events to occur for control concentrations of analyte.

Clause 128. A method for measuring an analyte present in a biological sample, the method comprising: (a) contacting the sample with a first binding member, wherein the first binding member is immobilized on a solid support and wherein the first binding member specifically binds to the analyte; (b) contacting the analyte with a second binding member, wherein the second binding member specifically binds to the analyte and wherein the second binding member comprises an aptamer; (c) removing aptamer not bound to the analyte bound to the solid substrate; (d) dissociating the aptamer bound to the analyte and (e) translocating the dissociated aptamer through one or more nanopores in a layer; and (f) assessing the aptamer translocating through the layer, wherein each aptamer translocating through the layer is a translocation event, wherein measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference standard comprising a calibration curve, standard addition, or digital polymerase chain reaction, wherein the standard curve in subsection i) is determined by measuring the number of translocation events for control concentrations of analyte during a set period of time; wherein the standard curve in subsection ii) is determined by measuring the time it takes for a set number of translocation events to occur for control concentrations of analyte; and wherein the standard curve in subsection iii) is determined by measuring the average time between translocation events to occur for control concentrations of analyte.

Clause 129. A method for measuring an analyte present in a biological sample, the method comprising: (a) contacting the sample with a binding member, wherein the binding member is immobilized on a solid support and wherein the binding member specifically binds to the analyte; (b) contacting the sample with a labeled analyte, wherein the labeled analyte is labeled with a cleavable tag; (c) removing labeled analyte not bound to the binding member; (d) cleaving the tag attached to the labeled analyte bound to the binding member; (e) translocating the tag through one or more nanopores in a layer; and (f) assessing the tags translocating through the layer, wherein each tag translocating through the layer is a translocation event, wherein measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference standard comprising a calibration curve, standard addition, or digital polymerase chain reaction, wherein the standard curve in subsection i) is determined by measuring the number of translocation events for control concentrations of analyte during a set period of time; wherein the standard curve in subsection ii) is determined by measuring the time it takes for a set number of translocation events to occur for control concentrations of analyte; and wherein the standard curve in subsection iii) is determined by measuring the average time between translocation events to occur for control concentrations of analyte.

Clause 130. A method for measuring an analyte present in a biological sample, the method comprising: (a) contacting the sample with a binding member, wherein binding member is immobilized on a solid support and wherein binding member specifically binds to the analyte; (b) contacting the sample with a labeled analyte, wherein the labeled analyte comprises an aptamer; (c) removing labeled analyte not bound to the binding member; (d) dissociating the aptamer bound to the labeled analyte and translocating the dissociated aptamer through one or more nanopores in a layer; and (e) assessing the aptamer translocating through the layer, wherein each aptamer translocating through the layer is a translocation event, wherein measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference standard comprising a calibration curve, standard addition, or digital polymerase chain reaction, wherein the standard curve in subsection i) is determined by measuring the number of translocation events for control concentrations of analyte during a set period of time; wherein the standard curve in subsection ii) is determined by measuring the time it takes for a set number of translocation events to occur for control concentrations of analyte; and wherein the standard curve in subsection iii) is determined by measuring the average time between translocation events to occur for control concentrations of analyte.

Clause 131. A method for measuring an analyte present in a biological sample, the method comprising: (a) contacting the sample with a binding member, wherein the binding member specifically binds to the analyte, and the binding member is labeled with a cleavable tag; (b) contacting the sample with a immobilized analyte, wherein the immobilized analyte is immobilized on a solid support; (c) removing binding member not bound to the immobilized analyte; (d) cleaving the tag attached to the binding member bound to the immobilized analyte; (e) translocating the tag through one or more nanopores in a layer; and (f) assessing the tag translocating through the layer, wherein each tag translocating through the layer is a translocation event, wherein measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference standard comprising a calibration curve, standard addition, or digital polymerase chain reaction, wherein the standard curve in subsection i) is determined by measuring the number of translocation events for control concentrations of analyte during a set period of time; wherein the standard curve in subsection ii) is determined by measuring the time it takes for a set number of translocation events to occur for control concentrations of analyte; and wherein the standard curve in subsection iii) is determined by measuring the average time between translocation events to occur for control concentrations of analyte.

Clause 132. A method for measuring an analyte present in a biological sample, the method comprising: (a) contacting the sample with a binding member, wherein the binding member specifically binds to the analyte, and the binding member comprises an aptamer; (b) contacting the sample with a immobilized analyte, wherein the immobilized analyte is immobilized on a solid support; (c) removing binding member not bound to the immobilized analyte; (d) dissociating the aptamer bound to the binding member bound to the immobilized analyte and translocating the dissociated aptamer through one or more nanopores in a layer; and (e) assessing the aptamer translocating through the layer, wherein each aptamer translocating through the layer is a translocation event, wherein measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference standard comprising a calibration curve, standard addition, or digital polymerase chain reaction, wherein the standard curve in subsection i) is determined by measuring the number of translocation events for control concentrations of analyte during a set period of time; wherein the standard curve in subsection ii) is determined by measuring the time it takes for a set number of translocation events to occur for control concentrations of analyte; and wherein the standard curve in subsection iii) is determined by measuring the average time between translocation events to occur for control concentrations of analyte.

Clause 133. A method for measuring or detecting an analyte present in a biological sample, the method comprising: (a) contacting the sample with a binding member, wherein the binding member is immobilized on a solid support, the binding member comprises a cleavable tag attached thereto, and the binding member specifically binds to the analyte; (b) removing binding member not bound to the analyte; (c) cleaving the tag attached to the binding member bound to the analyte; (d) translocating the tag through one or more nanopores in a layer; and (e) assessing the tag translocating through the layer, wherein each tag translocating through the layer is a translocation event, wherein measuring the number of translocation events measures the amount of analyte present in the sample, wherein the amount of analyte present in the sample is determined by: i) counting the number of translocation events during a set period of time and correlating the number of translocation events to a control; ii) measuring the amount of time for a set number of translocation events to occur and correlating to a control; or iii) measuring the average time between translocation events to occur and correlating to a control, wherein the control is a reference comprising a calibration curve, standard addition, or digital polymerase chain reaction.

Clause 134. The method of clauses 133, wherein the standard curve in subsection i) is determined by measuring the number of translocation events for control concentrations of analyte during a set period of time; wherein the standard curve in subsection ii) is determined by measuring the time it takes for a set number of translocation events to occur for control concentrations of analyte; and wherein the standard curve in subsection iii) is determined by measuring the average time between translocation events to occur for control concentrations of analyte.

Clause 135. An integrated digital microfluidics nanopore-enabled device comprising: a microfluidics module and a nanopore-enabled module; the microfluidics module, comprising an array of electrodes spaced apart from a single electrode sized to overlap with at least a portion of the array of electrodes, where the array of electrodes and the single electrode transport at least one droplet of fluid to a transfer electrode in the array of electrodes, wherein the transfer electrode is positioned at an interface between the microfluidics module and the nanopore-enabled module; the nanopore-enabled module comprising: a first microchannel positioned on a first surface of a first substrate; a second microchannel positioned on a first surface of a second substrate; wherein the first surface of the first substrate is in contact with the first surface of the second substrate thereby enclosing the first microchannel and the second microchannel to provide a first capillary channel and a second capillary channel, respectively, wherein at least the first capillary channel extends to the interface between the microfluidics module and the nanopore-enabled module and is adjacent to the transfer electrode, and is positioned to receive a fluid droplet positioned on the transfer electrode; wherein the first capillary channel intersects with the second capillary channel, wherein a layer is positioned in between the first and second substrates at the location where the first and the second capillary channels intersect, wherein the layer is devoid of a nanopore and separates an ionic liquid present in the first and second capillary channels, wherein the first and second capillary channels are in electrical connection with electrodes for driving a voltage from the first to the second capillary channel or vice versa for creating a nanopore in the layer at the intersection of the first and second capillary channels.

Clause 136. The device of clauses 135, wherein the ionic liquid is an aqueous solution.

Clause 137. The device of clauses 136, wherein the aqueous solution is salt solution.

Clause 138. The device of any one of clauses 135 to 137, wherein the ionic liquid comprises an analyte of interest, wherein the device is configured to detect the presence or absence of the analyte in the ionic liquid.

Clause 139. A method for generating a nanopore in an integrated digital microfluidics nanopore-enabled device, the method comprising: providing an integrated digital microfluidics nanopore-enabled device of any one of clauses 135 to 138; applying a voltage in the first and second capillary channels to drive current through the layer; measuring conductance across the layer; terminating application of voltage upon detection of a conductance indicative of generation of a nanopore in the layer.

Clause 140. An integrated digital microfluidics nanopore device comprising: a first substrate comprising an array of electrodes; a second substrate spaced apart from the first substrate; an opening in the first or second substrate in fluid communication with a nanopore layer comprising a nanopore; and a pair of electrodes configured to apply an electric field through the nanopore, wherein the array of electrodes are configured to transport at least one droplet of fluid to the opening.

Clause 141. The device of clauses 140, wherein the opening is a capillary channel.

Clause 142. The device of clauses 141, wherein the capillary channel has an opening on a first side of the first or second substrate that is wider than an opening on a second side of the first or second substrate.

Clause 143. The device of clauses 142, wherein the pair of detection electrodes comprises a first detection electrode that is the single electrode.

Clause 144. The device of clauses 142 or 143, wherein the pair of detection electrodes comprises a second detection electrode disposed on the second side.

Clause 145. A pair of integrated digital microfluidics nanopore devices comprising:
a first integrated digital microfluidics nanopore device according to clauses 142, wherein the single electrode is a first single electrode, and the capillary channel is a first capillary channel; and a second integrated digital microfluidics nanopore device comprising: a third substrate, comprising a fifth side and a sixth side opposite the fifth side, wherein the fifth side comprises an array of electrodes; a fourth substrate spaced apart from the third substrate, wherein the fourth substrate comprises a seventh side facing the fifth side of the third substrate and a eight side opposite the seventh side, wherein the seventh side comprises a second single electrode and wherein the nanopore layer is disposed on the eight side, wherein the fourth substrate comprises a second capillary channel extending from the seventh side to the eight side of the fourth substrate, wherein the nanopore layer is positioned over an opening of the capillary channel, wherein the nanopore layer is interposed between the second substrate and the fourth substrate such that the nanopore provides an electroosmotic conduit between the first capillary channel and the second capillary channel, wherein the pair of detection electrodes comprises a second detection electrode that is the second single electrode.

Clause 146. An integrated digital microfluidics nanopore-enabled device comprising: a first substrate, comprising a first side and a second side opposite the first side, wherein the first side comprises an array of electrodes; a second substrate spaced apart from the first substrate, wherein the second substrate comprises a third side facing the first side of the first substrate and a fourth side opposite the third side; a nanopore-enabled layer devoid of a nanopore and disposed on an external side of the device, wherein the external side is selected from the second side or the fourth side, wherein one of the first or second substrates comprising the external side comprises a capillary channel extending from the first side to the second side of the first substrate, or the third side to the fourth side of the second substrate, wherein the nanopore-enabled layer is positioned over an opening of the capillary channel; and a pair of electrodes configured to apply an electric field across the nanopore-enabled layer, wherein the array of electrodes are configured to transport at least one droplet of fluid to the capillary channel.

Clause 147. A method for generating a nanopore in an integrated digital microfluidics nanopore-enabled device, the method comprising: providing an integrated digital microfluidics nanopore-enabled device of clauses 143; submerging both sides of the nanopore-enabled layer in an ionic liquid such that the ionic liquid on each side of the layer is in electrical contact with either one of the pair of detection electrodes; applying a voltage between the pair of detection electrodes to drive current through the layer; measuring conductance across the layer; terminating application of voltage upon detection of a conductance indicative of generation of a nanopore in the layer.

Clause 148. The method of clauses 147, wherein the ionic liquid is a salt solution.

Clause 149. The method of clauses 147 or 148, wherein the ionic liquid comprises an analyte of interest, wherein the device is configured to detect the presence or absence of the analyte in the ionic liquid.

Clause 150. The method of any one of clauses 139 or 147 to 149, further comprising conditioning the generated nanopore.

Clause 151. The method of clauses 150, wherein the conditioning comprises: alternately applying a first voltage having a first polarity and a second voltage having a second polarity opposite the first polarity across the nanopore membrane, wherein the first and second voltages are each applied at least once; and measuring an electroosmotic property related to a size of the nanopore.

Clause 152. The method of clauses 150 or 151, further comprising measuring the electroosmotic property related to a size of the nanopore before the conditioning.

Clause 153. A composition comprising a binding member, a tag and a spacer.

Clause 154. The composition of clauses 153, wherein the spacer comprises a nitrobenzyl group, dithioethylamino, 6 carbon spacer, 12 carbon spacer, or 3-(9-((3-carboxypropyl)(tosyl)carbamoyl)acridin-10-ium-10-yl)propane-1-sulfonate.

Clause 155. The composition of 154, wherein the spacer comprises a nitrobenzyl group, and the tag is a DNA molecule.

Clause 156. The composition of 154, wherein the spacer is dithioethylamino and the tag is a carboxylated nanoparticle.

Clause 157. The composition of 154, wherein the spacer is 3-(9-((3-carboxypropyl)(tosyl)carbamoyl)acridin-10-ium-10-yl)propane-1-sulfonate and the tag is an oligonucleotide.

Clause 158. The composition of 154, wherein the spacer comprises a 6 carbon spacer or 12 carbon spacer and the tag is biotin.

Clause 159. The composition of 158, wherein the second binding member comprises a nucleic acid comprising a nucleotide sequence set forth in any one of SEQ ID NOs: 1-11.

Clause 160. The composition of any one of clauses 153-159, wherein the tag comprises a cleavable linker.

Clause 161. The composition of clauses 160, wherein the cleavable linker is selected from the group consisting of a photocleavable linker, a chemically cleavable linker, a thermally cleavable linker, a thermal-sensitive cleavable linker, and an enzymatic cleavable linker.

Clause 162. The composition of clauses 161, wherein the cleavable linker is a photocleavable linker, wherein the photocleavable linker comprising a photocleavable moiety derived from

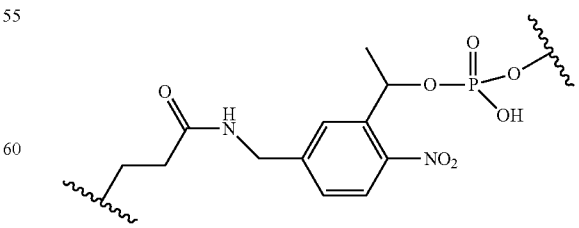

Clause 163. The composition of clauses 161, wherein the cleavable linker is a thermally cleavable linker and is cleaved using localized temperature elevation.

Clause 164. The composition of clauses 163, wherein the localized temperature elevation is generated photothermally or by microwave irradiation.

Clause 165. The composition of clauses 164, wherein energy from light is transferred to an absorbing target.

Clause 166. The composition of clauses 165, wherein the absorbing target comprises a dye, pigment, or water.

Clause 167. The composition of any one of clauses 163 to 166, wherein the cleavable linker comprises double stranded DNA.

Clause 168. The composition of clauses 161, wherein the cleavable linker is a chemically cleavable linker and cleavage is mediated by thiol.

Clause 169. The method of any one of clauses 29, 66, 68, 70, 72 to 86, 92-94, 98 to 105 127, 129, 131, 133, and 134, wherein the tag comprises a cleavable linker.

Clause 170. The method of clauses 169, wherein the cleavable linker is selected from the group consisting of a photocleavable linker, a chemically cleavable linker, a thermally cleavable linker, a thermal-sensitive cleavable linker, and an enzymatic cleavable linker.

Clause 171. The method of clauses 170, wherein the cleavable linker is a photocleavable linker and the photocleavable linker comprises a photocleavable moiety derived from

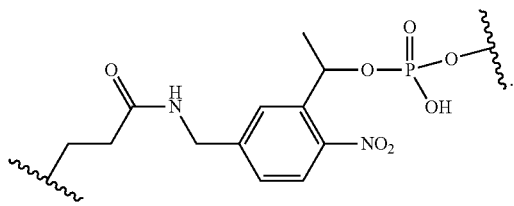 [SMILES: *CCC(=O)NCc1ccc([N+](=O)[O-])c(C(C)OP(=O)(O)O*)c1]

Clause 172. The method of clauses 170, wherein the cleavable linker is a thermally cleavable linker and is cleaved using localized temperature elevation.

Clause 173. The method of clauses 172, wherein the localized temperature elevation is generated photothermally or by microwave irradiation.

Clause 174. The method of clauses 173, wherein energy from light is transferred to an absorbing target.

Clause 175. The method of clauses 174, wherein the absorbing target comprises a dye, pigment, or water.

Clause 176. The method of any one of clauses 172 to 175, wherein the cleavable linker comprises double stranded DNA.

Clause 177. The method of clauses 30 and 170, wherein the cleavable linker is a chemically cleavable linker and is cleaved by thiol.

Clause 178. The method of any one of clauses 2-30, 31-45, 64, 70 to 105, 125, 127 to 134, and 169 to 177, wherein one or more translocation events corresponds to a binding event of a binding member to an analyte.

Clause 179. The method of clauses 178, wherein one translocation event corresponds to a binding event of a binding member to an analyte.

Clause 180. The method of clauses 178, wherein two or more translocation events corresponds to a binding event of a binding member to an analyte.

Clause 181. The method of clauses 180, wherein two or more tags are incorporated per binding member and two or more translocation events represents the binding of the binding member to the analyte.

Clause 182. The method of any one of clauses 1 to 45, 63 to 105, 124, 125, 127 to 134, and 169 to 181, wherein at least two or more nanopores are in the layer.

Clause 183. The method of clauses 182, wherein the at least two or more nanopores are presented side by side or in series.

Clause 184. An integrated digital microfluidics nanopore device comprising: a first substrate, comprising an array of electrodes; a second substrate spaced apart from the first substrate; and a nanopore layer having a first surface and a second surface disposed between the first and second substrates, wherein the array of electrodes are configured to position a first droplet at the first surface of the nanopore layer, wherein at least two electrodes of the array of electrodes are positioned across the nanopore layer, where the two electrodes form an anode and a cathode and operate to drive current through a nanopore in the nanopore layer when a liquid droplet is at the first surface of the nanopore layer.

Clause 185. The array of electrodes of clauses 173 is further configured to position a second droplet at a second surface of the nanopore layer.

Clause 186. An integrated digital microfluidics nanopore device comprising a microfluidics module and a nanopore module; the microfluidics module comprising an array of electrodes, where the array of electrodes transport at least one droplet of fluid to a transfer position in the array of electrodes, wherein the transfer position is at an interface between the microfluidics module and the nanopore module; the nanopore module comprising: a first capillary channel extending from the transfer position to a nanopore layer.

Clause 187. An integrated digital microfluidics nanopore device comprising: a first substrate, comprising an array of electrodes; a second substrate spaced apart from the first substrate; a first nanopore layer having one or more nanopores therein; a second nanopore layer having one or more nanopores therein; and at least two electrodes for creating an electric field to drive tags through a nanopore in the first and second nanopore layers.

Clause 188. The method of clauses 30, wherein the immobilization agent comprises biotin or streptavidin.

Clause 189. The method of clauses 188, wherein the immobilization agent comprises biotin and ligand comprises streptavidin.

Clause 190. The method of clauses 188, wherein the immobilization agent comprises streptavidin and ligand comprises biotin.

Clause 191. The method of any one of clauses 30 and 188 to 190, wherein the solid support, the first binding member, and second binding member are added sequentially or simultaneously to the sample.

Clause 192. The method of any one of clauses 1 to 45, 63 to 105, 124, 125, 127 to 134, 169 to 181, 183, and 188 to 191 wherein the ratio of the size of the pore to the tag is at or less than 1.0.

Clause 193. A method for measuring or detecting an analyte of interest present in a biological sample, the method comprising (a) contacting the sample with a solid support, a binding member, and a labeled analyte that is labeled with a cleavable tag, wherein the solid support comprises an immobilization agent, the binding member comprises a ligand for the immobilization agent, and the binding member specifically binds the analyte of interest so as to form either a solid support/binding member/analyte of interest complex or a solid support/binding member/labeled analyte complex; (b) removing labeled analyte not bound to the binding member in the solid support/binding member/labeled analyte complex; (c) cleaving the tag attached to the labeled analyte bound to the binding member in the solid support/binding member/labeled analyte complex; (d) translocating the tag through one or more nanopores in a layer; and (e) assessing the tags translocating through the layer, wherein measuring the number of tags translocating through the layer measures the amount of analyte present in the sample, or wherein detecting tags translocating through the layer detects that the analyte is present in the sample.

Clause 194. The method of clause 193, wherein the immobilization agent comprises biotin or streptavidin.

Clause 195. The method of clause 194, wherein the immobilization agent comprises biotin and ligand comprises streptavidin.

Clause 196. The method of clause 194, wherein the immobilization agent comprises streptavidin and ligand comprises biotin.

Clause 197. The method of any one of clauses 193 to 196, wherein the solid support, the binding member, and the labeled analyte are added sequentially or simultaneously to the sample.

Clause 198. A method for measuring or detecting an analyte of interest present in a biological sample, the method comprising (a) contacting the sample with a solid support, a binding member, and exogenous analyte, wherein the solid support comprises an immobilization agent, the exogenous analyte comprises a ligand for the immobilization agent and binds the solid support so as to form a solid support/immobilized analyte complex, and the binding member comprises a cleavable tag and specifically binds the analyte of interest so as to form either a solid support/analyte of interest/binding member complex or a solid support/immobilized analyte/binding member complex; (b) removing binding member not bound in either the solid support/immobilized analyte/binding member complex or the solid support/analyte of interest/binding member complex; (c) cleaving the tag attached to the binding member in the solid support/immobilized analyte/binding member complex; (d) translocating the tag through one or more nanopores in a layer; and (e) assessing the tags translocating through the layer, wherein measuring the number of tags translocating through the layer measures the amount of analyte present in the sample, or wherein detecting tags translocating through the layer detects that the analyte is present in the sample.

Clause 199. The method of clause 198, wherein the immobilization agent comprises biotin or streptavidin.

Clause 200. The method of clause 199, wherein the immobilization agent comprises biotin and ligand comprises streptavidin.

Clause 201. The method of clause 199, wherein the immobilization agent comprises streptavidin and ligand comprises biotin.

Clause 202. The method of any one of clauses 198 to 201, wherein the solid support, the binding member, and exogenous analyte are added sequentially or simultaneously to the sample.

Clause 203. The method of any one of clauses 198 to 201, wherein prior to cleaving the tag in step (c), the solid support/immobilized analyte/binding member complex is isolated.

Clause 204. The method of clause 203 wherein isolation can be done with use of a magnetic field.

Clause 205. A method for measuring or detecting an analyte of interest present in a biological sample, the method comprising (a) contacting the sample with a solid support, a binding member, and a labeled analyte that is labeled with an aptamer, wherein the solid support comprises an immobilization agent, the binding member comprises a ligand for the immobilization agent, and the binding member specifically binds the analyte of interest so as to form either a solid support/binding member/analyte of interest complex or a solid support/binding member/labeled analyte complex; (b) removing labeled analyte not bound to the binding member in the solid support/binding member/labeled analyte complex; (c) dissociating the aptamer attached to the labeled analyte bound to the binding member in the solid support/binding member/labeled analyte complex; (d) translocating the dissociated aptamer through one or more nanopores in a layer; and (e) assessing the aptamer translocating through the layer, wherein measuring the number of aptamers translocating through the layer measures the amount of analyte present in the sample, or wherein detecting aptamers translocating through the layer detects that the analyte is present in the sample.

Clause 206. The method of clause 205, wherein the immobilization agent comprises biotin or streptavidin.

Clause 207. The method of clause 206, wherein the immobilization agent comprises biotin and ligand comprises streptavidin.

Clause 208. The method of clause 206, wherein the immobilization agent comprises streptavidin and ligand comprises biotin.

Clause 209. The method of any one of clauses 205 to 208, wherein the solid support, the binding member, and the labeled analyte are added sequentially or simultaneously to the sample.

Clause 210. A method for measuring or detecting an analyte of interest present in a biological sample, the method comprising (a) contacting the sample with a solid support, a binding member, and exogenous analyte, wherein the solid support comprises an immobilization agent, the exogenous analyte comprises a ligand for the immobilization agent and binds the solid support so as to form a solid support/immobilized analyte complex, and the binding member comprises an aptamer and specifically binds the analyte of interest so as to form either a solid support/analyte of interest/binding member complex or a solid support/immobilized analyte/binding member complex; (b) removing binding member not bound in either the solid support/immobilized analyte/binding member complex or the solid support/analyte of interest/binding member complex; (c) dissociating the aptamer bound to the binding member in the solid support/immobilized analyte/binding member complex; (d) translocating the tag through one or more nanopores in a layer; and (e) assessing the tags translocating through the layer, wherein measuring the number of tags translocating through the layer measures the amount of analyte present in the sample, or wherein detecting tags translocating through the layer detects that the analyte is present in the sample.

Clause 211. The method of clause 210, wherein the immobilization agent comprises biotin or streptavidin.

Clause 212. The method of clause 211, wherein the immobilization agent comprises biotin and ligand comprises streptavidin.

Clause 213. The method of clause 211, wherein the immobilization agent comprises streptavidin and ligand comprises biotin.

Clause 214. The method of any one of clauses 210 to 213, wherein the solid support, the binding member, and exogenous analyte are added sequentially or simultaneously to the sample.

Clause 215. The method of any one of clauses 210 to 213, wherein prior to dissociating the aptamer in step (c), the solid support/immobilized analyte/binding member complex is isolated.

Clause 216. The method of clause 215 wherein isolation can be done with use of a magnetic field.

Clause 217. A method for measuring or detecting an analyte present in a biological sample, the method comprising:

I. (a) contacting the sample with a first binding member, wherein the first binding member is immobilized on a solid support and wherein the first binding member specifically binds to the analyte; (b) contacting the analyte with a second binding member, wherein the second binding member specifically binds to the analyte and wherein the second binding member comprises an aptamer; (c) removing aptamer not bound to the analyte bound to the solid substrate; (d) dissociating the aptamer bound to the analyte and translocating the dissociated aptamer through or across one or more nanopores in a layer; and (e) assessing the aptamer translocating through the layer, wherein measuring the number of aptamers translocating through the layer measures the amount of analyte present in the sample, or wherein detecting aptamers translocating through the layer detects that the analyte is present in the sample;

II. (a) contacting the sample with a binding member, wherein the binding member is immobilized on a solid support and wherein the binding member specifically binds to the analyte; (b) contacting the sample with a labeled analyte, wherein the labeled analyte is labeled with a cleavable tag; (c) removing labeled analyte not bound to the binding member; (d) cleaving the tag attached to the labeled analyte bound to the binding member; (e) translocating the cleaved tag through or across one or more nanopores in a layer; and (f) assessing the tag translocating through the layer, wherein measuring the number of tags translocating through the layer measures the amount of analyte present in the sample, or wherein detecting tags translocating through the layer detects that the analyte is present in the sample;

III. (a) contacting the sample with a binding member, wherein binding member is immobilized on a solid support and wherein binding member specifically binds to the analyte; (b) contacting the sample with a labeled analyte, wherein the labeled analyte comprises an aptamer; (c) removing labeled analyte not bound to the binding member; (d) dissociating the aptamer bound to the labeled analyte that is bound to the binding member and translocating the dissociated aptamer through or across one or more nanopores in a layer; and (e) assessing the aptamer translocating through the layer, wherein measuring the number of aptamers translocating through the layer measures the amount of analyte present in the sample, or detecting aptamers translocating through the layer detects that the analyte is present in the sample;

IV. (a) contacting the sample with a binding member, wherein the binding member specifically binds to the analyte, and the binding member is labeled with a cleavable tag; (b) contacting the sample with a immobilized analyte, wherein the immobilized analyte is immobilized on a solid support; (c) removing binding member not bound to the immobilized analyte; (d) cleaving the tag attached to the binding member bound to the immobilized analyte; (e) translocating the cleaved tag through or across one or more nanopores in a layer; and (f) assessing the tag translocating through the layer, wherein measuring the number of tags translocating through the layer measures the amount of analyte present in the sample, or detecting tags translocating through the layer detects that the analyte is present in the sample; and V. (a) contacting the sample with a binding member, wherein the binding member specifically binds to the analyte, and the binding member comprises an aptamer; (b) contacting the sample with a immobilized analyte, wherein the immobilized analyte is immobilized on a solid support; (c) removing binding member not bound to the immobilized analyte; (d) dissociating the aptamer bound to the binding member that is bound to the immobilized analyte and translocating the dissociated aptamer through or across one or more nanopores in a layer; and (e) assessing the aptamer translocating through the layer, wherein measuring the number of aptamers translocating through the layer measures the amount of analyte present in the sample, or detecting aptamers translocating through the layer detects that the analyte is present in the sample.

Clause 218. The method of any one of clauses 193 to 217, wherein the ratio of the size of the pore to the tag is at or less than 1.0.

What is claimed is:

1. An integrated digital microfluidics nanopore device comprising:
    a microfluidics module comprising a first substrate having an array of electrodes disposed in a grid pattern to generate electrical actuation forces on a liquid droplet disposed thereon; and
    a nanopore module in fluid communication with the microfluidics module and comprising at least one nanopore,
    wherein the microfluidics module is configured to introduce a liquid droplet to the at least one nanopore.

2. The device of claim 1, wherein the at least one nanopore is a solid state nanopore or a biological nanopore.

3. The device of claim 1, wherein the microfluidics module is configured to move the liquid droplet via a fluid manipulation force selected from an electrical force pressure, electrowetting, dielectrophoresis, electrode-mediated force, opto-electrowetting, electric-field mediated force, electrostatic actuation, and surface acoustic waves.

4. The device of claim 1, wherein the microfluidics module comprises:
    a second substrate spaced apart from the first substrate, wherein a first electrode in the array of electrodes forms an anode and a second electrode in the array of electrodes forms a cathode, to drive current through the nanopore.

5. The device of claim 4, wherein the at least one nanopore is disposed in a nanopore layer attached to at least one of the first substrate and the second substrate, and wherein the first electrode and the second electrode flank the nanopore layer.

6. The device of claim 4, wherein at least one of the first substrate and the second substrate is substantially transparent.

7. The device of claim 4, wherein the electrodes in the array of electrodes are interdigitated.

8. The device of claim 1, wherein the microfluidics module comprises a layer of surface acoustic wave (SAW) generation material.

9. The device of claim 1, further comprising at least one reagent disposed on the microfluidics module and configured to be carried by the liquid droplet.

10. The device of claim 9, wherein the reagent is selected from the group consisting of a binding member, a cleaveable tag, and a combination thereof.

11. The device of claim 9, wherein the cleavable tag comprises an anionic polymer, a cationic polymer, a dendrimer, or a nanoparticle and the binding member comprises a binding member or a receptor.

12. The device of claim 1, wherein the array of electrodes is operatively connected to a reagent reservoir.

* * * * *